US007018611B2

(12) United States Patent
Harris et al.

(10) Patent No.: US 7,018,611 B2
(45) Date of Patent: *Mar. 28, 2006

(54) VITRONECTIN RECEPTOR ANTAGONIST PHARMACEUTICALS

(75) Inventors: Thomas D. Harris, Salem, NH (US); John A. Barrett, Groton, MA (US); Alan P. Carpenter, Jr., Carlisle, MA (US); Milind Rajopadhye, Westford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 130 days.

This patent is subject to a terminal disclaimer.

(21) Appl. No.: 10/281,015

(22) Filed: Oct. 26, 2002

(65) Prior Publication Data

US 2003/0113336 A1    Jun. 19, 2003

Related U.S. Application Data

(60) Division of application No. 09/599,364, filed on Jun. 21, 2000, now Pat. No. 6,511,649, which is a continuation-in-part of application No. 09/465,300, filed on Dec. 17, 1999, now Pat. No. 6,511,648.

(60) Provisional application No. 60/112,732, filed on Dec. 18, 1998.

(51) Int. Cl.
*A61K 51/00* (2006.01)
*A61M 36/14* (2006.01)

(52) U.S. Cl. .............. 424/1.65; 424/1.11; 424/1.65; 424/9.1; 424/1.69; 424/9.3; 424/9.32; 424/9.323; 534/14

(58) Field of Classification Search .............. 424/1.11, 424/1.65, 1.69, 9.1, 9.2, 9.3, 9.4, 9.5, 9.6, 424/9.7, 9.8; 514/2; 206/223, 569, 570; 530/300; 534/10–16
See application file for complete search history.

(56) References Cited

U.S. PATENT DOCUMENTS

| | | | |
|---|---|---|---|
| 4,248,802 A | 2/1981 | Kuntz | |
| 4,472,509 A | 9/1984 | Gansow et al. | |
| 4,536,387 A | 8/1985 | Sakamoto et al. | |
| 4,859,777 A | 8/1989 | Toner | |
| 4,988,827 A | 1/1991 | Bergstein et al. | |
| 5,021,236 A | 6/1991 | Gries et al. | |
| 5,064,956 A | 11/1991 | Kruper | |
| 5,087,440 A | 2/1992 | Cacheris et al. | |
| 5,155,215 A | 10/1992 | Ranney | |
| 5,281,704 A | 1/1994 | Love et al. | |
| 5,342,757 A | 8/1994 | Garin-Chesa et al. | |
| 5,350,837 A | 9/1994 | Bridger et al. | |
| 5,376,356 A | 12/1994 | Morgan, Jr. | |
| 5,382,654 A | 1/1995 | Lyle et al. | |
| 5,395,609 A | 3/1995 | Stuttle | |
| 5,403,713 A | 4/1995 | Bevilacqua et al. | |
| 5,412,148 A | 5/1995 | Keana | |
| 5,417,959 A | 5/1995 | Wallace | |
| 5,520,904 A | 5/1996 | Nosco et al. | |
| 5,556,939 A | 9/1996 | Flanagan et al. | |
| 5,567,411 A | 10/1996 | Keana et al. | |
| 5,622,821 A | 4/1997 | Selvin et al. | ............ 435/6 |
| 5,650,134 A | 7/1997 | Albert et al. | |
| 5,659,013 A | 8/1997 | Senger et al. | |
| 5,659,041 A | 8/1997 | Pollak et al. | |
| 5,660,827 A | 8/1997 | Thorpe et al. | |
| 5,679,810 A | 10/1997 | Love et al. | |
| 5,739,789 A * | 4/1998 | Kronhamn | ............ 342/465 |
| 5,744,120 A | 4/1998 | Edwards et al. | |
| 5,760,191 A | 6/1998 | Snow et al. | |
| 5,766,591 A | 6/1998 | Brooks et al. | |
| 5,776,427 A | 7/1998 | Thorpe et al. | ........ 424/1.49 |
| 5,801,228 A | 9/1998 | Hollister et al. | |
| 5,804,161 A | 9/1998 | Long et al. | |
| 5,855,866 A | 1/1999 | Thorpe et al. | |
| 5,863,538 A | 1/1999 | Thorpe et al. | |
| 5,879,656 A | 3/1999 | Waldman | ............ 424/149 |
| 6,040,311 A | 3/2000 | Duggan et al. | |
| 6,051,207 A | 4/2000 | Klaveness et al. | |

(Continued)

FOREIGN PATENT DOCUMENTS

AU    5 314 694    7/1994

(Continued)

OTHER PUBLICATIONS

Abstract, *Nucl. Med. Proceeding of the 42nd Annual Meeting*, May 1995, 36(5), No. 287, p. 71.

(Continued)

*Primary Examiner*—Dameron Jones
(74) *Attorney, Agent, or Firm*—Woodcock Washburn LLP

(57) ABSTRACT

The present invention describes novel compounds of the formula:

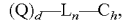

$(Q)_d-L_n-C_h,$ useful for the diagnosis and treatment of cancer, methods of imaging tumors in a patient, and methods of treating cancer in a patient. The present invention also provides novel compounds useful for monitoring therapeutic angiogenesis treatment and destruction of new angiogenic vasculature. The present invention further provides novel compounds useful for imaging atherosclerosis, restenosis, cardiac ischemia, and myocardial reperfusion injury. The present invention still further provides novel compounds useful for the treatment of rheumatoid arthritis. The pharmaceuticals are comprised of a targeting moiety that binds to a receptor that is upregulated during angiogenesis, an optional linking group, and a therapeutically effective radioisotope or diagnostically effective imageable moiety. The imageable moiety is a gamma ray or positron emitting radioisotope, a magnetic resonance imaging contrast agent, an X-ray contrast agent, or an ultrasound contrast agent.

26 Claims, No Drawings

U.S. PATENT DOCUMENTS

| | | | |
|---|---|---|---|
| 6,051,230 | A | 4/2000 | Thorpe et al. |
| 6,056,973 | A | 5/2000 | Allen et al. |
| 6,143,274 | A | 11/2000 | Tweedle et al. |
| 6,254,852 | B1 | 7/2001 | Glajch et al. ............... 424/9.52 |
| 6,264,917 | B1 | 7/2001 | Klaveness et al. ......... 424/9.52 |
| 6,511,648 | B1* | 1/2003 | Harris et al. ............... 424/1.65 |
| 6,511,649 | B1* | 1/2003 | Harris et al. ............... 424/1.69 |
| 6,569,402 | B1* | 5/2003 | Cheesman et al. ......... 424/1.65 |
| 6,610,269 | B1* | 8/2003 | Klaveness et al. ........... 424/9.1 |
| 6,683,163 | B1* | 1/2004 | Harris et al. .................. 534/15 |
| 2003/0124120 | A1* | 7/2003 | Harris ..................... 424/143.1 |
| 2003/0232053 | A1* | 12/2003 | Harris et al. ............. 424/178.1 |

FOREIGN PATENT DOCUMENTS

| | | |
|---|---|---|
| CA | 2 113 245 | 6/1988 |
| CA | 2 039 259 | 10/1991 |
| CA | 2 156 620 | 10/1994 |
| CA | 2 232 315 | 4/1997 |
| DE | 04 311 023 | 10/1994 |
| DE | 19 536 781 | 3/1997 |
| DE | 19 536 785 | 3/1997 |
| DE | 19 725 368 | 12/1998 |
| EP | 0 107 734 | 7/1987 |
| EP | 0 359 347 | 3/1990 |
| EP | 0 436 005 | 10/1991 |
| EP | 0 606 683 | 7/1994 |
| EP | 0 727 225 A2 | 8/1996 |
| WO | WO 81/01145 | 4/1981 |
| WO | WO 90/03801 | 4/1981 |
| WO | WO 90/05539 | 5/1990 |
| WO | WO 90/12585 | 11/1990 |
| WO | WO 90/13300 | 11/1990 |
| WO | WO 91/01144 | 2/1991 |
| WO | WO 91/14460 | 10/1991 |
| WO | WO 91/15244 | 10/1991 |
| WO | WO 92/12729 | 8/1992 |
| WO | WO 92/17215 | 10/1992 |
| WO | WO 92/19646 | 11/1992 |
| WO | WO 93/08174 | 4/1993 |
| WO | WO 93/08210 A1 | 4/1993 |
| WO | WO 93/17715 | 9/1993 |
| WO | WO 94/11499 | 5/1994 |
| WO | WO 94/22497 | 10/1994 |
| WO | WO 96/00574 | 1/1996 |
| WO | WO 96/01653 | 1/1996 |
| WO | WO 95/25543 | 10/1996 |
| WO | WO 96/31243 | 10/1996 |
| WO | WO 96/40637 | 12/1996 |
| WO | WO 96/41803 | 12/1996 |
| WO | WO 97/08145 | 3/1997 |
| WO | WO 94/05328 | 4/1997 |
| WO | WO 97/16474 | 5/1997 |
| WO | WO 97/18207 | 5/1997 |
| WO | WO 97/23480 | 7/1997 |
| WO | WO 93/23074 | 9/1997 |
| WO | WO 98/14220 | 4/1998 |
| WO | WO 98/16256 | 4/1998 |
| WO | WO 98/23608 | 6/1998 |
| WO | WO 98/47541 | 10/1998 |
| WO | WO 99/06049 | 2/1999 |
| WO | WO 99/13329 | 3/1999 |
| WO | WO 99/40947 | 8/1999 |
| WO | WO 99/59640 | 11/1999 |
| WO | WO 00/35492 A3 | 6/2000 |
| WO | WO 01/97860 A2 | 12/2001 |
| WO | WO 01/97861 A2 | 12/2001 |
| WO | WO 01/98294 A2 | 12/2001 |
| WO | WO 02/04030 A2 | 1/2002 |

OTHER PUBLICATIONS

Baker, et al., *Life Sci.*, 1991, 49, 1583-1591.
Batt, et al., *J. Med. Chem.*, 2000, 43, 41-58.
Bevilacqua, et al., *Proc. Natl. Acad. Sci.*, 1986, 84, 9238-9242.
Bousquet, et al., *Radiology*, 1988, 166, 693.
Brechbiel, M., et al., *J. Chem. Soc. Perkin Trans.*, 1992, 1, 1175.
Brechbiel, M., et al., *Bioconjugate Chem.*, 1991, 2, 187.
Brinkley, M., *Bioconjugate Chemistry*, 1992, 3(1).
Burrows, et al., *Proc. Nat. Acad. Sci. USA*, 1993, 90, 8996-9000.
Burrows, F.J., et al., *Cancer Research*, 1992, 52, 5954-5962.
Burrows, et al., *J. Controlled Release*, Jan. 1994, 28(1), 195-202.
Cheresh, et al., *Science*, 1995, 270, 1500-1502.
Clauss, et al., *J. Biological Chem.*, 1990, 265(12), 7078-7083.
*Clin. Can. Res.*, 1995, 1, 1623-1634.
DeGrado, et al., *J. Org. Chem.*, 1980, 45, 1295.
DeNardo, et al., *Cancer Biotherapy & Radiopharm.*, Feb. 2000, 15(1), 71-79.
Denekamp, J., et al., *Br. J. Cancer*, 1982, 45, 136-139.
Denekamp, J., et al., *Br. J. Cancer*, 1982, 46, 711-720.
Denekamp, J., *Acta Radiologica Oncology*, 1984, 23 Fasc. (4), 217-225.
Denekamp, J., *Cancer Meta. Rev.*, 1990, 9, 267-282.
Deshpande, S., et al., *J. Nucl. Med.*, 1990, 31, 473.
DiZio, et al., *Bioconjugate Chem.*, 1991, 2, 353-366.
Dvorak, et al., *Cancer Cells*, 1991, 3, 77-85.
Folkman, J., Nature Med., 1995, 1, 27-31.
Ghose, et al., *Meth. Enzymology*, 1983, 93, 280-333.
Hagemeier, H-H., et al., *Int. J. Cancer*, 1986, 38, 481-488.
Haubner, *V313 Nuclear-Medizin*, Mar. 1997.
Henry, T., et al., *J. Amer. College Cardiology*, 1998, 31, p. 65A
Horton, et al., *Int. J. Biochem. Cell. Biol.*, May 1997, 29(5), 721-725.
Hu, et al., *Oncology Res.*, 1994, 6(7), 321-327.
*J. Org. Chem.*, 1996, 61, 903-908.
Kennel, et al., *Nuclear Med. & Biol.*, 1998, 25, 241-246.
Kerr, et al., *Anticancer Res.*, Mar.-Apr. 1999, 19(2A), 958-968.
Knowles, et al., *Analytical Biochemistry*, 1987, 160, 440-443.
Krenning, et al., *Eur. J. Nucl. Med.* 1993, 20, 716-731.
Krenning, et al., *Digestion*, 1996, 57, 57-61.
*Liebigs Ann. Chem.*, 1979, 776-783.
Liu, et al., *Inorg. Chem.*, 1999, 38(6), 1326-1335.
Margerstadt, et al., *Magn. Reason, Med.*, 1986, 3, 808.
Molema, et al., *Biochemical Pharm.*, 1998, 55, 1939-1945.
Mueller, et al., *Proc. Natl. Acad. Sci. USA*, 1992, 89, 11832-11836.
Olson, et al., *Int. J. Cancer*, 1997, 73, 865-870.
O'Reilly, et al., *Cell*, 1997, 88, 277-285.
O'Reilly, et al., *Cell*, 1994, 79, 315-328.
Orlando, et al., *J. Biological Chem.*, Oct. 1991, 266(29), 19543-1955.
Remington's Pharmaceutical Sciences, 17th Ed., *Mack Publishing Co., Easton, PA*, 1985, p. 1418.
Runge, et al., *Radiology*, 1988, 166, 835.
Sellke, et al., *Drugs*, 1999, 58, 391-396.
Senger, et al., *Proc. Natl. Acad. Sci. USA*, 1997, 94, 13612-13617.
Sipkins, et al., *Nature Med.*, May 1998, 4(5), 623-62.

Srivatsa, et al., *Cardiovascular Res.*, 1997, 36 408-428.
Takeshita, S., et al., *J. Clin. Invest.*, 1994, 93, 662-670.
Tet. Lett., 1997, 53, 11937-11952.
Thorpe, et al., *Breast Cancer Res. & Treat.*, 1995, 36(2), 237-251.
Van Waes, et al., *International J. Oncology*, 2000, 16, 1189-1195.
Wellicome, et al., *J. Immunol.*, 1990, 144(7), 2558-2565.
Wilbur, D.S., et al., *Bioconjugate Chem.*, 1998, 9, 322-330.
Harris, T.D., et al., "Radiolabeled indazole-based αvβ3 antagonists as potential tumor imaging agents," *J. Labelled Cpd. Radiopharm.*, 2001, 44, Suppl. 1, XP008009503, S60-S62.
Kawai, K., et al., "Enhancement of anticancer effects of radiation and conventional anticancer agents by a quinolinone derivative, vesnarinone: studies on human gastric cancer tissue xenografts in nude mice," *Anticancer Research*, 1998, 18, XP008009504, 405-412.
Bundgaard, H., Design and Application of Prodrugs, *Elsevier*, 1985, Chapter 5, 113-191.
Bundgard, H., "Means to enhance penetration; prodrugs as a means to improve the delivery of peptide drugs," *Advanced Drug Delivery Reviews*, 1992, 8, 1-38.
Chen-AY, et al., "DNA topoisomerase I—targeting drugs as radiation sensitizers," *Oncology*, Oct. 1999, 13(Suppl. 5), 39-46.
Chou, T-C., et al., "Quantitative analysis of dose-effect relationships: the combined effects of multiples drugs or enzyme inhibitors," *Adv. Enzyme Regul.*, 1984, 22, 27-55.
Choy-H., "Taxanes iin combined—modality therapy for solid tumors," *Oncology*, Oct. 1999, 13(10) (Suppl. 5), 23-38.
Coker, M.L., et al., "Myocardial matrix metalloproteinase activity and abundance with congestive heart failure," *J. Am. Physiol.*, 1998, 274, H1516-H1523.
Herscher L.L, et al., "Principles of chemoradiation: theoretical and practical considerations," *Oncology*, Oct. 1999, Suppl. 5, 11-22.
Kakeya, N., et al., "Studies on prodrugs of cephalosporins. I. Synthesis and biological properties of glycylxybenzoyloxymethyl and glycylaminobenzoyloxymethyl esters of 7β-[2-(-aminothiazol-4-yl)-(Z)-2-methoxyiminoaccetamido]-3-methyl-3-cephem-4-carboxylic acid," *Chem. Pharm. Bull.*, 1984, 32, 692-698.
McNulty, P.H., et al., "Glycogen depletion contributes to ischemic preconditioning in the rat heart in vivo," *J. Am. Physiol.*, 1996, H2283-H2289.
Mousa, S.A., et al., "Recent advances in cell adhesion molecules and extracellular matrix proteins: potential clinical implications," *DDT*, May 1997, 2(5), 187-199.
Nielsen, N.M., et al., "Glycolamide esters as biolabile prodrugs of carboxylic acid agents: synthesis, stability, bioconversion, and physicochemical properties," *Journal of Pharmaceutical Sciences*, Apr. 1988, 77(4), 285-298.
Notari, R.E., "Theory and practice of prodrug kinetics," Methods in Enzymology, *Academic Press*, 1985, 112, 309-323.
Rowinsky-E,K. "Novel radiation sensitizers trargeting tissue hypoxia," *Oncology*, Oct. 1999, Suppl. 5, 61-70.
Samanen, J., et al., "Vascular indications for integrin αv antagonists," *Current Pharm. Design.*, 1997, 3, 545-584.
Sinusas, A.J., "Experimental evaluation of radiotracers: role of intact biological models," *J. Nucl. Cardiol.*, 1998, 5(2), 167-183.
Stein, R., et al., "Assessment of combined radioimmunotherapy and chemotherapy for treatment of medullary thyroid cancer," *Clin. Cancer Res.*, Oct. 1999, 5, 3199s-3206s.
Van Waes, C., et al., "Effects of the noval $\alpha_v$ integrin antagonist SM256 and cis-platinum on growth of murine squamous cell carcinoma PAM LY8," XP-000925238, *Int. J. Oncol.*, 2000, 16, 1189-1195.
Youker, K.A., et al., "Time-dependent neutrophil β1 and β3 integrin expression in the reperfused myocardium: role in tissue migration," *Circulation*, 1999, 100, Abstract No. 1433, p. I-275.
U.S. Appl. No. 08/646,886.
U.S. Appl. No. 60/013,360.

* cited by examiner

VITRONECTIN RECEPTOR ANTAGONIST PHARMACEUTICALS

This application is a divisional application of U.S. application Ser. No. 09/599,364 filed Jun. 21, 2000 now U.S. Pat. No. 6,511,649, which is a continuation-in-part of U.S. application Ser. No. 09/465,300 filed Dec. 17, 1999 now U.S. Pat. No. 6,511,648, which claims the benefit of U.S. Provisional Application No. 60/112,732 filed Dec. 18, 1998.

FIELD OF THE INVENTION

The present invention provides novel pharmaceuticals useful for the diagnosis and treatment of cancer, methods of imaging tumors in a patient, and methods of treating cancer in a patient. The invention is also directed to novel pharmaceutical compositions and combination therapy comprising a compound of the invention or a pharmaceutically acceptable salt thereof, and at least one agent selected from the group consisting of a chemotherapeutic agent and a radiosensitizer agent. The pharmaceuticals are comprised of a targeting moiety that binds to the vitronectin receptor that is expressed in tumor vasculature, an optional linking group, and a therapeutically effective radioisotope or diagnostically effective imageable moiety. The therapeutically effective radioisotope emits a gamma ray or alpha particle sufficient to be cytotoxic. The imageable moiety is a gamma ray or positron emitting radioisotope, a magnetic resonance imaging contrast agent, an X-ray contrast agent, or an ultrasound contrast agent.

BACKGROUND OF THE INVENTION

Cancer is a major public health concern in the United States and around the world. It is estimated that over 1 million new cases of invasive cancer will be diagnosed in the United States in 1998. The most prevalent forms of the disease are solid tumors of the lung, breast, prostate, colon and rectum. Cancer is typically diagnosed by a combination of in vitro tests and imaging procedures. The imaging procedures include X-ray computed tomography, magnetic resonance imaging, ultrasound imaging and radionuclide scintigraphy. Frequently, a contrast agent is administered to the patient to enhance the image obtained by X-ray CT, MRI and ultrasound, and the administration of a radiopharmaceutical that localizes in tumors is required for radionuclide scintigraphy.

Treatment of cancer typically involves the use of external beam radiation therapy and chemotherapy, either alone or in combination, depending on the type and extent of the disease. A number of chemotherapeutic agents are available, but generally they all suffer from a lack of specificity for tumors versus normal tissues, resulting in considerable side-effects. The effectiveness of these treatment modalities is also limited, as evidenced by the high mortality rates for a number of cancer types, especially the more prevalent solid tumor diseases. More effective and specific treatment means continue to be needed.

Despite the variety of imaging procedures available for the diagnosis of cancer, there remains a need for improved methods. In particular, methods that can better differentiate between cancer and other pathologic conditions or benign physiologic abnormalities are needed. One means of achieving this desired improvement would be to administer to the patient a metallopharmaceutical that localizes specifically in the tumor by binding to a receptor expressed only in tumors or expressed to a significantly greater extent in tumors than in other tissue. The location of the metallopharmaceutical could then be detected externally either by its imageable emission in the case of certain radiopharmaceuticals or by its effect on the relaxation rate of water in the immediate vicinity in the case of magnetic resonance imaging contrast agents.

This tumor specific metallopharmaceutical approach can also be used for the treatment of cancer when the metallopharmaceutical is comprised of a particle emitting radioisotope. The radioactive decay of the isotope at the site of the tumor results in sufficient ionizing radiation to be toxic to the tumor cells. The specificity of this approach for tumors minimizes the amount of normal tissue that is exposed to the cytotoxic agent and thus may provide more effective treatment with fewer side-effects.

Previous efforts to achieve these desired improvements in cancer imaging and treatment have centered on the use of radionuclide labeled monoclonal antibodies, antibody fragments and other proteins or polypeptides that bind to tumor cell surface receptors. The specificity of these radiopharmaceuticals is frequently very high, but they suffer from several disadvantages. First, because of their high molecular weight, they are generally cleared from the blood stream very slowly, resulting in a prolonged blood background in the images. Also, due to their molecular weight they do not extravasate readily at the site of the tumor and then only slowly diffuse through the extravascular space to the tumor cell surface. This results in a very limited amount of the radiopharmaceutical reaching the receptors and thus very low signal intensity in imaging and insufficient cytotoxic effect for treatment.

Alternative approaches to cancer imaging and therapy have involved the use of small molecules, such as peptides, that bind to tumor cell surface receptors. An In-111 labeled somatostatin receptor binding peptide, In-111-DTPA-D-Phe$^1$-octeotide, is in clinical use in many countries for imaging tumors that express the somatostatin receptor (Baker, et al. Life Sci., 1991, 49, 1583–91 and Krenning, et al., Eur. J. Nucl. Med., 1993, 20, 716–31). Higher doses of this radiopharmaceutical have been investigated for potential treatment of these types of cancer (Krenning, et al., Digestion, 1996, 57, 57–61). Several groups are investigating the use of Tc-99m labeled ananlogs of In-111-DTPA-D-Phe$^1$-octeotide for imaging and Re-186 labeled analogs for therapy (Flanagan, et al., U.S. Pat. No. 5,556,939, Lyle, et al., U.S. Pat. No. 5,382,654, and Albert et al., U.S. Pat. No. 5,650,134).

Angiogenesis is the process by which new blood vessels are formed from pre-existing capillaries or post capillary venules; it is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. Tumor released cytokines or angiogenic factors stimulate vascular endothelial cells by interacting with specific cell surface receptors for the factors. The activated endothelial cells secrete enzymes that degrade the basement membrane of the vessels. The endothelial cells then proliferate and invade into the tumor tissue. The endothelial cells differentiate to form lumens, making new vessel offshoots of pre-existing vessels. The new blood vessels then provide nutrients to the tumor permitting further growth and a route for metastasis.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the proangiogenic factors that have been identified include basic fibroblast growth factor (bFGF), angiogenin, TGF-alpha, TGF-beta, and vascular endothelium growth factor (VEGF). While interferon-alpha, interferon-beta and thrombospondin are examples of angiogenesis suppressors.

The proliferation and migration of endothelial cells in the extracellular matrix is mediated by interaction with a variety of cell adhesion molecules (Folkman, J., Nature Medicine, 1995, 1, 27–31). Integrins are a diverse family of heterodimeric cell surface receptors by which endothelial cells attach to the extracellular matrix, each other and other cells. The integrin $\alpha_v\beta_3$ is a receptor for a wide variety of extracellular matrix proteins with an exposed tripeptide Arg-Gly-Asp moiety and mediates cellular adhesion to its ligand: vitronectin, fibronectin, and fibrinogen, among others. The integrin $\alpha_v\beta_3$ is minimally expressed on normal blood vessels, but is significantly upregulated on vascular cells within a variety of human tumors. The role of the $\alpha_v\beta_3$ receptors is to mediate the interaction of the endothelial cells and the extracellular matrix and facilitate the migration of the cells in the direction of the angiogenic signal, the tumor cell population. Angiogenesis induced by bFGF or TNF-alpha depend on the agency of the integrin $\alpha_v\beta_3$, while angiogenesis induced by VEGF depends on the integrin $\alpha_v\beta_3$ (Cheresh et. al., Science, 1955, 270, 1500–2). Induction of expression of the integrins $\alpha_1\beta_1$ and $\alpha_2\beta_1$ on the endothelial cell surface is another important mechanism by which VEGF promotes angiogenesis (Senger, et. al., Proc. Natl. Acad, Sci USA, 1997, 84, 13612–7).

Angiogenic factors interact with endothelial cell surface receptors such as the receptor tyrosine kinases EGFR, FGFR, PDGFR, Flk-1/KDR, Flt-1, Tek, tie, neuropilin-1, endoglin, endosialin, and Axl. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

Because of the importance of angiogenesis to tumor growth and metastasis, a number of chemotherapeutic approaches are being developed to interfere with or prevent this process. One of these approaches, involves the use of anti-angiogenic proteins such as angiostatin and endostatin. Angiostatin is a 38 kDa fragment of plasminogen that has been shown in animal models to be a potent inhibitor of endothelial cell proliferation. (O'Reilly et. al., Cell, 1994, 79, 315–328) Endostatin is a 20 kDa C-terminal fragment of collagen XVIII that has also been shown to be a potent inhibitor. (O'Reilly et. al., Cell, 1997, 88, 277–285) Systemic therapy with endostatin has been shown to result in strong anti-tumor activity in animal models. However, human clinical trials of these two chemotherapeutic agents of biological origin have been hampered by lack of availability.

Another approach to anti-angiogenic therapy is to use targeting moieties that interact with endothelial cell surface receptors expressed in the angiogenic vasculature to which are attached chemotherapeutic agents. Burrows and Thorpe (Proc. Nat. Acad. Sci, USA, 1993, 90, 8996–9000) described the use of an antibody-immunotoxin conjugate to eradicate tumors in a mouse model by destroying the tumor vasculature. The antibody was raised against an endothelial cell class II antigen of the major histocompatibility complex and was then conjugated with the cytotoxic agent, deglycosylated ricin A chain. The same group (Clin. Can. Res., 1995, 1, 1623–1634) investigated the use of antibodies raised against the endothelial cell surface receptor, endoglin, conjugated to deglycosylated ricin A chain. Both of these conjugates exhibited potent anti-tumor activity in mouse models. However, both still suffer drawbacks to routine human use. As with most antibodies or other large, foreign proteins, there is considerable risk of immunologic toxicity which could limit or preclude administration to humans. Also, while the vasculature targeting may improve the local concentration of the attached chemotherapeutic agents, the agents still must be cleaved from the antibody carrier and be transported or diffuse into the cells to be cytotoxic.

Thus, it is desirable to provide anti-angiogenic pharmaceuticals and tumor or new vasculature imaging agents which do not suffer from poor diffusion or transportation, possible immunologic toxicity, limited availability, and/or a lack of specificity.

There continues to be a need for more effective treatment options for patients with solid tumors. This is especially true in cases of metastatic cancer in which current standard chemotherapy and external beam radiation regimens only result in marginal survival improvements.

Although improvements in cytotoxic chemotherapeutics have been made in recent years, the toxicity of these compounds to normal tissues has continued to severely limit their utility in extending survival in patients with solid tumors. Recently developed combinations of different therapeutic modalities, such as external beam irradiation and chemotherapy (i.e. chemoradiation), has provided some incremental benefit to the control of tumor progression and quality of life. However, neither systemic chemotherapeutics nor external beam irradiation have acceptable therapeutic indices, and are often limited due to unacceptable toxicity to normal tissues. The concept of combined therapy of cancer using anti-angiogenesis drugs in combination with chemotherapeutics is not new. Further, the concept of combining targeted in-vivo radiotherapy using radiolabeled antibodies and antibody fragments with chemotherapy has been reported (Stein R, Juweid M, Zhang C, et al., Clin. Cancer Res., 5: 3199s–3206s, 1999. However, the combination of a angiogenesis-targeted therapeutic radiopharmaceutical which is targeted to receptors, which are then upregulated in the neovasculature of tumors, together with chemotherapy has not been described before. Therefore, there is a need for a combination of a therapeutic radiopharmaceutical, which is targeted to localize in the neovasculature of tumors, with chemotherapeutics or a radiosensitizer agent, or a pharmaceutically acceptable salt thereof, to provide additive or synergistic therapeutic response without unacceptable additive toxicity in the treatment of solid tumors.

The major advantage of combined chemotherapy and angiogenesis-targeted therapeutic radiopharmaceuticals, over each therapeutic modality alone, is improved tumor response without substantial increases in toxicity over either treatment alone. The advantage of using neovascular-specific radiopharmaceuticals, versus a tumor-cell targeted antibody, is that there is much lower systemic radiation exposure to the subject being treated.

Further, if the receptor targets for the radiopharmaceutical compounds, used in this method of treatment, are expressed on the luminal side of tumor vessels, there is no requirement that these compounds traverse the capillary bed and bind to the tumor itself.

Thus, it is desirable to provide a combination of angiogenesis-targeted therapeutic radiopharmaceuticals and a chemotherapeutics or a radiosensitizer agent, or a pharmaceutically acceptable salt thereof, which target the luminal side of the neovasculature of tumors, to provide a surprising, and enhanced degree of tumor suppression relative to each treatment modality alone without significant additive toxicity.

Another application of anti-angiogenic therapy is in treating rheumatoid arthritis (RA). In RA, the ingrowth of a highly vascularized pannus is caused by the excessive production of angiogenic factors by the infiltrating macrophages, immune cells, or inflammatory cells. Therefore, it is desirable to have new pharmaceuticals to destroy the highly vascularized pannus that results and thus treat the disease.

There is also a growing interest in therapeutic angiogenesis to improve blood flow in regions of the body that have become ischemic or poorly perfused. Several investigators are using growth factors administered locally to cause new vasculature to form either in the limbs or the head. The growth factors VEGF and bFGF are the most common for this application. Recent publications include: Takeshita, S., et. al., J. Clin. Invest., 1994, 93, 662–670; and Schaper, W. and Schaper, J., Collateral Circulation: Heart, Brain, Kidney, Limbs, Kluwer Academic Publishers, Boston, 1993. The main applications that are under investigation in a number of laboratories are for improving cardiac blood flow and in improving peripheral vessel blood flow in the limbs. For example, Henry, T. et. al. (J. Amer. College Cardiology, 1998, 31, 65A) describe the use of recombinant human VEGF in patients for improving myocardial perfusion by therapeutic angiogenesis. Patients received infusions of rhVEGF and were monitored by nuclear perfusion imaging 30 and 60 days post treatment to determine improvement in myocardial perfusion. About 50% of patients showed improvement by nuclear perfusion imaging whereas 5/7 showed new collatoralization by angiography. Thus, it is desirable to discover a method of monitoring improved cardiac blood flow which is targeted to new collatoral vessels themselves and not, as in nuclear perfusion imaging, a regional consequence of new collatoral vessels.

The detection, imaging and diagnosis of a number of cardiovascular diseases need to be improved, including restenosis, atherosclerosis, myocardial reperfusion injury, and myocardial ischemia, stunning or infarction. It has recently been determined that in all of these disease conditions, the integrin receptor $\alpha v \beta 3$ plays an important role.

For example, in the restenosis complication that occurs in $-30-50\%$ of patients having undergone angioplasty or stent placement, neointimal hyperplasia and ultimate reocclusion is caused by aggressively proliferating vascular smooth muscle cells that express $\alpha v \beta 3$. (Cardiovascular Res., 1997, 36, 408–428; DDT, 1997, 2, 187–199; Current Pharm. Design, 1997, 3, 545–584)

Atherosclerosis proceeds from an intial endothelial damage that results in the recruitment and subintimal migration of monocytes at the site of the injury. Growth factors are released which induce medial smooth muscle cells to proliferate and migrate to the intimal layer. The migrating smooth muscle cells express $\alpha v \beta 3$.

In reperfusion injury, neutrophil transmigration is integrin dependent and the integrins moderate initial infiltration into the viable border zone. The induction of $\alpha 5 \beta 1$, $\alpha 4 \beta 1$ and $\alpha v \beta 5$ in infiltrating neutrophils occurs within 3 to 5 hours after reperfusion as neutrophils move from the border zone to the area of necrosis. (Circulation, 1999, 100, I-275)

Acute or chronic occlusion of a coronary artery is known to result in angiogenesis in the heart as native collateral vessels are recruited to attempt to relieve the ischemia. However, even a gradual occlusion usually results in areas of infarction as the resulting angiogenesis is not sufficient to prevent damage. Cardiac angiogenesis has been associated with increased expression of the growth factors VEGF and FGF and the upregulation of the growth factor receptors flt-1 and flk-1/KDR. (Drugs, 1999, 58, 391–396).

SUMMARY OF THE INVENTION

It is one object of the present invention to provide improved anti-angiogenic pharmaceuticals, comprised of a targeting moiety that binds to the vitronectin receptor that is expressed in tumor neovasculature, an optional linking group, and a radioisotope. The vitronectin receptor binding compounds target the radioisotope to the tumor neovasculature. The beta or alpha-particle emitting radioisotope emits a cytotoxic amount of ionizing radiation which results in cell death. The penetrating ability of radiation obviates the requirement that the cytotoxic agent diffuse or be transported into the cell to be cytotoxic.

It is another object of the present invention to provide pharmaceuticals to treat rheumatoid arthritis. These pharmaceuticals comprise a targeting moiety that binds to a receptor that is upregulated during angiogenesis, an optional linking group, and a radioisotope that emits cytotoxic radiation (i.e., beta particles, alpha particles and Auger or Coster-Kronig electrons). In rheumatoid arthritis, the ingrowth of a highly vascularized pannus is caused by the excessive production of angiogenic factors by the infiltrating macrophages, immune cells, or inflammatory cells. Therefore, the radiopharmaceuticals of the present invention that emit cytotoxic radiation could be used to destroy the new angiogenic vasculature that results and thus treat the disease.

It is another object of the present invention to provide imaging agents, comprised of vitronectin receptor binding compounds conjugated to an imageable moiety, such as a gamma ray or positron emitting radioisotope, a magnetic resonance imaging contrast agent, an X-ray contrast agent, or an ultrasound contrast agent. These imaging agents are useful for imaging tumor neovasculature, therapeutic angiogenesis interventions in the heart, natural angiogenic processes in response to acute or chronic coronary vessel occlusion, restenosis post-angioplasty, atherosclerosis and plaque formation, and reperfusion injury.

It is another object of the present invention to provide compounds useful for preparing the pharmaceuticals of the present invention. These compounds are comprised of a non-peptide quinolone containing targeting moiety that binds to a receptor that is upregulated during angiogenesis or during cardiovascular diseases, Q, an optional linking group, $L_n$, and a metal chelator or bonding moiety, $C_h$. The compounds may have one or more protecting groups attached to the metal chelator or bonding moiety. The protecting groups provide improved stability to the reagents for long-term storage and are removed either immediately prior to or concurrent with the synthesis of the radiopharmaceuticals. Alternatively, the compounds of the present invention are comprised of a peptide or peptidomimetic targeting moiety that binds to a receptor that is upregulated during angiogenesis or during cardiovascular diseases, Q, an optional linking group, $L_n$, and a surfactant, $S_f$.

The pharmaceuticals of the present invention may be used for diagnostic and/or therapeutic purposes. Diagnostic radiopharmaceuticals of the present invention are pharmaceuticals comprised of a diagnostically useful radionuclide (i.e., a radioactive metal ion that has imageable gamma ray or positron emissions). Therapeutic radiopharmaceuticals of the present invention are pharmaceuticals comprised of a therapeutically useful radionuclide, a radioactive metal ion that emits ionizing radiation such as beta particles, alpha particles and Auger or Coster-Kronig electrons.

The pharmaceuticals comprising a gamma ray or positron emitting radioactive metal ion are useful for imaging tumors and by gamma scintigraphy or positron emission tomography. The pharmaceuticals comprising a gamma ray or positron emitting radioactive metal ion are also useful for imaging therapeutic angiogenesis, natural angiogenic processes in response to acute or chronic coronary vessel occlusion, restenosis post-angioplasty, atherosclerosis and plaque formation, and reperfusion injury by gamma scintigraphy or positron emission tomography. The pharmaceuticals comprising a particle emitting radioactive metal ion are useful for treating cancer by delivering a cytotoxic dose of radiation to the tumors. The pharmaceuticals comprising a particle emitting radioactive metal ion are also useful for treating rheumatoid arthritis by destroying the formation of angiogenic vasculature. The pharmaceuticals comprising a paramagnetic metal ion are useful as magnetic resonance imaging contrast agents. The pharmaceuticals comprising one or more X-ray absorbing or "heavy" atoms of atomic number 20 or greater are useful as X-ray contrast agents. The pharmaceuticals comprising a microbubble of a biocompatible gas, a liquid carrier, and a surfactant microsphere, are useful as ultrasound contrast agents.

DETAILED DESCRIPTION OF THE INVENTION

[1] Thus, in a first embodiment, the present invention provides a novel compound, comprising: a targeting moiety and a chelator, wherein the targeting moiety is bound to the chelator, is a quinolone nonpeptide, and binds to a receptor that is upregulated during angiogenesis and the compound has 0–1 linking groups between the targeting moiety and chelator.

[2] In a preferred embodiment, the receptor is the integrin $\alpha_v\beta_3$ or $\alpha_v\beta_5$ and the compound is of the formula:

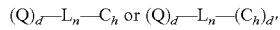

wherein, Q is a compound of Formula (II):

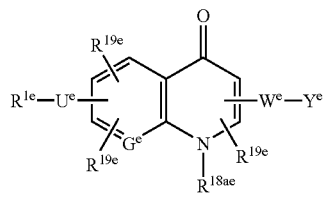

including stereoisomeric forms thereof, or mixtures of stereoisomeric forms thereof, or pharmaceutically acceptable salt or prodrug forms thereof wherein:

$R^{1e}$ is selected from:

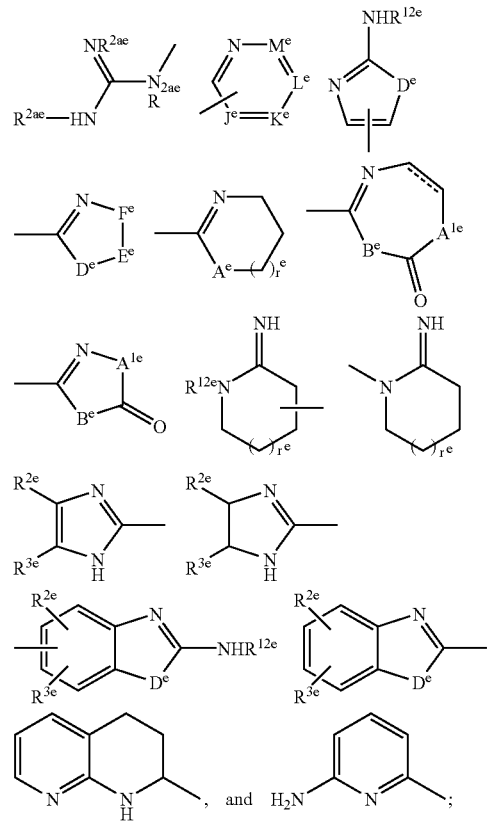

$A^e$ is —CH$_2$— or —N(R$^{10e}$)—;
$A^{1e}$ and $B^e$ are independently —CH$_2$— or —N(R$^{10e}$)—;
$D^e$ is —N(R$^{10e}$)— or —S—;
$E^e$—$F^e$ is —C(R$^{2e}$)=C(R$^{3e}$)— or —C(R$^{2e}$)$_2$C(R$^{3e}$)$_2$—;
$J^e$ is —C(R$^{2e}$)— or —N—;
$K^e$, $L^e$ and $M^e$ are independently —C(R$^{2e}$)— or —C(R$^{3e}$)—;
$R^{2e}$ and $R^{3e}$ are independently selected from:
 H, C$_1$–C$_4$ alkoxy, NR$^{11e}$R$^{12e}$, halogen, NO$_2$, CN, CF$_3$, C$_1$–C$_6$ alkyl, C$_3$–C$_6$ alkenyl, C$_3$–C$_7$ cycloalkyl, C$_3$–C$_7$ cycloalkyl(C$_1$–C$_4$ alkyl), aryl(C$_1$–C$_6$ alkyl)-, (C$_1$–C$_6$ alkyl)carbonyl, (C$_1$–C$_6$ alkoxy)carbonyl, arylcarbonyl, and aryl substituted with 0–4 R$^{7e}$,
 alternatively, when R$^{2e}$ and R$^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from C$_1$–C$_4$ alkyl, C$_1$–C$_4$ alkoxy, halo, cyano, amino, CF$_3$ and NO$_2$;
$R^{2ae}$ is selected from:
 H, C$_1$–C$_{10}$ alkyl, C$_2$–C$_6$ alkenyl, C$_3$–C$_{11}$ cycloalkyl, C$_3$–C$_7$ cycloalkyl(C$_1$–C$_4$ alkyl), aryl, aryl(C$_1$–C$_4$ alkyl)-, (C$_2$–C$_7$ alkyl)carbonyl, arylcarbonyl, (C$_2$–C$_{10}$ alkoxy)carbonyl, C$_3$–C$_7$ cycloalkoxycarbonyl, C$_7$–C$_{11}$ bicycloalkoxycarbonyl, aryloxycarbonyl, aryl (C$_1$–C$_{10}$ alkoxy) carbonyl, C$_1$–C$_6$ alkylcarbonyloxy(C$_1$–C$_4$ alkoxy)carbonyl, arylcarbonyloxy(C$_1$–C$_4$ alkoxy)carbonyl, and C$_3$–C$_7$ cycloalkylcarbonyloxy(C$_1$–C$_4$ alkoxy)carbonyl;

$R^{7e}$ is selected from:
  H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
  —$(CH_2)_n{}^e$—, —$(CH_2)_n{}^eO(CH_2)_m{}^e$—, —$(CH_2)_n{}^eN(R^{12})(CH_2)_m{}^e$—, —$NH(CH_2)_n{}^e$—, —$(CH_2)_n{}^eC(\!=\!O)(CH_2)_m{}^e$—, —$(CH_2)_n{}^eS(O)_p{}^e(CH_2)_m{}^e$—, —$(CH_2)_m{}^e$ $NHNH(CH_2)_m{}^e$—, —$N(R^{10e})C(\!=\!O)$—, —$NHC(\!=\!O)(CH_2)_n{}^e$—, —$C(\!=\!O)N(R^{10e})$—, and —$N(R^{10e})S(O)_p{}^e$—;

$G^e$ is N or $CR^{19e}$;

$W^e$ is —C(=O)—$N(R^{10e})$—($C_1$–$C_3$ alkylene)-, in which the alkylene group is substituted by $R^{8e}$ and by $R^{9e}$:

$R^{8e}$ and $R^{9e}$ are independently selected from:
  H, $CO_2R^{18be}$, $C(\!=\!O)R^{18be}$, $CONR^{17}R^{18be}$,
  $C_1$–$C_{10}$ alkyl substituted with 0–1 $R^{6e}$,
  $C_2$–$C_{10}$ alkenyl substituted with 0–1 $R^{6e}$,
  $C_2$–$C_{10}$ alkynyl substituted with 0–1 $R^{6e}$,
  $C_3$–$C_8$ cycloalkyl substituted with 0–1 $R^{6e}$,
  $C_5$–$C_6$ cycloalkenyl substituted with 0–1 $R^{6e}$,
  ($C_1$–$C_{10}$ alkyl) carbonyl,
  $C_3$–$C_{10}$ cycloalkyl($C_1$–$C_4$ alkyl)-,
  phenyl substituted with 0–3 $R^{6e}$,
  naphthyl substituted with 0–3 $R^{6e}$,
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$,
  $C_1$–$C_{10}$ alkoxy substituted with 0–2 $R^{7e}$,
  hydroxy, nitro, —$N(R^{10e})R^{11e}$, —$N(R^{16e})R^{17e}$, aryl ($C_0$–$C_6$ alkyl)carbonyl, aryl($C_3$–$C_6$ alkyl), heteroaryl ($C_1$–$C_6$ alkyl), $CONR^{18ae}R^{20e}$, $SO_2R^{18ae}$, and $SO_2NR^{18ae}R^{20e}$,
  providing that any of the above alkyl, cycloalkyl, aryl or heteroaryl groups may be unsubstituted or substituted independently with 1–2 $R^{7e}$;

$R^{6e}$ is selected from:
  H, $C_1$–$C_{10}$ alkyl, hydroxy, $C_1$–$C_{10}$ alkoxy, nitro, $C_1$–$C_{10}$ alkylcarbonyl, —$N(R^{11e})R^{12e}$, cyano, halo, $CF_3$, CHO, $CO_2R^{18be}$, $C(\!=\!O)R^{18be}$, $CONR^{17e}R^{18be}$, $OC(\!=\!O)R^{10e}$, $OR^{10e}$, $OC(\!=\!O)NR^{10e}R^{11e}$, $NR^{10e}C(\!=\!O)R^{10e}$, $NR^{10e}C(\!=\!O)OR^{21e}$, $NR^{10e}C(\!=\!O)NR^{10e}R^{11e}$, $NR^{10e}SO_2NR^{10e}R^{11e}$, $NR^{10e}SO_2R^{21e}$, $S(O)_pR^{11e}$, $SO_2NR^{10e}R^{11e}$,
  aryl substituted with 0–3 groups selected from halogen, $C_1$–$C_6$ alkoxy, $C_1$–$C_6$ alkyl, $CF_3$, $S(O)_m{}^e$Me, and —$NMe_2$,
  aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p{}^e$Me, and —$NMe_2$, and
  a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:
  H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:
  H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:
  H, $C_1$–$C_6$ alkyl, $C_3$–$C_7$ cycloalkyl, $C_3$–$C_7$ cycloalkyl ($C_1$–$C_4$ alkyl)-, ($C_1$–$C_{10}$ alkyl)carbonyl, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, alternatively, when $R^{10e}$ and $R^{11e}$ are both substituents on the same nitrogen atom (as in —$NR^{10e}R^{11e}$) they may be taken together with the nitrogen atom to which they are attached to form a heterocycle selected from:
  3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
  said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12e}$ is selected from:
  H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
  —$C(\!=\!O)OR^{18ae}$, —$C(\!=\!O)R^{18be}$, —$C(\!=\!O)N(R^{18be})_2$, —$C(\!=\!O)NHSO_2R^{18ae}$, —$C(\!=\!O)NHC(\!=\!O)R^{18be}$, —$C(\!=\!O)NHC(\!=\!O)OR^{18ae}$, —$C(\!=\!O)NHSO_2NHR^{18be}$, —$SO_2R^{18ae}$, —$SO_2N(R^{18be})_2$, and —$SO_2NHC(\!=\!O)OR^{18be}$;

$R^{17e}$ is selected from:
  H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:
  $C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
  H, halogen, $CF_3$, $CO_2H$, CN, $NO_2$, —$NR^{11e}R^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
$(R^{10e})(R^{11e})N$—$(C_1$–$C_{10}$ alkoxy)-;

$R^{21e}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^{7e}$;

$R^{22e}$ is selected from:
—C(=O)—$R^{18be}$, —C(=O)N($R^{18be}$)$_2$, —C(=O)NHSO$_2$$R^{18ae}$, —C(=O)NHC(=O)$R^{18be}$, —C(=O)NHC(=O)O$R^{18ae}$, and —C(=O)NHSO$_2$NH$R^{18be}$;

$Y^e$ is selected from:
—COR$^{20e}$, —SO$_3$H, —PO$_3$H, —CONHNHSO$_2$CF$_3$, —CONHSO$_2$R$^{18ae}$, —CONHSO$_2$NHR$^{18be}$, —NH-COCF$_3$, —NHCONHSO$_2$R$^{18ae}$, —NHSO$_2$R$^{18ae}$, —OPO$_3$H$_2$, —OSO$_3$H, —PO$_3$H$_2$, —SO$_2$NHCOR$^{18ae}$, —SO$_2$NHCO$_2$R$^{18ae}$,

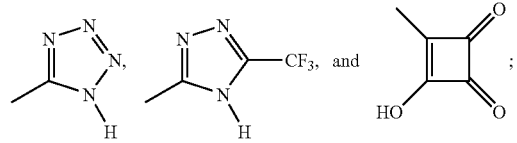

$m^e$ is 0–2;
$n^e$ is 0–4;
$p^e$ is 0–2;
$r^e$ is 0–2;
with the following proviso: $n^e$ and $m^e$ are chosen such that the number of atoms connecting $R^{1e}$ and $Y^e$ is in the range of 8–14;
d is selected from 1, 2, 3, 4, 5, 6, 7, 8, 9, and 10;
d' is 1–100;
$L_n$ is a linking group having the formula:

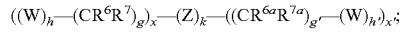

W is independently selected at each occurrence from the group: O, S, NH, NHC(=O), C(=O)NH, NR$^8$C(=O), C(=O)N R$^8$, C(=O), C(=O)O, OC(=O), NHC(=S)NH, NHC(=O)NH, SO$_2$, SO$_2$NH, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;
aa is independently at each occurrence an amino acid;
Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, SO$_3$H, PO$_3$H, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NHR$^{11}$, NHC(=O)NHR$^{11}$, NHR$^{11}$, $R^{11}$, and a bond to $C_h$;

$R^{10}$ is independently selected at each occurrence from the group: a bond to $C_h$, COOR$^{11}$, C(=O)NHR$^{11}$, NHC(=O)R$^{11}$, OH, NHR$^{11}$, SO$_3$H, PO$_3$H, —OPO$_3$H$_2$, —OSO$_3$H, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $C_h$;

$R^{12}$ is a bond to $C_h$;
k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5;
x' is selected from 0, 1, 2, 3, 4, and 5;
$C_h$ is a metal bonding unit having a formula selected from the group:

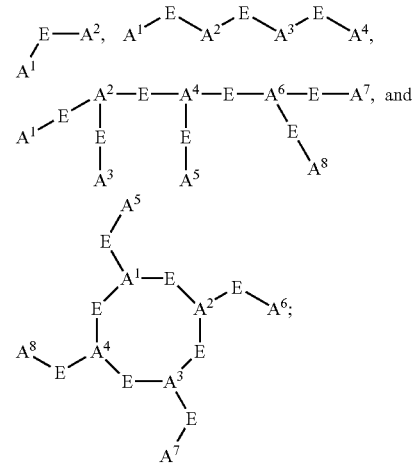

$A^1, A^2, A^3, A^4, A^5, A^6, A^7$, and $A^8$ are independently selected at each occurrence from the group: $NR^{13}$, $NR^{13}R^{14}$, S, SH, S(Pg), O, OH, $PR^{13}$, $PR^{13}R^{14}$, $P(O)R^{15}R^{16}$, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{13}$ and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form $=C(R^{20})(R^{21})$;

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, $=O$, F, Cl, Br, I, —$CF_3$, —CN, —$CO_2R^{18}$, —$C(=O)R^{18}$, —$C(=O)N(R^{18})_2$, —CHO, —$CH_2OR^{18}$, —$OC(=O)R^{18}$, —$OC(=O)OR^{18a}$, —$OR^{18}$, —$OC(=O)N(R^{18})_2$, —$NR^{19}C(=O)R^{18}$, —$NR^{19}C(=O)OR^{18a}$, —$NR^{19}C(=O)N(R^{18})_2$, —$NR^{19}SO_2N(R^{18})_2$, —$NR^{19}SO_2R^{18a}$, —$SO_3H$, —$SO_2R^{18a}$, —$SR^{18}$, —$S(=O)R^{18a}$, —$SO_2N(R^{18})_2$, —$N(R^{18})_2$, —$NHC(=S)NHR^{18}$, $=NOR^{18}$, $NO_2$, —$C(=O)NHOR^{18}$, —$C(=O)NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$, and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —$C(=O)R^{25}$, —$C(=O)N(R^{25})_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

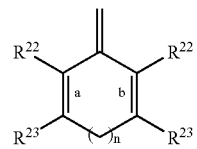

$R^{22}$ and $R^{23}$ are independently selected from the group: H, $R^{24}$, $C_1$–$C_{10}$ alkyl substituted with 0–3 $R^{24}$, $C_2$–$C_{11}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: $=O$, F, Cl, Br, I, —$CF_3$, —CN, —$CO_2R^{25}$, —$C(=O)R^{25}$, —$C(=O)N(R^{25})_2$, —$N(R^{25})_3^+$, —$CH_2OR^{25}$, —$OC(=O)R^{25}$, —$OC(=O)OR^{25a}$, —$OR^{25}$, —$OC(=O)N(R^{25})_2$, —$NR^{26}C(=O)R^{25}$, —$NR^{26}C(=O)OR^{25a}$, —$NR^{26}C(=O)N(R^{25})_2$, —$NR^{26}SO_2N(R^{25})_2$, —$NR^{26}SO_2R^{25a}$, —$SO_3H$, —$SO_2R^{25a}$, —$SR^{25}$, —$S(=O)R^{25a}$, —$SO_2N(R^{25})_2$, —$N(R^{25})_2$, $=NOR^{25}$, —$C(=O)NHOR^{25}$, —$OCH_2CO_2H$, and 2-(1-morpholino)ethoxy; and, $R^{25}$, $R^{25a}$, and $R^{26}$ are each independently selected at each occurrence from the group: hydrogen and $C_1$–$C_6$ alkyl;

and a pharmaceutically acceptable salt thereof.

[3] In a more preferred embodiment, the present invention provides a compound wherein: Q is a compound of Formula (IV):

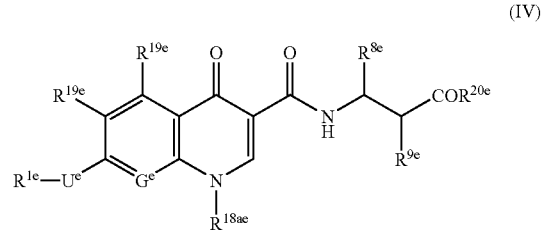

(IV)

including stereoisomeric forms thereof, or mixtures of stereoisomeric forms thereof, or pharmaceutically acceptable salt or prodrug forms thereof wherein:

$R^{1e}$ is selected from:

[Structures shown: guanidine-type $R^{2ae}$-HN-C(=NR$^{2ae}$)-N(R)(R$^{2ae}$); 2-methylimidazole with $R^{2e}$, $R^{3e}$ substituents; 2-methylimidazoline with $R^{2e}$, $R^{3e}$; tetrahydropyrimidine; tetrahydropyridine; 2-methylpyridine; 6-amino-2-methylpyridine ($H_2N$-); cis and trans fused benzimidazoles; azaindole-type bicyclics; 2-aminoimidazole ($H_2N$-); and 2-amino-thiazole ($H_2N$-)];

$R^{2e}$ and $R^{3e}$ are independently selected from:
   H, $C_1$–$C_4$ alkoxy, $NR^{11e}R^{12e}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^{7e}$,
   alternatively, when $R^{2e}$ and $R^{3e}$ are substituents on adjacent carbon atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2ae}$ is selected from:
   H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl ($C_1$–$C_{10}$ alkoxy) carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^{7e}$ is selected from:
   H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
   —$(CH_2)_n{}^e$—, —$(CH_2)_n{}^e O(CH_2)_m{}^e$—, —$NH(CH_2)_n{}^e$—, —$N(R^{10e})C(=O)$—, —$NHC(=O)(CH_2)_n{}^e$—, and —$C(=O)N(R^{10e})$—;

$G^e$ is N or $CR^{19e}$;

$R^{8e}$ is selected from:
   H, $CO_2R^{18be}$, $C(=O)R^{18be}$, $CONR^{17e}R^{18be}$,
   $C_1$–$C_{10}$ alkyl substituted with 0–1 $R^{6e}$,
   $C_2$–$C_{10}$ alkenyl substituted with 0–1 $R^{6e}$,
   $C_2$–$C_{10}$ alkynyl substituted with 0–1 $R^{6e}$,
   $C_3$–$C_8$ cycloalkyl substituted with 0–1 $R^{6e}$,
   $C_5$–$C_6$ cycloalkenyl substituted with 0–1 $R^{6e}$,
   ($C_1$–$C_{10}$ alkyl) carbonyl,
   $C_3$–$C_{10}$ cycloalkyl($C_1$–$C_4$ alkyl)-,
   phenyl substituted with 0–3 $R^{6e}$,
   naphthyl substituted with 0–3 $R^{6e}$,
   a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{9e}$ is selected from:
   $C_1$–$C_{10}$ alkyl substituted with 0–1 $R^{6e}$,
   $C_1$–$C_{10}$ alkoxy substituted with 0–2 $R^{7e}$,
   H, nitro, $N(R^{11e})R^{12e}$, $OC(=O)R^{10e}$, $OR^{10e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, hydroxy, $OR^{22e}$, —$N(R^{10e})R^{11e}$, —$N(R^{16e})R^{17e}$, aryl($C_0$–$C_6$ alkyl)carbonyl, aryl($C_1$–$C_6$ alkyl), heteroaryl($C_1$–$C_6$ alkyl), $CONR^{18ae}R^{20e}$, $SO_2R^{18ae}$, and $SO_2NR^{18ae}R^{20e}$,
   providing that any of the above alkyl, cycloalkyl, aryl or heteroaryl groups may be unsubstituted or substituted independently with 1–2 $R^{7e}$;

$R^{6e}$ is selected from:
   H, $C_1$–$C_{10}$ alkyl, hydroxy, $C_1$–$C_{10}$ alkoxy, nitro, $C_1$–$C_{10}$ alkylcarbonyl, —$N(R^{11e})R^{12e}$, cyano, halo, $CF_3$, CHO, $CO_2R^{18be}$, $C(=O)R^{18be}$, $CONR^{17e}R^{18be}$, $OC(=O)R^{10e}$, $OR^{10e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, $S(O)_p{}^e R^{11e}$, $SO_2NR^{10e}R^{11e}$,
   aryl substituted with 0–3 groups selected from halogen, $C_1$–$C_6$ alkoxy, $C_1$–$C_6$ alkyl, $CF_3$, $S(O)_m{}^e$Me, and —$NMe_2$,
   aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p{}^e$Me, and —$NMe_2$, and
   a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:
   H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:
   H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:
   H, $C_1$–$C_6$ alkyl, $C_3$–$C_7$ cycloalkyl, $C_3$–$C_7$ cycloalkyl($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^{12e}$ is selected from:
   H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl)

sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
 —C(=O)O$R^{18ae}$, —C(=O)$R^{18be}$, —C(=O)N($R^{18be}$)$_2$, —SO$_2$$R^{18ae}$, and —SO$_2$N($R^{18be}$)$_2$;

$R^{17e}$ is selected from:
 H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:
 $C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
 H, halogen, $CF_3$, $CO_2H$, CN, $NO_2$, —N$R^{11e}R^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
 hydroxy, $C_1$–$C_{10}$ alkyloxy, $C_3$–$C_{11}$ cycloalkyloxy, aryloxy, aryl($C_1$–$C_4$ alkyl)oxy,
 $C_2$–$C_{10}$ alkylcarbonyloxy($C_1$–$C_2$ alkyl)oxy-,
 $C_2$–$C_{10}$ alkoxycarbonyloxy($C_1$–$C_2$ alkyl)oxy-,
 $C_2$–$C_{10}$ alkoxycarbonyl($C_1$–$C_2$ alkyl)oxy-,
 $C_3$–$C_{10}$ cycloalkylcarbonyloxy($C_1$–$C_2$ alkyl)oxy-,
 $C_3$–$C_{10}$ cycloalkoxycarbonyloxy($C_1$–$C_2$ alkyl)oxy-,
 $C_3$–$C_{10}$ cycloalkoxycarbonyl($C_1$–$C_2$ alkyl)oxy-,
 aryloxycarbonyl($C_1$–$C_2$ alkyl)oxy-,
 aryloxycarbonyloxy($C_1$–$C_2$ alkyl)oxy-,
 arylcarbonyloxy($C_1$–$C_2$ alkyl)oxy-,
 $C_1$–$C_5$ alkoxy($C_1$–$C_5$ alkyl)carbonyloxy($C_1$–$C_2$ alkyl) oxy,
 (5-($C_1$–$C_5$ alkyl)-1,3-dioxa-cyclopenten-2-one-yl)methyloxy,
 (5-aryl-1,3-dioxa-cyclopenten-2-one-yl)methyloxy, and
 ($R^{10e}$)($R^{11e}$)N—($C_1$–$C_{10}$ alkoxy)-;

$R^{21e}$ is selected from:
 $C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^{7e}$;

$R^{22e}$ is selected from:
 —C(=O)—$R^{18be}$, —C(=O)N($R^{18be}$)$_2$, —C(=O) NHSO$_2$$R^{18ae}$, —C(=O)NHC(=O)$R^{18be}$, —C(=O) NHC(=O)O$R^{18ae}$, and —C(=O)NHSO$_2$NH$R^{18be}$;

$m^e$ is 0–2;
$n^e$ is 0–4; and
$p^e$ is 0–2;

with the following proviso: $n^e$ and $m^e$ are chosen such that the number of atoms connecting $R^1$ and —CO$R^{20e}$ in Formula (IV) is in the range of 8–14;

d is selected from 1, 2, 3, 4, and 5;
d' is 1–50;
W is independently selected at each occurrence from the group: O, NH, NHC(=O), C(=O)NH, N$R^8$C(=O), C(=O)N$R^8$, C(=O), C(=O)O, OC(=O), NHC(=S) NH, NHC(=O)NH, SO$_2$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, $SO_3H$, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O) NH$R^{11}$, NHC(=O)NH$R^{11}$, NH$R^{11}$, $R^{11}$, and a bond to $C_h$;

k is 0 or 1;
s is selected from 0, 1, 2, 3, 4, and 5;
s' is selected from 0, 1, 2, 3, 4, and 5;
s'' is selected from 0, 1, 2, 3, 4, and 5;
t is selected from 0, 1, 2, 3, 4, and 5;
$A^1, A^2, A^3, A^4, A^5, A^6, A^7$, and $A^8$ are independently selected at each occurrence from the group: N$R^{13}$, N$R^{13}R^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C($R^{20}$)($R^{21}$);

$R^{17}$ is independently selected at each occurrence from the group: a bond to $L_n$, =O, F, Cl, Br, I, —$CF_3$, —CN, —CO$_2R^{18}$, —C(=O)$R^{18}$, —C(=O)N($R^{18}$)$_2$, —CH$_2$O$R^{18}$, —OC(=O)$R^{18}$, —OC(=O)O$R^{18a}$, —O$R^{18}$, —OC(=O)N($R^{18}$)$_2$, —N$R^{19}$C(=O)$R^{18}$, —N$R^{19}$C(=O)O$R^{18a}$, —N$R^{19}$C(=O)N($R^{18}$)$_2$, —N$R^{19}$SO$_2$N($R^{18}$)$_2$, —N$R^{19}$SO$_2R^{18a}$, —SO$_3H$, —SO$_2R^{18a}$, —S(=O)$R^{18a}$, —SO$_2$N($R^{18}$)$_2$, —N($R^{18}$)$_2$, —NHC(=S)NH$R^{18}$, =NO$R^{18}$, —C(=O)NHN$R^{18}R^{18a}$, —OCH$_2$CO$_2$H, and 2-(1-morpholino)ethoxy;

$R^{18}$, $R^{18a}$, and $R^{19}$ are independently selected at each occurrence from the group: a bond to $L_n$, H, and $C_1$–$C_6$ alkyl;

$R^{20}$ and $R^{21}$ are independently selected from the group: H, $C_1$–$C_5$ alkyl, —CO$_2R^{25}$, $C_2$–$C_5$ 1-alkene substituted with 0–3 $R^{23}$, $C_2$–$C_5$ 1-alkyne substituted with 0–3 $R^{23}$, aryl substituted with 0–3 $R^{23}$, and unsaturated 5–10 membered heterocyclic ring system containing 1–4 heteroatoms independently selected from N, S, and O and substituted with 0–3 $R^{23}$;

alternatively, $R^{20}$ and $R^{21}$, taken together with the divalent carbon radical to which they are attached form:

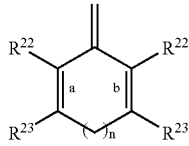

$R^{22}$ and $R^{23}$ are independently selected from the group: H, and $R^{24}$;

alternatively, $R^{22}$, $R^{23}$ taken together form a fused aromatic or a 5–10 membered heterocyclic ring system containing 1–4 heteroatoms independently selected from N, S, and O;

$R^{24}$ is independently selected at each occurrence from the group: —$CO_2R^{25}$, —C(=O)N($R^{25}$)$_2$, —$CH_2OR^{25}$, —OC(=O)$R^{25}$, —$OR^{25}$, —$SO_3H$, —N($R^{25}$)$_2$, and —$OCH_2CO_2H$; and, $R^{25}$ is independently selected at each occurrence from the group: H and $C_1$–$C_3$ alkyl.

[4] In an even more preferred embodiment, the present invention provides a compound including stereoisomeric forms thereof, or mixtures of stereoisomeric forms thereof, or pharmaceutically acceptable salt, or prodrug forms thereof wherein:

$R^{1e}$ is selected from:

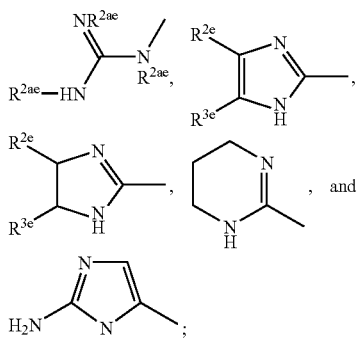

$R^{2e}$ and $R^{3e}$ are independently selected from:
H, $C_1$–$C_4$ alkoxy, $NR^{11e}R^{12e}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^{7e}$, alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2ae}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl) carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^{7e}$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
—($CH_2$)$_n^e$—, —NH($CH_2$)$_n^e$—, —N($R^{10e}$)C(=O)—, and —NHC(=O)($CH_2$)$_n^e$;

$G^e$ is N or $CR^{19e}$;

$R^{8e}$ is H;

$R^{9e}$ is selected from:
H, nitro, $N(R^{11e})R^{12e}$, OC(=O)$R^{10e}$, $OR^{10e}$, OC(=O)$NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, hydroxy, $OR^{22e}$, —N($R^{10e}$)$R^{11e}$, —N($R^{16e}$)$R^{17e}$, aryl($C_0$–$C_4$ alkyl)carbonyl, aryl($C_1$–$C_4$ alkyl), heteroaryl($C_1$–$C_4$ alkyl), $CONR^{18ae}R^{20e}$, $SO_2R^{18ae}$, and $SO_2NR^{18ae}R^{20e}$, providing that any of the above alkyl, cycloalkyl, aryl or heteroaryl groups may be unsubstituted or substituted independently with 1–2 $R^{7e}$;

$R^{10e}$ is selected from:
H, $CF_3$, $C_3$–$C_6$ alkenyl, $C_3$–$C_6$ cycloalkyl, aryl, ($C_3$–$C_6$ cycloalkyl)methyl, aryl($C_1$–$C_4$ alkyl), and $C_1$–$C_4$ alkyl substituted with 0–2 $R^{6e}$;

$R^{6e}$ is selected from:
H, $C_1$–$C_4$ alkyl, hydroxy, $C_1$–$C_4$ alkoxy, nitro, $C_1$–$C_4$ alkylcarbonyl, —N($R^{11e}$)$R^{12e}$, cyano, halo, $CF_3$, CHO, $CO_2R^{18be}$, C(=O)$R^{18be}$, $CONR^{17e}R^{18be}$, OC(=O)$R^{10e}$, $OR^{10e}$, OC(=O)$NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, $S(O)_pR^{11e}$, $SO_2NR^{10e}R^{11e}$, aryl substituted with 0–3 groups selected from halogen, $C_1$–$C_4$ alkoxy, $C_1$–$C_4$ alkyl, $CF_3$, $S(O)_m^e$Me, and —$NMe_2$, aryl($C_1$–$C_4$ alkyl)-, said aryl being substituted with 0–3 groups selected from halogen, $C_1$–$C_4$ alkoxy, $C_1$–$C_4$ alkyl, $CF_3$, $S(O)_p^e$Me, and —$NMe_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{11e}$ is selected from:
H, hydroxy, $C_1$–$C_4$ alkyl, $C_3$–$C_6$ alkenyl, $C_3$–$C_6$ cycloalkyl, ($C_3$–$C_6$ cycloalkyl)methyl, $C_1$–$C_4$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_4$ alkyl substituted with 0–2 $R^{4e}$;

$R^{4e}$ is selected from:
H, $C_1$–$C_4$ alkyl, $C_3$–$C_7$ cycloalkyl, $C_3$–$C_7$ cycloalkyl($C_1$–$C_4$ alkyl)-, aryl, heteroaryl, aryl($C_1$–$C_4$ alkyl)-, and heteroaryl($C_1$–$C_4$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^{12e}$ is selected from:
H, $C_1$–$C_4$ alkyl, ($C_1$–$C_4$ alkyl)carbonyl, ($C_1$–$C_4$ alkoxy) carbonyl, phenyl($C_1$–$C_4$ alkyl)-, phenylsulfonyl, phenyloxycarbonyl, and phenyl($C_1$–$C_4$ alkoxy)carbonyl, wherein said phenyl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
  —C(=O)OR$^{18ae}$, —C(=O)R$^{18be}$, —C(=O)N(R$^{18be}$)$_2$, —SO$_2$R$^{18ae}$, and —SO$_2$N(R$^{18be}$)$_2$;

$R^{17e}$ is selected from:
  H, C$_1$–C$_4$ alkyl, C$_3$–C$_6$ cycloalkyl, C$_3$–C$_6$ cycloalkyl (C$_1$–C$_4$ alkyl)-, aryl, aryl(C$_1$–C$_6$ alkyl)-, and heteroaryl (C$_1$–C$_6$ alkyl);

$R^{18ae}$ is selected from:
  C$_1$–C$_8$ alkyl optionally substituted with a bond to L$_n$, C$_3$–C$_{11}$ cycloalkyl optionally substituted with a bond to L$_n$, aryl(C$_1$–C$_6$ alkyl)- optionally substituted with a bond to L$_n$, heteroaryl(C$_1$–C$_6$ alkyl)- optionally substituted with a bond to L$_n$, (C$_1$–C$_6$ alkyl)heteroaryl optionally substituted with a bond to L$_n$, biaryl(C$_1$–C$_6$ alkyl) optionally substituted with a bond to L$_n$, heteroaryl optionally substituted with a bond to L$_n$, phenyl substituted with 3–4 R$^{19e}$ and optionally substituted with a bond to L$_n$, naphthyl substituted with 0–4 R$^{19e}$ and optionally substituted with a bond to L$_n$, and a bond to L$_n$, wherein said aryl or heteroaryl groups are optionally substituted with 0–4 R$^{19e}$;

$R^{18be}$ is H or R$^{18ae}$;

$R^{19e}$ is selected from:
  H, halogen, CF$_3$, CO$_2$H, CN, NO$_2$, —NR$^{11e}$R$^{12e}$, OCF$_3$, C$_1$–C$_6$ alkyl, C$_2$–C$_6$ alkenyl, C$_2$–C$_6$ alkynyl, C$_3$–C$_6$ cycloalkyl, C$_3$–C$_6$ cycloalkyl(C$_1$–C$_4$ alkyl)-, aryl(C$_1$–C$_4$ alkyl)-, C$_1$–C$_6$ alkoxy, C$_1$–C$_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, CF$_3$, C$_1$–C$_3$ alkyl, and C$_1$–C$_3$ alkoxy;

$R^{20e}$ is selected from:
  hydroxy, C$_1$–C$_6$ alkyloxy, C$_3$–C$_6$ cycloalkyloxy,
  aryloxy, aryl(C$_1$–C$_4$ alkyl)oxy,
  C$_2$–C$_{10}$ alkylcarbonyloxy(C$_1$–C$_2$ alkyl)oxy-,
  C$_2$–C$_{10}$ alkoxycarbonyloxy(C$_1$–C$_2$ alkyl)oxy-,
  C$_2$–C$_{10}$ alkoxycarbonyl(C$_1$–C$_2$ alkyl)oxy-,
  C$_3$–C$_{10}$ cycloalkylcarbonyloxy(C$_1$–C$_2$ alkyl)oxy-,
  C$_3$–C$_{10}$ cycloalkoxycarbonyloxy(C$_1$–C$_2$ alkyl)oxy-,
  C$_3$–C$_{10}$ cycloalkoxycarbonyl (C$_1$–C$_2$ alkyl)oxy-,
  aryloxycarbonyl(C$_1$–C$_2$ alkyl)oxy-,
  aryloxycarbonyloxy(C$_1$–C$_2$ alkyl)oxy-,
  arylcarbonyloxy(C$_1$–C$_2$ alkyl)oxy-,
  C$_1$–C$_5$ alkoxy(C$_1$–C$_5$ alkyl)carbonyloxy(C$_1$–C$_2$ alkyl)oxy,
  (5-(C$_1$–C$_5$ alkyl)-1,3-dioxa-cyclopenten-2-one-yl)methyloxy,
  (5-aryl-1,3-dioxa-cyclopenten-2-one-yl)methyloxy, and
  (R$^{10e}$)(R$^{11e}$)N—(C$_1$–C$_{10}$ alkoxy)-;

$R^{21e}$ is selected from:
  C$_1$–C$_4$ alkyl, C$_2$–C$_6$ alkenyl, C$_3$–C$_6$ cycloalkyl, (C$_3$–C$_6$ cycloalkyl)methyl, aryl, aryl(C$_1$–C$_4$ alkyl)-, and C$_1$–C$_{10}$ alkyl substituted with 0–2 R$^{7e}$;

$R^{22e}$ is selected from:
  —C(=O)—R$^{18be}$, —C(=O)N(R$^{18be}$)$_2$, —C(=O)NHSO$_2$R$^{18ae}$, —C(=O)NHC(=O)R$^{18be}$, —C(=O)NHC(=O)OR$^{18ae}$, and —C(=O)NHSO$_2$NHR$^{18be}$;

$m^e$ is 0–2;
$n^e$ is 0–4;
$p^e$ is 0–2;

$C_h$ is

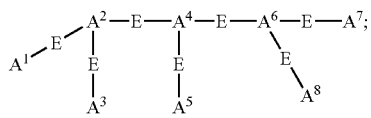

$A^1$ is selected from the group: OH, and a bond to L$_n$;
$A^2$, $A^4$, and $A^6$ are each N;
$A^3$, $A^5$, and $A^8$ are each OH;
$A^7$ is a bond to L$_n$ or NH-bond to L$_n$;
E is a C$_2$ alkyl substituted with 0–1 R$^{17}$;
$R^{17}$ is =O;
alternatively, $C_h$ is

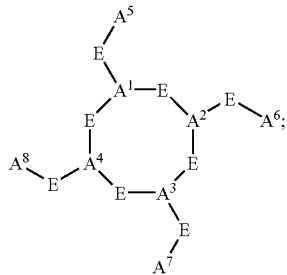

$A^1$ is selected from the group: OH, and a bond to L$_n$;
$A^2$, $A^3$ and $A^4$ are each N;
$A^5$, $A^6$ and $A^8$ are each OH;
$A^7$ is a bond to L$_n$;
E is a C$_2$ alkyl substituted with 0–1 R$^{17}$;
$R^{17}$ is =O;
alternatively, $C_h$ is

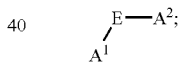

$A^1$ is NH$_2$ or N=C(R$^{20}$)(R$^{21}$);
E is a bond;
$A^2$ is NHR$^{13}$;
$R^{13}$ is a heterocycle substituted with R$^{17}$, the heterocycle being selected from pyridine and pyrimidine;
$R^{17}$ is selected from a bond to L$_n$, C(=O)NHR$^{18}$ and C(=O)R$^{18}$;
$R^{18}$ is a bond to L$_n$;
$R^{24}$ is selected from the group: —CO$_2$R$^{25}$, —OR$^{25}$, —SO$_3$H, and —N(R$^{25}$)$_2$; and,
$R^{25}$ is independently selected at each occurrence from the group: hydrogen and methyl.

[5] In another even more preferred embodiment, the present invention provides a compound including enantiomeric or diastereomeric forms thereof, or mixtures of enantiomeric or diastereomeric forms thereof, or pharmaceutically acceptable salt or prodrug forms thereof, wherein Q is selected from the group:
  3-[7-[(imidazolin-2-ylamino)methyl]-1-methyl-6,8-difluoroquinoline-4-one-3-ylcarbonylamino]-2-(3,5-dimethylisoxazol-4-ylsulfonylamino)propionic acid,
  3-[7-[(imidazolin-2-ylamino)methyl]-1-methyl-6,8-difluoroquinoline-4-one-3-ylcarbonylamino]-2-(benzyloxycarbonylamino)propionic acid, 3-[7-[(imidazolin-2-ylamino)methyl]-1-methyl-6,8-difluoroquinoline-4-one-3-ylcarbonylamino]-2-(n-butyloxycarbonylamino)propionic acid,
3-[7-[(imidazolin-2-ylamino)methyl]-1-methyl-6,8-difluoroquinoline-4-one-3-ylcarbonylamino]-2-(n-butylsulfonylamino)propionic acid,
3-[7-[(tetrahydropyrimid-2-ylamino)methyl]-1-methyl-6,8-difluoroquinoline-4-one-3-ylcarbonylamino]-2-(benzyloxycarbonylamino)propionic acid,
3-[7-[(tetrahydropyrimid-2-ylamino)methyl]-1-methyl-6,8-difluoroquinoline-4-one-3-ylcarbonylamino]-2-(n-butyloxycarbonylamino)propionic acid,
3-[7-[(tetrahydropyrimid-2-ylamino)methyl]-1-methyl-6,8-difluoroquinoline-4-one-3-ylcarbonylamino]-2-(phenylsulfonylamino)propionic acid,
3-[7-[(tetrahydropyrimid-2-ylamino)methyl]-1-methyl-6,8-difluoroquinoline-4-one-3-ylcarbonylamino]-2-(n-butylsulfonyl)aminopropionic acid,
3-[7-[(2-aminothiazol-4-yl)methyl]-1-methyl-6,8-difluoroquinoline-4-one-3-ylcarbonylamino]-2-(benzyloxycarbonylamino)propionic acid,
3-[7-[(imidazolin-2-ylamino)methyl]-1-methyl-6,8-difluoroquinoline-4-one-3-ylcarbonylamino]-2-((2,4,6-trimethylphenyl)sulfonylamino)propionic acid,
3-[7-[(tetrahydropyrimid-2-ylamino)methyl]-1-methyl-6,8-difluoroquinoline-4-one-3-ylcarbonylamino]-2-((2,4,6-trimethylphenyl)sulfonylamino)propionic acid,
3-[7-[(imidazol-2-ylamino)methyl]-1-methyl-6,8-difluoroquinoline-4-one-3-ylcarbonylamino]-2-(3,5-dimethylisoxazol-4-ylsulfonylamino)propionic acid,
3-[7-[(imidazol-2-ylamino)methyl]-1-methyl-6,8-difluoroquinoline-4-one-3-ylcarbonylamino]-2-(benzyloxycarbonylamino)propionic acid,
3-[7-[(imidazol-2-ylamino)methyl]-1-methyl-6,8-difluoroquinoline-4-one-3-ylcarbonylamino]-2-((2,4,6-trimethylphenyl)sulfonylamino)propionic acid,
3-[7-[(imidazol-2-ylamino)methyl]-1-methyl-6,8-difluoroquinoline-4-one-3-ylcarbonylamino]-2-((4-biphenyl)sulfonylamino)propionic acid,
3-[7-[(imidazol-2-ylamino)methyl]-1-methyl-6,8-difluoroquinoline-4-one-3-ylcarbonylamino]-2-(1-naphthylsulfonylamino)propionic acid,
3-[7-[(benzimidazol-2-ylamino)methyl]-1-methyl-6,8-difluoroquinoline-4-one-3-ylcarbonylamino]-2-((2,4,6-trimethylphenyl)sulfonylamino)propionic acid,
3-[7-[(4-methylimidazol-2-ylamino)methyl]-1-methyl-6,8-difluoroquinoline-4-one-3-ylcarbonylamino]-2-((2,4,6-trimethylphenyl)sulfonylamino)propionic acid,
3-[7-[(4,5-dimethylimidazol-2-ylamino)methyl]-1-methyl-6,8-difluoroquinoline-4-one-3-ylcarbonylamino]-2-((2,4,6-trimethylphenyl)sulfonylamino)propionic acid,
3-[7-[(4,5,6,7-tetrahydrobenzimidazol-2-ylamino)methyl]-1-methyl-6,8-difluoroquinoline-4-one-3-ylcarbonylamino]-2-((2,4,6-trimethylphenyl)sulfonylamino)propionic acid,
3-[7-[(pyridin-2-ylamino)methyl]-1-methyl-6,8-difluoroquinoline-4-one-3-ylcarbonylamino]-2-((2,4,6-trimethylphenyl)sulfonylamino)propionic acid,
3-[7-(2-aminopyridin-6-yl)-1-methyl-6,8-difluoroquinoline-4-one-3-ylcarbonylamino]-2-((2,4,6-trimethylphenyl)sulfonylamino)propionic acid,
3-[7-[(7-azabenzimidazol-2-yl)methyl]-1-methyl-6,8-difluoroquinoline-4-one-3-ylcarbonylamino]-2-((2,4,6-trimethylphenyl)sulfonylamino)propionic acid,
3-[7-[(benzimidazol-2-ylamino)methyl]-1-(2-phenylethyl)-6,8-difluoroquinoline-4-one-3-ylcarbonylamino]propionic acid,
3-[7-[(pyridin-2-ylamino)methyl]-1-(2-phenylethyl)-6,8-difluoroquinoline-4-one-3-ylcarbonylamino]propionic acid,
3-[7-[(imidazolin-2-ylamino)methyl]-1-(2-phenylethyl)-6,8-difluoroquinoline-4-one-3-ylcarbonylamino]propionic acid,
3-[7-[(imidazol-2-ylamino)methyl]-1-(2-phenylethyl)-6,8-difluoroquinoline-4-one-3-ylcarbonylamino]propionic acid,
3-[7-[(imidazolin-2-ylamino)methyl]-1-(2-phenylethyl)-6,8-difluoroquinoline-4-one-3-ylcarbonylamino]-2-(benzyloxycarbonylamino)propionic acid,
3-[7-[(imidazolin-2-ylamino)methyl]-1-(2-phenylethyl)-6,8-difluoroquinoline-4-one-3-ylcarbonylamino]-2-(n-butyloxycarbonylamino)propionic acid,
3-[7-[(imidazolin-2-ylamino)methyl]-1-(2-phenylethyl)-6,8-difluoroquinoline-4-one-3-ylcarbonylamino]-2-(phenylsulfonylamino)propionic acid,
3-[7-[(imidazolin-2-ylamino)methyl]-1-(2-phenylethyl)-6,8-difluoroquinoline-4-one-3-ylcarbonylamino]-2-(n-butylsulfonylamino)propionic acid,
3-[7-[(tetrahydropyrimid-2-ylamino)methyl]-1-(2-phenylethyl)-6,8-difluoroquinoline-4-one-3-ylcarbonylamino]-2-(benzyloxycarbonylamino)propionic acid,
3-[7-[(tetrahydropyrimid-2-ylamino)methyl]-1-(2-phenylethyl)-6,8-difluoroquinoline-4-one-3 -ylcarbonylamino]-2-(n-butyloxycarbonylamino)propionic acid,
3-[7-[(tetrahydropyrimid-2-ylamino)methyl]-1-(2-phenylethyl)-6,8-difluoroquinoline-4-one-3-ylcarbonylamino]-2-(phenylsulfonylamino)propionic acid,
3-[7-[(tetrahydropyrimid-2-ylamino)methyl]-1-(2-phenylethyl)-6,8-difluoroquinoline-4-one-3-ylcarbonylamino]-2-(n-butylsulfonyl)aminopropionic acid,
3-[7-[(2-aminothiazol-4-yl)methyl]-1-(2-phenylethyl)-6,8-difluoroquinoline-4-one-3-ylcarbonylamino]-2-(phenylsulfonylamino)propionic acid,
3-[7-[(2-aminothiazol-4-yl)methyl]-1-(2-phenylethyl)-6,8-difluoroquinoline-4-one-3-ylcarbonylamino]-2-(benzyloxycarbonylamino)propionic acid,
3-[7-[(imidazolin-2-ylamino)methyl]-1-(2-phenylethyl)-6,8-difluoroquinoline-4-one-3-ylcarbonylamino]-2-((2,4,6-trimethylphenyl)sulfonylamino)propionic acid,
3-[7-[(tetrahydropyrimid-2-ylamino)methyl]-1-(2-phenylethyl)-6,8-difluoroquinoline-4-one-3-ylcarbonylamino]-2-((2,4,6-trimethylphenyl)sulfonylamino)propioflic acid,
3-[7-[(imidazol-2-ylamino)methyl]-1-(2-phenylethyl)-6,8-difluoroquinoline-4-one-3-ylcarbonylamino]-2-(benzyloxycarbonylamino)propionic acid,
3-[7-[(imidazol-2-ylamino)methyl]-1-(2-phenylethyl)-6,8-difluoroquinoline-4-one-3-ylcarbonylamino]-2-(phenylsulfonylamino)propionic acid,
3-[7-[(imidazol-2-ylamino)methyl]-1-(2-phenylethyl)-6,8-difluoroquinoline-4-one-3-ylcarbonylamino]-2-((2,6,dichlorophenyl)sulfonylamino)propionic acid,
3-[7-[(imidazol-2-ylamino)methyl]-1-(2-phenylethyl)-6,8-difluoroquinoline-4-one-3-ylcarbonylamino] -2-((2,4,6-trimethylphenyl)sulfonylamino)propionic acid,
3-[7-[(imidazol-2-ylamino)methyl]-1-(2-phenylethyl)-6,8-difluoroquinoline-4-one-3-ylcarbonylamino]-2-((4-biphenyl)sulfonylamino)propionic acid,
3-[7-[(benzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid,
3-[7-[(4-methylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid,
3-[7-[(4,5-dimethylimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(4,5,6,7-tetrahydrobenzimidazol-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-[(pyridin-2-ylamino)methyl]-1-(2-phenylethyl)-6,8-difluoroquinoline-4-one-3-ylcarbonylamino]-2-((2,4,6-trimethylphenyl)sulfonylamino)propionic acid, 3-[7-(2-aminopyridin-6-yl)-1-(2-phenylethyl)-6,8-difluoroquinoline-4-one-3-ylcarbonylamino]-2-((2,4,6-trimethylphenyl)sulfonylamino)propionic acid, and 3-[7-[(7-azabenzimidazol-2-yl)methyl]-1-(2-phenylethyl)-6,8-difluoroquinoline-4-one-3-ylcarbonylamino]-2-((2,4,6-trimethylphenyl)sulfonylamino)propionic acid.

[6] In another even more preferred embodiment, the present invention provides a compound selected from the group:

2-(((4-(4-(((3-(2-(2-(3-((6-((1-aza-2-(2-sulfophenyl)vinyl)amino)(3-pyridyl))carbonylamino)propoxy)ethoxy)ethoxy)propyl)amino)sulfonyl)phenyl)phenyl)sulfonyl)amino)-3-((7-((imidazol-2-ylamino)methyl)-1-methyl-4-oxo(3-hydroquinolyl))carbonylamino)propanoic acid;

3-((7-((imidazol-2-ylamino)methyl)-1-methyl-4-oxo(3-hydroquinolyl))carbonylamino)-2-(((4-(4-(((3-(2-(2-(3-(2-(1,4,7,10-tetraaza-4,7,10-tris(carboxylmethyl)cyclododecyl)acetylamino)propoxy)ethoxy)ethoxy)propyl)amino)sulfonyl)phenyl)phenyl)sulfonyl)amino)propanoic acid;

2-(((4-(3-(N-(3-(2-(2-(3-((6-((1-aza-2-(2-sulfophenyl)vinyl)amino)(3-pyridyl))carbonylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic;

3-((1-(3-((6-((1-aza-2-(2-sulfophenyl)vinyl)amino)(3-pyridyl))carbonylamino)propyl)-7-((imidazole-2-ylamino)methyl)-4-oxo(3-hydroquinolyl))carbonylamino)-2-(((2,4,6-trimethylphenyl)sulfonyl)amino)propanoic acid;

3-((1-(3-((6-((1-aza-2-(2-sulfophenyl)vinyl)amino)(3-pyridyl))carbonylamino)propyl)-7-(((1-hydroxyimidazole-2-yl)amino)methyl)-4-oxo(3-hydroquinolyl))carbonylamino)-2-(((2,4,6-trimethylphenyl)sulfonyl)amino)propanoic acid;

3-((1-(3-(3-(N-(3-(2-(2-(3-((6-((1-aza-2-(2-sulfophenyl)vinyl)amino)(3-pyridyl))carbonylamino)propoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic acid;

2-(2-aza-2-(5-(N-(1,3-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)proproxy)ethoxy)ethoxy)propyl)carbamoyl)(2-pyridyl))amino)vinyl)benzenesulfonic acid;

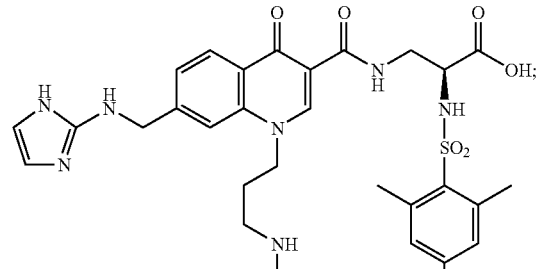

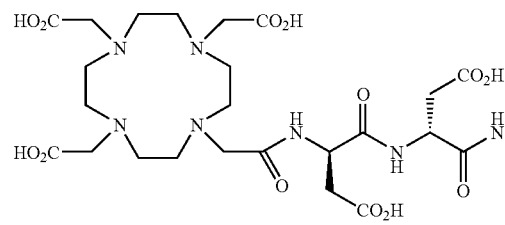

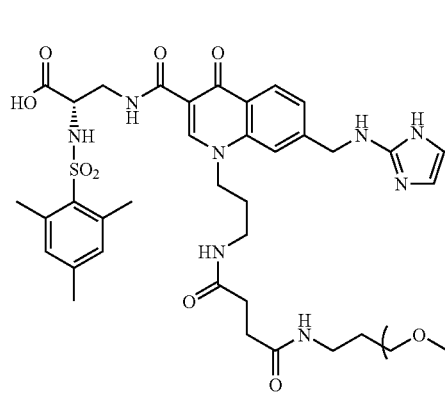

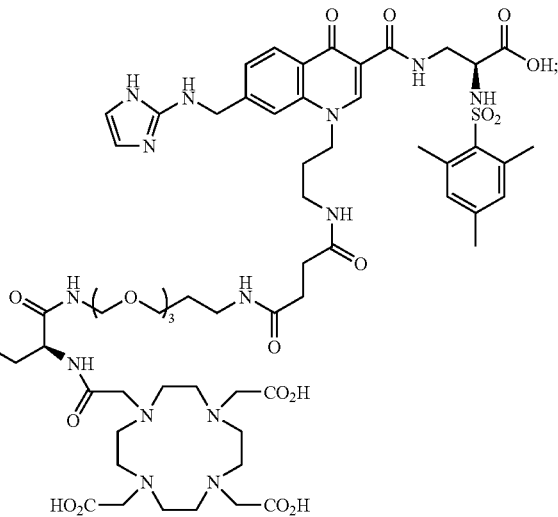

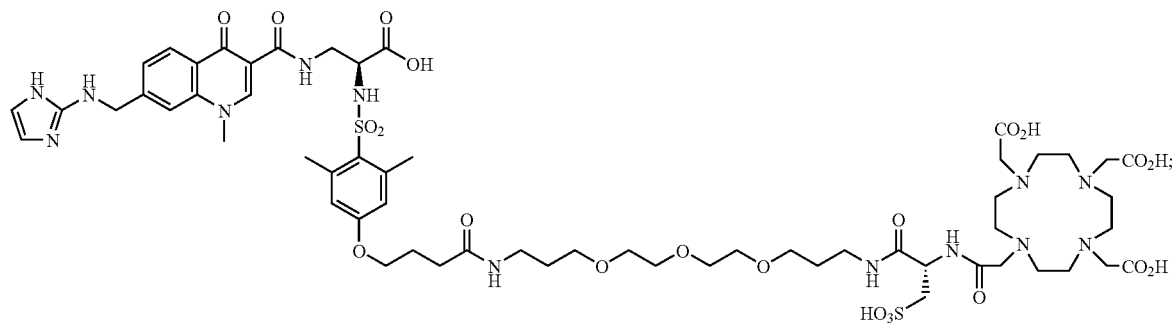
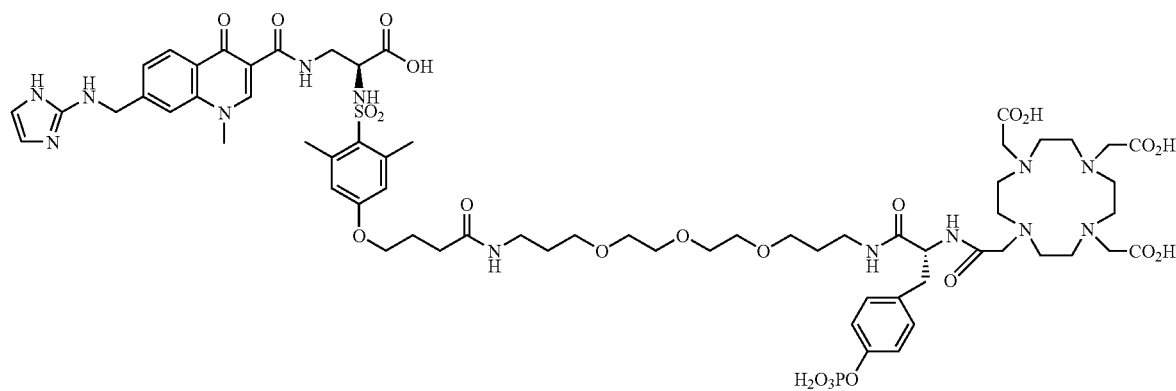
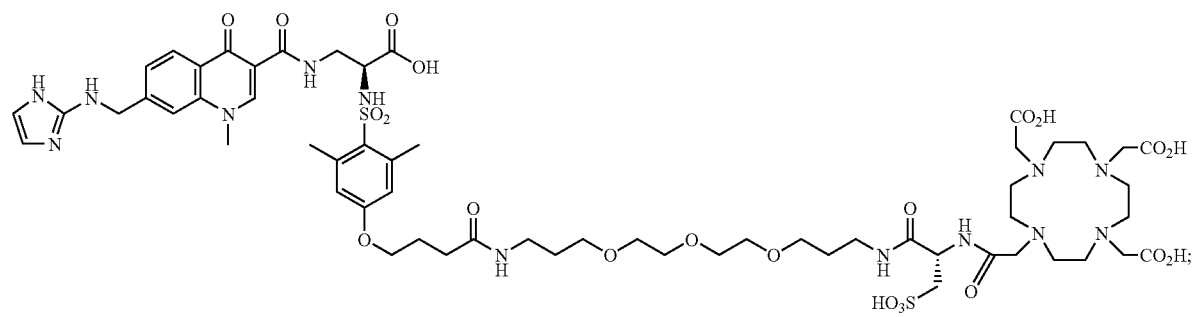
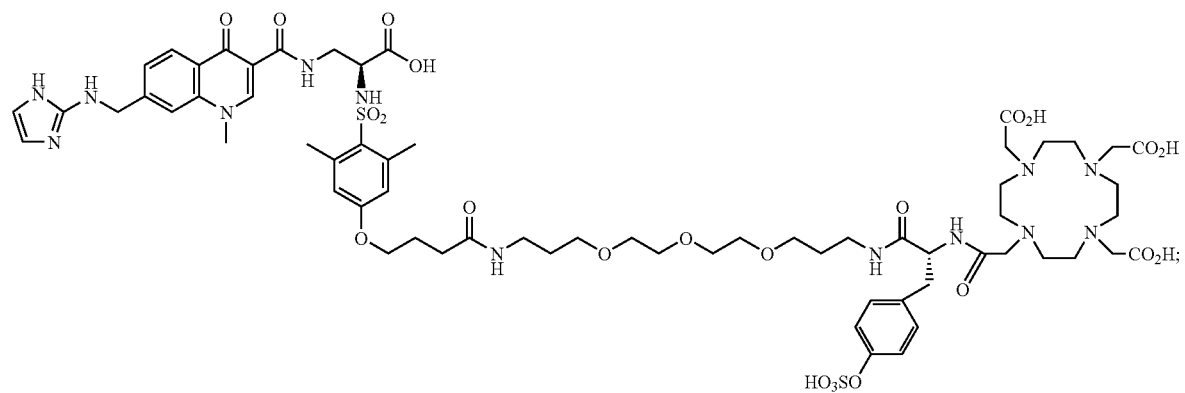

-continued

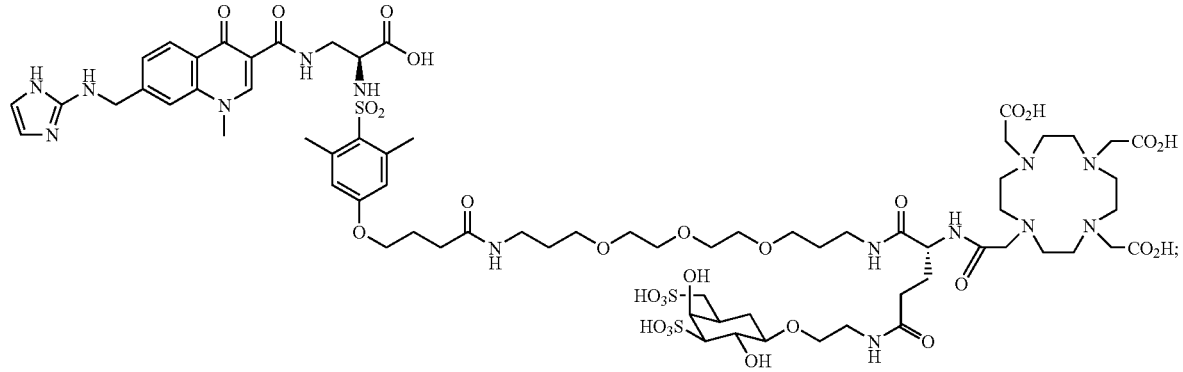

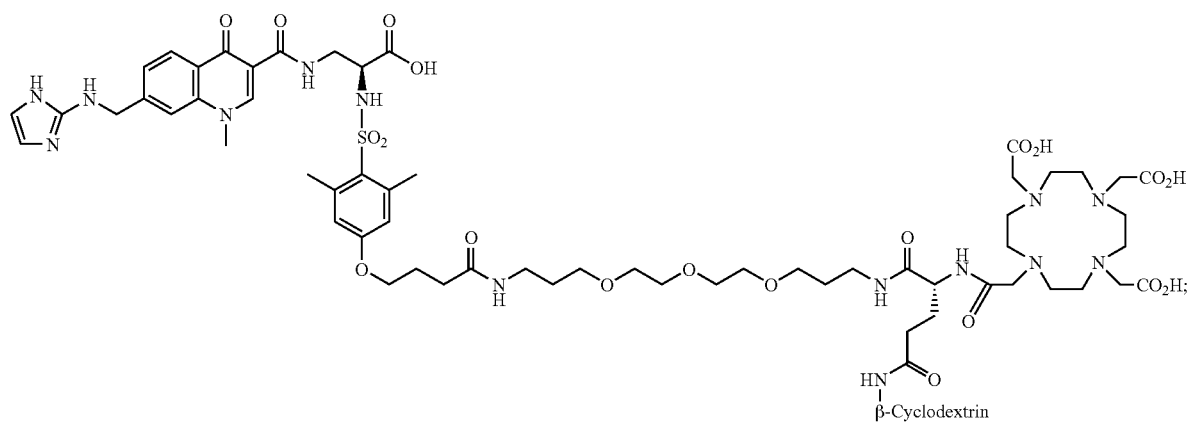

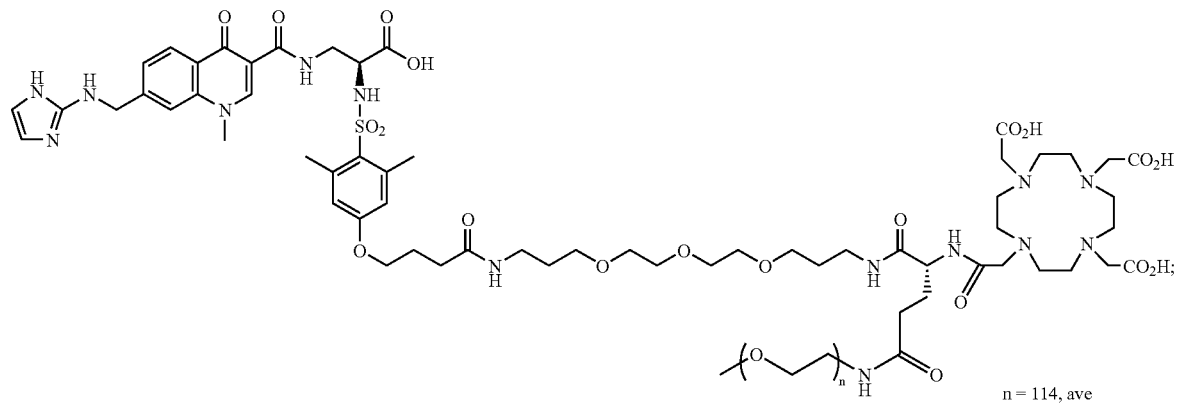

2-(((4-(3-(N-(3-(2-(2-(3-(2-(1,4,7,10-tetraaza-4,7,10-tris(carboxymethyl)cyclododecylacetylamino)-6-aminohexanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic acid;

2-(((4-(3-(N-(3-(2-(2-(3-(2-(1,4,7,10-tetraaza-4,7,10-tris(carboxymethyl)cyclododecylacetylamino)-6-(2-(bis(phosphonomethyl)amino)acetylamino)hexanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic acid conjugate; and 2-(((4-(3-(N-(3-(2-(2-(3-(2-(2-((2-((2-(bis(carboxymethyl)amino)ethyl)(carboxymethyl)amino)ethyl)(carboxymethyl)amino)acetylamino)-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic acid;

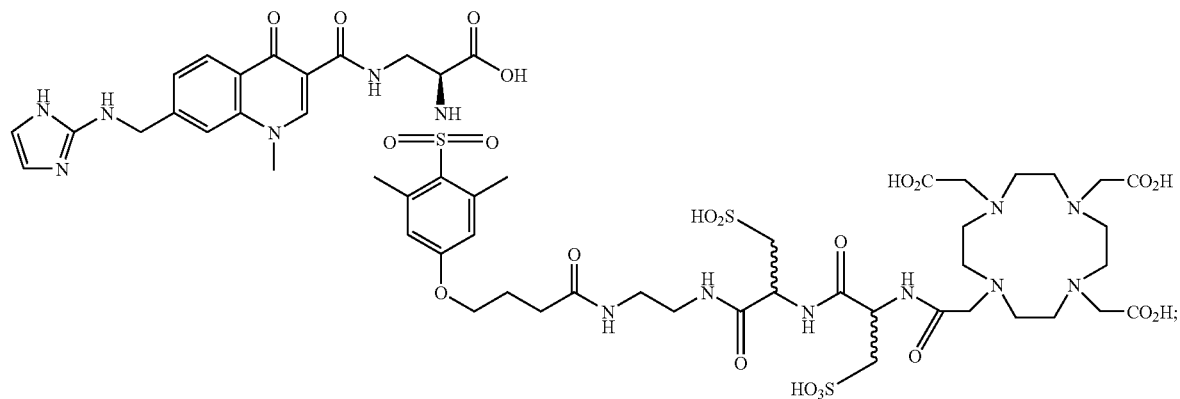
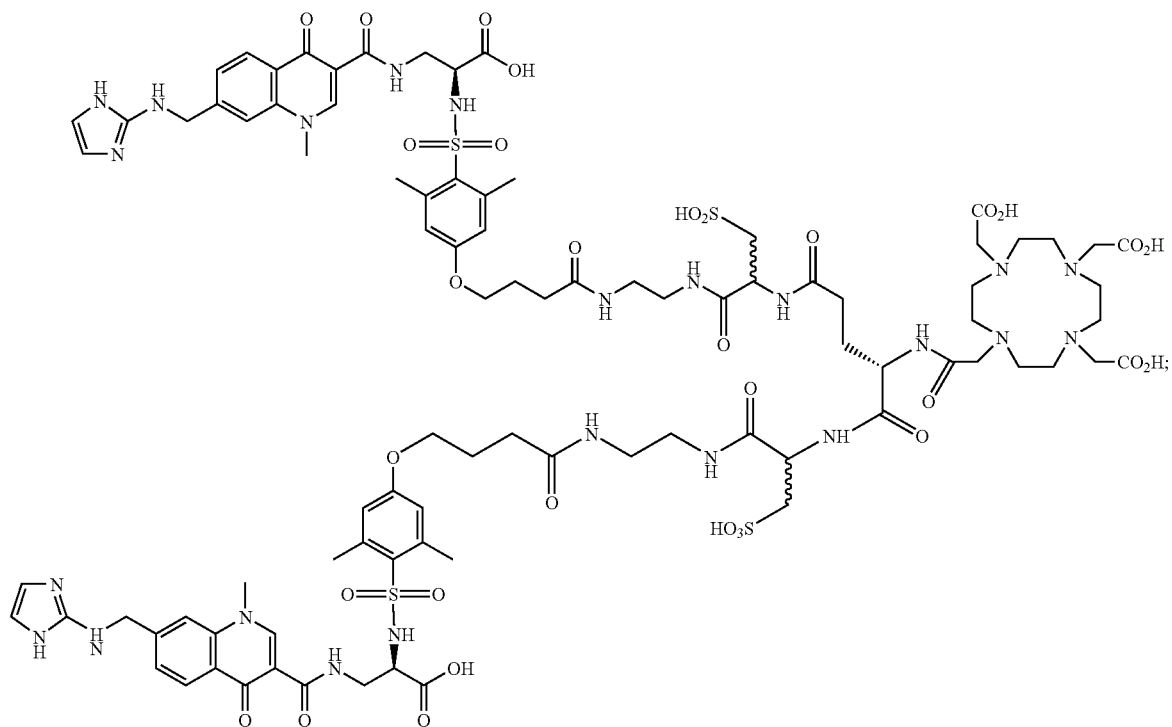
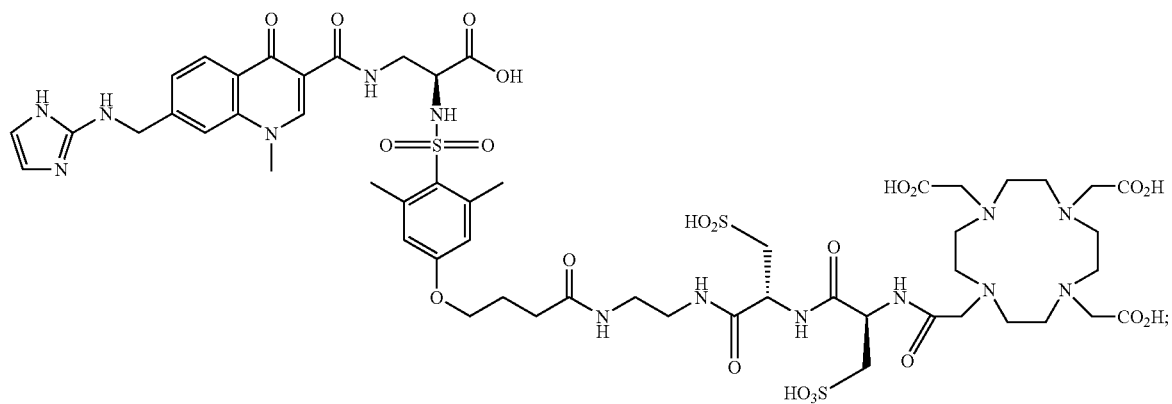

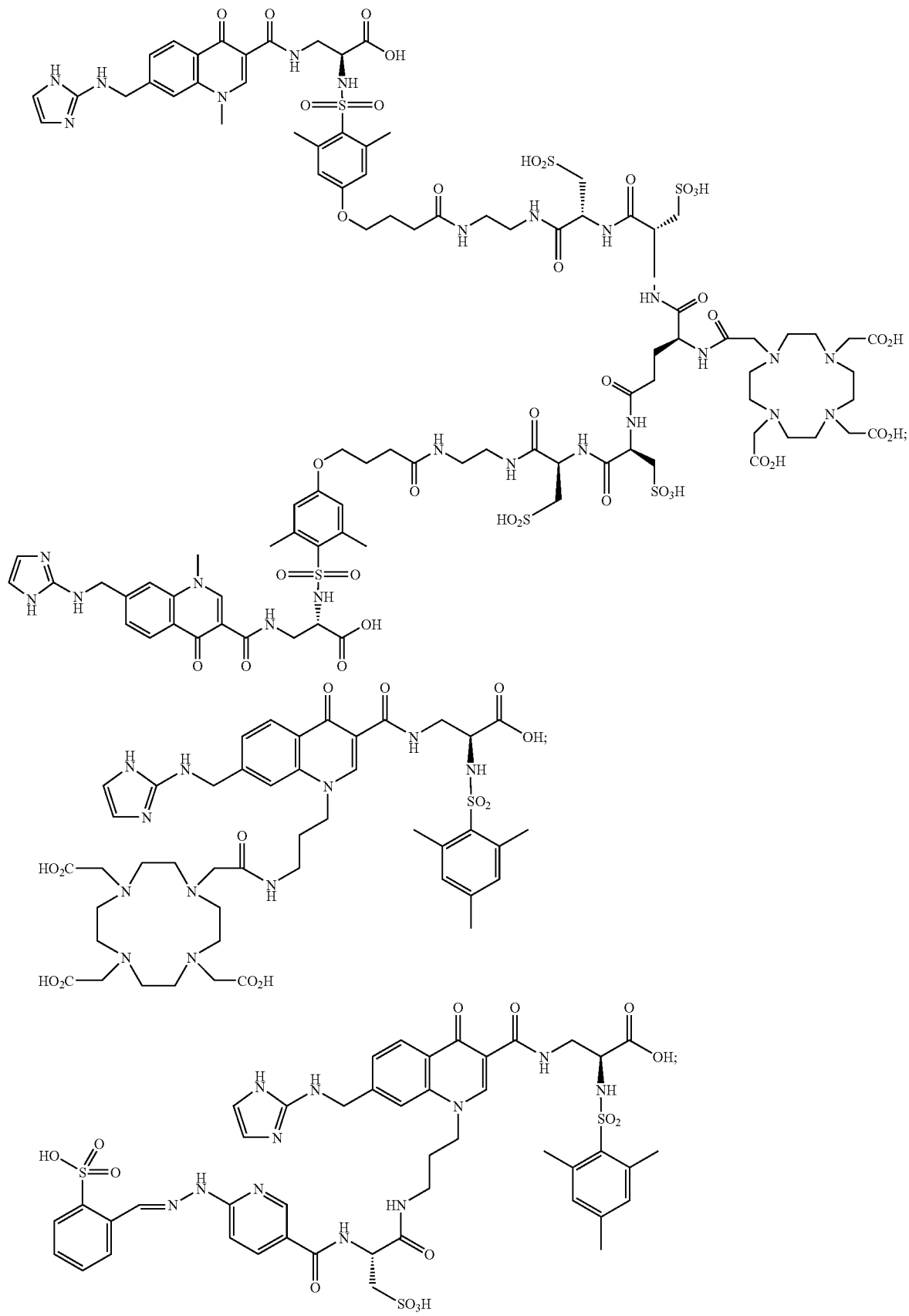

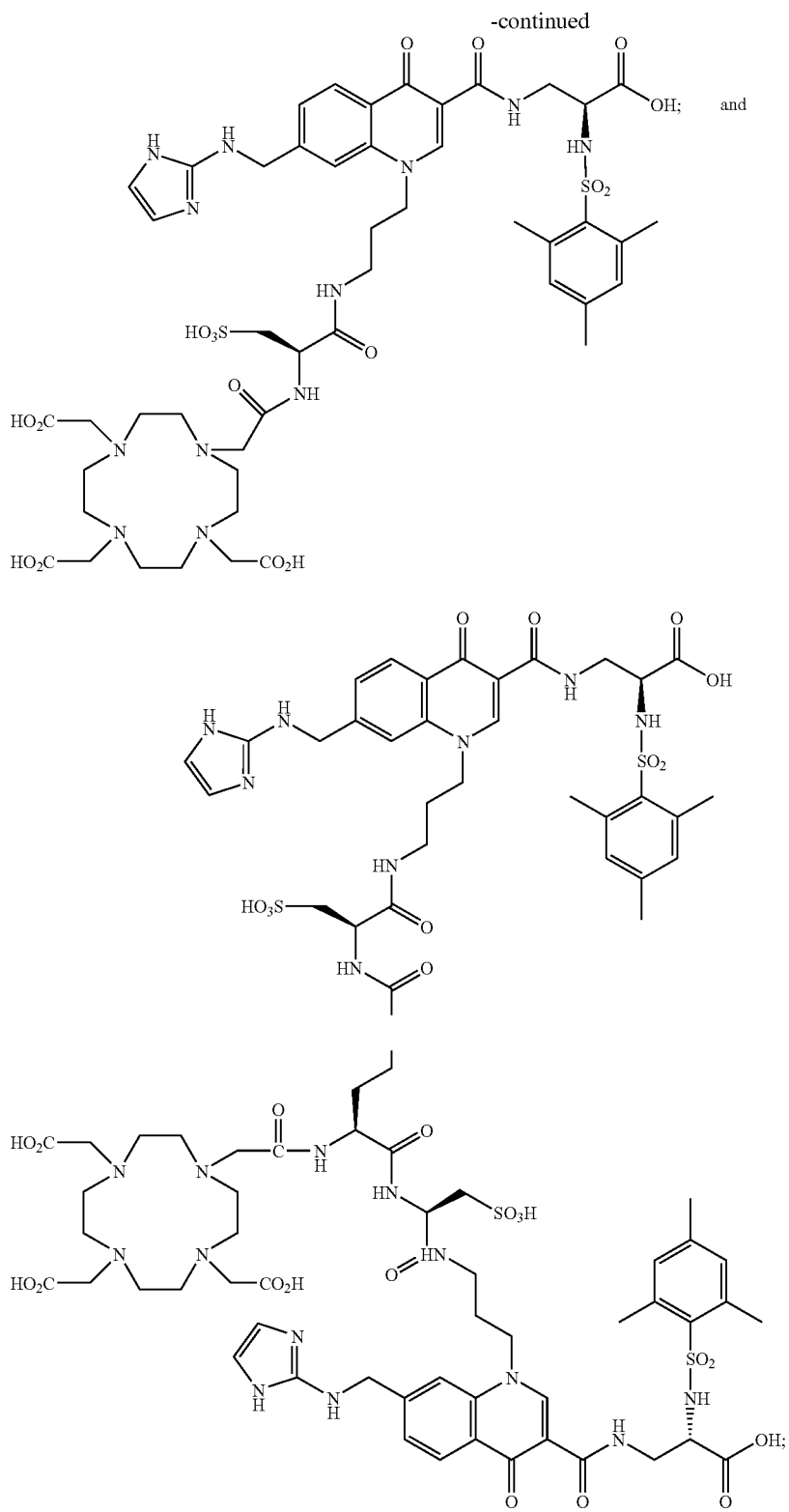

or a pharmaceutically acceptable salt form thereof.

[7] In a further preferred embodiment, the present invention provides a kit comprising a compound of Embodiment 2, or a pharmaceutically acceptable salt form thereof and a pharmaceutically acceptable carrier.

[8] In an even further preferred embodiment, the kit further comprises one or more ancillary ligands and a reducing agent.

[9] In a still further preferred embodiment, the ancillary ligands are tricine and TPPTS.

[10] In another still further preferred embodiment, the reducing agent is tin(II).

[11] In a second embodiment, the present invention provides a novel diagnostic or therapeutic metallopharmaceutical composition, comprising: a metal, a chelator capable of chelating the metal and a targeting moiety, wherein the targeting moiety is bound to the chelator, is a quinolone non-peptide and binds to a receptor that is upregulated during angiogenesis and the compound has 0–1 linking groups between the targeting moiety and chelator.

[12] In a preferred embodiment, wherein the metallopharmaceutical is a diagnostic radiopharmaceutical, the metal is a radioisotope selected from the group: $^{99m}$Tc, $^{95}$Tc, $^{111}$In, $^{62}$Cu, $^{64}$Cu, $^{67}$Ga, and $^{68}$Ga, and the linking group is present between the non-peptide targeting moiety and chelator.

[13] In another preferred embodiment, the targeting moiety is a quinolone non-peptide and the receptor is $\alpha_v\beta_3$ or $\alpha_v\beta_5$.

[14] In another preferred embodiment, the radioisotope is $^{99m}$Tc or $^{95}$Tc, the radiopharmaceutical further comprises a first ancillary ligand and a second ancillary ligand capable of stabilizing the radiopharmaceutical.

[15] In another preferred embodiment, the radioisotope is $^{99m}$Tc.

[16] In another preferred embodiment, the radiopharmaceutical is selected from the group:

$^{99m}$Tc(2-(((4-(4-(((3-(2-(2-(3-(((6-(diazenido)(3-pyridyl))carbonylamino)propoxy)ethoxy)ethoxy)propyl)amino)sulfonyl)phenyl)phenyl)sulfonyl)amino)-3-((7-((imidazol-2-ylamino)methyl)-1-methyl-4-oxo(3-hydroquinolyl))carbonylamino)propanoic acid)(tricine) (TPPTS);

$^{99m}$Tc(2-(((4-(3-(N-(3-(2-(2-(3-(((6-(diazenido)(3-pyridyl))carbonylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic acid)(tricine) (TPPDS);

$^{99m}$Tc(3-((1-(3-((6-(diazenido)(3-pyridyl))carbonylamino)propyl)-7-((imidazole-2-ylamino)methyl)-4-oxo(3-hydroquinolyl))carbonylamino)-2-(((2,4,6-trimethylphenyl)sulfonyl)amino)propanoic acid)(tricine)(TPPTS);

$^{99m}$Tc(3-((1-(3-((6-(diazenido)(3-pyridyl))carbonylamino)propyl)-7-(((1-hydroxyimidazole-2-yl)amino)methyl)-4-oxo(3-hydroquinolyl))carbonylamino)-2-(((2,4,6-trimethylphenyl)sulfonyl)amino)propanoic acid)(tricine) (TPPTS);

$^{99m}$Tc(3-((1-(3-(3-(N-(3-(2-(2-(3-((6-(diazenido)(3-pyridyl))carbonylamino)propoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic acid)(tricine)(TPPTS);

$^{99m}$Tc(2-(2-(5-(N-(1,3-bis (3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy)ethoxy)ethoxy)propyl)carbamoyl)(2-pyridyl)diazenido))(tricine)(TPPTS);

$^{99m}$Tc(3-{[1-(3-{2-[(6-(diazenido)(3-pyridyl))carbonylamino](2R)-3-sulfopropyl}propyl)-7-[(imidazol-2-ylamino)methyl]-4-oxo(3-hydroquinolyl)]carbonylamino}(2S)-2-{[(2,4,6 -trimethylphenyl)sulfonyl]amino}propanoic acid) (tricine)(TPPTS).

[17] In another preferred embodiment, the radioisotope is $^{111}$In.

[18] In another preferred embodiment, the radiopharmaceutical is selected from the group:

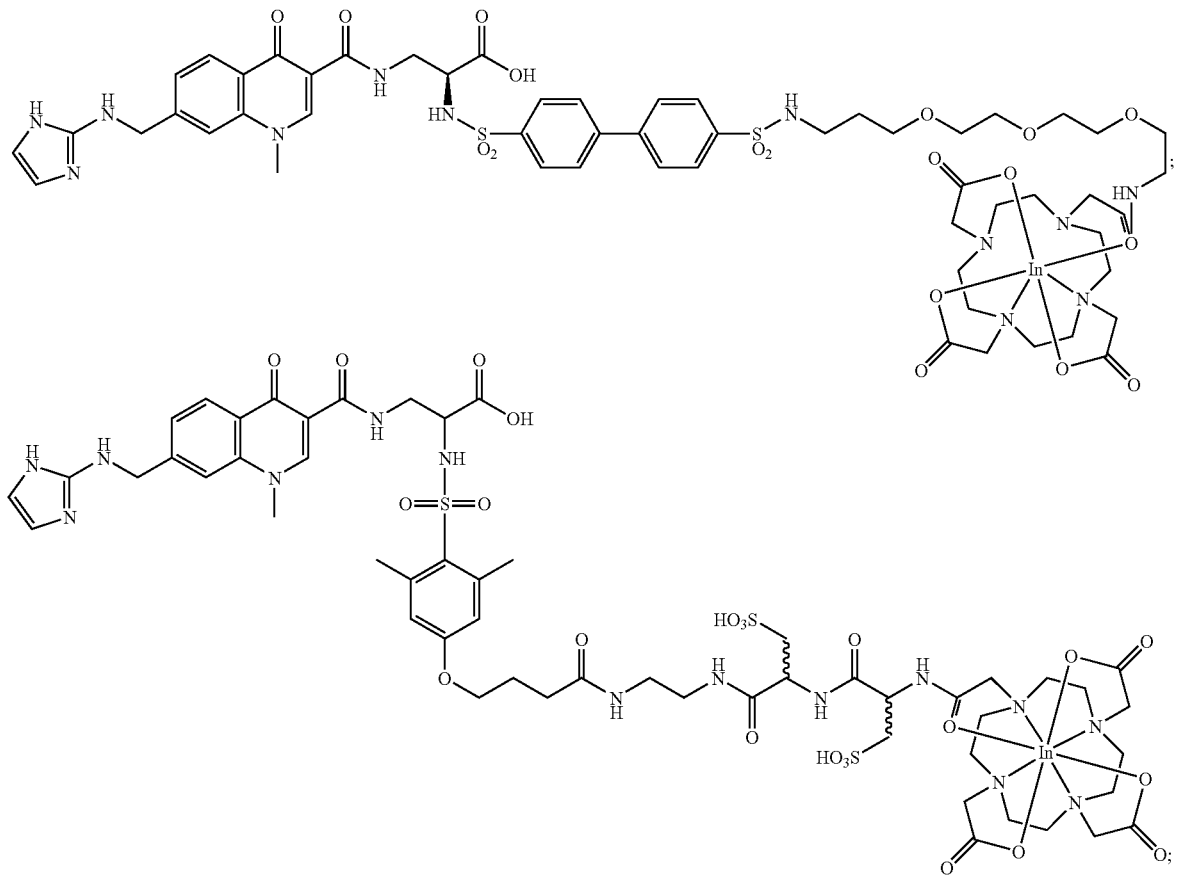

-continued
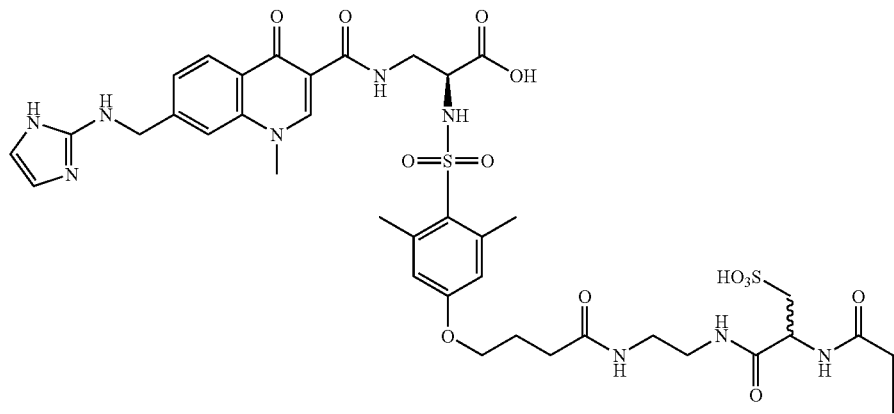
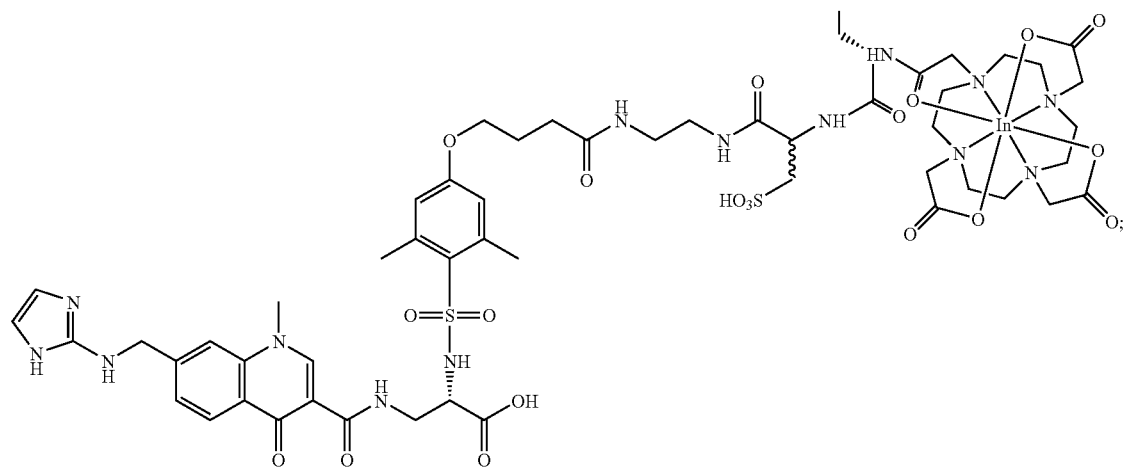
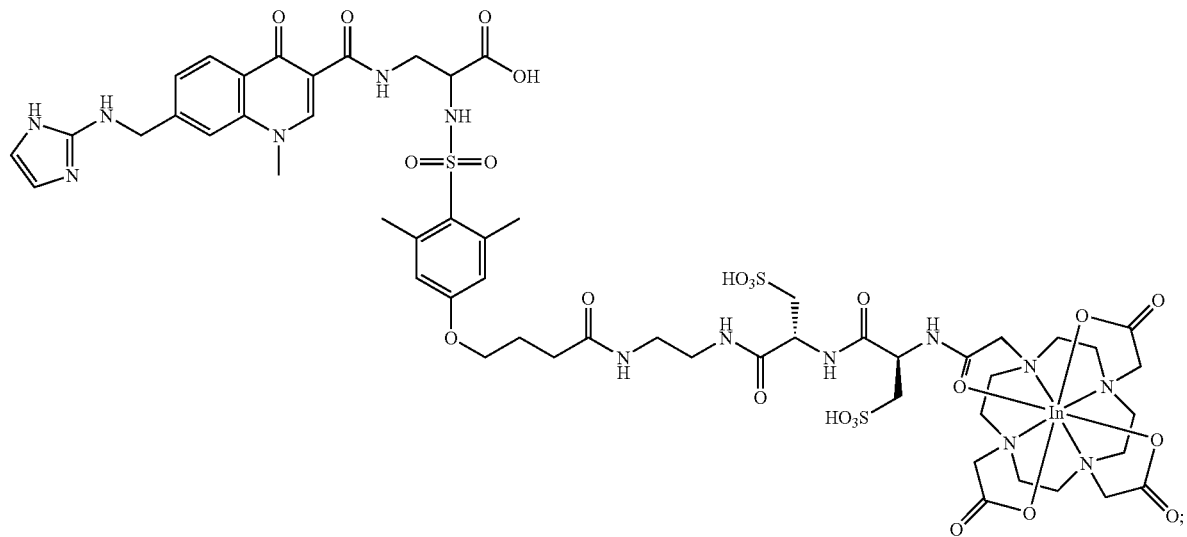

-continued
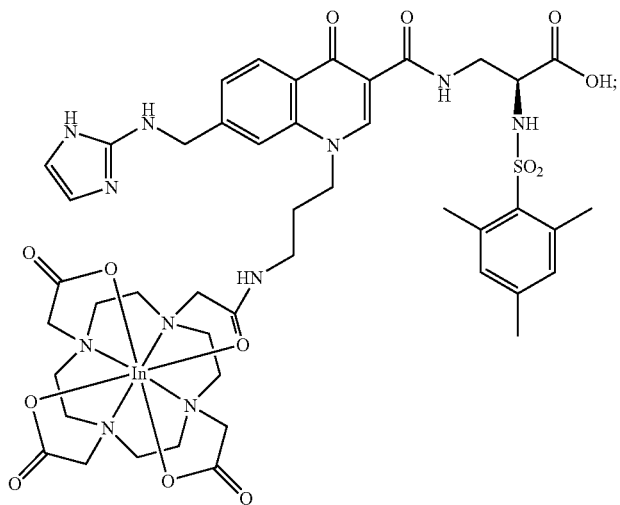
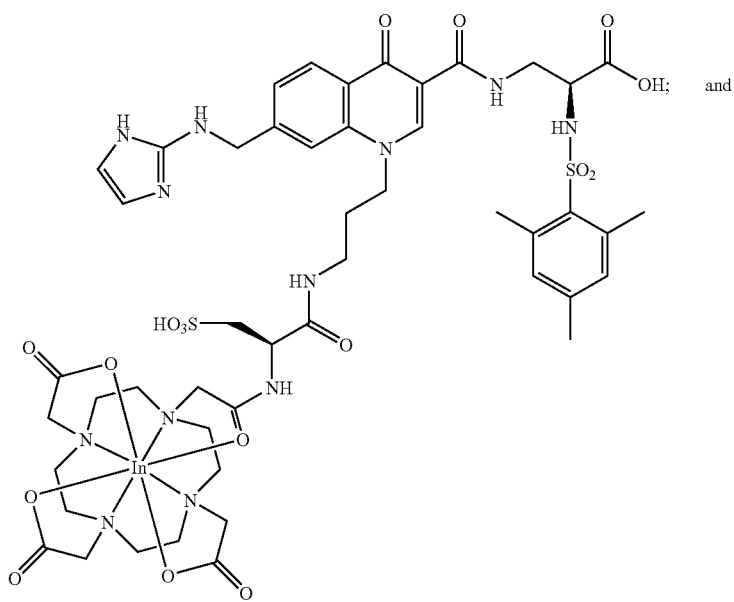
and
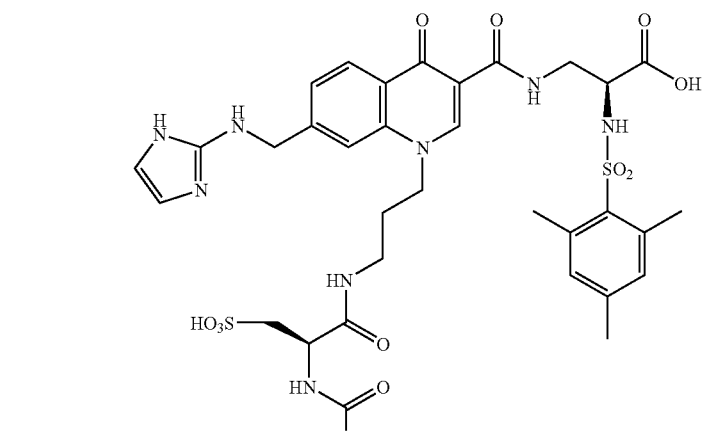

-continued

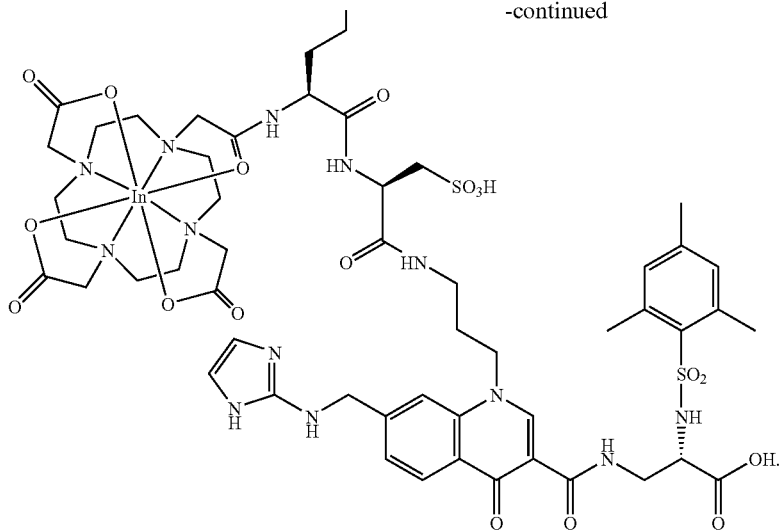

[19] In another preferred embodiment wherein the metallopharmaceutical is a therapeutic radiopharmaceutical, the metal is a radioisotope selected from the group: $^{33}$P, $^{125}$I, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, and the linking group is present between the non-peptide targeting moiety and chelator.

[20] In another preferred embodiment, the targeting moiety is a quinolone non-peptide and the receptor is $\alpha_v\beta_3$ or $\alpha_v\beta_5$.

[21] In another preferred embodiment, the radioisotope is $^{153}$Sm.

[22] In another preferred embodiment, the radioisotope is $^{177}$Lu.

[23] In another preferred embodiment, the radiopharmaceutical is selected from the group:

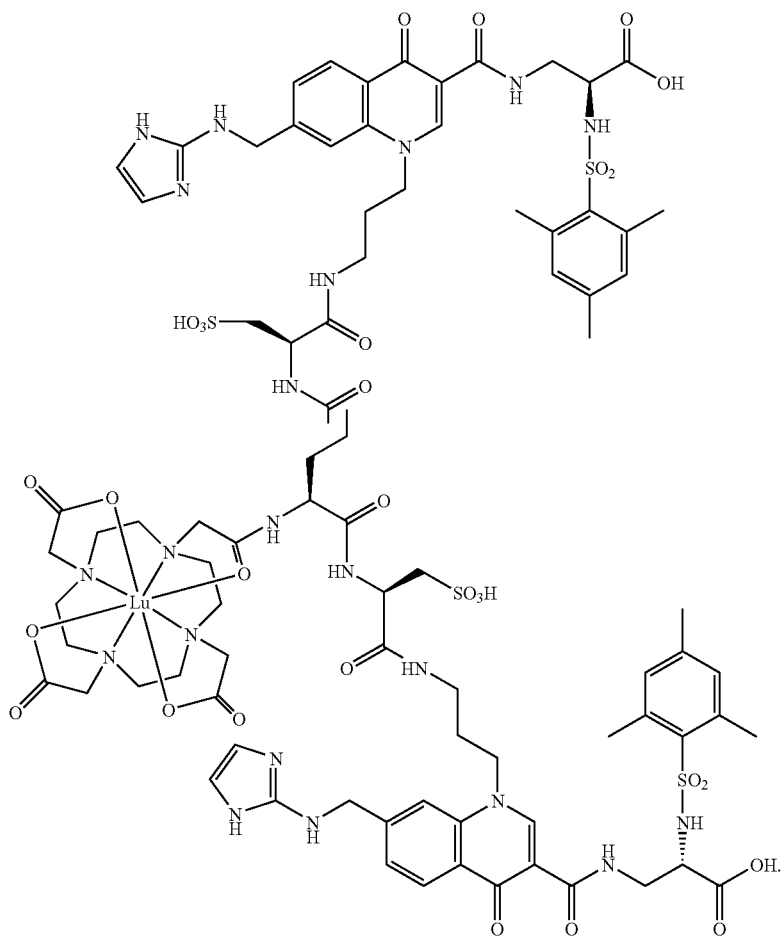

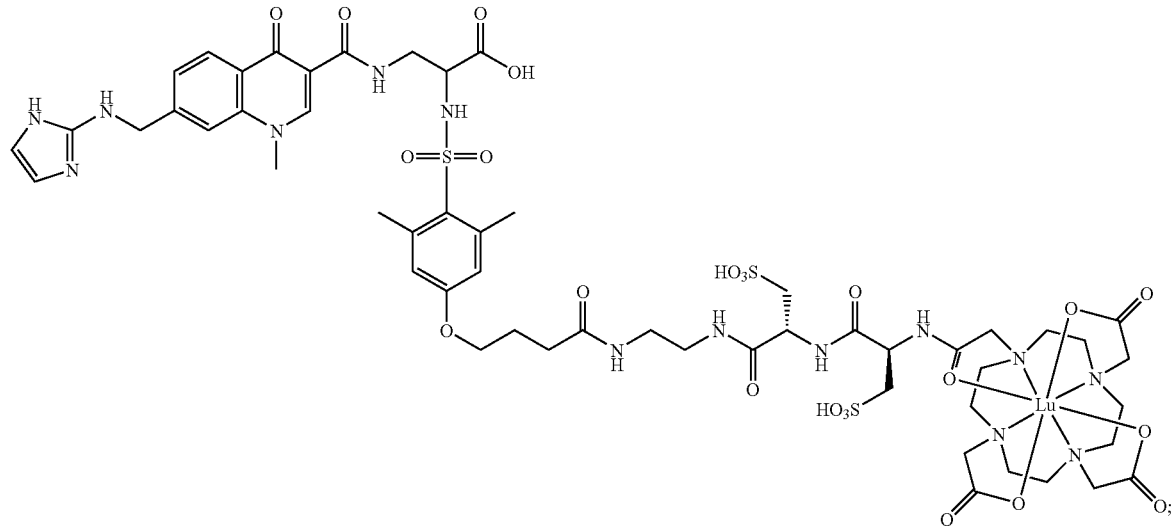
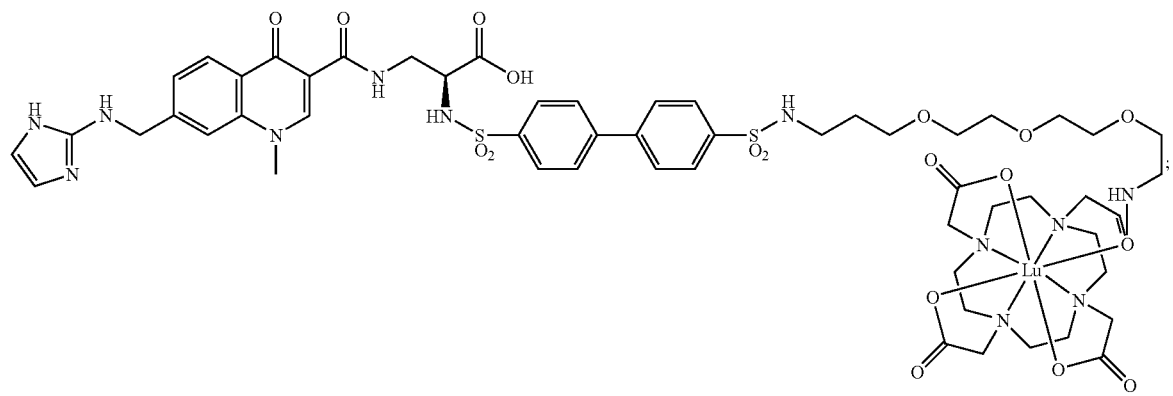
and
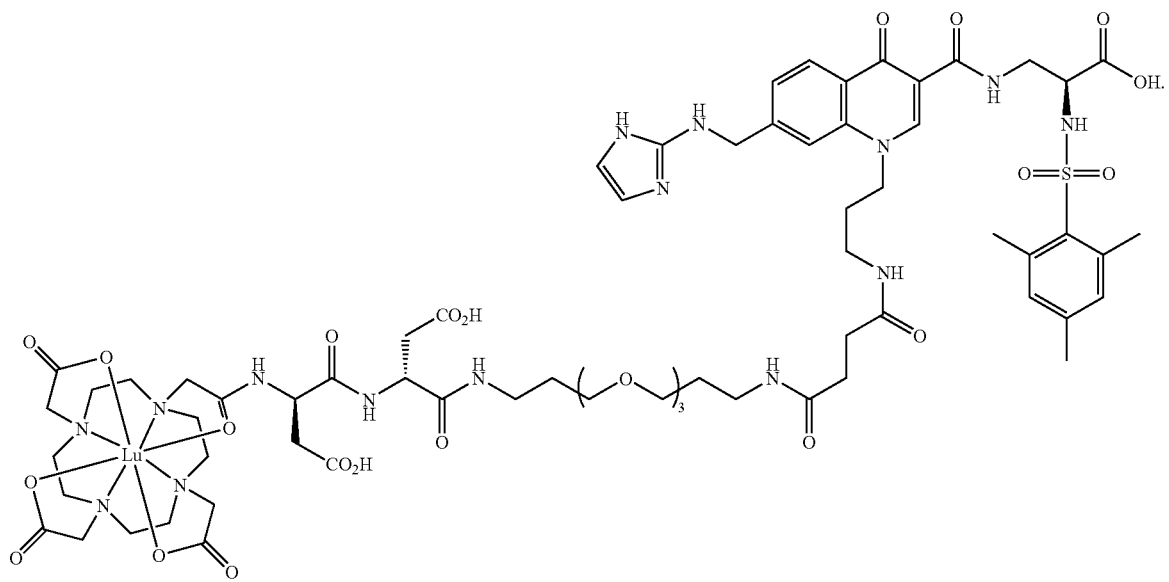

[24] In another preferred embodiment, the radiopharmaceutical is $^{90}Y$.
[25] In another preferred embodiment, the radiopharmaceutical is selected from the group;
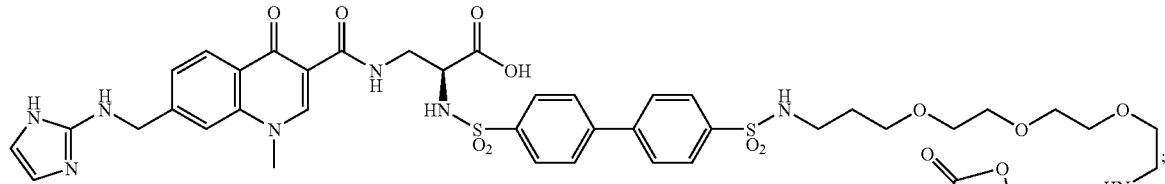
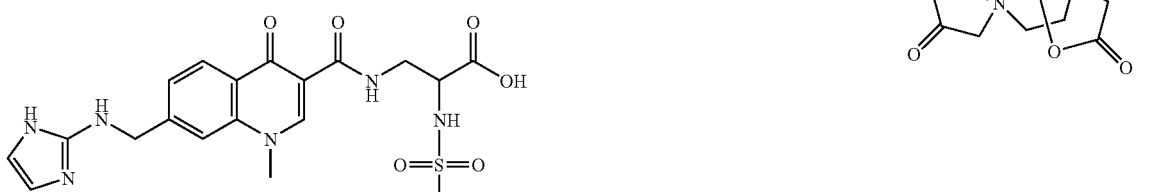
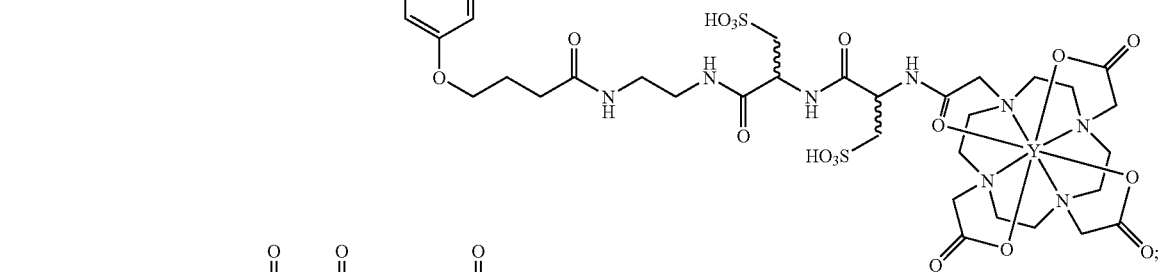
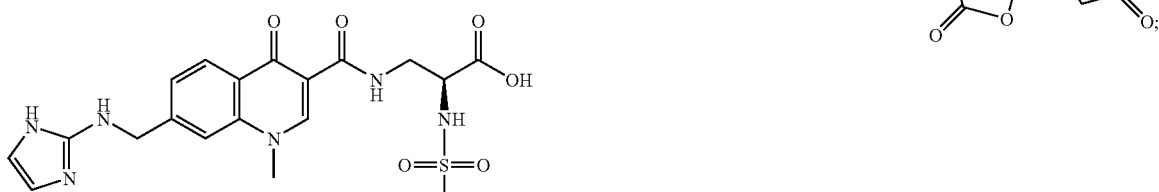
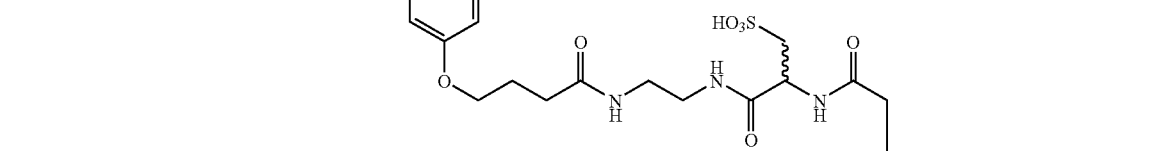
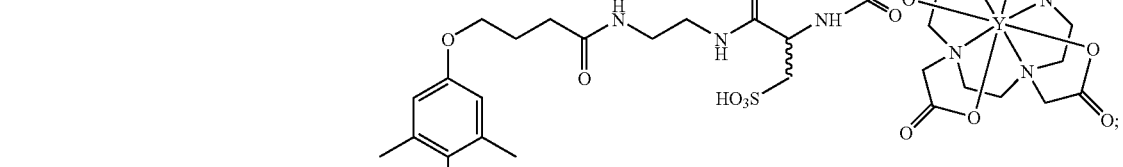
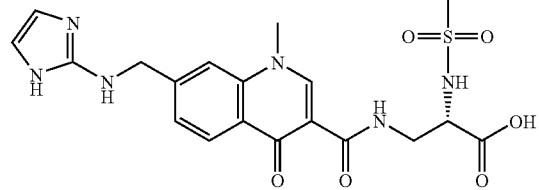

-continued
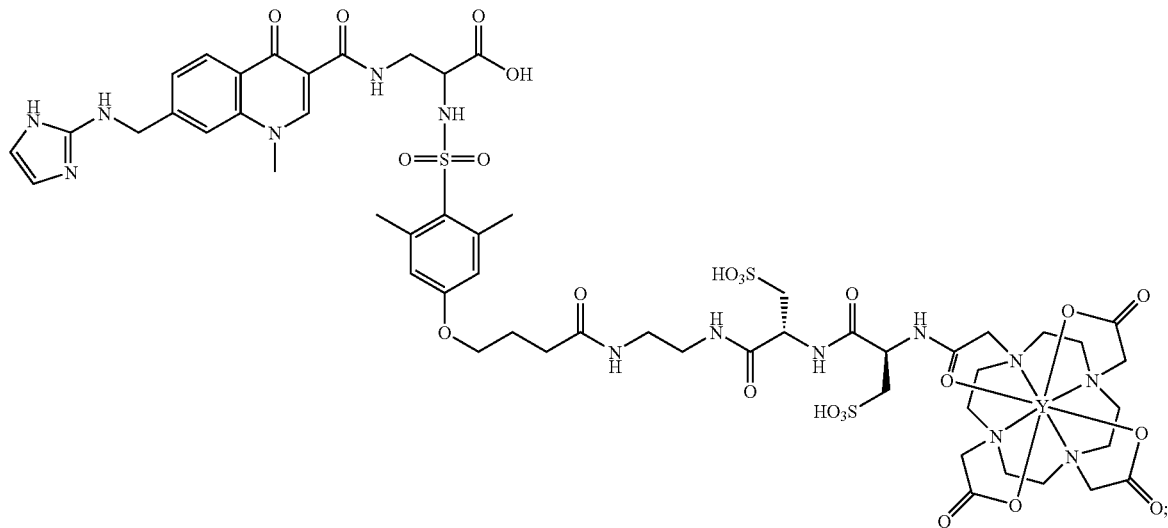
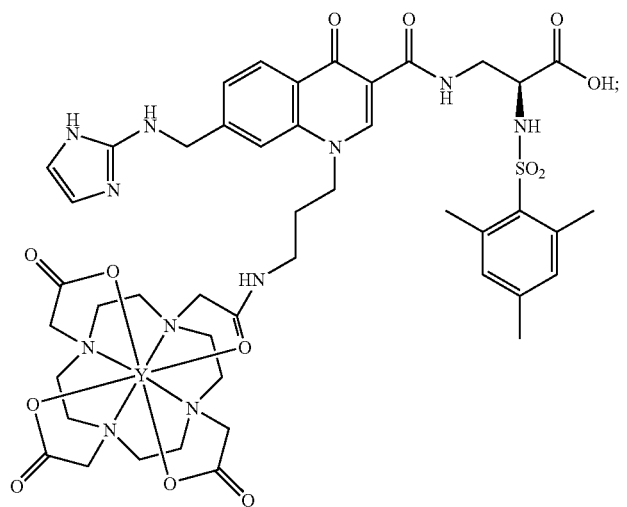
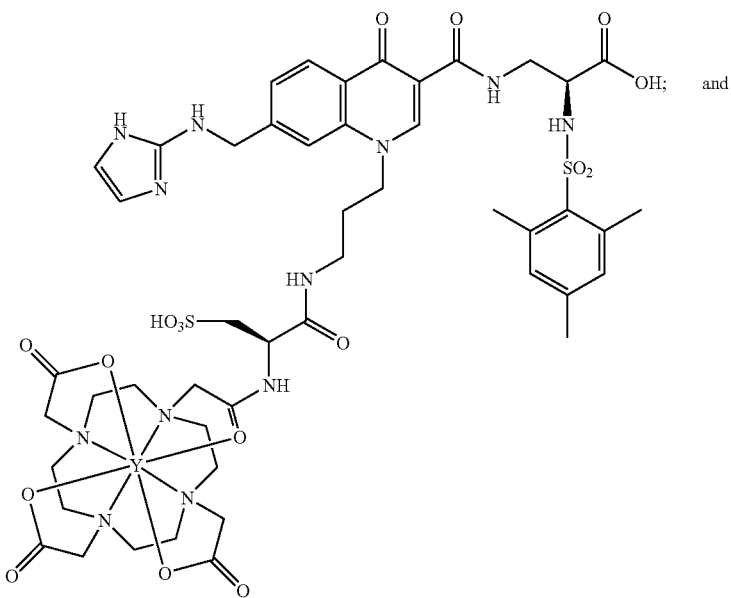

-continued

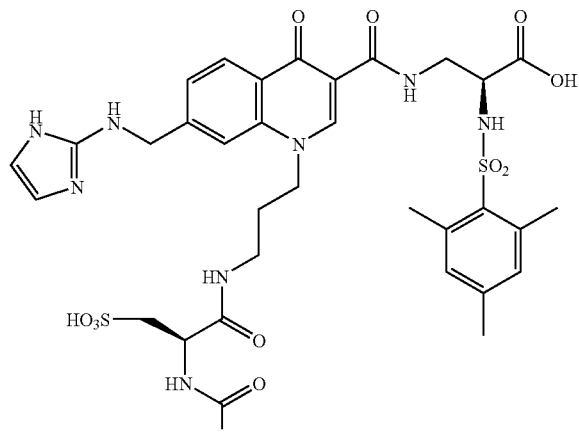

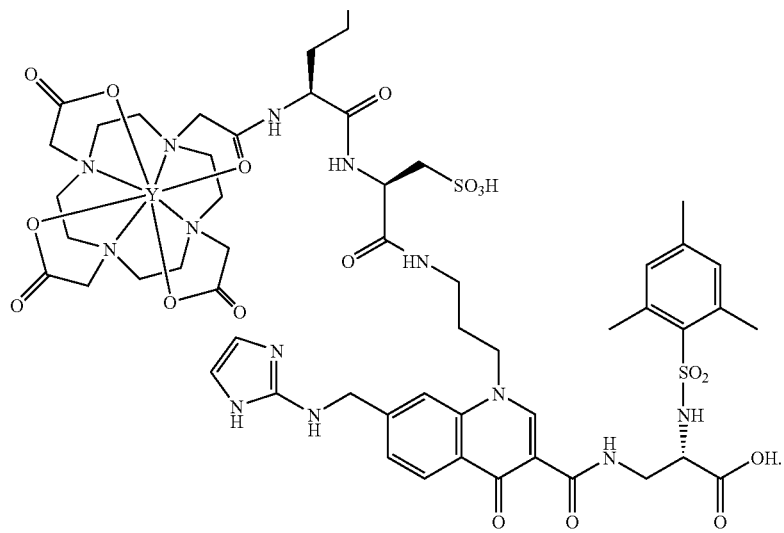

[26] In another preferred embodiment wherein the metallopharmaceutical is a MRI contrast agent, the metal is a paramagnetic metal ion selected from the group: Gd(III), Dy(III), Fe(III), and Mn(II), the targeting moiety is a quinolone nonpeptide and the linking group is present between the targeting moiety and chelator.

[27] In another preferred embodiment, the targeting moiety is quinolone non-peptide and the receptor is $\alpha_v\beta_3$ or $\alpha_v\beta_5$.

[28] In another preferred embodiment, the metal ion is Gd(III).

[29] In another preferred embodiment, the contrast agent is

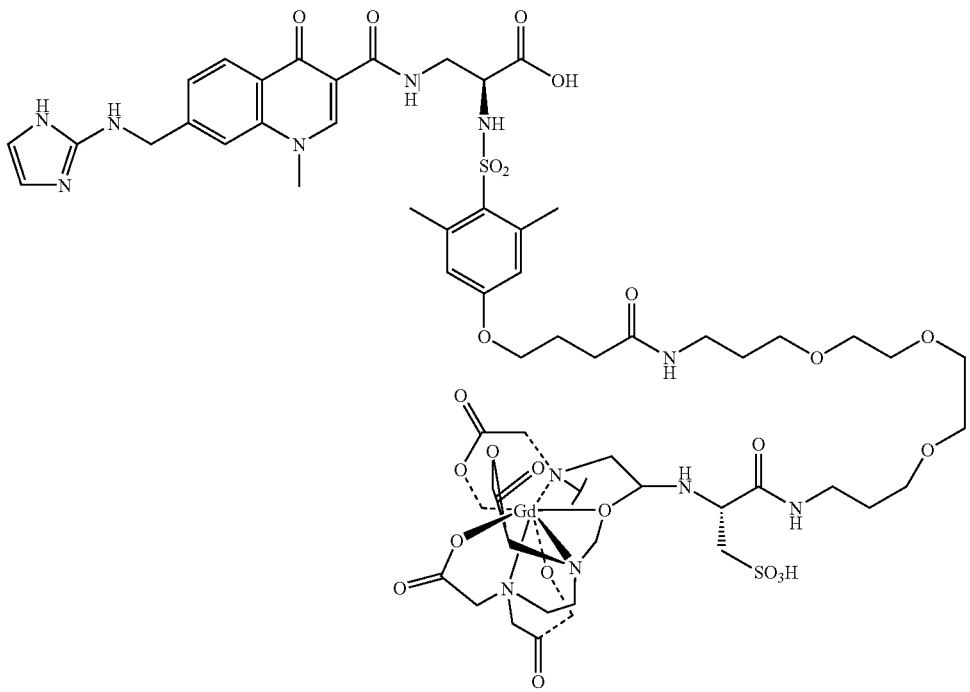

[30] In another preferred embodiment wherein the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, the targeting moiety is a quinolone non-peptide, the receptor is $\alpha_v\beta_3$ or $\alpha_v\beta_5$, and the linking group is present between the targeting moiety and chelator.

[31] In another preferred embodiment, the present invention provides a novel method of treating rheumatoid arthritis in a patient comprising: administering a therapeutic radiopharmaceutical of Embodiment 19 capable of localizing in new angiogenic vasculature to a patient by injection or infusion.

[32] In another preferred embodiment, the present invention provides a novel method of treating cancer in a patient comprising: administering to a patient in need thereof a therapeutic radiopharmaceutical of Embodiment 19 by injection or infusion.

[33] In another preferred embodiment, the present invention provides a novel method of imaging therapeutic angiogenesis in a patient comprising: (1) administering a diagnostic radiopharmaceutical, a MRI contrast agent, or a X-ray contrast agent of Embodiment 11 to a patient by injection or infusion; (2) imaging the area of the patient wherein the desired formation of new blood vessels is located.

[34] In another preferred embodiment, the present invention provides a novel method of imaging cancer in a patient comprising: (1) administering a diagnostic radiopharmaceutical of Embodiment 12 to a patient by injection or infusion; (2) imaging the patient using planar or SPECT gamma scintigraphy, or positron emission tomography.

[35] In another preferred embodiment, the present invention provides a novel method of imaging cancer in a patient comprising: (1) administering a MRI contrast agent of Embodiment 26; and (2) imaging the patient using magnetic resonance imaging.

[36] In another preferred embodiment, the present invention provides a novel method of imaging cancer in a patient comprising: (1) administering a X-ray contrast agent of Embodiment 30; and (2) imaging the patient using X-ray computed tomography.

[37] In a third embodiment, the present invention provides a novel compound, comprising: a targeting moiety and a surfactant, wherein the targeting moiety is bound to the surfactant, is a nonpeptide, and binds to a receptor that is upregulated during angiogenesis and the compound has 0–1 linking groups between the targeting moiety and surfactant.

[38] In a preferred embodiment, the targeting moiety comprises a quinolone non-peptide and the linking group is present between the targeting moiety and surfactant.

[39] In another preferred embodiment, the receptor is the integrin $\alpha_v\beta_3$ or $\alpha_v\beta_5$ and the compound is of the formula:

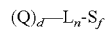

wherein, Q is a compound of Formula (II):

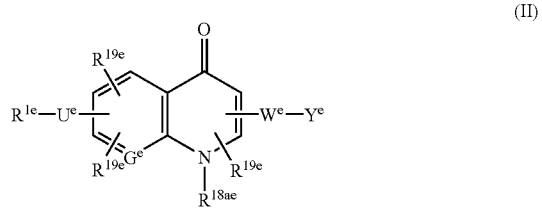

including stereoisomeric forms thereof, or mixtures of stereoisomeric forms thereof, or pharmaceutically acceptable salt or prodrug forms thereof wherein:

$R^{1e}$ is selected from:

[chemical structures]

$A^e$ is —$CH_2$— or —$N(R^{10e})$—;
$A^{1e}$ and $B^e$ are independently —$CH_2$— or —$N(R^{10e})$—;
$D^e$ is —$N(R^{10e})$— or —$S$—;
$E^e$—$F^e$ is —$C(R^{2e})$=$C(R^{3e})$— or —$C(R^{2e})_2C(R^{3e})_2$—;
$J^e$ is —$C(R^{2e})$— or —$N$—;
$K^e$, $L^e$ and $M^e$ are independently —$C(R^{2e})$— or —$C(R^{3e})$—;
$R^{2e}$ and $R^{3e}$ are independently selected from:
H, $C_1$–$C_4$ alkoxy, $NR^{11e}R^{12e}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^{7e}$, alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2ae}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^{7e}$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
—$(CH_2)_n{}^e$—, —$(CH_2)_n{}^eO(CH_2)_m{}^e$—, —$(CH_2)_n{}^eN(R^{12})(CH_2)_m{}^e$—, —$NH(CH_2)_n{}^e$—, —$(CH_2)_n{}^eC$(=O)$(CH_2)_m{}^e$—, —$(CH_2)_n{}^eS(O)_p{}^e(CH_2)_m{}^e$—, —$(CH_2)_n{}^e$NHNH$(CH_2)_m{}^e$—, —$N(R^{10e})C$(=O)—, —NHC(=O)$(CH_2)_n{}^e$—, —C(=O)N($R^{10e}$)—, and —N($R^{10e}$)S(O)$_p{}^e$—;

$G^e$ is N or $CR^{19e}$;
$W^e$ is —C(=O)—N($R^{10e}$)—($C_1$–$C_3$ alkylene)-, in which the alkylene group is substituted by $R^{8e}$ and by $R^{9e}$;
$R^{8e}$ and $R^{9e}$ are independently selected from:
H, $CO_2R^{18be}$, C(=O)$R^{18be}$, $CONR^{17e}R^{18be}$,
$C_1$–$C_{10}$ alkyl substituted with 0–1 $R^{6e}$,
$C_2$–$C_{10}$ alkenyl substituted with 0–1 $R^{6e}$,
$C_2$–$C_{10}$ alkynyl substituted with 0–1 $R^{6e}$,
$C_3$–$C_8$ cycloalkyl substituted with 0–1 $R^{6e}$,
$C_5$–$C_6$ cycloalkenyl substituted with 0–1 $R^{6e}$,
($C_1$–$C_{10}$ alkyl) carbonyl,
$C_3$–$C_{10}$ cycloalkyl($C_1$–$C_4$ alkyl)-,
phenyl substituted with 0–3 $R^{6e}$,
naphthyl substituted with 0–3 $R^{6e}$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$,
$C_1$–$C_{10}$ alkoxy substituted with 0–2 $R^{7e}$,
hydroxy, nitro, —N($R^{10e}$)$R^{11e}$, —N($R^{16e}$)$R^{17e}$, aryl ($C_0$–$C_6$ alkyl)carbonyl, aryl($C_3$–$C_6$ alkyl), heteroaryl ($C_1$–$C_6$ alkyl), $CONR^{18ae}R^{20e}$, $SO_2R^{18ae}$, and $SO_2NR^{18ae}R^{20e}$, providing that any of the above alkyl, cycloalkyl, aryl or heteroaryl groups may be unsubstituted or substituted independently with 1–2 $R^{7e}$;

$R^{6e}$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11e}$)$R^{12e}$, cyano, halo, $CF_3$, CHO, $CO_2R^{18be}$, C(=O)$R^{18be}$, $CONR^{17e}R^{18be}$, OC(=O)$R^{10e}$, $OR^{10e}$, OC(=O)$NR^{10e}R^{11e}$, $NR^{10e}$C(=O)$R^{10e}$, $NR^{10e}$C(=O)$OR^{21e}$, $NR^{10e}$C(=O)$NR^{10e}R^{11e}$, $NR^{10e}SO_2NR^{10e}R^{11e}$, $NR^{10e}SO_2R^{21e}$, S(O)$_pR^{11e}$, $SO_2NR^{10e}R^{11e}$,
aryl substituted with 0–3 groups selected from halogen, $C_1$–$C_6$ alkoxy, $C_1$–$C_6$ alkyl, $CF_3$, S(O)$_m{}^e$Me, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, S(O)$_p{}^e$Me, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:
H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:
H, $C_1$–$C_6$ alkyl, $C_3$–$C_7$ cycloalkyl, $C_3$–$C_7$ cycloalkyl ($C_1$–$C_4$ alkyl)-, ($C_1$–$C_{10}$ alkyl)carbonyl, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, alternatively, when $R^{10e}$ and $R^{11e}$ are both substituents on the same nitrogen atom (as in —$NR^{10e}R^{11e}$) they may be taken together with the nitrogen atom to which they are attached to form a heterocycle selected from:
3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12e}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
—C(=O)O$R^{18ae}$, —C(=O)$R^{18be}$, —C(=O)N($R^{18be}$)$_2$, —C(=O)NHSO$_2$$R^{8ae}$, —C(=O)NHC(=O)$R^{18be}$, —C(=O)NHC(=O)O$R^{18ae}$, —C(=O)NHSO$_2$NH$R^{18be}$, —SO$_2$$R^{18ae}$, —SO$_2$N($R^{18be}$)$_2$, and —SO$_2$NHC(=O)O$R^{18be}$;

$R^{17e}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:
$C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
H, halogen, $CF_3$, $CO_2H$, CN, $NO_2$, —$NR^{11e}R^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_0$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl) oxy,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and ($R^{10e}$)($R^{11e}$)N—($C_1$–$C_{10}$ alkoxy)-;

$R^{21e}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$-$C_{10}$ alkyl substituted with 0–2 $R^{7e}$;

$R^{22e}$ is selected from:
—C(=O)—$R^{18be}$, —C(=O)N($R^{18be}$)$_2$, —C(=O) NHSO$_2$$R^{18ae}$, —C(=O)NHC(=O)$R^{18be}$, —C(=O) NHC(=O)O$R^{18ae}$, and —C(=O)NHSO$_2$NH$R^{18be}$;

$Y^e$ is selected from:
—COR$^{20e}$, —SO$_3$H, —PO$_3$H, —CONHNHSO$_2$CF$_3$, —CONHSO$_2$$R^{18ae}$,
—CONHSO$_2$NH$R^{18be}$, —NHCOCF$_3$, —NHCONHSO$_2$$R^{18ae}$,
—NHSO$_2$$R^{18ae}$, —OPO$_3$H$_2$, —OSO$_3$H, —PO$_3$H$_2$, —SO$_2$NHCOR$^{18ae}$,
—SO$_2$NHCO$_2$$R^{18ae}$,

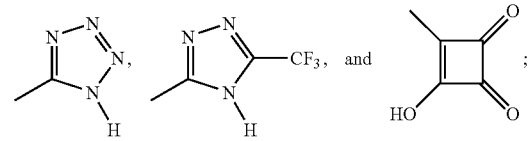

$m^e$ is 0–2;
$n^e$ is 0–4;
$p^e$ is 0–2;
$r^e$ is 0–2;
with the following proviso: $n^e$ and $m^e$ are chosen such that the number of atoms connecting $R^{1e}$ and $Y^e$ is in the range of 8–14;
d is selected from 1, 2, 3, 4, 5, 6, 7, 8, 9, and 10;
$L_n$ is a linking group having the formula:

$((W)_h—(CR^6R^7)_g)_x—(Z)_k—((CR^{6a}R^{7a})_{g'}—(W)_{h'})_{x'}$;

W is independently selected at each occurrence from the group: O, S, NH, NHC(=O), C(=O)NH, $NR^8$C(=O), C(=O)N $R^8$, C(=O), C(=O)O, OC(=O), NHC(=S) NH, NHC(=O)NH, SO$_2$, SO$_2$NH, (OCH$_2$CH$_2$)$_{20-200}$, (CH$_2$CH$_2$O)$_{20-200}$, (OCH$_2$CH$_2$CH$_2$)$_{20-200}$, (CH$_2$CH$_2$CH$_2$O)$_{20-200}$, and (aa)$_r$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NHR$^{11}$, NHC(=O)NHR$^{11}$, NHR$^{11}$, $R^{11}$, and a bond to $S_f$;

$R^{10}$ is independently selected at each occurrence from the group: a bond to $S_f$, COOR$^{11}$, C(=O)NHR$^{11}$, NHC(=O)R$^{11}$, OH, NHR$^{11}$, $SO_3H$, $PO_3H$, —OPO$_3H_2$, —OSO$_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

$$E^1—A^{10};$$
$$\diagup$$
$$A^9$$

$A^9$ is selected from the group: OH and OR$^{27}$;

$A^{10}$ is OR$^{27}$;

$R^{27}$ is C(=O)$C_{1-20}$ alkyl;

$E^1$ is $C_{1-10}$ alkylene substituted with 1–3 $R^{28}$;

$R^{28}$ is independently selected at each occurrence from the group: $R^{30}$, —PO$_3$H—$R^{30}$, =O, —CO$_2R^{29}$, —C(=O)$R^{29}$, —C(=O)N(R$^{29}$)$_2$, —CH$_2$OR$^{29}$, —OR$^{29}$, —N(R$^{29}$)$_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

and a pharmaceutically acceptable salt thereof.

[40] In another preferred embodiment, the compound is of the formula:

$$Q—L_n—S_f$$

wherein, Q is a compound of Formula (IV):

(IV)

including stereoisomeric forms thereof, or mixtures of stereoisomeric forms thereof, or pharmaceutically acceptable salt or prodrug forms thereof wherein:

$R^{1e}$ is selected from:

$R^{2e}$ and $R^{3e}$ are independently selected from:
H, $C_1$–$C_4$ alkoxy, NR$^{11e}$R$^{12e}$, halogen, NO$_2$, CN, CF$_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^{7e}$, alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, CF$_3$ and NO$_2$;

$R^{2ae}$ is selected from:
H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^{7e}$ is selected from:
H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
—$(CH_2)_n{}^e$—, —$(CH_2)_n{}^e O(CH_2)_m{}^e$—, —$NH(CH_2)_n{}^e$—, —$N(R^{10e})C(=O)$—, —$NHC(=O)(CH_2)_n{}^e$—, and —$C(=O)N(R^{10e})$—;

$G^e$ is N or $CR^{19e}$;

$R^{8e}$ is selected from:
H, $CO_2R^{18be}$, $C(=O)R^{18be}$, $CONR^{17e}R^{18be}$,
$C_1$–$C_{10}$ alkyl substituted with 0–1 $R^{6e}$,
$C_2$–$C_{10}$ alkenyl substituted with 0–1 $R^{6e}$,
$C_2$–$C_{10}$ alkynyl substituted with 0–1 $R^{6e}$,
$C_3$–$C_8$ cycloalkyl substituted with 0–1 $R^{6e}$,
$C_5$–$C_6$ cycloalkenyl substituted with 0–1 $R^{6e}$,
($C_1$–$C_{10}$ alkyl) carbonyl,
$C_3$–$C_{10}$ cycloalkyl($C_1$–$C_4$ alkyl)-,
phenyl substituted with 0–3 $R^{6e}$,
naphthyl substituted with 0–3 $R^{6e}$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{9e}$ is selected from:
$C_1$–$C_{10}$ alkyl substituted with 0–1 $R^{6e}$,
$C_1$–$C_{10}$ alkoxy substituted with 0–2 $R^{7e}$,
H, nitro, $N(R^{11e})R^{12e}$, $OC(=O)R^{10e}$, $OR^{11e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, hydroxy, $OR^{22e}$, —$N(R^{10e})R^{11e}$, —$N(R^{16e})R^{17e}$, aryl($C_0$–$C_6$ alkyl)carbonyl, aryl($C_1$–$C_6$ alkyl), heteroaryl($C_1$–$C_6$ alkyl), $CONR^{18ae}R^{20e}$, $SO_2R^{18ae}$, and $SO_2NR^{18ae}R^{20e}$,
providing that any of the above alkyl, cycloalkyl, aryl or heteroaryl groups may be unsubstituted or substituted independently with 1–2 $R^{7e}$;

$R^{6e}$ is selected from:
H, $C_1$–$C_{10}$ alkyl, hydroxy, $C_1$–$C_{10}$ alkoxy, nitro, $C_1$–$C_{10}$ alkylcarbonyl, —$N(R^{11e})R^{12e}$, cyano, halo, $CF_3$, CHO, $CO_2R^{18be}$, $C(=O)R^{18be}$, $CONR^{17e}R^{18be}$, $OC(=O)R^{10e}$, $OR^{10e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, $S(O)_p{}^e R^{11e}$, $SO_2NR^{10e}R^{11e}$,
aryl substituted with 0–3 groups selected from halogen, $C_1$–$C_6$ alkoxy, $C_1$–$C_6$ alkyl, $CF_3$, $S(O)_m{}^e Me$, and —$NMe_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p{}^e Me$, and —$NMe_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:
H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$, $R^{12e}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
—$C(=O)OR^{18ae}$, —$C(=O)R^{18be}$, —$C(=O)N(R^{18be})_2$, —$SO_2R^{18ae}$, and —$SO_2N(R^{18be})_2$;

$R^{17e}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:
$C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
H, halogen, $CF_3$, $CO_2H$, CN, $NO_2$, —$NR^{11e}R^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-, aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10e}$)($R^{11e}$)N—($C_1$–$C_{10}$ alkoxy)-;
$R^{21e}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^{7e}$;
$R^{22e}$ is selected from:
—C(=O)—$R^{18be}$, —C(=O)N($R^{18be}$)$_2$, —C(=O)NHSO$_2R^{18ae}$,
—C(=O)NHC(=O)$R^{18be}$, —C(=O)NHC(=O)O$R^{18ae}$, and
—C(=O)NHSO$_2$NH$R^{18be}$;
$m^e$ is 0–2;
$n^e$ is 0–4; and
$p^e$ is 0–2;
with the following proviso: $n^e$ and $m^e$ are chosen such that the number of atoms connecting $R^1$ and —CO$R^{20e}$ in Formula (IV) is in the range of 8–14;
W is independently selected at each occurrence from the group: O, S, NH, NHC(=O), C(=O)NH, N$R^8$C(=O), C(=O)N $R^8$, C(=O), C(=O)O, OC(=O), NHC(=S)NH, NHC(=O)NH, SO$_2$, SO$_2$NH, (OCH$_2$CH$_2$)$_{20-200}$, (CH$_2$CH$_2$O)$_{20-200}$, (OCH$_2$CH$_2$CH$_2$)$_{20-200}$, (CH$_2$CH$_2$CH$_2$O)$_{20-200}$, and (aa)$_t$;
aa is independently at each occurrence an amino acid;
Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;
$R^6$, $R^{6a}$, $R^7$, $R^{7a}$, and $R^8$ are independently selected at each occurrence from the group: H, =O, COOH, SO$_3$H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to S$_f$;
k is 0 or 1;
S$_f$ is a surfactant which is a lipid or a compound of the formula:

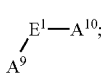

$A^9$ is O$R^{27}$;
$A^{10}$ is O$R^{27}$;
$R^{27}$ is C(=O)$C_{1-5}$ alkyl;
$E^1$ is $C_{1-4}$ alkylene substituted with 1–3 $R^{28}$;
$R^{28}$ is independently selected at each occurrence from the group: $R^{30}$, —PO$_3$H—$R^{30}$, =O, —CO$_2R^{29}$, —C(=O)$R^{29}$, —CH$_2$O$R^{29}$, —O$R^{29}$, and $C_1$–$C_5$ alkyl;
$R^{29}$ is independently selected at each occurrence from the group: $R^{30}$, H, $C_1$–$C_6$ alkyl, phenyl, and benzyl;
$R^{30}$ is a bond to $L_n$;
and a pharmaceutically acceptable salt thereof.

[41] In another more preferred embodiment, the present invention provides a novel ultrasound contrast agent composition, comprising:

(a) a compound of Embodiment 39, comprising: an quinolone that binds to the integrin $\alpha_v\beta_3$, a surfactant and a linking group between the quinolone and the surfactant;
(b) a parenterally acceptable carrier; and,
(c) an echogenic gas.

[42] In another more preferred embodiment, the present invention provides a novel ultrasound contrast agent composition, further comprising: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

[43] In another more preferred embodiment, the echogenic gas is a $C_{2-5}$ perfluorocarbon.

[44] In another preferred embodiment, the present invention provides a method of imaging cancer in a patient comprising: (1) administering, by injection or infusion, a ultrasound contrast agent composition of Embodiment 41 to a patient; and (2) imaging the patient using sonography.

[45] In another preferred embodiment, the present invention provides a method of imaging formation of new blood vessels in a patient comprising: (1) administering, by injection or infusion, a ultrasound contrast agent composition of of Embodiment 41 to a patient; (2) imaging the area of the patient wherein the desired formation of new blood vessels is located.

[46] In another preferred embodiment, the present invention provides a method of imaging therapeutic angiogenesis in a patient comprising: (1) administering, by injection or infusion, an ultrasound contrast agent composition of Embodiment 41 to a patient; (2) imaging the area of the patient wherein the desired formation of new blood vessels is located.

[47] In another preferred embodiment, the present invention provides a method of imaging atherosclerosis in a patient comprising: (1) administering, by injection or infusion, an ultrasound contrast agent composition of Embodiment 41 to a patient; (2) imaging the area of the patient wherein the atherosclerosis is located.

[48] In another preferred embodiment, the present invention provides a method of imaging restenosis in a patient comprising: (1) administering, by injection or infusion, an ultrasound contrast agent composition of Embodiment 41 to a patient; (2) imaging the area of the patient wherein the restenosis is located.

[49] In another preferred embodiment, the present invention provides a method of imaging cardiac ischemia in a patient comprising: (1) administering, by injection or infusion, an ultrasound contrast agent composition of Embodiment 41 to a patient; (2) imaging the area of the myocardium wherein the ischemic region is located.

[50] In another preferred embodiment, the present invention provides a method of imaging myocardial reperfusion injury in a patient comprising: (1) administering, by injection or infusion, an ultrasound contrast agent composition of Embodiment 41 to a patient; (2) imaging the area of myocardium wherein the reperfusion injury is located.

[51] In another preferred embodiment, the present invention provides a novel therapeutic radiopharmaceutical composition, comprising:

(a) a therapeutic radiopharmaceutical of Embodiment 19; and,
(b) a parenterally acceptable carrier.

[52] In another preferred embodiment, the present invention provides a novel diagnostic pharmaceutical composition, comprising:
(a) a diagnostic radiopharmaceutical, a MRI contrast agent, or a X-ray contrast agent of Embodiment 11; and,
(b) a parenterally acceptable carrier.

[53] In another preferred embodiment, the present invention provides a method of treating restenosis in a patient comprising: administering to a patient, either systemically or locally, a therapeutic radiopharmaceutical of Embodiment 19 capable of localizing in the restenotic area and delivering an effective dose of radiation.

[54] In another preferred embodiment, the present invention provides a method of imaging atherosclerosis in a patient comprising: (1) administering a diagnostic radiopharmaceutical, a MRI contrast agent, or a X-ray contrast agent of Embodiment 11 to a patient by injection or infusion; (2) imaging the area of the patient wherein the atherosclerosis is located.

[55] In another preferred embodiment, the present invention provides a method of imaging restenosis in a patient comprising: (1) administering a diagnostic radiopharmaceutical, a MRI contrast agent, or a X-ray contrast agent of Embodiment 11 to a patient by injection or infusion; (2) imaging the area of the patient wherein the restenosis is located.

[56] In another preferred embodiment, the present invention provides a method of imaging cardiac ischemia in a patient comprising: (1) administering a diagnostic radiopharmaceutical, a MRI contrast agent, or a X-ray contrast agent of Embodiment 11 to a patient by injection or infusion; (2) imaging the area of the myocardium wherein the ischemic region is located.

[57] In another preferred embodiment, the present invention provides a method of imaging myocardial reperfusion injury in a patient comprising: (1) administering a diagnostic radiopharmaceutical, a MRI contrast agent, or a X-ray contrast agent of Embodiment 11 to a patient by injection or infusion; (2) imaging the area of myocardium wherein the reperfusion injury is located.

[58] In another preferred embodiment, the present invention provides a kit for treating cancer, comprising a compound of Embodiment 2, or a pharmaceutically acceptable salt thereof, and at least one agent selected from the group consisting of a chemotherapeutic agent and a radiosensitizer agent, or a pharmaceutically acceptable salt thereof, and a pharmaceutically acceptable carrier.

[59] In another preferred embodiment, the present invention provides a kit according to Embodiment 58 wherein said kit comprises a plurality of separate containers, wherein at least one of said containers contains a compound of Embodiment 2, or a pharmaceutically acceptable salt thereof, and at least another of said containers contains one or more agents selected from the group consisting of a chemotherapeutic agent and a radiosensitizer agent, or a pharmaceutically acceptable salt thereof, and a pharmaceutically acceptable carrier.

[60] In another preferred embodiment, the present invention provides a kit according to Embodiment 58, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[61] In another preferred embodiment, the present invention provides a kit according to Embodiment 58, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, and lisuride.

[62] In another preferred embodiment, the present invention provides a kit according to Embodiment 58 wherein the chemotherapeutic agent is selected from the group consisting of oxymetholone, tamoxifen, progesterone, mepitiostane, epitiostanol, and formestane.

[63] In another preferred embodiment, the present invention provides a kit according to Embodiment 58 wherein the chemotherapeutic agent is selected from the group consisting of interferon-alpha, interferon-2 alpha, interferon-beta, interferon-gamma, colony stimulating factor-1, colony stimulating factor-2, denileukin diftitox, interleukin-2, and leutinizing hormone releasing factor.

[64] In another preferred embodiment, the present invention provides a kit according to Embodiment 58, wherein radiosensitizer agent is selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[65] In another preferred embodiment, the present invention provides a therapeutic metallopharmaceutical composition according to Embodiment 11, wherein the metallopharmaceutical is a therapeutic radiopharmaceutical, further comprising at least one agent selected from the group consisting of a chemotherapeutic agent and a radiosensitizer agent, or a pharmaceutically acceptable salt thereof.

[66] In another preferred embodiment, the present invention provides a therapeutic metallopharmaceutical composition according to Embodiment 65, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[67] In another preferred embodiment, the present invention provides a therapeutic metallopharmaceutical composition according to Embodiment 65, wherein radiosensitizer agent is selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[68] In another preferred embodiment, the present invention provides a method of treating cancer in a patient comprising: administering to a patient in need thereof a therapeutic radiopharmaceutical of Embodiment 19 or a pharmaceutically acceptable salt thereof, and at least one agent selected from the group consisting of a chemotherapeutic agent and a radiosensitizer agent, or a pharmaceutically acceptable salt thereof.

[69] In another preferred embodiment, the present invention provides a method of treating cancer according to Embodiment 68, wherein the administration is by injection or infusion.

[70] In another preferred embodiment, the present invention provides a method according to Embodiment 68 wherein administering the therapeutic radiopharmaceutical and agent is concurrent.

[71] In another preferred embodiment, the present invention provides a method according to Embodiment 68 wherein administering the therapeutic radiopharmaceutical and agent is sequential.

[72] In another preferred embodiment, the present invention provides a method according to Embodiment 68 wherein the cancer is selected from the group consisting of carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, and neuroblastomas.

[73] In another preferred embodiment, the present invention provides a method according to Embodiment 68 wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[74] In another preferred embodiment, the present invention provides a method according to claim 68 wherein the radiosensitizer agent is selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[75] In another preferred embodiment, the present invention provides a process for the preparation of diagnostic or therapeutic metallopharmaceutical composition, said process comprising generating a macrostructure from a plurality of molecular components wherein the plurality of components includes a targeting moiety and a chelator, wherein the targeting moiety is a quinolone nonpeptide, which is bound to the chelator, and binds to a receptor that is upregulated during angiogenesis and the compound has 0–1 linking groups between the targeting moiety and chelator.

Another aspect of the present invention are diagnostic kits for the preparation of radiopharmaceuticals useful as imaging agents for cancer. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the(kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates a method of imaging cancer in a patient involving: (1) synthesizing a diagnostic radiopharmaceutical of the present invention, using a reagent of the present invention, capable of localizing in tumors; (2) administering said radiopharmaceutical to a patient by injection or infusion; (3) imaging the patient using planar or SPECT gamma scintigraphy, or positron emission tomography.

Another aspect of the present invention contemplates a method of imaging cancer in a patient involving: (1) administering a paramagnetic metallopharmaceutical of the present invention capable of localizing in tumors to a patient by injection or infusion; and (2) imaging the patient using magnetic resonance imaging.

Another aspect of the present invention contemplates a method of imaging cancer in a patient involving: (1) administering a X-ray contrast agent of the present invention capable of localizing in tumors to a patient by injection or infusion; and (2) imaging the patient using X-ray computed tomography.

Another aspect of the present invention contemplates a method of imaging cancer in a patient involving: (1) administering a ultrasound contrast agent of the present invention capable of localizing in tumors to a patient by injection or infusion; and (2) imaging the patient using sonography.

Another aspect of the present invention contemplates a method of treating cancer in a patient involving: (1) administering a therapeutic radiopharmaceutical of the present invention capable of localizing in tumors to a patient by injection or infusion.

Another aspect of the present invention contemplates the combination of chemotherapeutics and angiogenesis-targeted therapeutic radiopharmaceuticals of the invention, which target the luminal side of the neovasculature of tumors, to provide a surprising, and enhanced degree of tumor suppression relative to each treatment modality alone without significant additive toxicity.

Another aspect of the present invention contemplates the compounds of the present invention (i.e. a compound comprising: a targeting moiety and a chelator, wherein the targeting moiety is bound to the chelator, is a quinolone nonpeptide, and binds to a receptor that is upregulated during angiogenesis and the compound has 0–1 linking groups between the targeting moiety and chelator) which is administered in combination therapy, with one or more chemotherapeutic agent(s) selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

This combination therapy may further, optionally, include a radiosensitizer agent, or a pharmaceutically acceptable salt thereof, to enhance the radiotherapeutic effect together with the chemotherapeutic agent, said radiosensitizer agent being selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol. A thorough discussion of radiosensitizer agents is provided in the following: Rowinsky-EK, Oncology-Huntingt., 1999 Oct.; 13(10 Suppl 5): 61–70; Chen.-AY et al., Oncology-Huntingt. 1999 Oct.; 13(10 Suppl 5): 39–46; Choy-H, Oncology-Huntingt. 1999 Oct.; 13(10 Suppl 5): 23–38; and Herscher-LL et al, Oncology-Huntingt. 1999 Oct.; 13(10 Suppl 5): 11–22, which are incorporated herein by reference.

It is a further aspect of the invention to provide kits having a plurality of active ingredients (with or without carrier) which, together, may be effectively utilized for carrying out the novel combination therapies of the invention.

It is another aspect of the invention to provide a novel pharmaceutical composition which is effective, in and of itself, for utilization in a beneficial combination therapy because it includes compounds of the present invention, and a chemotherapeutic agent or a radiosensitizer agent, which may be utilized in accordance with the invention.

In another aspect, the present invention provides a method for treating cancer in a patient in need of such treatment, said method including the steps of administering a therapeutically effective amount of a compound of the present invention and administering a therapeutically effective amount of at least one agent selected from the group consisting of a chemotherapeutic agent and a radiosensitizer agent.

It is to be understood that this invention covers all appropriate combinations of the particular and preferred groupings and embodiments referred to herein.

Definitions

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

The term "nonpeptide" means preferably less than three amide bonds in the backbone core of the targeting moiety or preferably less than three amino acids or amino acid mimetics in the targeting moiety.

The term "metallopharmaceutical" means a pharmaceutical comprising a metal. The metal is the cause of the imageable signal in diagnostic applications and the source of the cytotoxic radiation in radiotherapeutic applications. Radiopharmaceuticals are metallopharmaceuticals in which the metal is a radioisotope.

By "reagent" is meant a compound of this invention capable of direct transformation into a metallopharmaceutical of this invention. Reagents may be utilized directly for the preparation of the metallopharmaceuticals of this invention or may be a component in a kit of this invention.

The term "binding agent" means a metallopharmaceutical of this invention having affinity for and capable of binding to the vitronectin receptor. The binding agents of this invention have Ki<1000 nM.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; "Design and Applications of Prodrugs" p. 113–191, 1991; Advanced Drug Delivery Reviews, H. Bundgard, 8, p.1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, hexyl, heptyl, octyl, nonyl, and decyl; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" or "bicyclic" is intended to include saturated bicyclic ring groups such as [3.3.0]bicyclooctane, [4.3.0]bicyclononane, [4.4.0]bicyclodecane (decalin), [2.2.2]bicyclooctane, and so forth.

As used herein, the term "alkene" or "alkenyl" is intended to include hydrocarbon chains having the specified number of carbon atoms of either a straight or branched configuration and one or more unsaturated carbon-carbon bonds which may occur in any stable point along the chain, such as ethenyl, propenyl, and the like.

As used herein, the term "alkyne" or "alkynyl" is intended to include hydrocarbon chains having the specified number of carbon atoms of either a straight or branched configuration and one or more unsaturated carbon-carbon triple bonds which may occur in any stable point along the chain, such as propargyl, and the like.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, •-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydroturanyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals, X-ray contrast agent pharmaceuticals, ultrasound contrast agent pharmaceuticals and metallopharmaceuticals for magnetic resonance imaging contrast are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate hynic boc-hydrazinonicotinyl group or 2-[[[5-[carbonyl]-2-pyridinyl]hydrazono]methyl]-benzenesulfonic acid, NMeArg or MeArga-N-methyl arginine |
| NMAsp | a-N-methyl aspartic acid |
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

| | |
|---|---|
| Ala = | alanine |
| Arg = | arginine |
| Asn = | asparagine |
| Asp = | aspartic acid |
| Cys = | cysteine |
| Gln = | glutamine |
| Glu = | glutamic acid |
| Gly = | glycine |
| His = | histidine |
| Ile = | isoleucine |
| Leu = | leucine |
| Lys = | lysine |
| Met = | methionine |
| Nle = | norleucine |
| Orn = | ornithine |
| Phe = | phenylalanine |
| Phg = | phenylglycine |
| Pro = | proline |
| Sar = | sarcosine |
| Ser = | serine |

-continued

| | |
|---|---|
| Thr = | threonine |
| Trp = | tryptophan |
| Tyr = | tyrosine |
| Val = | valine |

As used herein, the term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

As used herein, the term "lipid" refers to a synthetic or naturally-occurring amphipathic compound which comprises a hydrophilic component and a hydrophobic component. Lipids include, for example, fatty acids, neutral fats, phosphatides, glycolipids, aliphatic alchols and waxes, terpenes and steroids.

As used herein, the term "lipid composition" refers to a composition which comprises a lipid compound. Exemplary lipid compositions include suspensions, emulsions and vesicular compositions.

As used herein, the term "lipid formulation" refers to a composition which comprises a lipid compound and a bioactive agent.

As used herein, the term "vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

As used herein, the term "vesicular composition" refers to a composition which is formulate from lipids and which comprises vesicles.

As used herein, the term "vesicle formulation" refers to a composition which comprises vesicles and a bioactive agent.

As used herein, the term "lipsomes" refers to a generally spherical cluster or aggregate of amphipathic compounds, including lipid compounds, typically in the form of one or more concentric layers, for example, bilayers. They may also be referred to herein as lipid vesicles.

Angiogenesis is the process of formation of new capillary blood vessels from existing vasculature. It is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. The activated endothelial cells secrete enzymes that degrade the basement membrane of the vessels. The endothelial cells then proliferate and migrate into the extracellular matrix first forming tubules and subsequently new blood vessels.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the pro-angiogenic factors that have been identified include basic fibroblast growth factor (bFGF), angiogenin, TGF-alpha, TGF-beta, and vascular endothelium growth factor (VEGF), while interferon-alpha, interferon-beta and thrombospondin are examples of angiogenesis suppressors.

Angiogenic factors interact with endothelial cell surface receptors such as the receptor tyrosine kinases EGFR, FGFR, PDGFR, Flk-1/KDR, Flt-1, Tek, Tie, neuropilin-1, endoglin, endosialin, and Axl. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

The proliferation and migration of endothelial cells in the extracellular matrix is mediated by interaction with a variety of cell adhesion molecules. Integrins are a diverse family of heterodimeric cell surface receptors by which endothelial cells attach to the extracellular matrix, each other and other cells. Angiogenesis induced by bFGF or TNF-alpha depend on the agency of the integrin avb3, while angiogenesis induced by VEGF depends on the integrin avb5 (Cheresh et. al., Science, 1995, 270, 1500–2). Induction of expression of the integrins a1b1 and a2b1 on the endothelial cell surface is another important mechanism by which VEGF promotes angiogenesis (Senger, et. al., Proc. Natl. Acad, Sci USA, 1997, 94, 13612–7).

The pharmaceuticals of the present invention are comprised of a non-peptide targeting moiety for the vitronectin receptor that is expressed or upregulated in angiogenic tumor vasculature.

The ultrasound contrast agents of the present invention comprise a plurality of vitronectin receptor targeting moieties attached to or incorporated into a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, which provides the difference in echogenicity and thus the contrast in ultrasound imaging. The gas is encapsulated or contained in the microsphere to which is attached the biodirecting group, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents of the present invention are comprised of one or more vitronectin receptor targeting moieties attached to one or more X-ray absorbing or "heavy" atoms of atomic number 20 or greater, further comprising an optional linking moiety, $L_n$, between the targeting moieties and the X-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215).

MRI contrast agents of the present invention are comprised of one or more vitronectin receptor targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. Nos. 5,801,228, 5,567,411, and 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

Administration of a compound of the present invention in combination with such additional therapeutic agents, may afford an efficacy advantage over the compounds and agents alone, and may do so while permitting the use of lower doses of each. A lower dosage minimizes the potential of side effects, thereby providing an increased margin of safety. The combination of a compound of the present invention with such additional therapeutic agents is preferably a synergistic combination. Synergy, as described for example by Chou and Talalay, Adv. Enzyme Regul. 22:27–55 (1984), occurs when the therapeutic effect of the compound and agent when administered in combination is greater than the additive effect of the either the compound or agent when administered alone. In general, a synergistic effect is most clearly demonstrated at levels that are (therapeutically) sub-optimal for either the compound of the present invention, a chemotherapeutic agent or a radiosensitizer agent alone, but which are highly efficacious in combination. Synergy can be in terms of improved tumor response without substantial increases in toxicity over individual treatments alone, or some other beneficial effect of the combination compared with the individual components.

The compounds of the present invention, and a chemotherapeutic agent or a radiosensitizer agent, utilized in combination therapy may be administered simultaneously, in either separate or combined formulations, or at different times e.g., sequentially, such that a combined effect is achieved. The amounts and regime of administration will be adjusted by the practitioner, by preferably initially lowering their standard doses and then titrating the results obtained.

The invention also provides kits or single packages combining two or more active ingredients useful in treating cancer. A kit may provide (alone or in combination with a pharmaceutically acceptable diluent or carrier), the compound of the present invention and additionally at least one agent selected from the group consisting of a chemotherapeutic agent and a radiosensitizer agent (alone or in combination with diluent or carrier).

The pharmaceuticals of the present invention have the formulae, $(Q)_d-L_n-(C_h-X)$, $(Q)_d-L_n-(C_h-X^1)_{d'}$, $(Q)_d-L_n-(X^2)_{d''}$, and $(Q)_d-L_n-(X^3)$, wherein Q represents a non-peptide that binds to a receptor expressed in angiogenic tumor vasculature, d is 1–10, $L_n$ represents an optional linking group, $C_h$ represents a metal chelator or bonding moiety, X represents a radioisotope, $X^1$ represents paramagnetic metal ion, $X^2$ represents a paramagnetic metal ion or heavy atom containing insoluble solid particle, d'' is 1–100, and $X^3$ represents a surfactant microsphere of an echogenic gas. The interaction of the non-peptide recognition sequences of the vitronectin receptor binding portion of the pharmaceuticals with the $\alpha v \beta 3$ receptor results in localization of the pharmaceuticals in angiogenic tumor vasculature, which express the $\alpha v \beta 3$ receptor.

The pharmaceuticals of the present invention can be synthesized by several approaches. One approach involves the synthesis of the targeting non-peptide moiety, Q, and direct attachment of one or more moieties, Q, to one or more metal chelators or bonding moieties, $C_h$, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach involves the synthesis of a non-peptide, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The non-peptide vitronectin binding moieties, Q, optionally bearing a linking group, $L_n$, or a fragment of the linking group, can be synthesized using standard synthetic methods known to those skilled in the art. Preferred methods include but are not limited to those methods described below.

The attachment of linking groups, $L_n$, to the non-peptides, Q; chelators or bonding units, $C_h$, to the non-peptides, Q, or to the linking groups, $L_n$; and non-peptides, bearing a fragment of the linking group to the remainder of the linking group, in combination forming the moiety, $(Q)_d-L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

A number of methods can be used to attach the non-peptides, Q, to paramagnetic metal ion or heavy atom containing solid particles, $X^2$, by one of skill in the art of the surface modification of solid particles. In general, the targeting moiety Q or the combination $(Q)_d L_n$ is attached to a coupling group that react with a constituent of the surface of the solid particle. The coupling groups can be any of a number of silanes which react with surface hydroxyl groups on the solid particle surface, as described in co-pending U.S. patent application Ser. No. 09/356,178 (now U.S. Pat. No. 6,254,852), and can also include polyphosphonates, polycarboxylates, polyphosphates or mixtures thereof which couple with the surface of the solid particles, as described in U.S. Pat. No. 5,520,904.

A number of reaction schemes can be used to attach the non-peptides, Q, to the surfactant microsphere, $X^3$. These are illustrated in following reaction schemes where $S_f$ represents a surfactant moiety that forms the surfactant microsphere.

Acylation Reaction:

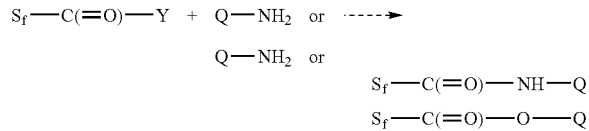

Y is a leaving group or active ester

Disulfide Coupling:

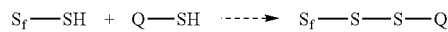

Sulfonamide Coupling:

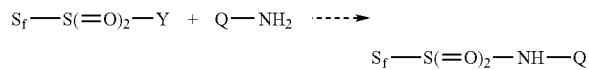

Reductive Amidation:

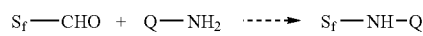

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the non-peptides, Q, so as to minimize the possibility that the moieties $C_h$—X, $C_h$—$X^1$, $X^2$, and $X^3$, will interfere with the interaction of the recognition sequences of Q with angiogenic tumor vasculature receptors. The necessity of incorporating a linking group in a reagent is dependent on the identity of Q, $C_h$—X, $C_h$—$X^1$, $X^2$, and $X^3$. If $C_h$—X, $C_h$—$X^1$, $X^2$, and $X^3$, cannot be attached to Q without substantially diminishing its affinity for the receptors, then a linking group is used. A linking group also provides a means of independently attaching multiple non-peptides, Q, to one group that is attached to $C_h$—X, $C_h$—$X^1$, $X^2$, or $X^3$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, Q, with the vitronectin receptors expressed in the tumor neovasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}$Tc, $^{95}$Tc, $^{111}$In, $^{62}$Cu, $^{60}$Cu, $^{64}$Cu, $^{67}$Ga, $^{68}$Ga, $^{86}$Y.

Chelators for technetium, copper and gallium isotopes are selected from diaminedithiols, monoamine-monoamidedithiols, triamide-monothiols, monoamine-diamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl;aryl and heterocycle. Particularly preferred hydrazones are described in co-pending U.S. Ser. No. 08/476,296 (now U.S. Pat. No. 5,750,088) the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}$In and $^{86}$Y are selected from cyclic and acyclic polyaminocarboxylates such as DTPA, DOTA, DO3A, 2-benzyl-DOTA, alpha-(2-phenethyl)1,4,7,10 -tetraazazcyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine. Procedures for synthesizing these chelators that are not commercially available can be found in Brechbiel, M. and Gansow, O., J. Chem. Soc. Perkin Trans. 1992, 1, 1175; Brechbiel, M. and Gansow, O., Bioconjugate Chem. 1991, 2, 187; Deshpande, S., et. al., J. Nucl. Med. 1990, 31, 473; Kruper, J., U.S. Pat. No. 5,064, 956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1, 2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908 (now U.S. Pat. No. 5,744,120), and U.S. Ser. No. 60/013360 and Ser. No. 08/646,886 (and corresponding International Publication No. WO 97/33627), the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

Chelators or bonding moieties for therapeutic radiopharmaceuticals are selected to form stable complexes with the radioisotopes that have alpha particle, beta particle, Auger or Coster-Kronig electron emissions, such as $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir. Chelators for rhenium, copper, palladium, platinum, iridium, rhodium, silver and gold isotopes are selected from diaminedithiols, monoaminemonoamidedithiols, triamide-monothiols, monoamine-diamide-monothiols, diaminedioximes, and hydrazines. Chelators for yttrium, bismuth, and the lanthamide isotopes are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl]-4'-(3-amino-4-methoxyphenyl)-2,2':6',2"-terpyridine.

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl]-4'-(3-amino-4-methoxyphenyl)-2,2':6',2"-terpyridine.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 μg to 10 mg, or more preferably from 0.5 μg to 200 μg. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 μg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, silver, palladium, rhodium, gold, platinum, bismuth, yttrium and lanthamide radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 µL of the echogenic gas per kg body weight or by infusion at a rate of approximately 3 µL/kg/min. Imaging is performed using known techniques of sonography.

Other features of the invention will become apparent in the course of the following descriptions of exemplary embodiments which are given for illustration of the invention and are not intended to be limiting thereof.

EXAMPLES

Representative materials and methods that may be used in preparing the compounds of the invention are described further below. 1-methyl-4-oxo-7-(((1-(triphenylmethyl)imidazol-2-yl)amino)methyl)hydroquinoline-3-carboxylic acid, ethyl 7-bromo-4-oxohydroquinoline-3-carboxylate, 1-(triphenylmethyl)imidazole-2-ylamine, and methyl 3-amino-2-(((2,4,6-trimethylphenyl)sulfonyl)amino)propanoate hydrochloride were prepared as described in PCT WO 98/23608. Boc-L-cysteic acid, Boc-L-cysteic acid N-hydroxyphenyl ester, and Boc-L-cysteic acid p-nitrophenyl ester were prepared as described in Liebigs Ann. Chem. 1979, 776–783. Benzotriazole-1-yloxy-tris-pyrrolidinophosphonium hexafluorophosphate (PyBOP) was purchased from Novabiochem. (tert-butoxy)-N-(3-bromopropyl)formamide and 2-(2-aza-2-((5-((2,5-dioxopyrrolidinyl)carbonyl)(2-pyridyl))-amino)vinyl)benzenesulfonic acid were prepared as described in PCT WO 96/40637. All other chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 1,2,4-triazole, stannous chloride dihydrate, 1-(3-dimethylaminopropyl)-3-ethylcarbodiimide hydrochloride (EDC), triethylsilane ($Et_3SiH$) and tris(3-sulfonatophenyl)phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-Sulfonatophenyl)diphenylphosphine monosodium salt (TPPMS)was purchased from TCI America, Inc. Tricine was obtained from Research Organics, Inc. Technetium-99m-pertechnetate ($^{99m}TcO_4^-$) was obtained from a DuPont Pharma $^{99}Mo/^{99m}Tc$ Technelite® generator. In-111-chloride (Indichlor®) was obtained from Amersham Medi-Physics, Inc. Sm-153-chloride and Lutetium-177-chloride were obtained from the University of Missouri Research Reactor (MURR). Yttrium-90 chloride was obtained from the Pacific Northwest Research Laboratories. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation.

Synthesis of Boc-Glu-(OTFP)-OTFP

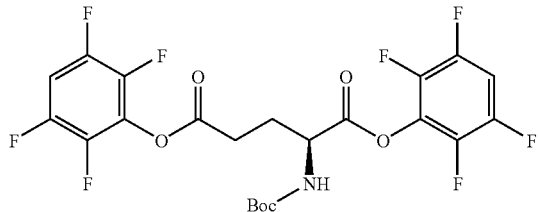

To a solution of Boc-Glu-OH (28.9 g, 117 mmol) in DMF (500 mL) at room temperature, and under nitrogen, was added a solution of 2,3,5,6-tetrafluorophenol (48.2 g, 290 mmol) in DMF (50 mL). After stirring for 10 min. EDC (55.6 g, 290 mmol) was added and the reaction mixture was stirred for about 96 h. The volatiles were removed in vacuo and the residue was triturated in 0.1 N HCl (750 mL). To this mixture was added ethyl acetate (600 mL), the layers separated. The aqueous layer was extracted with ethyl acetate (3×~500 mL), and all the ethyl acetate fractions were combined, washed with water (300 mL) and brine (300 mL), dried (MgSO$_4$), and concentrated to give a tan solid (62 g). The tan solid was washed with acetonitrile to give the title compound (45.5 g, 73%) in purified form.

ESMS: Calculated for $C_{22}H_{17}F_8NO_6$, 543.09; found, 566.0 [M+Na]$^{+1}$.

Example 1

2-(((4-(4-(((3-(2-(2-(3-((6-((1-Aza-2-(2-sulfophenyl) vinyl)amino)(3-pyridyl))carbonylamino)propoxy) ethoxy)ethoxy)propyl)amino)sulfonyl)phenyl)phenyl)sulfonyl)amino)-3-((7-(((imidazol-2-ylamino) methyl)-1-methyl-4-oxo(3-hydroquinolyl)) carbonylamino)propanoic Acid Trifluoroacetate Salt Part A—N-(3-(2-(2-(3-aminopropoxy)ethoxy) ethoxy)propyl)(phenylmethoxy)formamide A solution of 4,7,10-trioxa-1,13-tridecanediamine (158 mL, 0.72 mol), TEA (16.7 mL, 0.12 mol), and MeOH (300 mL) in peroxide-free THF (1,000 mL) was placed in a 3 liter 3-neck flask fitted with a mechanical stirrer, a thermometer, and an addition funnel with nitrogen line. The addition funnel was charged with a solution of benzyl chloroformate (17.1 mL, 0.12 mol) in peroxide-free THF (1,000 mL). The contents of the flask were cooled below 5° C. The contents of the addition funnel were added to the flask with rapid stirring over 4 h while keeping the temperature below 5° C. The solution was stirred an additional 30 min and concentrated to give a thick syrup. This syrup was taken up in saturated NaCl (1800 mL) and 10% Na$_2$CO$_3$ (200 mL) and extracted with ether (3×1,000 mL). The combined ether extracts were washed with saturated NaCl (500 mL), dried (MgSO$_4$), and concentrated to give a pale yellow oil (36.74 g). Flash chromatography on a 7×29 cm silica gel column (DCM/MeOH/TEA, 20/15/0.5) gave the title compound as a colorless syrup (19.14 g, 45%). $^1$H NMR (CDCl$_3$): 7.33–7.25 (m, 5H), 5.59 (s, 1H), 5.06 (s, 2H), 3.62–3.45 (m, 12H), 3.32–3.25 (m, 2H), 2.74 (t, J=6.7 Hz, 2H), 1.75 (pentet, J=6.0 Hz, 2H), 1.67 (pentet, J=6.4 Hz, 2H), 1.33 (s, 2H); MS: m/e 355.4 [M+H]; High Resolution MS: Calcd for $C_{18}H_{31}N_2O_5$ [M+H]: 355.2233, Found: 355.2222.

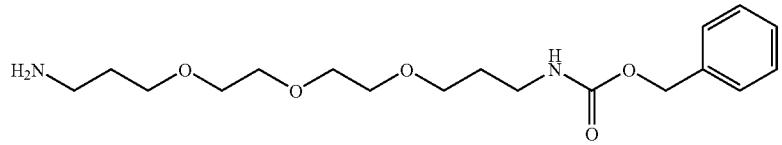

Part B—Methyl 3-((tert-Butoxy)carbonylamino)-2-(((4-(4-(((3-(2-(2-(3-((phenylmethoxy)carbonylamino)propoxy)ethoxy)ethoxy)propyl)amino)sulfonyl)phenyl)phenyl)sulfonyl)amino)propanoate Biphenyl-4,4'-disulfonyl chloride (2.64 g, 7.5 mmol, freshly recrystallized from CHCl$_3$) and DCM (200 mL) were placed in a 500 mL 3-neck flask fitted with a thermometer, an addition funnel, and a nitrogen line. The addition funnel was charged with a solution of N-(3-(2-(2-(3-aminopropoxy)ethoxy)ethoxy)propyl)(phenylmethoxy)formamide (1.77 g, 5.0 mmol) and DIEA (0.87 mL, 5.0 mmol) in DCM (40 mL). The contents of the flask were cooled below 5° C. The contents of the addition funnel were added to the flask with rapid stirring over 3 h while keeping the temperature of the flask below 5° C. The addition funnel was charged with a solution of N-β-Boc-L-α,β,-diaminopropionic acid methyl ester hydrochloride (2.55 g, 10 mmol) and DIEA (3.8 mL, 22 mmol) in DCM (25 mL). This solution was added to the flask with stirring at 5° C. over 15 min, and stirred at ambient temperatures for an additional 20 h. The reaction solution was washed consecutively with 0.1 N HCl (100 mL) and water (2×100 mL), dried (MgSO$_4$), and concentrated to give a viscous oil (5.79 g). Flash chromatography on a 5×21 cm silica gel column (85/15 EtOAc/hexanes, followed by 100% EtOAc) gave a colorless amorphous solid. Recrystallization from toluene (85 mL) gave the title compound as a colorless solid (2.52 g, 59%). MP: 104.5–106.5° C.; $^1$H NMR (CDCl$_3$): 8.00–7.90 (m, 4H), 7.72–7.64 (m, 4H), 7.46–7.24 (m, 5H), 5.96–5.88 (m, 1H), 5.86–5.73 (m, 1H), 5.41 (s, 1H), 5.16–5.00 (m, 3H), 4.15–4.02 (m, 1H), 3.68–3.39 (m, 17H), 3.34–3.22 (m, 2H), 3.13–3.03 (m, 2H), 1.80–1.62 (m, 4H), 1.39 (s, 9H); $^{13}$C NMR (CDCl$_3$): 170.2, 156.5, 156.1, 143.9, 143.0, 140.4, 139.4, 136.7, 128.4, 128.1, 128.0, 127.9, 127.9, 127.8, 127.3, 80.1, 70.6, 70.5, 70.2, 70.1, 70.0, 69.6, 66.5, 56.1, 52.9, 43.2, 42.4, 39.3, 29.4, 28.5, 28.2; MS: m/e 868.3 [M+NH$_4$]; High Resolution MS: Calcd for $C_{39}H_{55}N_4O_{13}S_2$ [M+H]: 851.3207, Found: 851.3226.

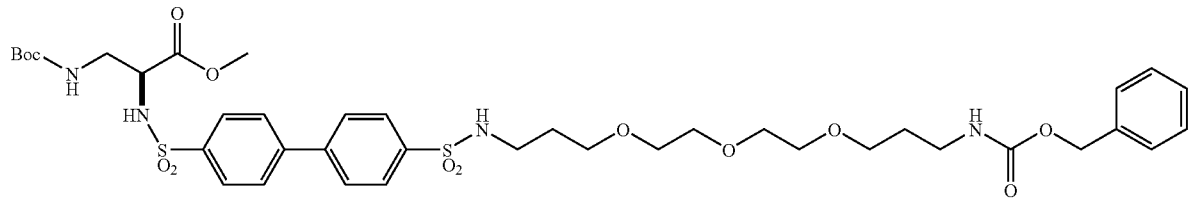

Part C—Methyl 3-((1-Methyl-4-oxo-7-(((1-(triphenylmethyl)imidazol-2-yl)amino)methyl)(3-hydroquinolyl))carbonylamino)-2-(((4-(4-(((3-(2-(2-(3-((phenylmethoxy)carbonylamino)propoxy)ethoxy)ethoxy)propyl)amino)sulfonyl)phenyl)phenyl)sulfonyl)amino)propanoate The product of Part B, above (748 mg, 0.88 mmol) was dissolved in 25/75 TFA/DCM (15 mL) and allowed to stand at ambient temperatures under nitrogen for 15 min. The TFA was removed under vacuum and the resulting amber oil was taken up in 50/50 ACN/water (50 mL), and treated portion wise with Bio-Rad AG-3-X4A resin, hydroxide form, to raise the pH from 2 to 6. The resin was removed by filtration and the filtrate was lyophilized to give a sticky pale yellow foam.

In a separate flask, 1-methyl-4-oxo-7-(((1-(triphenylmethyl)imidazol-2-yl)amino)methyl)hydroquinoline-3-carboxylic acid (432 mg, 0.80 mmol), TEA (0.33 mL), and HBTU (364 mg, 0.96 mmol) were dissolved in anhydrous DMF (25 mL). The resulting solution was stirred at ambient temperatures under a nitrogen atmosphere for 10 min and combined with a solution of the yellow foam in anhydrous DMF (15 mL). The DMF was removed under vacuum after 18 h to give a viscous yellow oil. This oil was taken up in EtOAc (175 mL), washed consecutively with water (25 mL), saturated NaHCO$_3$ (50 mL), and saturated NaCl (25 mL), dried (MgSO$_4$), and concentrated to give a viscous yellow oil. Purification by flash chromatography on a 7×25 cm silica gel column using a CHCl$_3$/EtOAc/MeOH step gradient (47/47/6, 46/46/8, 60/30/10) gave the title compound as a pale yellow solid (510 mg, 50%). MP: 136–140° C.; MS: m/e 1273.4 [M+H]; High Resolution MS: Calcd for C$_{68}$H$_{73}$N$_8$O$_{13}$S$_2$ [M+H]: 1273.4738, Found: 1273.4730.

Part D—3-((1-Methyl-4-oxo-7-(((1-(triphenylmethyl)imidazol-2-yl)amino)methyl)(3-hydroquinolyl))carbonylamino)-2-(((4-(4-(((3-(2-(2-(3-((phenylmethoxy)carbonylamino)propoxy)ethoxy)ethoxy)propyl)amino)sulfonyl)phenyl)phenyl)sulfonyl)amino)propanoic Acid The product form Part C, above (295 mg, 0.232 mmol) was dissolved in a mixture of peroxide-free THF (12 mL), water (1.8 mL), and 3 N LiOH (1.2 mL), and stirred at ambient temperatures under a nitrogen atmosphere for 30 min. The THF was removed under vacuum and the resulting mixture was dissolved in CHCl$_3$ (75 mL) and water (50 mL). The aqueous layer was adjusted to pH 3 with 0.5 N HCl and the layers were thoroughly mixed. The aqueous layer was extracted with additional CHCl$_3$ (2×25 mL). The combined CHCl$_3$ extracts were washed with saturated NaCl (50 mL), dried (MgSO$_4$), and concentrated to give the title compound as a pale yellow solid (291 mg, 100%). MS: m/e 1259.3 [M+H]; High Resolution MS: Calcd for C$_{67}$H$_{71}$N$_8$O$_{13}$S$_2$ [M+H]: 1259.4582, Found: 1259.4610.

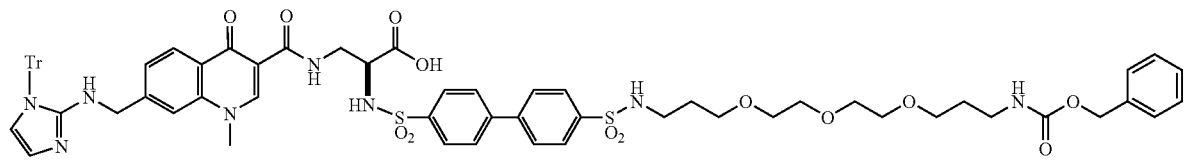

Part E—2-(((4-(4-(((3-(2-(2-(3-Aminopropoxy)ethoxy)ethoxy)propyl)amino)sulfonyl)phenyl)phenyl)sulfonyl)amino)-3-((7-((imidazol-2-yl)methyl)-1-methyl-4-oxo(3-hydroquinolyl))carbonylamino)propanoic Acid The product from Part D, above (279 mg, 0.222 mmol) was dissolved in degassed TFA (30 mL) and treated with Et$_3$SiH (0.424 mL, 2.66 mmol). The solution was heated at 70° C. under a nitrogen atmosphere for 1 h and concentrated to a viscous oil. This oil was dissolved in water (20 mL) and

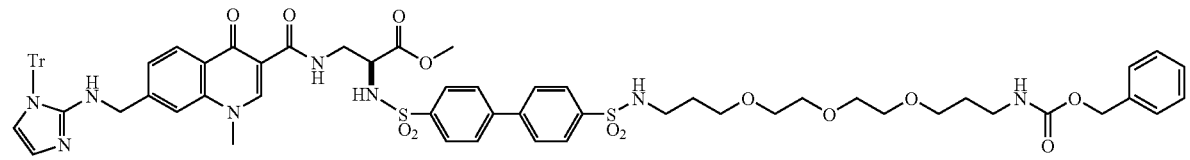

washed with ether (2×20 mL). The combined ether washings were back-extracted with water (10 mL). The combined water extracts were diluted with an equal volume of ACN and treated with Bio-Rad AG-3-X4A resin, hydroxide form to raise the pH from 4 to 6. The resin was removed by filtration and the filtrate was lyophilized to give the title compound as a colorless solid (220 mg). MS: m/e 883.4 [M+H], 442.5 [M+2H]; High Resolution MS: Calcd for $C_{40}H_{51}N_8O_{11}S_2$ [M+H]: 833.3118, Found: 833.3118.

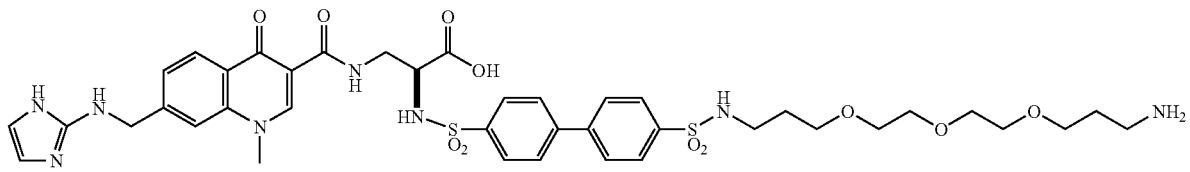

Part F—2-(((4-(4-(((3-(2-(2-(3-((6-((1-Aza-2-(2-sulfophenyl)vinyl)amino)(3-pyridyl))carbonylamino)propoxy)ethoxy)ethoxy)propyl)amino)sulfonyl)phenyl)phenyl)sulfonyl)amino)-3-((7-((imidazol-2-ylamino)methyl)-1-methyl-4-oxo(3-hydroquinolyl))carbonylamino)propanoic Acid Trifluoroacetate Salt A solution of the product from Part F, above (15 mg, 0.0135 mmol), TEA (0.007 mL), and 2-(2-aza-2-((5-((2,5-dioxopyrrolidinyl)carbonyl)(2-pyridyl))amino)vinyl)benzenesulfonic acid (9.0 mg, 0.0204 mmol) in anhydrous DMF (2.5 mL) was allowed to stand at ambient temperatures under a nitrogen atmosphere for 22 h. The DMF was removed under vacuum and the glassy solid was dissolved in 20% ACN and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 21.2 min was collected and lyophilized to give the title compound as a colorless powder (3.5 mg, 20%). MS: m/e 1186.7 [M+H]; High Resolution MS: Calcd for $C_{53}H_{60}N_{11}O_{15}S_3$ [M+H]: 1186.3432, Found: 1186.3410.

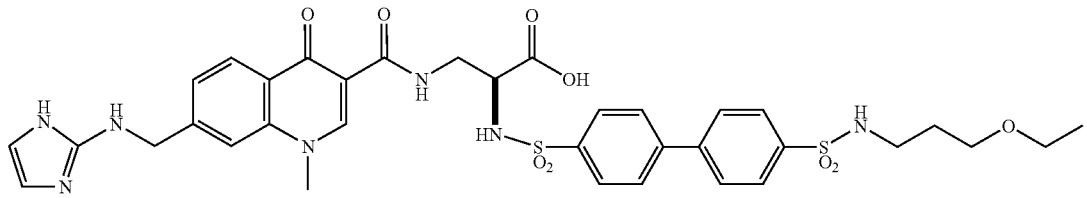

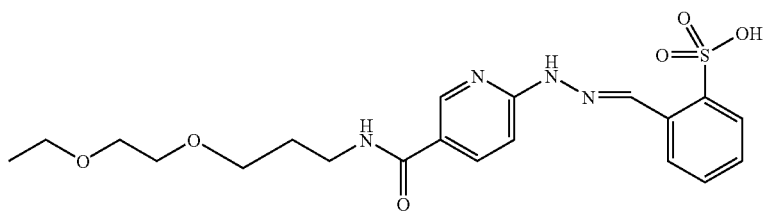

·TFA

Example 2

3-((7-((Imidazol-2-ylamino)methyl)-1-methyl-4-oxo (3-hydroquinolyl))carbonylamino)-2-(((4-(4-(((3-(2-(2-(3-(2-(1,4,7,10-tetraaza-4,7,10-tris(carboxylm-ethyl)cyclododecyl)acetylamino)propoxy)ethoxy) ethoxy)propyl)amino)sulfonyl)phenyl)phenyl) sulfonyl)amino)propanoic Acid Bis(trifluoroacetate) Salt

Part A—Phenylmethyl 2-(1,4,7,10-Tetraaza-4,7,10-tris(((tert-butyl)oxycarbonyl)methyl)cyclododecyl)acetate A solution of tert-butyl (1,4,7,10-tetraaza-4,7-bis(((tert-butyl)oxycarbonyl)methyl)cyclododecyl)acetate (0.922 g, 1.79 mmol), TEA (1.8 mL) and benzyl bromoacetate (0.86 mL, 5.37 mmol) in anhydrous DMF (24 mL) was stirred at ambient temperatures under a nitrogen atmosphere for 24 h. The DMF was removed under vacuum and the resulting oil was dissolved in EtOAc (300 mL). This solution was washed consecutively with water (2×50 mL) and saturated NaCl (50 mL), dried (MgSO₄), and concentrated to give the title compound as an amorphous solid (1.26 g). MS: m/e 663.5 [M+H].

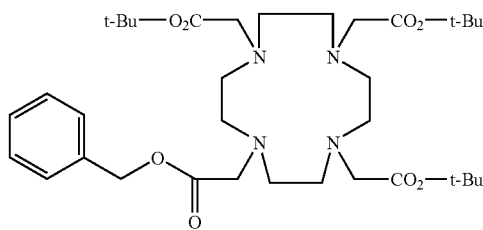

Part B—2-(1,4,7,10-tetraaza-4,7,10-tris(((tert-butyl)oxycarbonyl)methyl)cyclododecyl)acetic Acid The product from Part A, above (165 mg, 0.25 mmol) was hydrogenolyzed over 10% Pd on carbon (50 mg) in EtOH (15 mL) at 60 psi for 24 h. The catalyst was removed by filtration through filter aid and washed with EtOH. The filtrates were concentrated to give the title compound as an amorphous solid (134 mg, 94%). MS: m/e 573.5 [M+H].

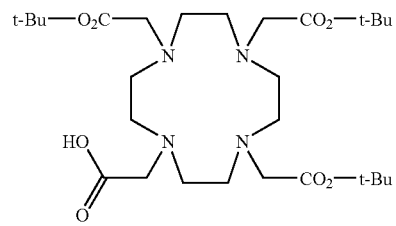

Part C—Methyl 3-((7-((Imidazol-2-ylamino)methyl)-1-methyl-4-oxo(3-hydroquinolyl))carbonylamino)-2-(((4-(4-(((3-(2-(2-(3-(2-(1,4,7,10-tetraaza-4,7,10-tris(((tert-butyl)oxycarbonyl)methyl) cyclododecyl)acetylamino) propoxy)ethoxy)ethoxy) propyl)amino)sulfonyl)phenyl)phenyl)sulfonyl) amino)propanoate Pentakis(trifluoroacetate) Salt A solution of the product of Example 1, Part C (68 mg, 0.0534 mmol) and Et₃SiH (0.051 mL, 0.32 mmol) in degassed TFA (5.0 mL) was stirred at 70° C. under a nitrogen atmosphere for 1 h and concentrated to dryness. The resulting amber oil was dissolved in anhydrous DMF (2 mL) and treated with TEA until basic to pH paper. A solution of the product of Part B, above (46 mg, 0.080 mmol) in anhydrous DMF (1.0 mL) was added, followed by HBTU (24 mg, 0.064 mmol), and the solution was stirred at ambient temperatures under a nitrogen atmosphere for 3 h. The DMF was removed under vacuum and the residue was dissolved in 50% ACN and purified by preparative HPLC on a Vydac C-18 column (22×250 mm) using a 2.1%/min gradient of 0 to 63% ACN containing 0.1% TFA at a flow rate of 20 mL/min. The main product peak eluting at 23.8 min was collected and lyophilized to give the title compound as a colorless powder (16 mg, 15%). MS: m/e 1451.7 [M+H]; High Resolution MS: Calcd for $C_{69}H_{103}N_{12}O_{18}S_2$ [M+H]: 1451.6954, Found: 1451.698.

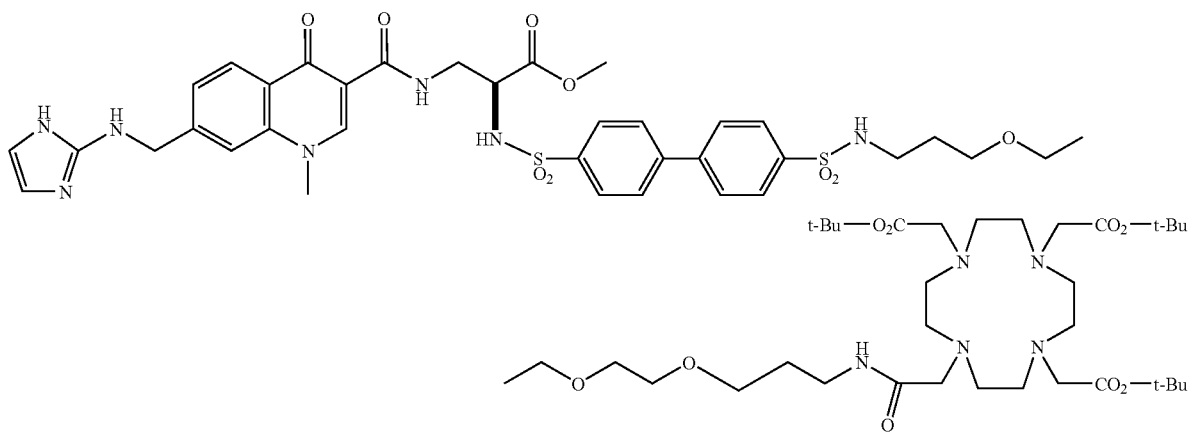

•5 TFA

Part D—3-((7-((Imidazol-2-ylamino)methyl)-1-methyl-4-oxo(3-hydroquinolyl))carbonylamino)-2-(((4-(4-(((3-(2-(2-(3-(2-(1,4,7,10-tetraaza-4,7,10-tris(carboxylmethyl)cyclododecyl)acetylamino)propoxy)ethoxy)ethoxy)propyl)amino)sulfonyl)phenyl)phenyl)sulfonyl)amino)propanoic Acid Bis (trifluoroacetate) Salt The product of Part C, above (16 mg, 0.0102 mmol) was dissolved in a mixture of peroxide-free THF (1 mL), water (0.115 mL), and 3 N LiOH (0.075 mL), and stirred at ambient temperatures under a nitrogen atmosphere for 24 h. The reaction was concentrated to give an oily solid. This solid was dissolved in 50% ACN and purified by preparative HPLC on a Vydac C-18 column (22×250 mm) using a 2.52%/min gradient of 0 to 63% ACN containing 0.1% TFA at a flow rate of 20 mL/min. The main product peak eluting at 24.0 min was collected and lyophilized to give a colorless powder (6.0 mg). This solid was dissolved in degassed TFA (2.0 mL) and Et$_3$SiH (0.050 mL), stirred at 70° C. under a nitrogen atmosphere for 4.5 h, and concentrated to dryness. The resulting oil was dissolved in 25% ACN and purified by preparative HPLC on a Vydac C-18 column (22×250 mm) using a 1.5%/min gradient of 0 to 45% ACN containing 0.1% TFA at a flow rate of 20 mL/min. The main product peak eluting at 19.0 min was collected and lyophilized to give the title compound as a colorless powder (2.0 mg, 17%). MS: m/e 1269.5 [M+H], 635.5 [M+2H], 424.3 [M+3H]; High Resolution MS: Calcd for $C_{56}H_{77}N_{12}O_{18}S_2$ [M+H]: 1269.4920, Found: 1269.4950.

ambient temperatures under a nitrogen atmosphere for 28 h. The EtOH was removed under vacuum and the oily solid was partitioned between water (1 L) and EtOAc (500 mL). The aqueous layer was extracted with additional EtOAc (500 mL). The combined EtOAc extracts were washed consecutively with saturated NaHCO$_3$ (300 mL) and saturated NaCl (300 mL), dried (MgSO$_4$), and concentrated to give an amber liquid. This liquid was vacuum fractional distilled through a 15 cm Vigreux column. The main fraction was collected from 91–117° C./6 mm Hg to gave the title compound as a colorless liquid (77.77 g, 89%). $^1$H NMR (CDCl$_3$): 6.59 (s, 1H), 6.52 (s, 2H), 4.16 (q, J=7.16 Hz, 2H), 3.98 (t, J=6.14 Hz, 2H), 2.49 (t, J=7.34 Hz, 2H), 2.28 (s, 6H), 2.11–2.07 (m, 2H), 1.26 (t, J=7.16 Hz, 3H); Anal. calcd for $C_{14}H_{20}O_3$: C, 71.16; H, 8.53, Found: C, 71.35; H, 8.59.

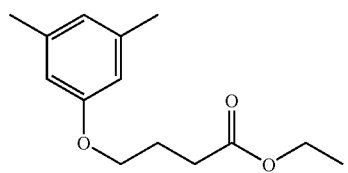

Part B—4-(3,5-Dimethylphenoxy)butanoic Acid

The product of part A, above (75.52 g, 0.320 mol) and KOH pellets (38.5 g, 0.584 mol) were dissolved in absolute

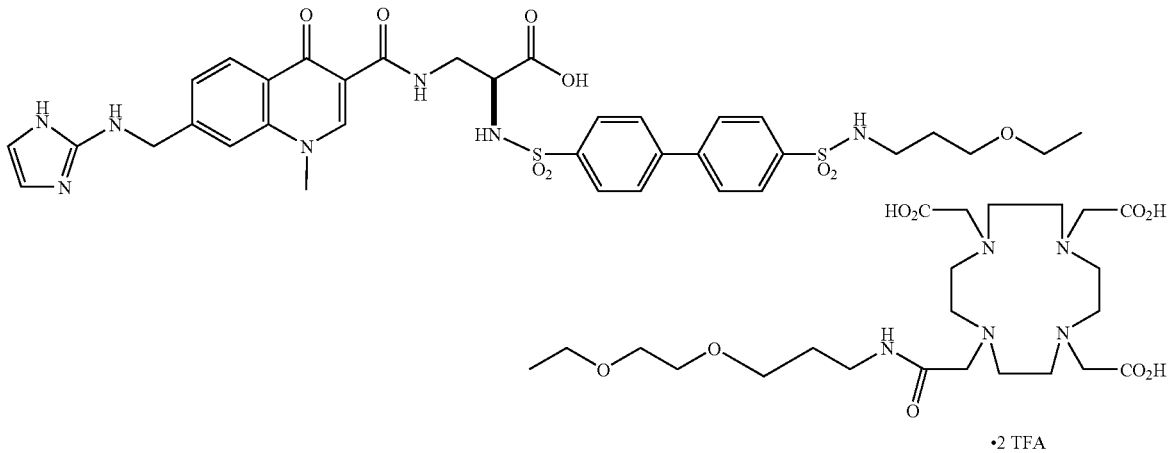

•2 TFA

Example 3

2-(((4-(3-(N-(3-(2-(2-(3-((6-((1-Aza-2-(2-sulfophenyl)vinyl)amino)(3-pyridyl))carbonylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt Part A—Ethyl 4-(3,5-Dimethylphenoxy)butanoate Sodium metal (17.12 g, 0.744 mol) was added to anhydrous EtOH (350 mL) and stirred until dissolved. 3,5-Dimethylphenol was added and the solution was stirred 15 min at ambient temperatures. Ethyl 4-bromoacetate (58.7 mL, 0.41 mol) was added and the solution was stirred at EtOH (1.50 L) and heated at reflux for 3 h. The solution was concentrated to a colorless solid, which was taken up in water (2.0 L) and washed with ether (2×750 mL). The aqueous layer was adjusted to pH 1 with concd HCl (55 mL) and the resulting oily ppt was extracted into EtOAc (2×500 mL). The combined EtOAc extracts were washed consecutively with water (300 mL) and saturated NaCl, dried (MgSO$_4$), and concentrated to give a colorless solid (64.13 g). Recrystallization from hexanes (500 mL) gave the title compound as a colorless solid (59.51 g, 89%). MP: 66–68.5° C.; $^1$H NMR (CDCl$_3$): 11.70 (bs, 1H), 6.59 (s, 1H), 6.52 (s, 2H), 3.99 (t, J=6.06 Hz, 2H), 2.57 (t, J=7.29 Hz, 2H), 2.28 (s, 6H), 2.12–2.08 (m, 2H); Anal. calcd for $C_{12}H_{16}O_3$: C, 69.21; H, 7.74, Found: C, 69.23; H, 7.40.

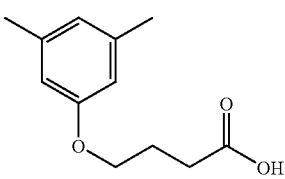

Part C—4-(4-(Chlorosulfonyl)-3,5-dimethylphenoxy)butanoic Acid

A solution of the product of Part B, above (20.8 g, 0.100 mol) in CHCl$_3$ (100 mL) was cooled to 0° C. and treated with chlorosulfonic acid (36 mL, 0.54 mol) dropwise and with rapid stirring while keeping the temperature of the reaction at 0° C. The resulting gelatinous mixture was stirred an additional 10 min and poured onto an ice/water mixture (600 mL). The resulting solid ppt was collected by filtration, washed with water (3×75 mL), and dried under vacuum to give a colorless solid (12.52 g). MP: 114–115° C. (with decomp); $^1$H NMR (CDCl$_3$): 13.84 (bs, 1H), 6.50 (s, 2H), 3.91 (t, J=6.48 Hz, 2H), 2.48 (s, 6H), 2.32 (t, J=7.32 Hz, 2H), 1.89–1.84 (m, 2H); IR (KBr cm$^{-1}$): 1705 (s), 1370 (s), 1175 (s) MS: m/e 305.1 [M−H].

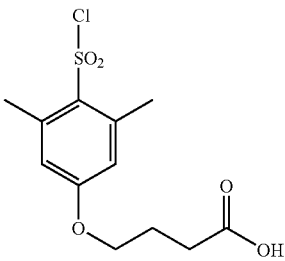

Part D—4-(4-(((2-((tert-Butoxy)carbonylamino)-1-(methoxycarbonyl)ethyl)amino)sulfonyl)-3,5-dimethylphenoxy)butanoic Acid A solution of N-β-Boc-L-α,β-diaminopropionic acid methyl ester hydrochloride (568 mg, 2.10 mmol) and DIEA (0.73 mL, 4.2 mmol) in DCM (5 mL) was cooled to 0° C. and treated with a suspension of the product of Part C, above (656 mg, 2.10 mmol) in DCM (20 mL) in small portions over a 15 min period. The reaction was stirred at ambient temperatures under a nitrogen atmosphere for 18 h. The reaction was diluted with DCM (100 mL) and washed with water (3×75 mL). The organic phase was dried (MgSO$_4$), and concentrated to give crude product (698 mg), which was purified by preparative HPLC on a Vydac C-18 column (50×250 mm) using a 0.96%/min gradient of 18 to 58.5% ACN containing 0.1% TFA at a flow rate of 80 mL/min. The main product fraction eluting at 23.8 min was collected adjusted to pH 3, partially concentrated to remove ACN, and extracted with DCM (2×100 mL). The DCM extracts were dried (MgSO$_4$) and concentrated to give the title compound as a colorless solid (297 mg, 29%). $^1$H NMR (CDCl$_3$): δ 6.61 (s, 2H), 5.66 (d, J=7.2 Hz, 1H), 4.90 (s, 1H), 4.03 (bs, 2H), 3.86 (bs, 1H), 3.59 (s, 3H), 3.49 (bs, 2H), 2.62 (s, 6H), 2.58–2.51 (m, 2H), 2.18–2.07 (m, 2H), 1.41 (s, 9H); MS: m/e 489.4 [M+H]; High Resolution MS: Calcd for C$_{21}$H$_{33}$N$_2$O$_9$S [M+Na]: 511.1726, Found: 511.1747; Anal. calcd for C$_{21}$H$_{32}$N$_2$O$_9$S: C, 51.62; H, 6.61; N, 5.74, Found: C, 51.47; H, 6.27; N, 5.48.

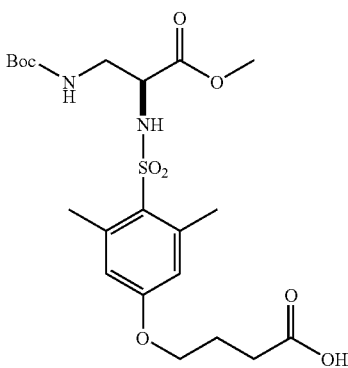

Part E—Methyl 3-((tert-Butoxy)carbonylamino)-2-(((2,6-dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)propanoate A solution of the product from Part D, above (233 mg, 0.477 mmol), the product of Example 1, Part A (190 mg, 0.536 mmol), TEA (0.2 mL, 1.43 mmol), and HBTU (226 mg, 0.701 mmol) in anhydrous DMF (8 mL) was stirred at ambient temperatures under a nitrogen atmosphere for 1 h. The DMF was removed under vacuum and the oily residue was taken up in EtOAc (50 mL) and washed consecutively with 0.1 N HCl (35 mL), water (35 mL), and saturated NaCl (35 mL), dried (MgSO$_4$), and concentrated to give crude product as a yellow viscous oil. Flash chromatography on a 3×18 cm silica gel column (EtOAc/MeOH, 95/5) gave the title compound as a colorless viscous oil (393 mg, 100%). $^1$H NMR (CDCl$_3$): δ 7.34–7.28 (m, 5H), 6.60 (s, 2H), 6.26 (bs, 1H), 5.67 (bs, 1H), 5.29 (bs, 1H), 5.08 (s, 2H), 4.88 (bs, 1H), 3.99 (t, J=6.1 Hz, 2H), 3.88–3.84 (m, 1H), 3.62–3.40 (m, 17H), 3.37–3.26 (m, 4H), 2.62 (s, 6H), 2.32 (t, J=7.2 Hz, 2H), 2.08 (t, J=6.3 Hz, 2H), 1.79–1.70 (m, 4H), 1.41 (s, 9H); MS: m/e 825.5 [M+H]; High Resolution MS: Calcd for C$_{39}$H$_{61}$N$_4$O$_{13}$S [M+H]: 825.3955, Found: 825.3940.

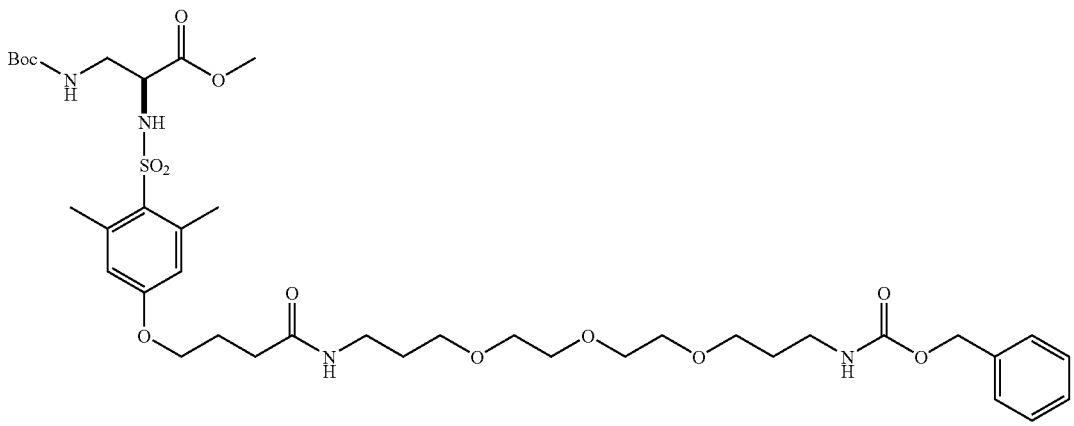

Part F—Methyl 3-Amino-2-(((2,6-dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)propanoate The product of Part E, above (750 mg, 0.91 mmol) was dissolved in 4 M HCl/dioxane (25 mL) and stirred at ambient temperatures for 1 h. The solution was diluted with ether (500 mL) and the resulting gummy ppt was triturated with fresh ether (2×250 mL). The gummy solid was dissolved in water (100 mL) and adjusted to pH 9 with NaHCO₃, causing an oily ppt to form. This ppt was extracted into DCM (2×75 mL). The DCM extracts were dried (MgSO₄) and concentrated to give the title compound as a colorless oil (386 mg, 56%). MS: m/e 725.5 [M+H].

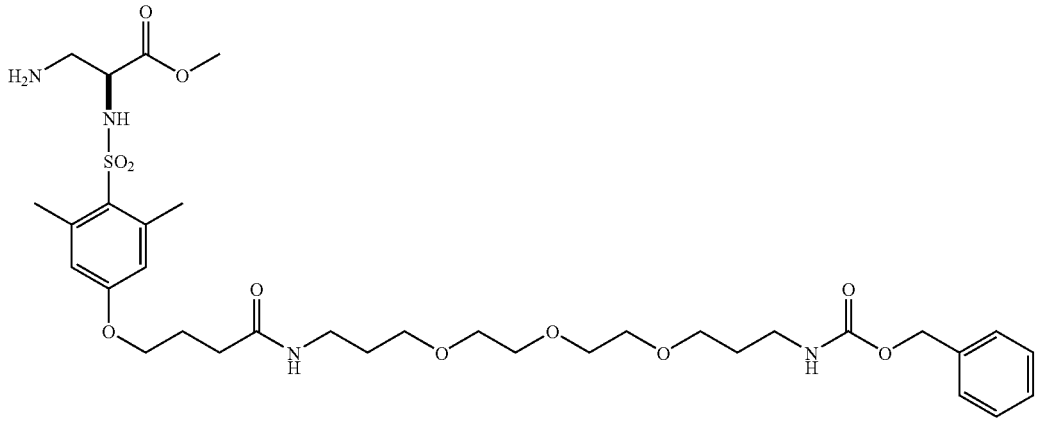

Part G—Methyl 2-(((2,6-Dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)-3-((1-methyl-4-oxo-7-(((1-(triphenylmethyl)imidazol-2-yl)amino)methyl)(3-hydroquinolyl))carbonylamino)propanoate A solution of 1-methyl-4-oxo-7-(((1-(triphenylmethyl)imidazol-2-yl)amino)methyl)hydroquinoline-3-carboxylic acid (274 mg, 0.51 mmol), TEA (0.22 mL, 1.52 mmol), and HBTU (192 mg, 0.51 mmol) in anhydrous DMF (3 mL) was stirred at ambient temperatures for 5 min. A solution of the product of Part F, above (367 mg, (0.51 mmol) in anhydrous DMF (7 mL) was added and the resulting solution was stirred at ambient temperatures under a nitrogen atmosphere for 2 h. The DMF was removed under vacuum and the resulting oily solid was dissolved in EtOAc (150 mL). The EtOAc solution was washed consecutively with water (50 mL), saturated NaHCO₃ (25 mL), and saturated NaCl (25 mL), dried (MgSO₄), and concentrated to give a yellow solid. Purification by flash chromatography on a silica gel column using a EtOAc/MeOH step gradient (95/5, 92.5/7.5) gave the title compound as a pale yellow solid (254 mg, 43%). MS: m/e 1247.7 [M+H], 624.6 [M+2H].

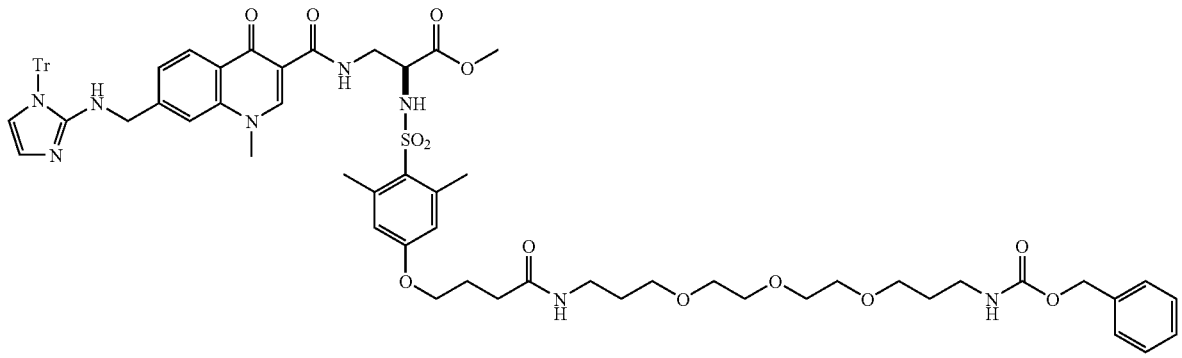

Part H—2-(((2,6-Dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)-3-((1-methyl-4-oxo-7-(((1-(triphenylmethyl)imidazol-2-yl)amino)methyl)(3-hydroquinolyl))carbonylamino)propanoic Acid The product of Part G, above (60.0 mg, 0.048 mmol) was dissolved in a mixture of peroxide-free THF (2.5 mL), water (0.37 mL), and 3 N LiOH (0.244 mL), and stirred at ambient temperatures under a nitrogen atmosphere for 30 min. The THF was removed under vacuum and the resulting mixture was dissolved in CHCl$_3$ (25 mL) and water (20 mL). The aqueous layer was adjusted to pH 3 with 0.1 N HCl and the layers were thoroughly mixed. The aqueous layer was extracted with additional CHCl$_3$ (2×20 mL). The combined CHCl$_3$ extracts were washed with saturated NaCl (30 mL), dried (MgSO$_4$), and concentrated to give the title compound as a pale yellow solid (44.0 mg, 74%). MS: m/e 1233.7 [M+H]; High Resolution MS: Calcd for C$_{67}$H$_{77}$N$_8$O$_{13}$S [M+H]: 1233.5330, Found: 1233.5330.

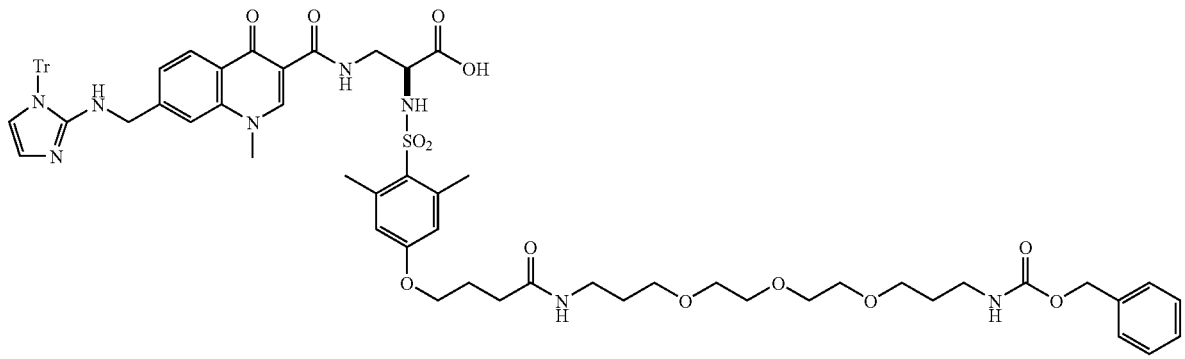

Part I—2-(((4-(3-(N-(3-(2-(2-(3-Aminopropoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid The product of Part H, above (42.1 mg, 0.0341 mmol) and Et$_3$SiH (0.033 mL, 0.205 mmol) were dissolved in degassed TFA (3.5 mL), heated at 70° C. under a nitrogen atmosphere for 1 h, and concentrated to give a viscous amber oil. This oil was dissolved in water (20 mL) and washed with ether (2×20 mL). The combined ether washings were back-extracted with water (10 mL). The combined water extracts were diluted with an equal volume of ACN and treated with Bio-Rad AG-3-X4A resin, hydroxide form to raise the pH from 4 to 6. The resin was removed by filtration and the filtrate was lyophilized to give the title compound as a colorless solid (34 mg). MS: m/e 857.5 [M+H], 429.4 [M+2H].

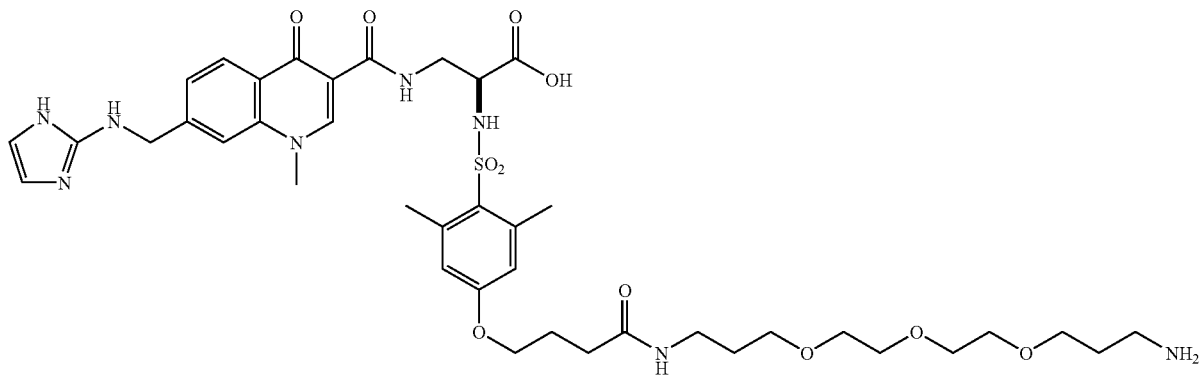

Part J—2-(((4-(3-(N-(3-(2-(2-(3-((6-((1-Aza-2-(2-sulfophenyl)vinyl)amino)(3-pyridyl))carbonylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt A solution of the product from Part I, above (30 mg, 0.035 mmol), DIEA (0.018 mL, 0.105 mmol) and 2-(2-aza-2-((5-((2,5-dioxopyrrolidinyl)carbonyl)(2-pyridyl))amino)vinyl) benzenesulfonic acid (18.5 mg, 0.042 mmol) in anhydrous DMF (1.5 mL) was allowed to stand at ambient temperatures under a nitrogen atmosphere for 20 h. The DMF was removed under vacuum and the amber oil was dissolved in 50% ACN and purified by preparative HPLC on a Zorbax C-18 RX column (21.2×250 mm) using a 1.5%/min gradient of 0 to 45% ACN containing 0.1% TFA at a flow rate of 20 mL/min. The main product peak eluting at 21.0 min was collected and lyophilized to give the title compound as a colorless powder (8.9 mg, 20%). MS: m/e 1160.6 [M+H], 581.0 [M+2H].

mopropyl)formamide (30.3 g, 0.127 mol), and anhydrous $K_2CO_3$ (12.5 g, 0.904 mol) in anhydrous DMF (200 mL) was stirred at 60° C. under a nitrogen atmosphere for 4 h, and then at ambient temperatures for 72 h. The DMF was removed under vacuum and the resulting oily solid was dissolved in EtOAc (500 mL). The EtOAc solution was washed consecutively with water (500 mL), saturated $NaHCO_3$ (500 mL), and saturated NaCl (500 mL), dried ($MgSO_4$), and concentrated to give a red oil. This oil was taken up in EtOAc (250 mL) and cooled, causing a solid ppt to form. This ppt was collected by filtration, washed with cold EtOAc, and dried to give the title compound as a colorless solid (6.25 g, 65%). MP: 140–142° C.; $^1$H NMR ($CDCl_3$): 8.49 (s, 1H), 8.39 (d, J=8.6 Hz, 1H), 7.58 (s, 1H), 7.53 (d, J=8.6 Hz, 1H), 4.72 (bs, 1H), 4.39 (q, J=7.1 Hz, 2H), 4.20 (t, J=7.6 Hz, 2H), 3.28–3.24 (m, 2H), 2.10–2.06 (m, 2H), 1.46 (s, 9H), 1.40 (t, J=7.1 Hz, 3H); MS: m/e 455.2. [M+H]; High Resolution MS: Calcd for $C_{20}H_{26}BrN_2O_5$ [M+H]: 453.1025, Found: 453.1028.

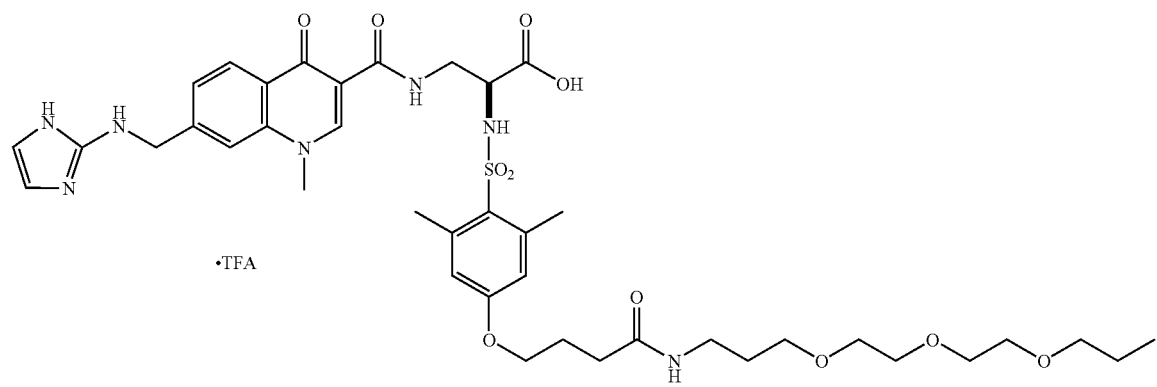

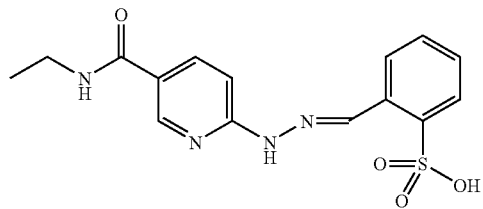

Example 4

3-((1-(3-((6-((1-Aza-2-(2-sulfophenyl)vinyl)amino)(3-pyridyl))carbonylamino)propyl)-7-((imidazole-2-ylamino)methyl)-4-oxo(3-hydroquinolyl))carbonylamino)-2-(((2,4,6-trimethylphenyl)sulfonyl)amino) propanoic Acid Trifluoroacetate Salt Part A—Ethyl 1-(3-((tert-Butoxy)carbonylamino)propyl)-7-bromo-4-oxohydroquinoline-3-carboxylate A mixture of ethyl 7-bromo-4-oxohydroquinoline-3-carboxylate (6.28 g, 0.0212 mol), (tert-butoxy)-N-(3-bro-

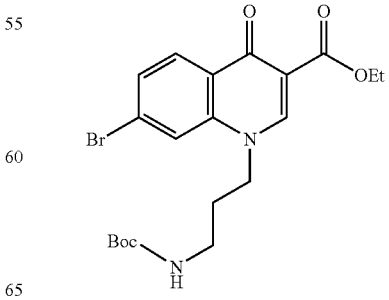

Part B—Ethyl 1-(3-((tert-Butoxy)carbonylamino) propyl)-4-oxo-7-vinylhydroquinoline-3-carboxylate The product from Part A, above (2.98 g, 6.60 mmol) was dissolved in toluene (50 mL) at a temperature of 100° C. and treated with tetrakis(triphenylphosphine)palladium(0) (152 mg, 0.132 mmol). After 5 min the mixture was treated with tributyl(vinyl)tin (1.93 mL, 6.60 mmol) and stirred 4.5 h at 100° C. under a nitrogen atmosphere, and 18 h at ambient temperatures. Additional tributyl(vinyl)tin (0.386 mL) and tetrakis(triphenylphosphine)palladium(0) (152 mg) were added and the mixture was heated at 100° C. for an additional 17 h. The toluene was removed under vacuum and the solid residue was triturated with ether to give the title compound as a pale green solid (1.67 g, 63%). MP: 133–135° C.; $^1$H NMR (CDCl$_3$): 8.52 (d, J=8.4 Hz, 1H), 8.51 (s, 1H), 7.55 (d, J=8.4 Hz, 1H), 7.38 (s, 1H), 6.88–6.82 (m, 1H), 5.97 (d, J=17.4 Hz, 1H), 5.51 (d, J=10.8 Hz, 1H), 4.75 (bs, 1H), 4.42 (q, J=7.2 Hz, 2H), 4.27 (t, J=7.8 Hz, 2H), 3.6–3.25 (m, 2H), 2.16–2.11 (m, 2H), 1.49 (s, 9H), 1.45 (t, J=7.2 Hz, 3H); MS: m/e 401.3 [M+H]; High Resolution MS: Calcd for C$_{22}$H$_{29}$N$_2$O$_5$ [M+H]: 401.2076, Found: 401.2075.

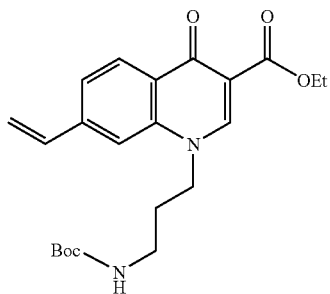

Part C—Ethyl 1-(3-((tert-Butoxy)carbonylamino) propyl)-7-formyl-4-oxohydroquinoline-3-carboxylate A solution of the product of Part B, above (1.50 g, 3.75 mmol) in dioxane (119 mL) and water (39 mL) was treated with a solution of osmium tetroxide (19.6 mg, 0.077 mmol) in dioxane (0.600 mL) and stirred at ambient temperatures under a nitrogen atmosphere for 5 min. Sodium periodate (2.40 g, 11.2 mmol) was added and the stirred at ambient temperatures for 2 h. The dioxane was removed under vacuum and the residue was taken up in DCM (500 mL). The DCM solution was washed consecutively with water (500 mL) and saturated NaCl (500 mL), dried (MgSO$_4$), and concentrated to give the title compound as an orange oily solid (1.52 g, 100%). $^1$H NMR (CDCl$_3$): 10.17 (s, 1H), 8.68 (d, J=8.2 Hz, 1H), 8.64 (s, 1H), 8.01 (s, 1H), 7.88 (d, J=8.2 Hz, 1H), 4.82 (bs, 1H), 4.41–4.35 (m, 4H), 3.28 (s, 2H), 2.15–2.07 (m, 2H), 1.45 (s, 9H), 1.41 (t, J=7.1 Hz, 3H); MS: m/e 403.3 [M+H]; High Resolution MS: Calcd for C$_{21}$H$_{27}$N$_2$O$_6$ [M+H]: 403.1870, Found: 403.1875.

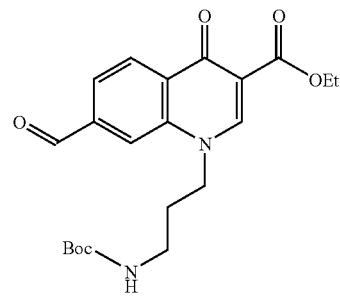

Part D—Ethyl 1-(3-((tert-Butoxy)carbonylamino) propyl)-4-oxo-7-(((1-(triphenylmethyl)imidazole-2-yl)amino)methyl)hydroquinoline-3-carboxylate A solution of the product of Part C, above (544 mg, 1.35 mmol) and 1-(triphenylmethyl)imidazole-2-ylamine (456 mg, 1.35 mmol) in toluene (60 mL) was heated at reflux under a nitrogen atmosphere with removal of water for 5 h. The solution was cooled, treated with Na(OAc)$_3$BH (1.14 g, 5.38 mmol) and stirred at ambient temperatures for 18 h. The mixture was diluted with EtOAc (400 mL), washed consecutively with water (500 mL) and saturated NaCl (500 mL), dried (MgSO$_4$), and concentrated to give an orange solid. This solid was dissolved in 50% ACN and purified by preparative HPLC on a Vydac C-18 column (50×250 mm) using a 0.60%/min gradient of 18 to 52% ACN containing 0.1% TFA at a flow rate of 49 mL/min. The main product peak eluting at 30.8 min was collected and lyophilized to give the title compound as a pale yellow solid (407 mg, 60%). MS: m/e 712.4 [M+H]; High Resolution MS: Calcd for C$_{43}$H$_{46}$N$_5$O$_5$ [M+H]: 712.3499, Found: 712.3485.

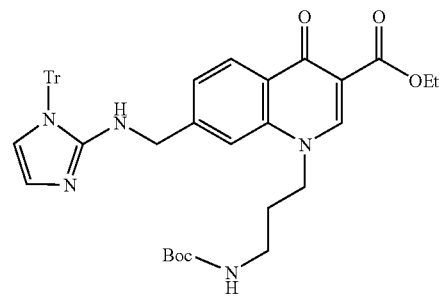

Part E—1-(3-((tert-Butoxy)carbonylamino)propyl)-4-oxo-7-(((1-(triphenylmethyl)imidazole-2-yl)amino)methyl)hydroquinoline-3-carboxylic Acid A mixture of the product of Part D, above (997 mg, 1.40 mmol), water (7.3 mL), 3 N LiOH (3.5 mL), and THF (50 mL) was stirred at ambient temperatures under a nitrogen atmosphere for 3 h. The THF was removed under vacuum and the resulting mixture was dissolved in CHCl$_3$ (500 mL) and water (100 mL). The aqueous layer was adjusted-to pH 3 with 1.0 N HCl and the layers were thoroughly mixed. The organic layer was washed consecutively with water (500 mL) and saturated NaCl (500 mL), dried (MgSO$_4$), and concentrated to give the title compound as a pale yellow solid (998 mg). MP: 153–160° C.; $^1$H NMR (CDCl$_3$): δ 14.83 (s, 1H), 8.76 (s, 1H), 8.68 (s, 1H), 824 (d, J=6 Hz, 1H), 7.49–7.35 (m, 9H), 7.12–7.10 (m, 6H), 6.82 (s, 1H), 6.52 (s, 1H), 6.24 (d, J=6 Hz, 1H), 5.75 (bs, 1H), 4.87–4.83 (m, 2H), 4.77 (bs, 1H), 4.51 (t, J=9 Hz, 2H), 3.38 (s, 2H), 2.23 (s, 2H), 1.42 (s, 9H); MS: m/e 684.3 [M+H]; High Resolution MS: Calcd for C$_{41}$H$_{42}$N$_5$O$_5$ [M+H]: 684.3186, Found: 684.3181.

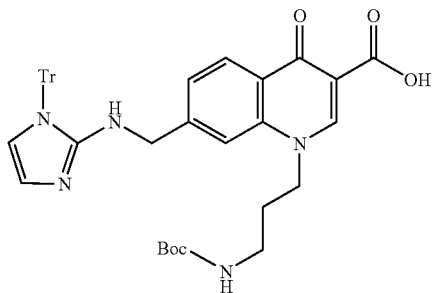

Part F—Methyl 3-((1-(3-((tert-Butoxy)carbonylamino)propyl)-4-oxo-7-(((1-(triphenylmethyl)imidazole-2-yl)amino)methyl)(3-hydroquinolyl))carbonylamino)-2-(((2,4,6-trimethylphenyl)sulfonyl)amino)propanoate A solution of the product of Part E, above (300 mg, 0.437 mmol), TEA (0.243 mL, 1.75 mmol), and HBTU (230 mg, 0.606 mmol) in anhydrous DMF (4 mL) was stirred at ambient temperatures for 5 min. A solution of methyl 3-amino-2-(((2,4,6-trimethylphenyl)sulfonyl)amino)propanoate hydrochloride (184 mg, 0.637 mmol) in anhydrous DMF (3 mL) was added and the solution was stirred at ambient temperatures under a nitrogen atmosphere for 2 h. The solution was diluted with EtOAc (200 mL) and washed consecutively with water (2×50 mL), saturated NaHCO$_3$ (50 mL), and saturated NaCl (50 mL), dried (MgSO$_4$), and concentrated to give a viscous amber oil. Purification by flash chromatography on a 2.5×24 cm silica gel column using a EtOAc/MeOH step gradient (98/2, 95/5, 75/25) gave the title compound as a pale yellow oil (330 mg, 78%). MS: m/e 966.6 [M+H]; High Resolution MS: Calcd for C$_{54}$H$_{60}$N$_7$O$_8$S [M+H]: 966.4224, Found: 966.4224.

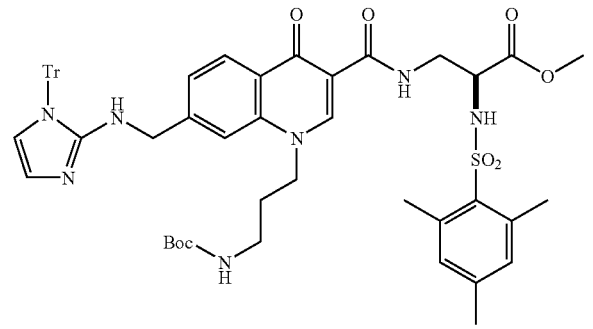

Part G—3-((1-(3-((tert-Butoxy)carbonylamino)propyl)-4-oxo-7-(((1-(triphenylmethyl)imidazole-2-yl)amino)methyl)(3-hydroquinolyl))carbonylamino)-2-(((2,4,6-trimethylphenyl)sulfonyl)amino)propanoic Acid A solution of the product of Part F, above (51 mg, 0.052 mmol), water (0.27 mL), and 3 N LiOH (0.13 mL) in MeOH (2 mL) was allowed to stand at ambient temperatures for 3.5 h and concentrated under vacuum. The resulting solid was dissolved in water (10 mL) and adjusted to pH 3 with 1.0 N HCl. The aqueous mixture was extracted with DCM (2×30 mL). The combined DCM extracts were washed with saturated NaCl (30 mL), dried (MgSO$_4$), and concentrated to give the title compound as a colorless solid (72 mg). MS: m/e 952.5 [M+H]; High Resolution MS: Calcd for C$_{53}$H$_{58}$N$_7$O$_8$S [M+H]: 952.4067, Found: 952.4056.

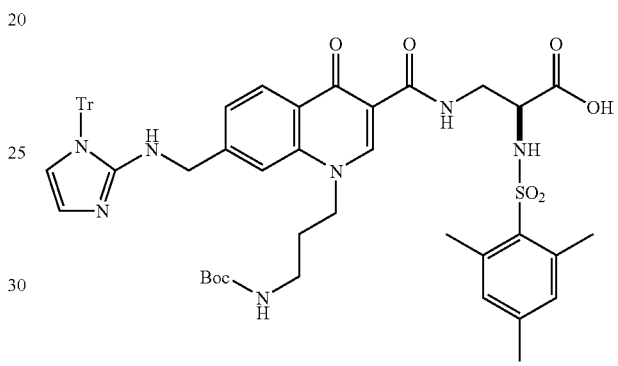

Part H—3-((1-(3-Aminopropyl)-7-((imidazole-2-ylamino)methyl)-4-oxo(3-hydroquinolyl))carbonylamino)-2-(((2,4,6-trimethylphenyl)sulfonyl)amino)propanoic Acid Bis(trifluoroacetate) Salt The product of Part I, above (0.052 mmol) and Et$_3$SiH (0.042 mL, 0.26 mmol) were dissolved in degassed TFA (2 mL), heated at 70° C. for 2.5 h, and concentrated to give an amber oil. This oil was dissolved in water (25 mL) and washed with ether (2×15 mL). The combined ether washings were back-extracted with water (15 mL). The combined water extracts were lyophilized to give the title compound as a colorless powder (34 mg, 78%). MS: m/e 610.4 [M+H]; High Resolution MS: Calcd for C$_{29}$H$_{36}$N$_7$O$_6$S [M+H]: 610.2448, Found: 610.2462.

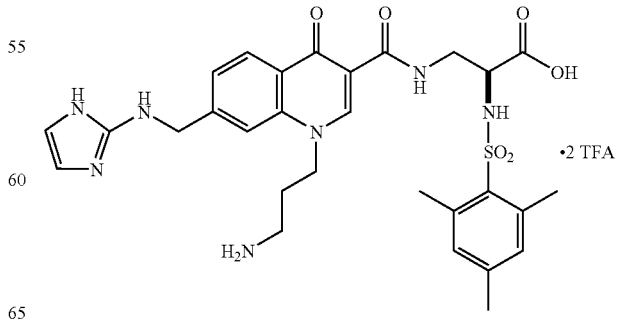

Part I—3-((1-(3-((6-((1-Aza-2-(2-sulfophenyl)vinyl)amino)(3-pyridyl))carbonylamino)propyl)-7-((imidazole-2-ylamino)methyl)-4-oxo(3-hydroquinolyl))carbonylamino)-2-(((2,4,6-trimethylphenyl)sulfonyl)amino)propanoic Acid Trifluoroacetate Salt A solution of the product of Part H, above (13.7 mg, 0.0163 mmol), TEA (0.015 mL, 0.108 mmol), and 2-(2-aza-2-((5-((2,5-dioxopyrrolidinyl)carbonyl)(2-pyridyl))amino)vinyl)benzenesulfonic acid (8.2 mg, 0.0186 mmol) in anhydrous DMF (2.0 mL) was allowed to stand at ambient temperatures under a nitrogen atmosphere for 24 h. The DMF was removed under reduced pressure and the amber oil was dissolved in 50% ACN and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 21.4 min was collected and lyophilized to give the title compound as a colorless powder (12.5 mg, 75%). MS: m/e 913.3 [M+H]; High Resolution MS: Calcd for $C_{42}H_{45}N_{10}O_{10}S_2$ [M+H]: 913.2761, Found: 913.2751.

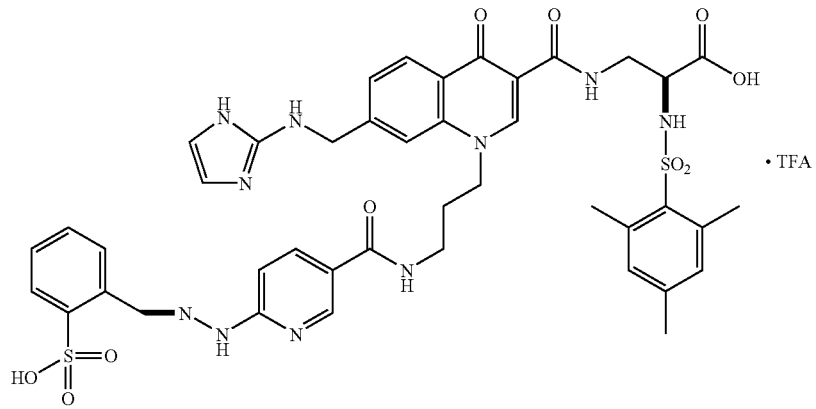

Example 5

3-((1-(3-((6-((1-Aza-2-(2-sulfophenyl)vinyl)amino)(3-pyridyl))carbonylamino)propyl)-7-(((1-hydroxyimidazole-2-yl)amino)methyl)-4-oxo(3-hydroquinolyl))carbonylamino)-2-(((2,4,6-trimethylphenyl)sulfonyl)amino)propanoic Acid Trifluoroacetate Salt Part A—Methyl 3-((1-(3-Aminopropyl)-7-((imidazole-2-ylamino)methyl)-4-oxo(3-hydroquinolyl))carbonylamino)-2-(((2,4,6-trimethylphenyl)sulfonyl)amino)propanoate Bis(trifluoroacetate) Salt A solution of the product of Example 4, Part F (120 mg, 0.124 mmol) and Et₃SiH (0.99 mL, 6.20 mmol) in TFA (10 mL) was heated at 70° C. for 1 h, and concentrated to give an amber oil. This oil was dissolved in water (50 mL) and washed with ether (2×30 mL). The combined ether washings were back-extracted with water (20 mL). The combined water extracts were lyophilized to give the title compound as a colorless powder (105 mg, 100%). MS: m/e 624.4 [M+H]; High Resolution MS: Calcd for $C_{30}H_{38}N_7O_6S$ [M+H]: 624.2604, Found: 624.2608.

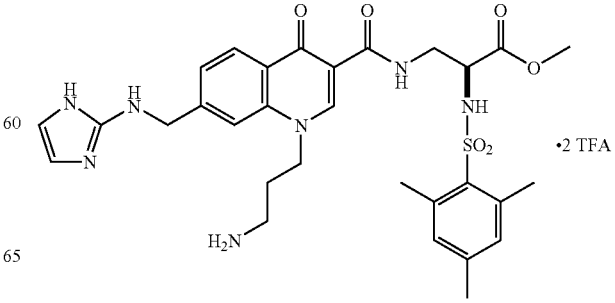

Part B—3-((1-(3-Aminopropyl)-7-(((1-hydroxyimidazol-2-yl)amino)methyl)-4-oxo(3-hydroquinolyl))carbonylamino)-2-(((2,4,6-trimethylphenyl)sulfonyl)amino)propanoic Acid Trifluoroacetate Salt A mixture of the product of Part A, above (105 mg, 0.126 mmol), water (3.0 mL), and 3 N LiOH (1.82 mL) in peroxide-containing THF (4 mL) was allowed to stand at ambient temperatures for 1 h and concentrated under vacuum. The resulting solid was dissolved in water (10 mL) and adjusted to pH 5 with 1.0 N HCl. Insoluble impurities were removed by filtration and the filtrate was lyophilized to give a colorless solid. This solid was dissolved in water and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 19.5 min was collected and lyophilized to give the title compound as a colorless powder (10.0 mg, 11%). MS: m/e 314.0 [M+2H]

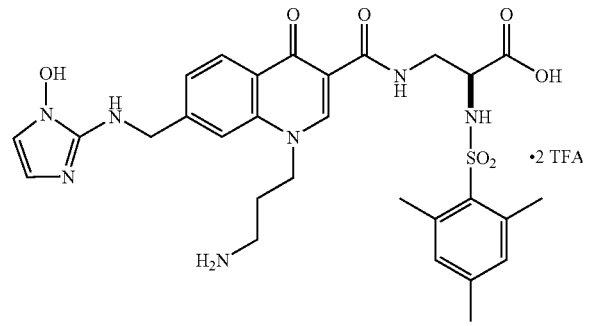

Part C—3-((1-(3-((6-(((1-Aza-2-(2-sulfophenyl)vinyl)amino)(3-pyridyl))carbonylamino)propyl)-7-(((1-hydroxyimidazol-2-yl)amino)methyl)-4-oxo(3-hydroquinolyl))carbonylamino)-2-(((2,4,6-trimethylphenyl)sulfonyl)amino)propanoic Acid Trifluoroacetate Salt A solution of the product of Part B, above (10.0 mg, 0.0135 mmol), TEA (0.018 mL, 0.129 mmol), and 2-(2-aza-2-((5-((2,5-dioxopyrrolidinyl)carbonyl)(2-pyridyl))amino) vinyl)benzenesulfonic acid (7.2 mg, 0.0163 mmol) in anhydrous DMF (4 mL) was allowed to stand at ambient temperatures under a nitrogen atmosphere for 20 h. The DMF was removed under vacuum and the amber oil was dissolved in 30% ACN and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 21.5 min was collected and lyophilized to give the title compound as a colorless powder (3.5 mg, 25%). MS: m/e 929.4 [M+H]; High Resolution MS: Calcd for $C_{42}H_{45}N_{10}O_{11}S_2$ [M+H]: 929.2710, Found: 929.2698.

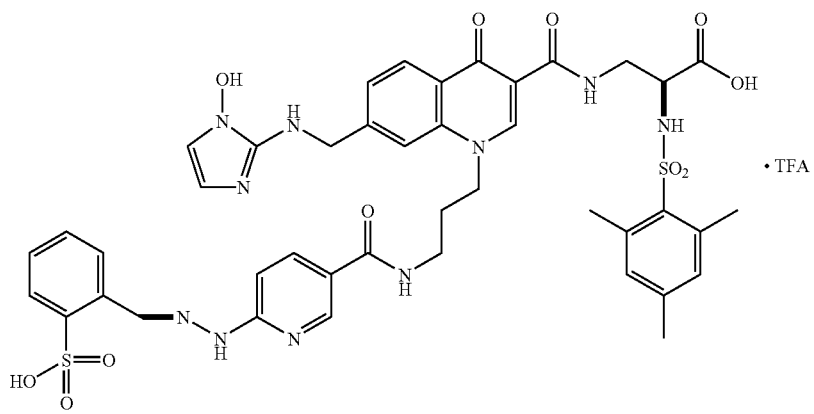

Example 6

3-((1-(3-(3-(N-(3-(2-(2-(3-(((6-(((1-Aza-2-(2-sulfophenyl)vinyl)amino)(3-pyridyl))carbonylamino)propoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic Acid Trifluoroacetate Salt

Part A—3-(N-(3-(2-(2-(3-((tert-Butoxy)carbonylamino)propoxy)ethoxy)ethoxy)propyl)carbamoyl) propanoic Acid A solution of N-(3-(2-(2-(3-aminopropoxy)ethoxy)ethoxy)propyl)(tert-butoxy)formamide (as described by D. S. Wilbur et al. in *Bioconjugate Chem.* 1998, 9, 322–330) (2.00 g, 6.24 mmol), TEA (1.0 mL, 7.49 mmol), and succinic anhydride (624 mg, 6.24 mmol) in anhydrous DMF (5 mL) was stirred at ambient temperatures under a nitrogen atmosphere for 4 h. The DMF was removed under reduced pressure to give the title compound as a pale yellow oil (2.80 g). MS: m/e 839.5 [2M−H], 419.4 [M−H].

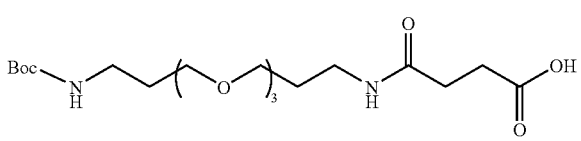

Part B—Methyl 3-((1-(3-(3-(N-(3-(2-(2-(3-((tert-Butoxy)carbonylamino)propoxy)ethoxy)ethoxy)propyl)carbamo yl)propanoylamino)propyl-4-oxo-7-(((1-(triphenylmethyl)imidazole-2-yl)amino)methyl)(3-hydroquinolyl))carbonylamino)-2-(((2,4,6-trimethylphenyl)sulfonyl)amino)propanoate The product of Example 4, Part F (46.1 mg, 0.477 mmol) was dissolved in 50% TFA/DCM (2.0 mL) for 15 min at ambient temperatures and concentrated to give a yellow oil. This oil was dissolved in anhydrous DMF (1.0 mL) and made basic to pH paper with TEA. In a separate flask, the product of Part A, above (26.1 mg, 0.062 mmol), TEA (0.014 mL, 0.099 mmol), and HBTU (27.7 mg, 0.074 mmol) were dissolved in anhydrous DMF (1.0 mL). The resulting solution was allowed to react for 5 min and combined with the DMF solution from the TFA deprotection reaction. The combined solutions were allowed to stand at ambient temperatures under a nitrogen atmosphere for 20 min and concentrated under vacuum. The resulting oil was dissolved in 50% ACN and purified by preparative HPLC on a Vydac C-18 column (22×250 mm) using a 1.8%/min gradient of 18 to 72% ACN containing 0.1% TFA at a flow rate of 20 mL/min. The main product peak eluting at 26.8 min was collected and lyophilized to give the title compound as a colorless powder (44.5 mg, 68%). MS: m/e 1268.6 [M+H]; High Resolution MS: Calcd for $C_{68}H_{86}N_9O_{13}S$ [M+H]: 1268.6065, Found: 1268.6070.

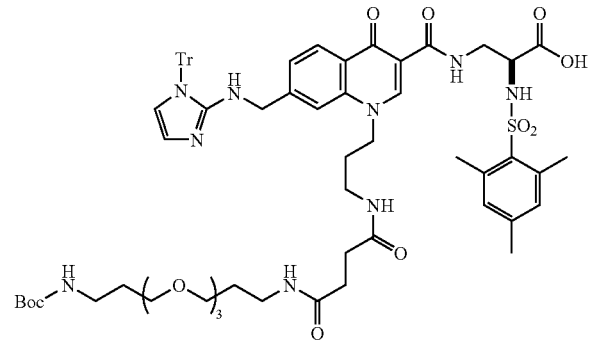

Part D—3-((1-(3-(3-(N-(3-(2-(2-(3-aminopropoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic Acid Bis(trifluoroacetate) Salt A solution of the product of Part C, above (24.6 mg, 0.0194 mmol) and Et₃SiH (0.016 mL, 0.097 mmol) in TFA (2.0 mL) was heated at 70° C. under a nitrogen atmosphere for 3 h, and concentrated to give a yellow solid. This solid

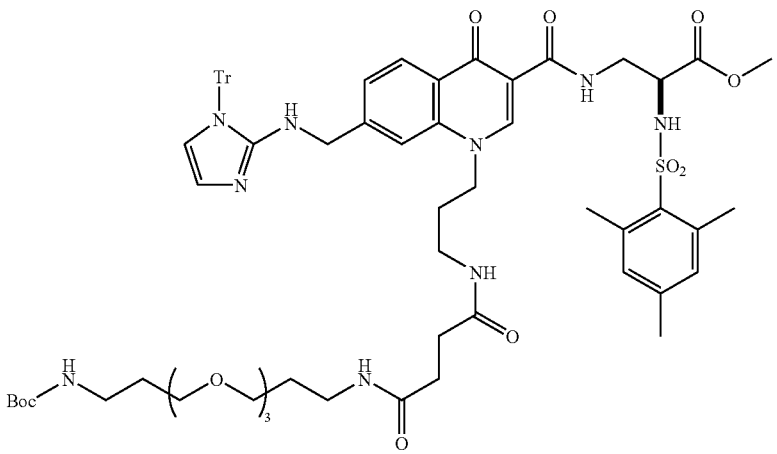

Part C—(2S)-3-[(1-{3-[3-(N-{3-[2-(2-{3-[(tert-Butoxy)carbonylamino]propoxy}ethoxy)ethoxy]propyl}carbamoyl)propanoylamino]propyl}-4-oxo-7-({[1-(triphenylmethyl)imidazole-2-yl]amino}methyl)(3-hydroquinolyl))carbonylamino]-2-{[(2,4,6-trimethylphenyl)sulfonyl]amino}propanoic Acid A solution of the product of Part B, above (31.1 mg, 0.0227 mmol), 3 n LiOH (0.091 mL), and water (0.117 mL) in MeOH (1.30 mL) was stirred at ambient temperatures for 8.5 h. The MeOH was removed under vacuum and the aqueous mixture was diluted with water (30 mL) and adjusted to pH 4 with 1.0 N HCl. The resulting aqueous mixture was extracted with DCM (2×50 mL). The combined DCM extracts were washed with saturated NaCl (50 mL), dried (MgSO₄), and concentrated to give the title compound as a colorless solid (24.6 mg, 86%).

was dissolved in water (50 mL) and washed with ether (2×25 mL). The aqueous layer was lyophilized to give the title compound as a pale yellow solid (20.7 mg, 93%). MS: m/e 912.5 [M+H].

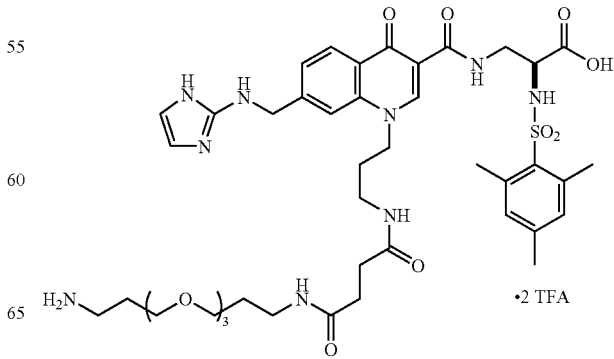

Part E—3-((1-(3-(3-(N-(3-(2-(2-(3-((6-((1-Aza-2-(2-sulfophenyl)vinyl)amino)(3-pyridyl))carbonylamino)propoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic Acid Trifluoroacetate Salt A solution of the product of Part D, above (15.5 mg, 0.0136 mmol), TEA (0.010 mL, 0.0746 mmol), and 2-(2-aza-2-((5-((2,5-dioxopyrrolidinyl)carbonyl)(2-pyridyl))amino)vinyl)benzenesulfonic acid (8.0 mg, 0.0182 mmol) in anhydrous DMF (2.0 mL) was allowed to stand at ambient temperatures under a nitrogen atmosphere for 24 h. The DMF was removed under vacuum and the resulting yellow oil was dissolved in 50% ACN and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 21.7 min was collected and lyophilized to give the title compound as a colorless powder (7.2 mg, 40%). MS: m/e 1215.5 [M+H]; High Resolution MS: Calcd for $C_{56}H_{71}N_{12}O_{15}S_2$ [M+H]: 1215.4603, Found: 1215.4580.

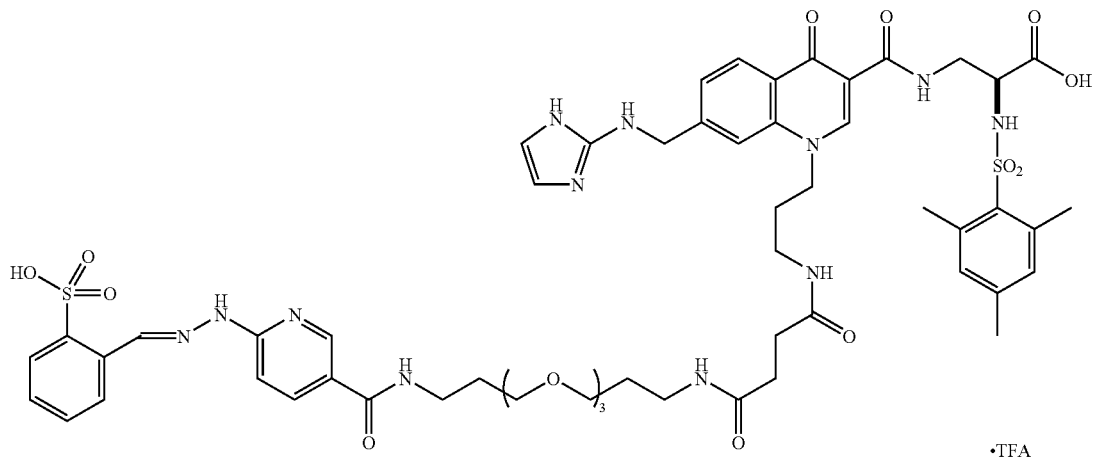

Example 7

2-(2-Aza-2-(5-(N-(1,3-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy)ethoxy)ethoxy)propyl)carbamoyl)(2-pyridyl))amino)vinyl)benzenesulfonic Acid Bis(trifluoroacetate) Salt Part A—N,N'-Bis(3-(2-(2-(3-(3-(N-(3-(3-(N-(3-carbomethoxy-2-(((2,4,6-trimethylphenyl) sulfonyl)amino)ethyl)carbamoyl)-4-oxo-7-(((1-(triphenylmethyl)imidazole-2-yl)amino)methyl)hydroquinolyl)propyl)carbamoyl)propanoylamino)propoxy)ethoxy)ethoxy)propyl)-2-((tert-butoxy)carbonylamino)pentane-1,5-diamide A solution of the product of Example 6, Part B (50.5 mg, 0.0398 mmol) in 50/50 TFA/DCM (2 mL) was allowed to react for 20 min at ambient temperatures and concentrated to a viscous oil. This oil was taken up in anhydrous DMF and made basic to pH paper with TEA. This solution was treated with Boc-L-Glu-OH (4.5 mg, 0.0181 mmol) and HBTU (16.6 mg, 0.0438 mmol), and allowed to stand at ambient temperatures for 2 h. The DMF was removed under vacuum and the resulting oil was dissolved in 60% ACN and purified by preparative HPLC on a Vydac C-18 column (22×250 mm) using a 1.8%/min gradient of 18 to 72% ACN containing 0.1% TFA at a flow rate of 20 mL/min. The main product peak eluting at 21.5 min was collected and lyophilized to give the title compound as a colorless powder (38.8 mg, 84%). MS: m/e 2306.5 [M+H−Tr], 2064.4 [M+H−2Tr], 1275.0 [M+2H]; High Resolution MS: Calcd for $C_{117}H_{154}N_{19}OS_2$ [M+H−Tr]: 2305.0753, Found: 2305.0770.

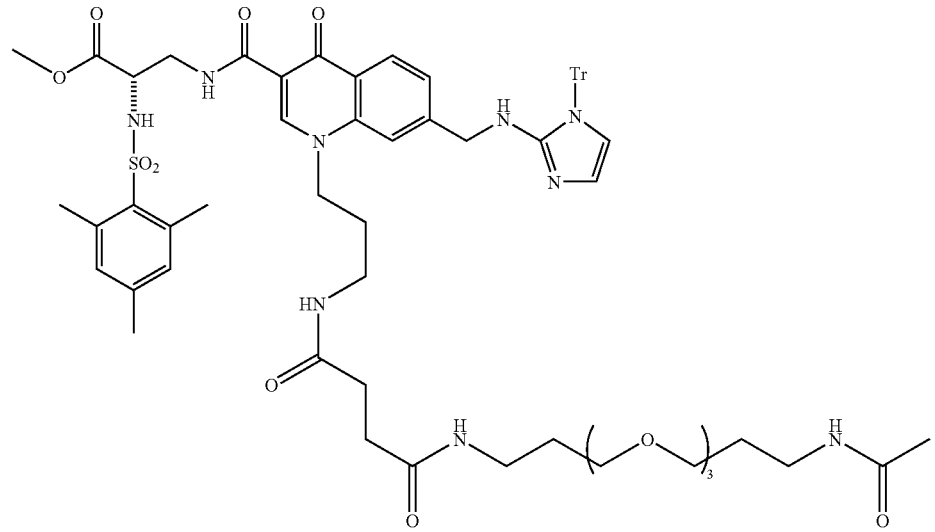

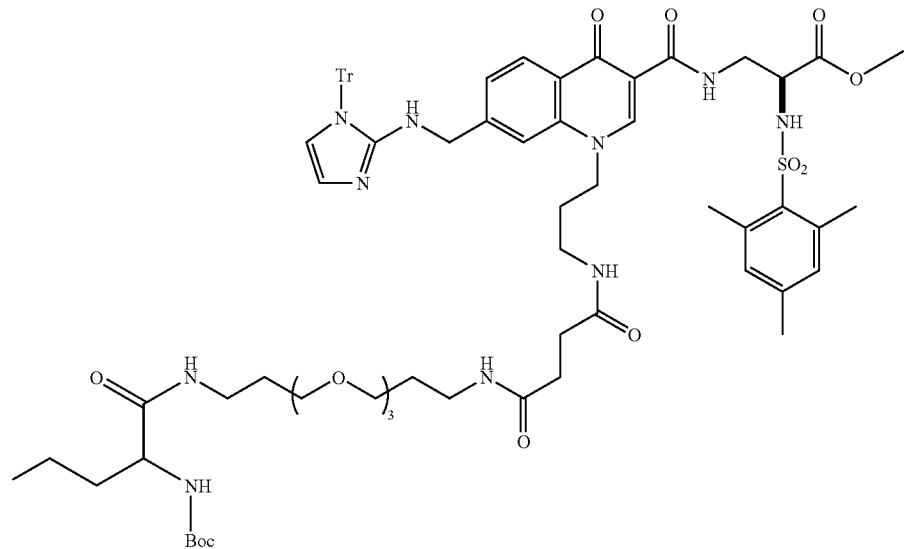

Part B—2-Amino-N,N'-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy) ethoxy)ethoxy)propyl) pentane-1,5-diamide Tris(trifluoroacetate) Salt A solution of the product from Part A, above (38.8 mg, 0.0152 mmol), 3 N LiOH (0.075 mL), and water (0.156 mL) in MeOH (2.0 mL) was stirred at ambient temperatures for 18 h. The MeOH was removed under vacuum and the aqueous mixture was diluted with water (50 mL) and adjusted to pH 3 using 0.5 N HCl. The mixture was extracted with DCM (2×50 mL). The combined DCM extracts were washed with saturated NaCl (50 mL), dried (MgSO₄), and concentrated to give a colorless solid. This solid was dissolved in TFA (3.0 mL) along with Et₃SiH (0.031 mL, 0.178 mol), heated at 70° C. under a nitrogen atmosphere for 11 h, and concentrated to give a yellow oil. This oil was dissolved in water (25 mL) and washed with ether (2×25 mL). The aqueous solution was lyophilized to give a pale yellow solid. This solid was dissolved in water and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 22.4 min was collected and lyophilized to give the title compound as a colorless powder (5.1 mg, 18%). MS: m/e 968.2 [M+2H], 646.0 [M+3H].

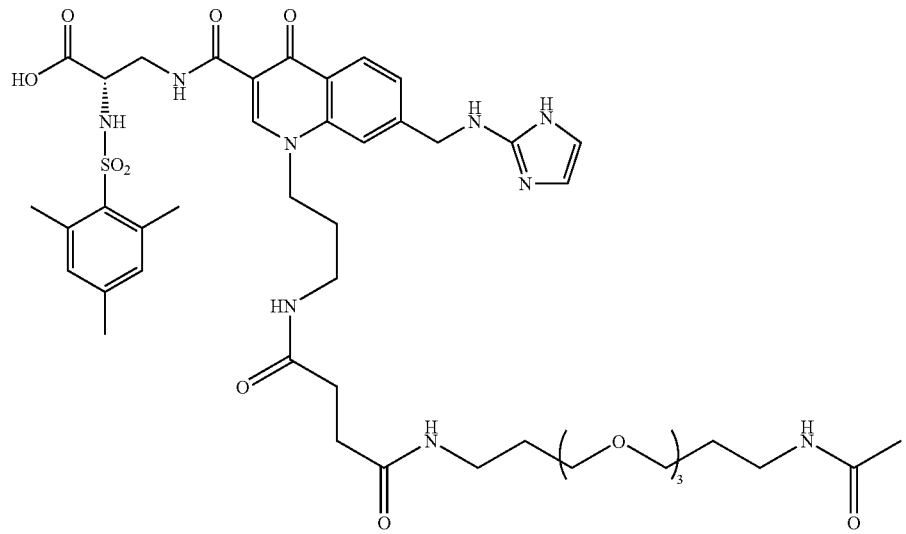

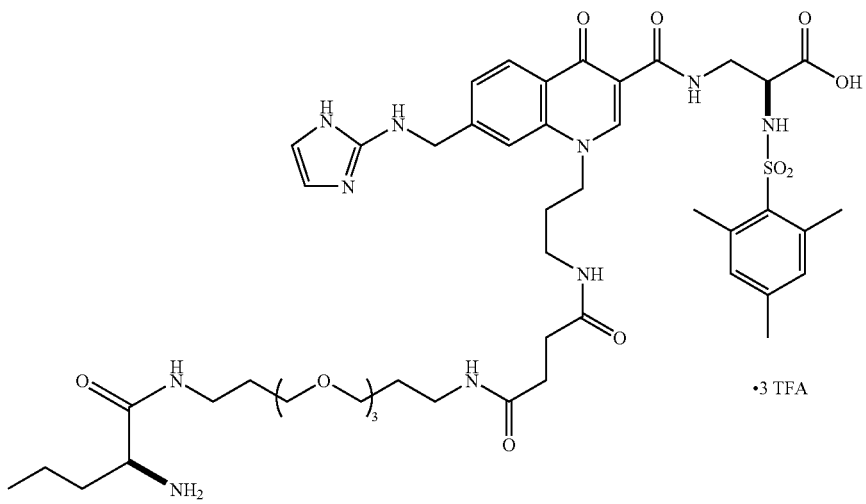

Part C—2-(2-Aza-2-(5-(N-(1,3-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy) ethoxy) ethoxy)propyl)carbamoyl)(2-pyridyl))amino)vinyl) benzenesulfonic Acid Bis(trifluoroacetate) Salt A solution of the product of Part B, above (5.1 mg, 0.00224 mmol), TEA (0.002 mL, 0.0115 mmol), and 2-(2-aza-2-((5-(((2,5-dioxopyrrolidinyl)carbonyl)(2-pyridyl)) amino)vinyl)benzenesulfonic acid (1.2 mg, 0.00272 mmol) in anhydrous DMF (2.0 mL) was allowed to stand at ambient temperatures under nitrogen for 72 h. The DMF was removed under vacuum and the resulting oil was dissolved in 50% ACN and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 23.5 min was collected and lyophilized to give the title compound as a colorless powder (0.5 mg, 9.0%). MS: m/e 1120.0 [M+2H]; High Resolution MS: Calcd for $C_{104}H_{137}N_{22}O_{28}S_3$ [M+]: 2237.9055, Found: 2237.9120.

123
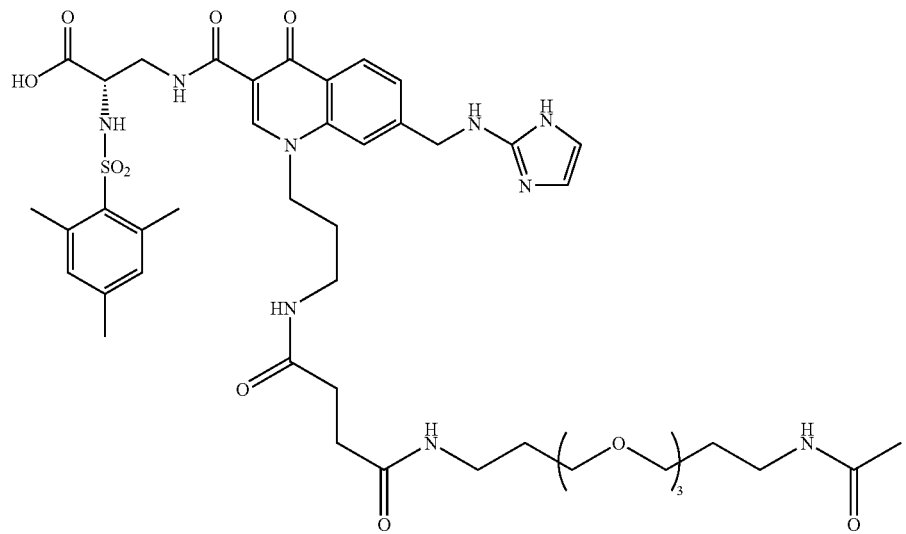
124
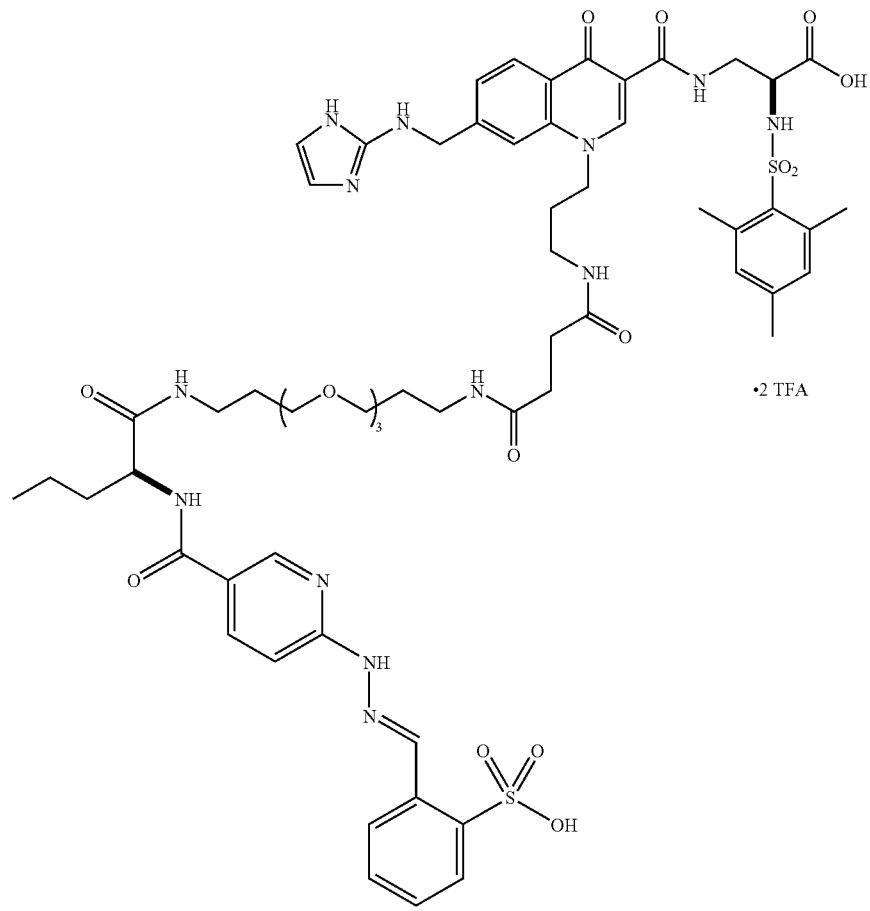
•2 TFA

Example 8

DOTA Conjugate of 3-((1-(3-(3-(N-(3-(2-(2-(N-(L-Asp-L-Asp)3-aminopropoxy)ethoxy)propyl)carbamoyl)propanoylamino)propyl)-7-((imidazole-2-ylamino)methyl)-4-oxo-(3-hydroquinolyl))carbonylamino)-2-(((2,4,6-trimethylphenyl)sulfonyl)amino)propanoic Acid Bis(trifluoroacetate) Salt

Part A—Carbobenzyloxy-L-Asp(O-t-Bu)-L-Asp(O-t-Bu)-OMe

A solution of Cbz-Asp(O-t-Bu)-OH (1.54 g, 4.76 mmol), H-Asp(O-t-Bu)-OMe.HCl (1.14 g, 4.76 mmol), DIEA (1.85 mL, 10.5 mmol), and HBTU (1.99 g, 5.24 mmol) in DMF (20 mL) was stirred at ambient temperatures for 18 h. Water (100 mL) and EtOAc (50 mL) were added and the layers were separated. The water layer was extracted with EtOAc (2×50 mL). The combined EtOAc extracts were washed consecutively with water (50 mL), 10% $KHSO_4$ (2×50 mL), and 10% $NaHCO_3$ (50 mL). The organic phase was dried ($MgSO_4$), and concentrated to give an oily solid. This material was triturated with ether to give the title compound as a colorless solid (2.14 g, 89%). MS: m/e 1017.6 [2M+H], 509.4 [M+H].

Part B—Carbobenzyloxy-L-Asp(O-t-Bu)-L-Asp(O-t-Bu)-OH

A mixture of the product of Part A, above (200 mg, 0.393 mmol), LiOH (38 mg, 0.865 mmol), water (40 mL), and THF (200 mL) was stirred at ambient temperatures for 28 h, and concentrated to remove THF. The aqueous mixture was diluted with additional water (20 mL) and washed with EtOAc (20 mL). The aqueous phase was adjusted to pH 4 with 1.0 N HCl and extracted with EtOAc (20 mL). The EtOAc extract was washed with saturated NaCl (15 mL), dried ($MgSO_4$), and concentrated to give a colorless solid. This solid was dissolved in 60% ACN and purified by preparative HPLC on a Vydac C-18 column (22×250 mm) using a 2.4%/min gradient of 18 to 90% ACN containing 0.1% TFA at a flow rate of 20 mL/min. The main product peak eluting at 19.0 min was collected and lyophilized to give the title compound as a colorless powder (95 mg, 49%).

Part C—Methyl (2S)-3-((1-(3-(3-(N-(3-(2-(2-(N-(Benzyloxycarbonyl-L-Asp(O-t-Bu)-L-Asp(O-t-Bu))3-aminopropoxy)ethoxy)ethoxy)propyl)carbamoyl)propanoylamino)propyl)-4-oxo-7-(((1-(triphenylmethyl)imidazole-2-yl)amino)methyl)(3-hydroquinolyl))carbonylamino)-2-(((2,4,6-trimethylphenyl)sulfonyl)amino)propanoate The product of Example 6, Part B (44.0 mg, 0.0894 mmol) in TFA (1.5 mL) was allowed to stand at ambient temperatures for 45 min and concentrated to a yellow oil. This oil was dissolved in anhydrous DMF (2.0 mL) and made basic to pH paper with TEA. In a separate flask, the product of Part B, above (69.3 mg, 0.0547 mmol) was dissolved in anhydrous DMF (2.0 mL) and pre-activated by treatment with TEA (0.015 mL, 0.104 mmol) and HBTU (32.6 mg, 0.0859 mmol). After 10 min this solution was added to the DMF solution from the TFA deprotection reaction, and the combined solutions were stirred at ambient temperatures for 30 min. The DMF was removed under vacuum and the resulting oil dissolved in 60% ACN and purified by preparative HPLC on a Vydac C-18 column (22×250 mm) using a 1.54%/min gradient of 18 to 72% ACN containing 0.1% TFA at a flow rate of 20 mL/min. The main product peak eluting at 29.9 min was adjusted to pH 8 with saturated $NaHCO_3$ and concentrated to remove the ACN. The remaining aqueous mixture was extracted with EtOAc (2×40 mL). The combined EtOAc extracts were washed with saturated NaCl (40 mL), dried ($MgSO_4$), and concentrated to give the title compound as a colorless solid (56.4 mg, 63%). MS: m/e 1644.8 [M+H]; High Resolution MS: Calcd for $C_{87}H_{110}N_{11}O_{19}S$ [M+H]: 1644.7700, Found: 1644.771.

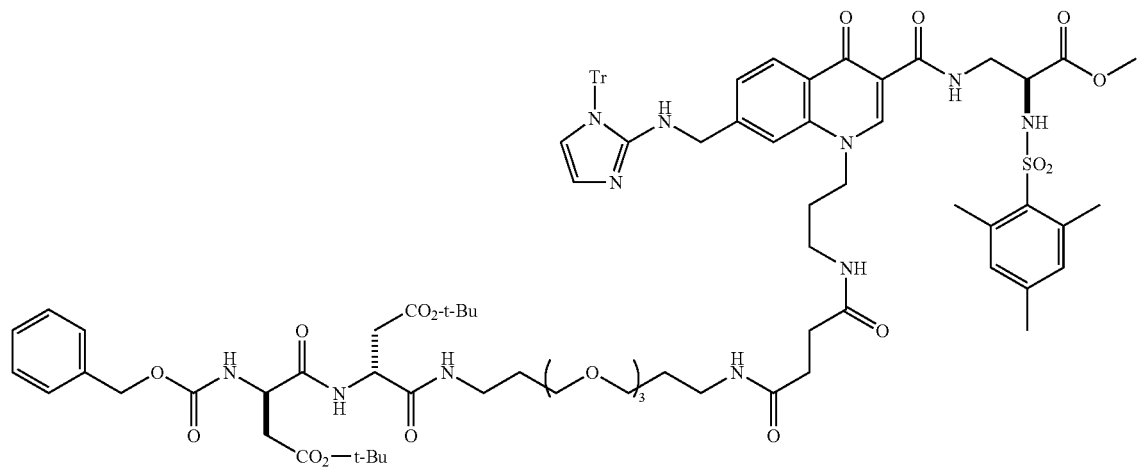

Part D—Methyl (2S)-3-((1-(3-(3-(N-(3-(2-(2-(N-(L-Asp(O-t-Bu)-L-Asp(O-t-Bu))3-aminopropoxy)ethoxy)ethoxy)propyl)carbamoyl)propanoylamino)propyl)-4-oxo-7-(((1-(triphenylmethyl)imidazole-2-yl)amino)methyl)(3-hydroquinolyl))carbonylamino)-2-(((2,4,6-trimethylphenyl)sulfonyl)amino)propanoate The product of Part C, above (55.0 mg, 0.0335 mmol) was hydrogenolyzed over 10% Pd/C (25 mg) in MeOH (15 mL)

at 40 psi for 3.5 h. The catalyst was removed by filtration through filter aid and the filtrate was concentrated to give the title compound as a pale yellow oil (41.8 mg, 83%). MS: m/e 1510.8 [M+H].

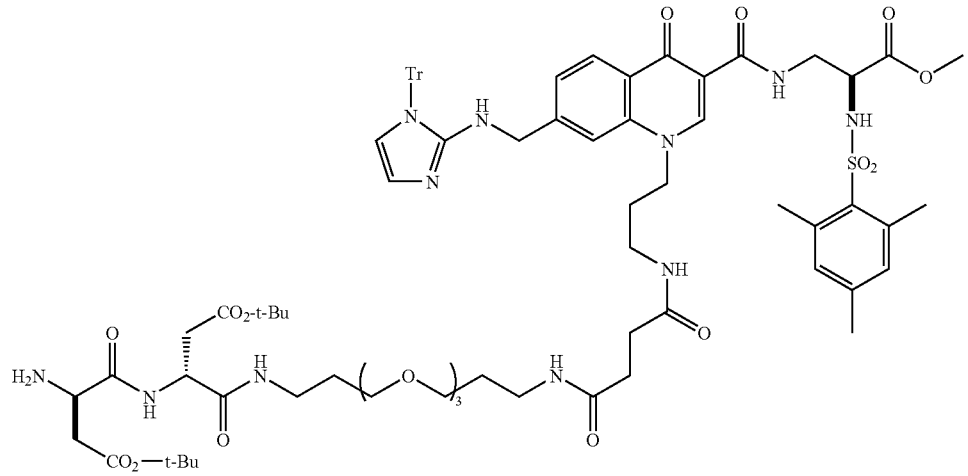

Part E—DOTA-tri-t-butyl Ester Conjugate of Methyl 3-((1-(3-(3-(N-(3-(2-(2-(N-(L-Asp(O-t-Bu)-L-Asp(O-t-Bu))3-aminopropoxy)ethoxy)ethoxy) propyl)carbamoyl)propanoylamino)propyl-4-oxo-7-(((1-(triphenylmethyl)imidazole-2-yl)amino)methyl) (3-hydroquinolyl))carbonylamino)-2-(((2,4,6-trimethylphenyl)sulfonyl)amino)propanoate A solution of the product of Part D, above (41.8 mg, 0.0277 mmol), the product of Example 2, Part B, 39.9 mg, 0.0436 mmol), TEA (0.023 mL, 0.166 mmol), and HBTU (15.6 mg, 0.0411 mmol) in anhydrous DMF (3.0 mL) was allowed to stand at ambient temperatures under a nitrogen atmosphere for 20 h. The DMF was removed under vacuum and the resulting oil was dissolved in 60% ACN and purified by preparative HPLC on a Vydac C-18 column (22×250 mm) using a 2.4%/min gradient of 18 to 90% ACN containing 0.1% TFA at a flow rate of 20 mL/min. The main product peak eluting at 21.2 min was collected and lyophilized to give the title compound as a colorless powder (24.8 mg, 43%). MS: m/e 2066.3 [M+H], 1033.6 [M+2H]; High Resolution MS: Calcd for $C_{107}H_{154}N_{15}O_{24}S$ [M+H]: 2065.1011, Found: 2065.1030.

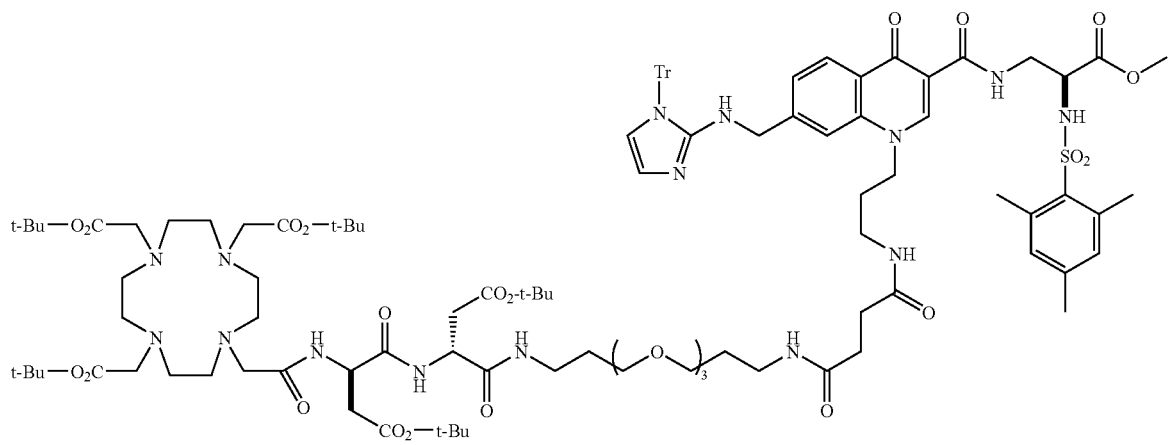

Part F—DOTA Conjugate of 3-((1-(3-(3-(N-(3-(2-(2-(N-(L-Asp-L-Asp)3-aminopropoxy)ethoxy)ethoxy)propyl)carbamoyl)propanoylamino)propyl)-7-((imidazole-2-ylamino)methyl)-4-oxo(3-hydroquinolyl)carbonylamino)-2-(((2,4,6-trimethylphenyl)sulfonyl)amino)propanoic Acid Bis(trifluoroacetate) Salt A mixture of the product of Part G, above (18.8 mg. 0.0091 mmol), water (0.150 mL), 3 N LiOH (0.015 mL), and peroxide-free THF (1.5 mL) was stirred at ambient temperatures for 3 h. The THF was removed under vacuum and the aqueous mixture was diluted with water (40 mL) and adjusted to pH 7 with 0.1 N HCl. The mixture was extracted with DCM (2×30 mL) and the combined extracts were concentrated to give a yellow oil. This oil was dissolved in TFA (1.0 mL) along with Et$_3$SiH (0.030 mL, 0.184 mmol) and heated at 40° C. under a nitrogen atmosphere for 48 h. The solution was concentrated and the resulting oil was dissolved in water and purified by preparative HPLC on a Vydac C-18 column (22×250 mm) using 0.1% TFA in water for 5 min followed by a 2.52%/min gradient of 0 to 63% ACN containing 0.1% TFA at a flow rate of 20 mL/min. The main product peak eluting at 19.9 min was collected and lyophilized to give the title compound as a colorless powder (1.5 mg, 9.4%). MS: m/e 1528.9 [M+2H], 765.1 [M+2H], 510.7 [M+3H].

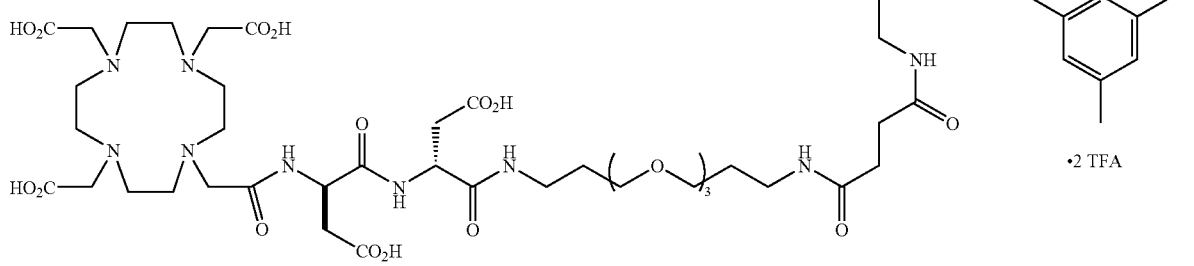

Example 9

DOTA/2-Amino-N,N'-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy)ethoxy)ethoxy)propyl)pentane-1,5-diamide Tris(trifluoroacetate) Salt Conjugate

Part A—DOTA-tri-t-butyl Ester/2-Amino-N,N'-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy)ethoxy)ethoxy)propyl)pentane-1,5-diamide Hexakis(trifluoroacetate) Salt Conjugate A solution of the product of Example 2, Part B, HBTU, and DIEA in anhydrous DMF is stirred at ambient temperatures under nitrogen for 15 min and treated with the product of Example 7, Part B. The resulting solution is stirred an additional 18 h and the DMF is removed under vacuum. The resulting residue is purified by preparative HPLC on a C18 column using a water:ACN:0.1% TFA gradient. The product fraction is lyophilized to give the title compound.

Part B—DOTA/2-Amino-N,N'-bis(3-(2-(2-(3-(3-(N-(3-(3-(N-(3-carboxy-2-(((2,4,6-trimethylphenyl)sulfonyl)amino)ethyl)carbamoyl)-7-((imidazole-2-ylamino)methyl)4-oxohydroquinolyl)propyl)carbamoyl)propanoylamino)propoxy)ethoxy)ethoxy)propyl)pentane-1,5-diamide Tris(trifluoroacetate) Salt Conjugate The product of Part B, above, is dissolved in degassed TFA, treated with triethylsilane, and heated at 50° C. under nitrogen for 1 h. The solution is concentrated under vacuum and the resulting residue is purified by preparative HPLC on a C18 column using a water:ACN:0.1% TFA gradient. The product fraction is lyophilized to give the title compound.

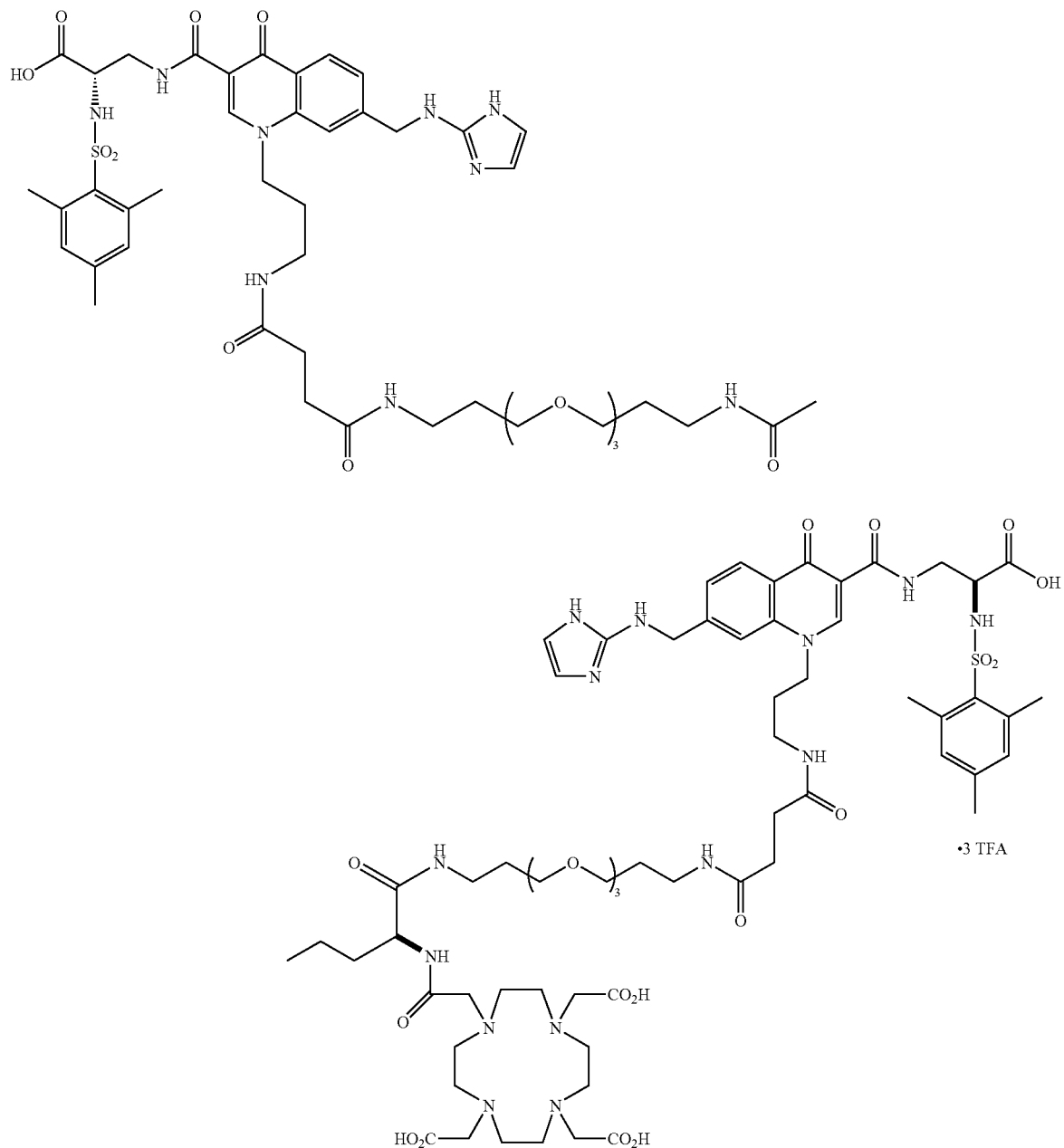

Example 10

DOTA/2-(((4-(3-(N-(3-(2-(2-(3-(2-Amino-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt Conjugate Part A—2-(((4-(3-(N-(3-(2-(2-(3-(2-((tert-Butoxy)carbonylamino)-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid The product of Example 3, Part I is dissolved in anhydrous DMF and treated with the N-hydroxysuccinimide ester of Boc-cysteic acid (as described in *Liebigs Ann. Chem.* 1979, 776–783) and DIEA. The solution is stirred at ambient temperatures under nitrogen for 18 h, and the DMF is removed under vacuum. The resulting residue is purified by preparative HPLC on a C18 column using a water:ACN: 0.1% TFA gradient. The product fraction is lyophilized to give the title compound.

Part B—DOTA-tri-t-butyl Ester/2-(((4-(3-(N-(3-(2-(2-(3-(2-Amino-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Tetrakis (trifluoroacetate) Salt Conjugate The product of Part A, above, is dissolved in degassed TFA and stirred at ambient temperatures for 15 min. The solution is concentrated under vacuum, and the resulting residue is dissolved in 50% ACN and lyophilized to remove the last traces of TFA.

In a separate flask, a solution of the product of Example 2, Part B and DIEA in anhydrous DMF are treated with HBTU and allowed to react 15 min at ambient temperatures under nitrogen. The deprotected product from above is added to this solution and stirring is continued at ambient temperatures under nitrogen for 18 h. The DMF is removed under vacuum and the resulting residue is purified by preparative HPLC on a C18 column using a water:ACN: 0.1% TFA gradient. The product fraction is lyophilized to give the title compound.

Part C—DOTA/2-(((4-(3-(N-(3-(2-(2-(3-(2-Amino-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt Conjugate The product of Part B, above, and $Et_3SiH$ are dissolved in degassed TFA and heated at 50° C. under nitrogen for 1 h. The solution is concentrated and the resulting residue is purified by preparative HPLC on a C18 column using a water:ACN:0.1% TFA gradient. The product fraction is lyophilized to give the title compound.

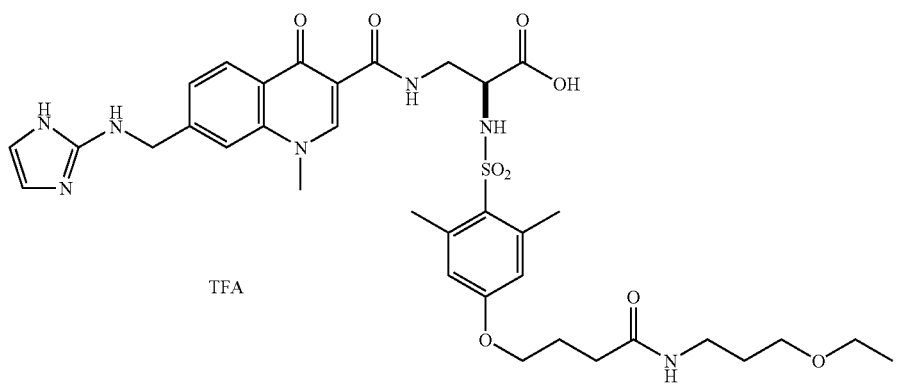

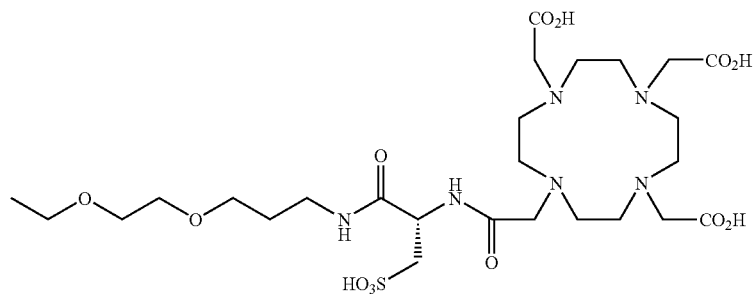

135
Example 11

DOTA/2-(((4-(3-(N-(3-(2-(2-(3-(2-Amino-3-(4-(phosphonooxy)phenyl)propanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt Conjugate The title compound is prepared by the same procedure described for Example 10 by substituting Boc-Tyr(PO$_3$H$_2$)—OSu for Boc-Cys(O$_3$H)—OSu.

136
Example 12

DOTA/2-(((4-(3-(N-(3-(2-(2-(3-(2-Amino-3-(4-(sulfooxy)phenyl)propanoylamino)propoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Trifluoroacetate Salt Conjugate The title compound is prepared by the same procedure described for Example 10 by substituting Boc-Tyr(SO$_3$H)—OSu for Boc-Cys(O$_3$H)—OSu.

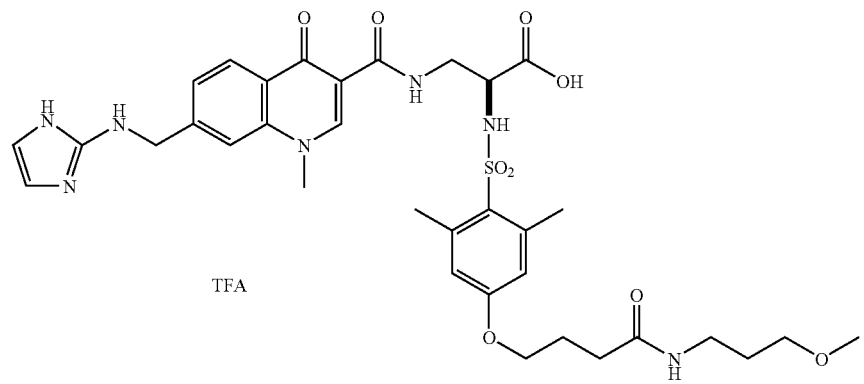

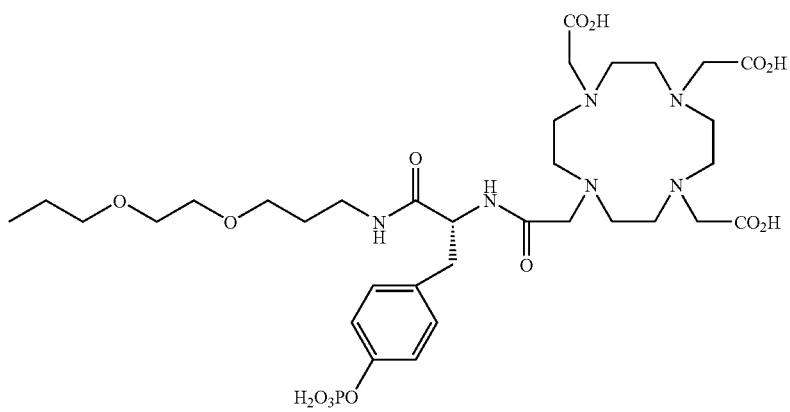

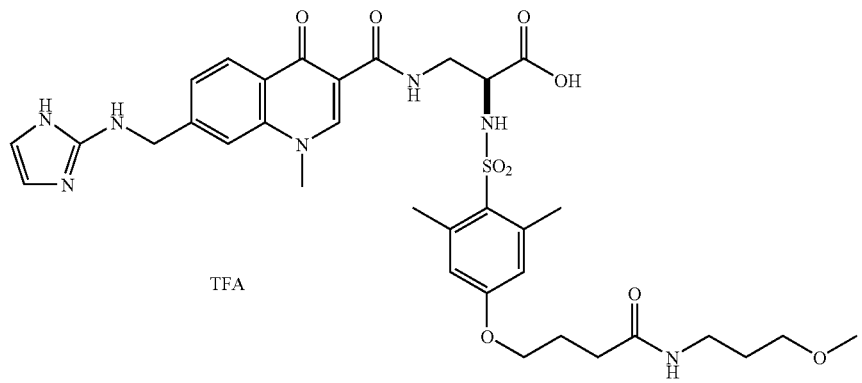

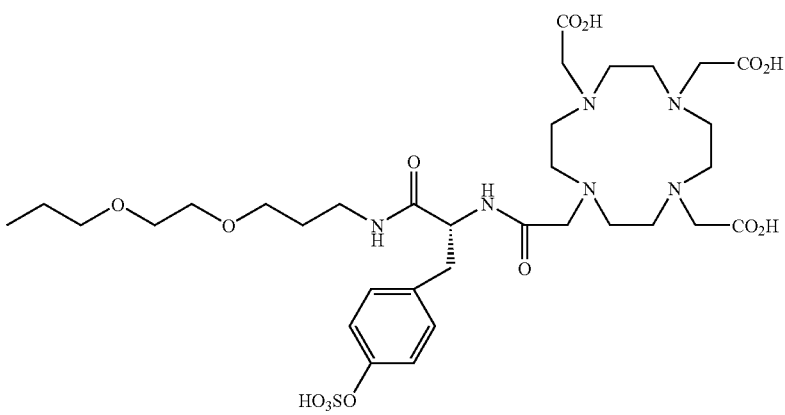

Example 13

DOTA/2-(((4-(3-(N-(3-(2-(2-(3-(2-Amino-4-(N-(ethyl-3,6-O-disulfo-β-D-galactopyranosyl)carbamoyl)butanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino) propanoic Acid Conjugate

Part A—Preparation of Boc-Glu(aminoethyl-3,6-O-disulfo-β-D-galactopyranosyl)-OSu A solution of Boc-Glu-OMe, aminoethyl-3,6-O-disulfo-β-D-galactopyranoside (as described in *Tet. Lett.* 1997, 53, 11937–11952), DIEA, and HBTU in anhydrous DMF is stirred at ambient temperatures under nitrogen for 18 h. The DMF is removed under vacuum and the resulting residue is hydrolyzed using aqueous NaOH. The reaction solution is adjusted to pH 7 and purified by preparative anion exchange chromatography using a resin such as DEAE Cellulose and a Et$_3$NH$_2$CO$_3$ gradient. The product fraction is treated with a cation exchange resin, sodium form, to give the intermediate carboxylic acid as the sodium salt.

The above compound, N-hydroxysuccinimide, and DCC are dissolved in anhydrous DMF and stirred at ambient temperatures under nitrogen for 18 h. The DMF is removed under vacuum and the resulting residue is purified by preparative anion exchange chromatography as above to give the title compound as the triethylammonium salt.

Part B—DOTA/2-(((4-(3-(N-(3-(2-(2-(3-(2-Amino-4-(N-(ethyl-3,6-O-disulfo-β-D-galactopyranosyl) carbamoyl)butanoylamino)propoxy)ethoxy) propyl)carbamoyl)propoxy)-2,6-dimethylphenyl) sulfonyl)amino)-3-((7-((imidazol-2-ylamino) methyl)-1-methyl-4-oxo(3-hydroquinolyl)) carbonylamino)propanoic Acid Conjugate The title compound is prepared by the same procedure described for Example 10 by substituting Boc-Glu(aminoethyl-3,6-O-disulfo-β-D-galactopyranosyl)-OSu for Boc-Cys(O$_3$H)—OSu.

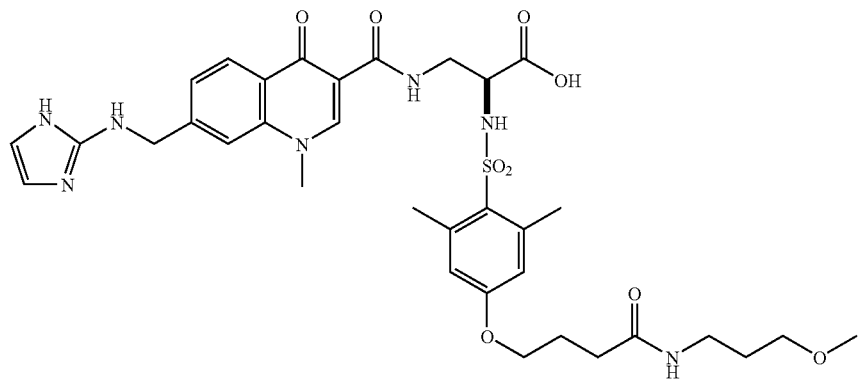

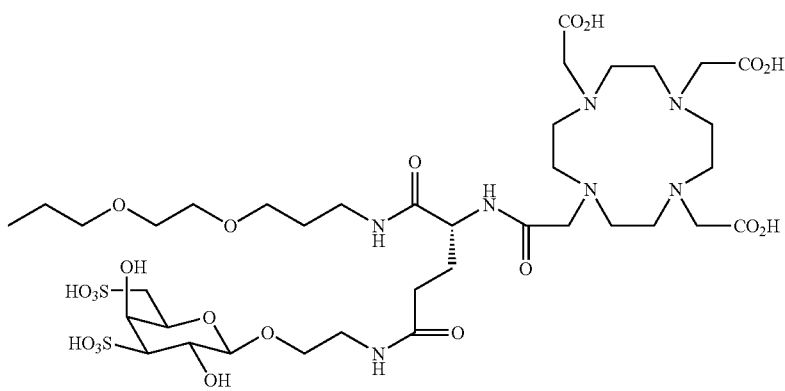

Example 14

DOTA/2-(((4-(3-(N-(3-(2-(2-(3-(2-Amino-4-(N-(6-deoxy-β-cyclodextryl)carbamoyl)butanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Bis(trifluoroacetate) Salt Conjugate Part A—Preparation of Boc-Glu(6-amino-6-deoxy-β-cyclodextryl)-OMe A solution of Boc-Glu-OMe, 6-amino-6-deoxy-β-cyclodextrin (as described in *J. Org. Chem.* 1996, 61, 903–908), DIEA, and HBTU in anhydrous DMF is stirred at ambient temperatures under nitrogen for 18 h. The DMF is removed under vacuum and the resulting residue is purified by preparative HPLC on a C18 column using a water:ACN: 0.1% TFA gradient. The product fraction is lyophilized to give the title compound.

Part B—Preparation of Boc-Glu(6-amino-6-deoxy-β-cyclodextryl)-OSu

The product of Part A, above, is hydrolyzed by stirring in a mixture of LiOH, THF, and water at ambient temperatures under nitrogen for 4 h. The THF is removed under vacuum and the resulting mixture is diluted with water and adjusted to pH 3 using 0.1 N HCl. The mixture is extracted with EtOAc, and the combined extracts are dried (MgSO$_4$) and concentrated. The resulting material is dissolved in anhydrous DMF along with N-hydroxysuccinimide, and DCC, and stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part C—DOTA/2-(((4-(3-(N-(3-(2-(2-(3-(2-Amino-4-(N-(6-deoxy-β-cyclodextryl)carbamoyl)butanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Bis(trifluoroacetate) Salt Conjugate The title compound is prepared by the same procedure described for Example 10 by substituting Boc-Glu(6-amino-6-deoxy-β-cyclodextryl)-OSu for Boc-Cys(O$_3$H)—OSu.

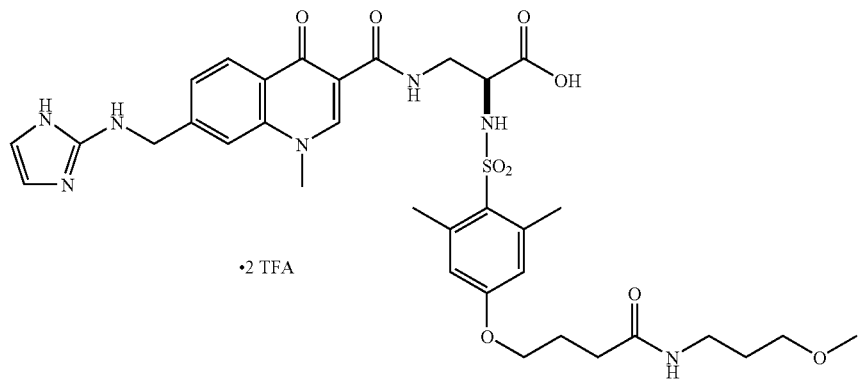

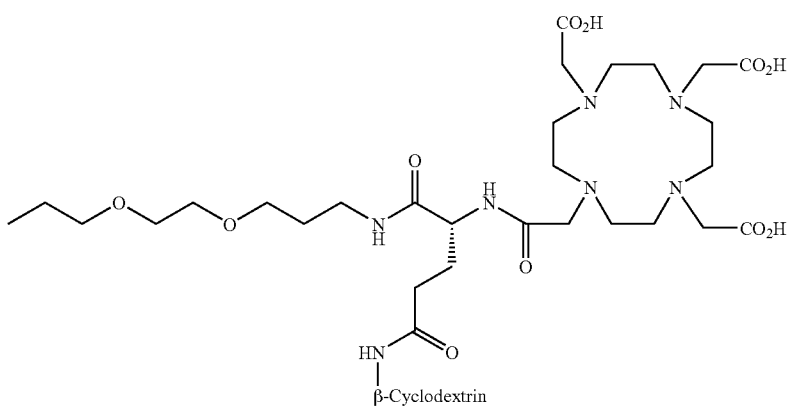

Example 15

DOTA/2-(((4-(3-(N-(3-(2-(2-(3-(2-Amino-4-(N-(ω-methoxypolyethylene(5,000)glycoxyethyl)carbamoyl)butanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Bis(trifluoroacetate) Salt Conjugate

Part A—Preparation of Boc-Glu(amino-ω-methoxypolyethylene glycol)-OMe

A solution of Boc-Glu-OMe, amino-ω-methoxypolyethylene glycol, (MW=5,000), DIEA, and HBTU in anhydrous DMF is stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part B—Preparation of Boc-Glu(amino-ω-methoxypolyethylene glycol)-OSu

The product of Part A, above, is hydrolyzed by stirring in a mixture of LiOH, THF, and water at ambient temperatures under nitrogen for 4 h. The THF is removed under vacuum and the resulting solution is adjusted to pH 7 using 0.1 N HCl. The solution is desalted using a Sephadex PD-10 desalting column and the product eluant is lyophilized. The resulting material is dissolved in anhydrous DMF along with N-hydroxysuccinimide, and DCC, and stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part C—DOTA/2-(((4-(3-(N-(3-(2-(2-(3-(2-Amino-4-(N-(ω-methoxypolyethylene(5,000)glycoxyethyl)carbamoyl)butanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Bis(trifluoroacetate) Salt Conjugate The title compound is prepared by the same procedure described for Example 10 by substituting Boc-Glu(amino-ω-methoxypolyethylene glycol)-OSu for Boc-Cys(O$_3$H)—OSu.

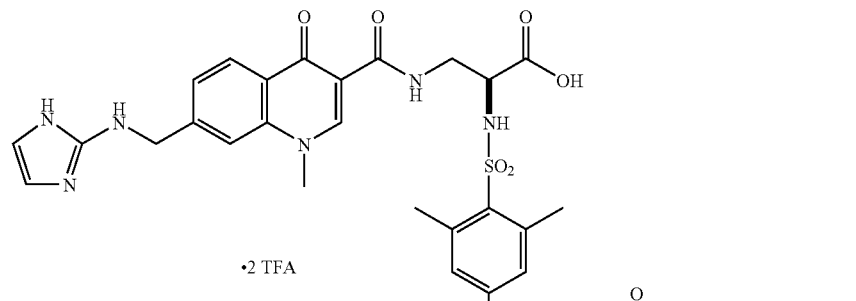
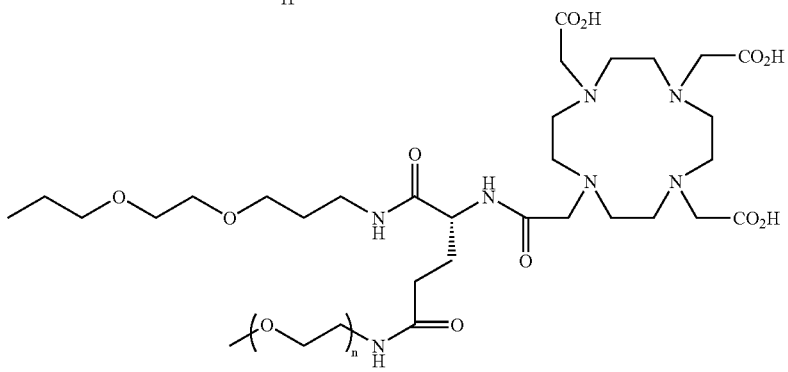

Example 16

2-(((4-(3-(N-(3-(2-(2-(3-(2-(1,4,7,10-Tetraaza-4,7,10-tris(carboxymethyl)cyclododecylacetylamino)-6-aminohexanoylamino)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid Tris(trifluoroacetate) Salt The title compound is prepared by the same procedure described for Example 10 by substituting Boc-Lys(Cbz)-OSu for Boc-Cys(O$_3$H)—OSu.

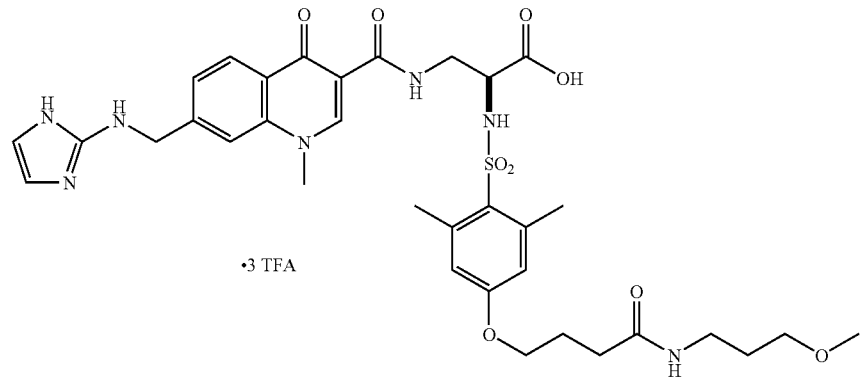

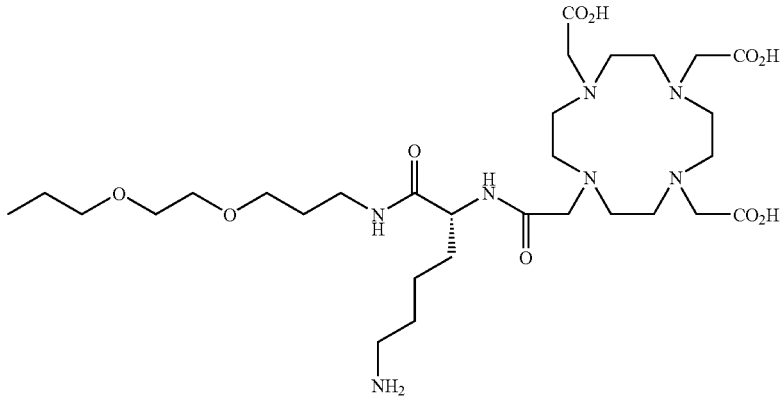

Example 17
2-(((4-(3-(N-(3-(2-(2-(3-(2-(1,4,7,10-Tetraaza-4,7,10-tris(carboxymethyl)cyclododecylacetylamino)-6-(2-(bis (phosphonomethyl) amino) acetylamino) hexanoylamino)propoxy)ethoxy)ethoxy)propyl)carbamoyl)propoxy)-2,6-dimethylphenyl)sulfonyl) amino)-3-((7-((imidazol-2-ylamino)methyl)-1-methyl-4-oxo (3-hydroquinolyl))carbonylamino) propanoic Acid Conjugate A solution of bis(phosphonomethyl)glycine, DIEA, and HBTU in anhydrous DMF is stirred at ambient temperatures under nitrogen for 15 min, and treated with the product of Example 16. Stirring is continued for 18 h and the DMF is removed under vacuum. The resulting residue is purified by ion exchange chromatography.

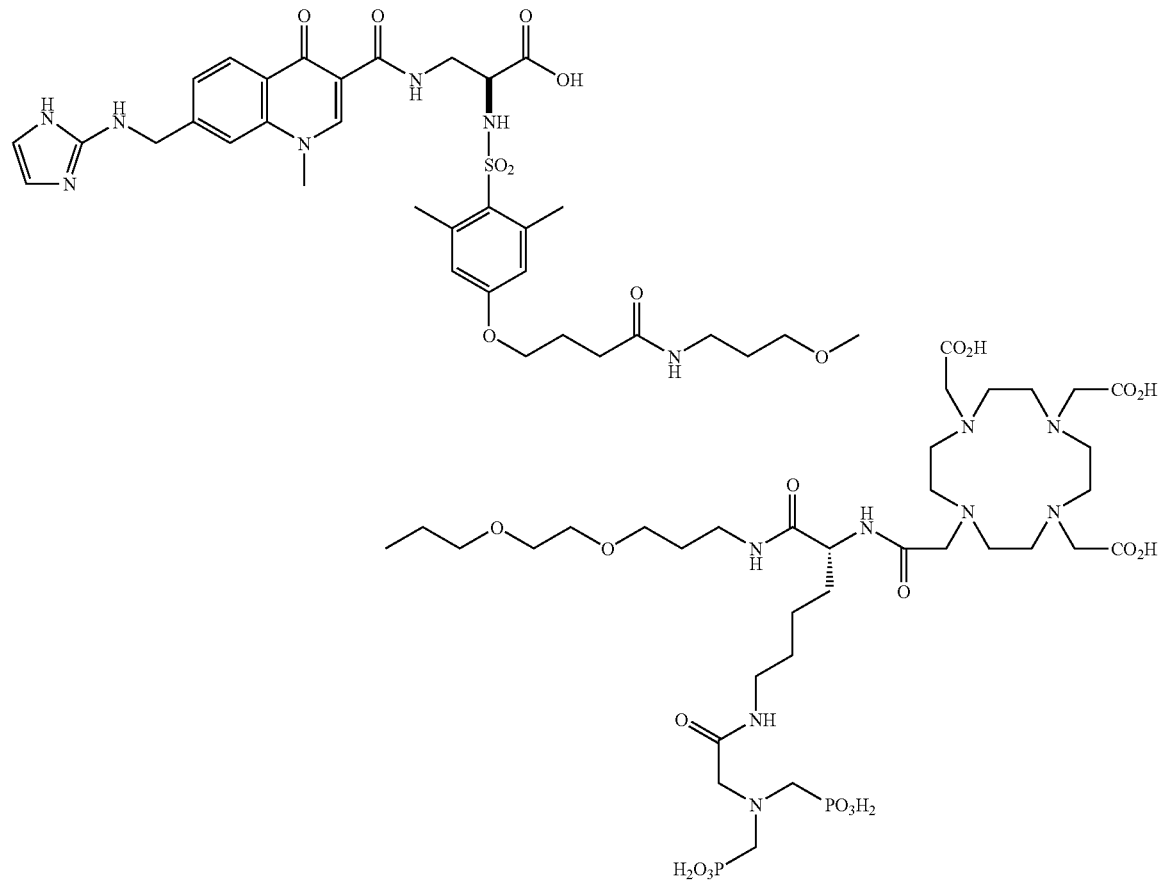

Example 18

2-(((4-(3-(N-(3-(2-(2-(3-(2-(2-((2-((2-(bis(car-boxymethyl)amino)ethyl)(carboxymethyl)amino)ethyl)(carboxymethyl)amino)acetylamino)-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid The product of Example 10, Part A is dissolved in degassed TFA and stirred at ambient temperatures for 15 min. The solution is concentrated under vacuum, and the resulting residue is dissolved in 50% ACN and lyophilized to remove the last traces of TFA. The material is dissolved in anhydrous DMF along with DIEA and diethylenetriaminepentaacetic dianhydride. The resulting solution is stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Examples 19–23

Synthesis of Complexes [$^{99m}$Tc (HYNIC-VnA) (tricine) (TPPTS)]

To a lyophilized vial containing 4.84 mg TPPTS, 6.3 mg tricine, 40 mg mannitol, succinic acid buffer, pH 4.8, and 0.1% Pluronic F-64 surfactant, was added 1.1 mL sterile water for injection, 0.2 mL (20 µg) of the appropriate HYNIC-conjugated vitronectin antagonist (VnA) in deionized water or 50% aqueous ethanol, and 0.2 mL of $^{99m}$TcO$_4^-$ (50±5 mCi) in saline. The reconstituted kit was heated in a 100° C. water bath for 15 minutes, and was allowed to cool 10 minutes at room temperature. A sample of the reaction mixture was analyzed by HPLC. The RCP results are listed in the Table 1.

HPLC Method

Column: Zorbax C18, 25 cm×4.6 mm

Flow rate: 1.0 mL/min

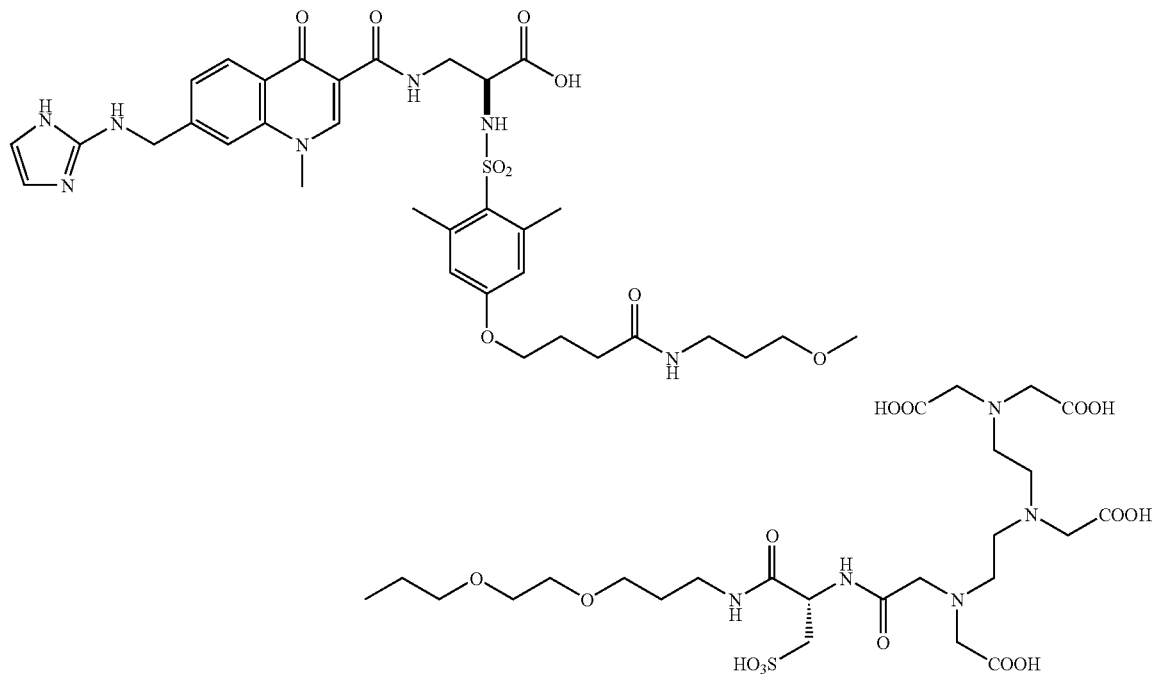

The following procedures describe the synthesis of radiopharmaceuticals of the present invention of the formula $^{99m}$Tc(VnA)(tricine)(phosphine), in which (VnA) represents a vitronectin receptor antagonist compound of the present invention bonded to the Tc through a diazenido (—N═N—) or hydrazido (═N—NH—) moiety. The diazenido or hydrazido moiety results from the reaction of the hydrazinonicotinamido group, present either as the free hydrazine or protected as a hydrazone, with the Tc-99m. The other two ligands in the Tc coordination sphere are tricine and a phosphine.

Solvent A: 10 mM sodium phosphate buffer, pH 6.0

Solvent B: 100% CH3CN

| Gradient A (Exs. 19, 20, 21) | | | | | |
|---|---|---|---|---|---|
| t (min) | 0 | 20 | 21 | 30 | 31 | 40 |
| % Solvent B | 0 | 25 | 75 | 75 | 0 | 0 |

| Gradient B (Ex. 22) | | | | | |
|---|---|---|---|---|---|
| t (min) | 0 | 20 | 30 | 31 | 40 |
| % Solvent B | 0 | 50 | 50 | 0 | 0 |

| Gradient C (Ex. 23) | | | | | | |
|---|---|---|---|---|---|---|
| t (min) | 0 | 20 | 21 | 30 | 31 | 40 |
| % Solvent B | 10 | 30 | 75 | 75 | 0 | 0 |

TABLE 1

Analytical and Yield Data for
$^{99m}$Tc (VnA) (tricine) (TPPTS) Complexes

| Example No. | Reagent No. | Ret. Time (min) | % Yield |
|---|---|---|---|
| 19 | 1 | 8.8 | 73 |
| 20 | 3 | 17.2 | 81 |
| 21 | 4 | 17.6 | 68 |
| 22 | 6 | 11.7 | 79 |
| 23 | 7 | 16.4 | 52 |

Example 24

Synthesis of the In-111 Complex of 3-((7-((Imidazol-2-ylamino)methyl)-1-methyl-4-oxo(3-hydroquinolyl))carbonylamino)-2-(((4-(4-(((3-(2-(2-(3-(2-(1,4,7,10-tetraaza-4,7,10-tris(carboxylmethyl)cyclododecyl)acetylamino)propoxy)ethoxy)ethoxy)propyl)amino)sulfonyl)phenyl)phenyl)sulfonyl)amino)propanoic Acid To a lead shielded and crimped autosampler vial was added 35 μg of the conjugate of Example 2 and 1.0 mg gentisic acid, sodium salt dissolved in 70 μL ammonium acetate buffer (0.4 M, pH 4.7) followed by the addition of 2 mCi, 20 μL In-111 in 0.05 N HCl (specific activity: 17 μg/mCi). The reaction mixture was heated at 70–80° C. for 60 min and analyzed by HPLC and ITLC. The complex was formed in 93% yield and had a retention time of 19.6 min.

HPLC Method

Column: Zorbax Rx C18, 25 cm×4.6 mm

Column Temperature: Ambient

Flow: 1.0 mL/min

Solvent A: 10% Acetonitrile/0.1% TFA/H$_2$O

Solvent B: Acetonitrile

Detector: Sodium iodide (NaI) radiometric probe

Gradient

| t (min) | 0 | 25 | 26 | 35 | 36 | 45 |
|---|---|---|---|---|---|---|
| % B | 10 | 20 | 60 | 60 | 10 | 10 |

Examples 25–26

Synthesis of $^{177}$Lu and $^{90}$Y Complexes of 3-((7-((Imidazol-2-ylamino)methyl)-1-methyl-4-oxo(3-hydroquinolyl))carbonylamino)-2-(((4-(4-(((3-(2-(2-(3-(2-(1,4,7,10-tetraaza-4,7,10-tris(carboxylmethyl)cyclododecyl)acetylamino)propoxy)ethoxy)ethoxy)propyl)amino)sulfonyl)phenyl)phenyl)sulfonyl)amino)propanoic Acid To a clean sealed 5 mL vial was added 0.3 mL of a solution of the comjugate of Example 2 (200 μg/mL in 0.5 M ammonium acetate buffer, pH 6.9), followed by 0.05 mL of gentisic acid (sodium salt, 10 mg/mL in 0.5 M ammonium acetate buffer, pH 6.9) solution, 0.3 mL of 0.5 M ammonium acetate buffer (pH 6.9), and 0.010 mL of $^{177}$LuCl$_3$ or $^{90}$YCl$_3$ solution (1000 mCi/mL for $^{177}$LuCl$_3$ and 500 mCi/mL for $^{90}$YCl$_3$) in 0.05 N HCl. The resulting mixture was heated at 100° C. for 30 min. After cooling to room temperature, a sample of the resulting solution was analyzed by radio-HPLC and ITLC. The radiolabeling yields were=90% (after correction for small amount of colloid) for both complex, and the retention time was 19.2 min.

HPLC Method

Column: Zorbax C18, 25 cm×4.6 mm

Flow rate: 1.0 mL/min

Solvent A: 0.1% TFA aqueous solution

Solvent B: 100% CH$_3$CN

| t (min) | 0 | 20 | 25 | 30 | 31 | 40 |
|---|---|---|---|---|---|---|
| % Solvent B | 10 | 25 | 60 | 60 | 10 | 10 |

The instant thin layer chromatography (ITLC) method used Gelman Sciences silica-gel strips and a 1:1 mixture of acetone and saline as eluant.

Example 27

Synthesis of $^{177}$Lu Complex of the DOTA Conjugate of 3-((1-(3-(3-(N-(3-(2-(2-(N-(L-Asp-L-Asp)3-aminopropoxy)ethoxy)ethoxy)propyl)carbamoyl)propanoylamino)propyl)-7-((imidazole-2-ylamino)methyl)-4-oxo(3-hydroquinolyl))carbonylamino)-2-(((2,4,6-trimethylphenyl)sulfonyl)amino)propanoic Acid To a clean sealed 5 mL vial was added 0.5 mL of a solution of the conjugate of Example 8 (200 μg/mL in 0.5 M ammonium acetate buffer, pH 6.9), followed by 0.05 mL of gentisic acid (sodium salt, 10 mg/mL in 0.5 M ammonium acetate buffer, pH 6.9) solution, 0.25 mL of 0.5 M ammonium acetate buffer (pH 6.9), and 0.05 mL of $^{177}$LuCl$_3$ solution (200 mCi/mL) in 0.05 N HCl. The resulting mixture was heated at 100° C. for 30 min. After cooling to room temperature, a sample of the resulting solution was analyzed by radio-HPLC and ITLC. The radiolabeling yield was 75% (after correction for colloid), and the retention time was 20 min.

HPLC Method

Column: Zorbax C18, 25 cm×4.6 mm

Flow rate: 1.0 mL/min

Solvent A: 10 mM phosphate buffer, pH=6

Solvent B: 100% CH₃CN

| t (min) | 0 | 20 | 25 | 30 | 31 | 40 |
|---|---|---|---|---|---|---|
| % Solvent B | 0 | 20 | 50 | 50 | 0 | 0 |

Example 28

Synthesis of the Gadolinium Complex of 2-(((4-(3-(N-(3-(2-(2-(3-(2-(2-((2-((2-(bis(carboxymethyl)amino)ethyl)(carboxymethyl)amino)ethyl)(carboxymethyl) amino)acetylamino)-3-sulfopropyl)propoxy)ethoxy)ethoxy)propyl)carbamoyl)propoxy)-2,6-dimethylphenyl)sulfonyl)amino)-3-((7-((imidazol-2-ylamino)methyl)-1-methyl-4-oxo(3-hydroquinolyl))carbonylamino)propanoic Acid The gadolinium complex of the conjugate of Example 18 is prepared according to the following procedure. 3–3.5 mg of the conjugate is dissolved in 2 mL 1 M ammonium acetate buffer at pH 7.0, and one equivalent Gd(NO₃)₃ solution (0.02 M in water) is added to it. The reaction mixture is allowed to stay at room temperature for 3–5 hours and the product is isolated by HPLC. The fraction containing the complex is lyophilized and dissolved in 1 mL H₂O. The identity of the complex is confirmed by mass spectroscopy.

Example 29

Synthesis of (2S)-2-[({2,6-Dimethyl-4-[3-(N-{2-[3-sulfo-2-(3-sulfo-2-{2-[1,4,7,10-tetraaza-4,7,10-tris(carboxymethyl) cyclododecyl]acetylamino}propyl)propyl]ethyl}carbamoyl)propoxy]phenyl}sulfonyl) amino]-3-({7-[(imidazol-2-ylamino)methyl]-1-methyl-4-oxo(3-hydroquinolyl)}carbonylamino) propanoic Acid Trifluoroacetate Salt Part A—Preparation of Methyl (2S)-3-[(tert-Butoxy)carbonylamino]-2-[({2,6-dimethyl-4-[3-(N-{2-[(phenylmethoxy)carbonylamino]ethyl}carbamoyl)propoxy]-phenyl}sulfonyl)amino]propanoate

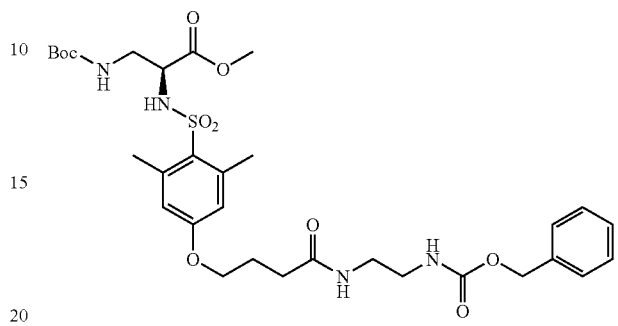

A solution of the product of Example 3, Part D (369 mg, 0.756 mmol), DIEA (0.52 mL, 3.0 mmol), and HBTU (315 mg, 0.832 mmol) in anhydrous DMF (14 mL) was stirred at ambient temperatures under nitrogen for 5 min, and treated with benzyl N-(2-aminoethyl)carbamate hydrochloride (192 mg, 0.832 mmol), and stirred an additional 1 h. The DMF was removed under vacuum, and the oily residue was taken up in EtOAc (150 mL), washed consecutively with 0.1 N HCl (40 mL), water (40 mL), and saturated NaCl (40 mL), dried (MgSO₄), and concentrated to give a colorless viscous oil. Flash chromatography on a 3×16 cm silica gel column (EtOAc) gave the title compound as a colorless viscous oil (450 mg, 89.6%). ¹H NMR (CDCl₃): δ 7.34–7.27 (m, 5H), 6.58 (s, 2H), 6.31 (bs, 1H), 5.86 (bs, 1H), 5.36 (bs, 1H), 5.14–5.03 (m, 3H), 3.96 (t, J=6.0 Hz, 2H), 3.88–3.83 (m, 1H), 3.56 (s, 3H), 3.47–3.25 (m, 6H), 2.59 (s, 6H), 2.31 (t, J=6.9 Hz, 2H), 2.05 (p, J=6.6 Hz, 2H), 1.39 (s, 9H); ¹³C NMR (CDCl₃): δ 172.9, 170.5, 160.6, 157.3, 155.9, 141.8, 136.3, 128.5, 128.2, 128.0, 116.6, 79.9, 66.9, 55.5, 52.8, 43.1, 40.9, 40.3, 32.4, 28.2, 24.9, 23.3; MS: m/e 665.4 [M+H]; 687.3 [M+Na]; High Resolution MS: Calcd for $C_{31}H_{45}N_4O_{10}S$ [M+H]: 665.2856, Found: 665.2883.

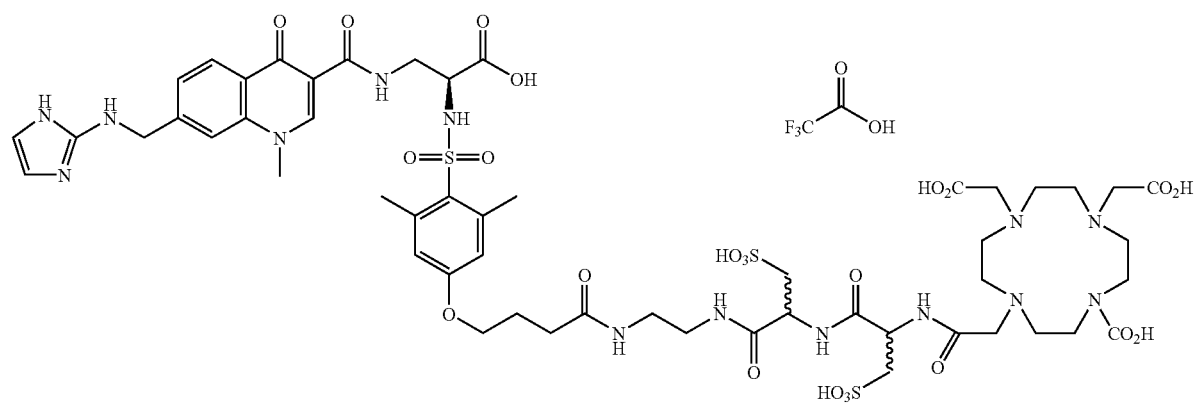

Part B—Preparation of Methyl (2S)-3-Amino-2-[({2,6-dimethyl-4-[3-(N-{2-[(phenylmethoxy)carbonylamino]ethyl}carbamoyl)propoxy]phenyl}sulfonyl)amino]propanoate Trifluoroacetate Salt

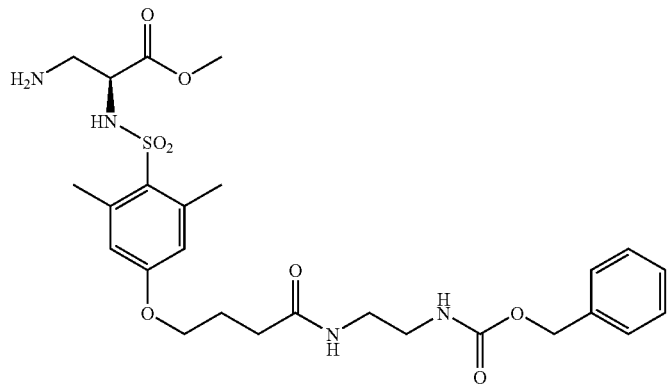
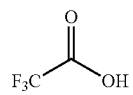

The product of Part A, above (420 mg, 0.632 mmol) was dissolved in 25/75 DCM/TFA (20 mL) and allowed to stand at ambient temperatures under nitrogen for 10 min. The solution was concentrated, and the resulting viscous oil was dissolved in 50% ACN and lyophilized to give the title compound as a colorless solid (437 mg, 102%). MS: m/e 565.3 [M+H].

Part C—Preparation of Methyl (2S)-2-[({2,6-Dimethyl-4-[3-(N-{2-[(phenylmethoxy)carbonylamino]ethyl}carbamoyl)propoxy]phenyl}sulfonyl)amino]-3-{[1-methyl-4-oxo-7-({[1-(triphenylmethyl)imidazol-2-yl]amino}methyl)(3-hydroquinolyl)]carbonylamino}propanoate

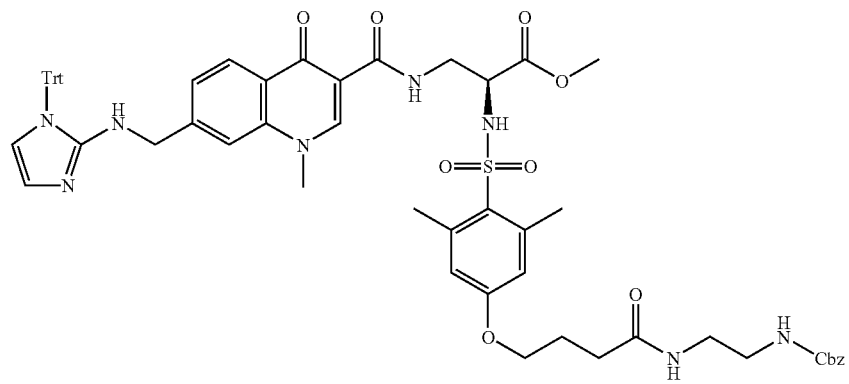

A solution of 1-methyl-4-oxo-7-(((1-(triphenylmethyl)imidazol-2-yl)amino)methyl)hydroquinoline-3-carboxylic acid (702 mg, 1.30 mmol), DIEA (0.678 mL, 3.90 mmol), and HBTU (542 mg, 1.43 mmol) in anhydrous DMF (60 mL) was stirred at ambient temperatures under nitrogen for 10 min, and treated with the product of Step B, above (881 mg, 1.30 mmol). After 75 min the DMF was removed under vacuum and the resulting oil was purified by HPLC on a Vydac C-18 column (50×250 mm) using a 1.24%/min gradient of 18 to 67.5% ACN containing 0.1% TFA at a flow rate of 80 mL/min. A peak eluting at 18.9 min was lyophilized to give unreacted 1-methyl-4-oxo-7-(((1-(triphenylmethyl)imidazol-2-yl)amino)methyl)hydroquinoline-3-carboxylic acid (308 mg). The main product peak eluting at 23.7 min was lyophilized to give the title compound as a colorless solid (890 mg, 63.0%). $^1$H NMR (CDCl$_3$/D$_2$O): δ 8.50 (s, 1H) 8.18 (d, J=8.3 Hz, 1H), 7.70 (s, 1H), 7.51–7.25 (m, 15H), 7.25–7.12 (m, 5H), 6.97 (s, 1H), 6.58 (d, J=2.3 Hz, 1H), 6.34 (s, 2H), 6.32 (d, J=8.5 Hz, 1H), 5.09 (s, 2H), 4.65 (s, 2H), 4.29–4.23 (m, 1H), 3.88 (s, 3H), 3.80–3.50 (m, 7H), 3.41–3.28 (m, 4H), 2.61 (s, 6H), 2.26–2.11 (m, 2H), 1.92–1.76 (m, 2H); MS: m/e 1087.4 [M+H]; 845.3 [M+H–Tr]; High Resolution MS: Calcd for C$_{60}$H$_{63}$N$_8$O$_{10}$S [M+H]: 1087.4388; found: 1087.440.

Part D—Preparation of Methyl (2S)-2-{[(4-{3-[N-(2-Aminoethyl)carbamoyl]propoxy}-2,6-dimethylphenyl)sulfonyl]amino}-3-{[1-methyl-4-oxo-7-({[1-(triphenylmethyl)imidazol-2-yl]amino} methyl)(3-hydroquinolyl)]carbonylamino}propanoate

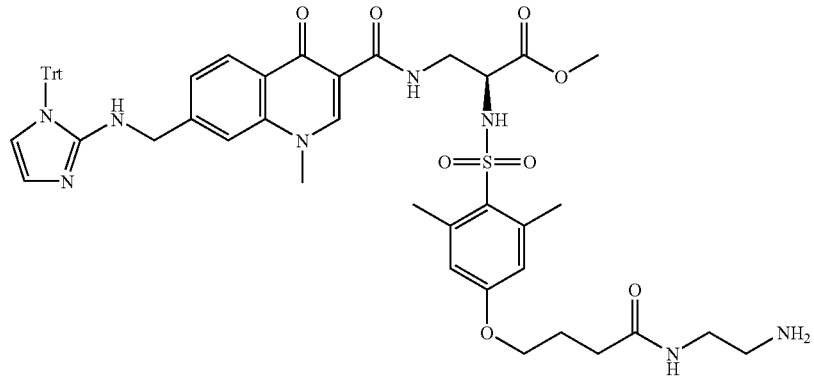

Hydrogenolysis of the product of Part C, above (468 mg, 0.431 mmol) was accomplished in MeOH (100 mL) over 10% Pd/C (95 mg) at 60 psi for 1 h. The catalyst was removed by filtration through Celite® and the filtrate was concentrated to give the title compound as a pale amber oil (405 mg, 98.7%). MS: m/e 953.3 [M+H], 711.3 [M+H–Trityl].

Part E—Preparation of (2R)-N-{2-[4-(4-{[((1S)-1-(Methoxycarbonyl)-2-{[1-methyl-4-oxo-7-({[1-(triphenylmethyl)imidazol-2-yl]amino}methyl)(3-hydroquinolyl)]carbonylamino}ethyl)amino]sulfonyl}-3,5-dimethylphenoxy)butanoylamino]ethyl}-2-[(tert-butoxy)carbonylamino] propanesulfonic Acid

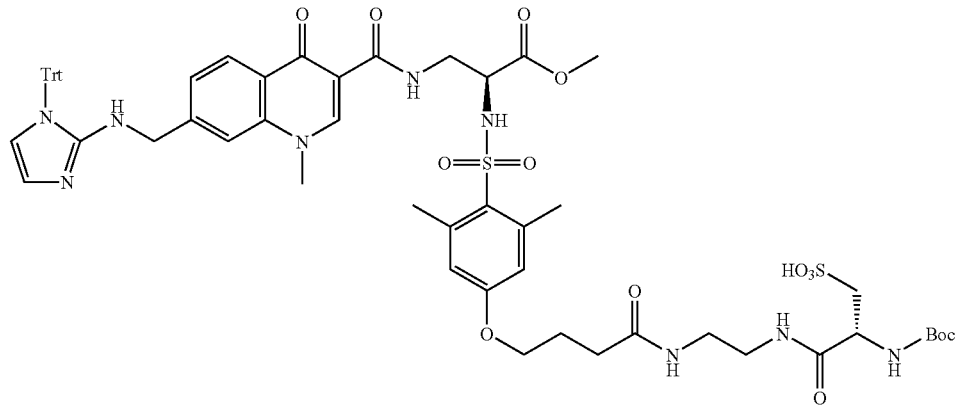

A solution of the product of Part E, above (405 mg, 0.425 mmol), the p-nitrophenyl ester of Boc-L-cysteic acid (425 mg, 1.03 mmol), and DIEA (0.435 mL, 2.55 mmol) in anhydrous DMF (20 mL) was stirred at ambient temperatures under nitrogen for 3 h. The DMF was removed under vacuum and the resulting oil was purified by HPLC on a Vydac C-18 column (50×250 mm) using a 1.12%/min gradient of 9 to 54% ACN containing 0.1% TFA at a flow rate of 80 mL/min. The main product peak eluting at 37.3 min was lyophilized to give the title compound as a colorless solid (410 mg, 80.2%). MS: m/e 1204.4 [M+H], 962.3 [M+H−Trt].

Part F—Preparation of (2R)-N-{2-[4-(4-{[((1S)-1-(Methoxycarbonyl)-2-{[1-methyl-4-oxo-7-({[1-(triphenylmethyl)imidazol-2-yl]amino}methyl)(3-hydroquinolyl)]carbonylamino}ethyl)amino]sulfonyl}-3,5-dimethylphenoxy)butanoylamino]ethyl}-2-aminopropanesulfonic Acid

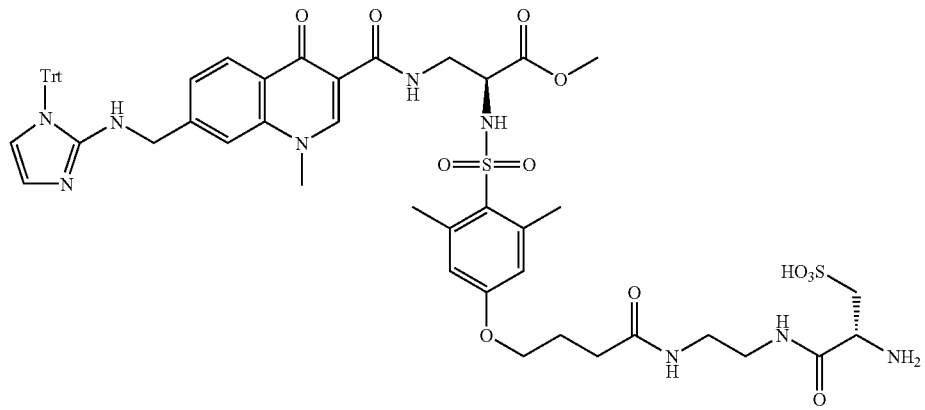

The product of Part E, above (410 mg, 0.341 mmol) was dissolved in 50/50 TFA/DCM (20 mL) and allowed to react at ambient temperatures for 10 min. The solution was concentrated and the resulting amber oil was dissolved in 50% ACN (50 mL) and lyophilized to give the title compound as a colorless solid (371 mg, 98.6%). MS: m/e 1104.4 [M+H], 862.3 [M+H−Trt]; High Resolution MS: Calcd for $C_{55}H_{62}N_9O_{12}S_2$ [M+H]: 1104.3959; Found: 1104.393.

Part G—Preparation of (2R)-N-[(1R)-1-(N-{2-[4-(4-{[((1S)-1-(Methoxycarbonyl)-2-{[1-methyl-4-oxo-7-({[1-(triphenylmethyl)imidazol-2-yl]amino}methyl)(3-hydroquinolyl)]carbonylamino}ethyl)amino]sulfonyl}-3,5-dimethylphenoxy)butanoylamino]ethyl}carbamoyl)-2-sulfoethyl]-2-[(tert-butoxy)carbonylamino]propanesulfonic Acid

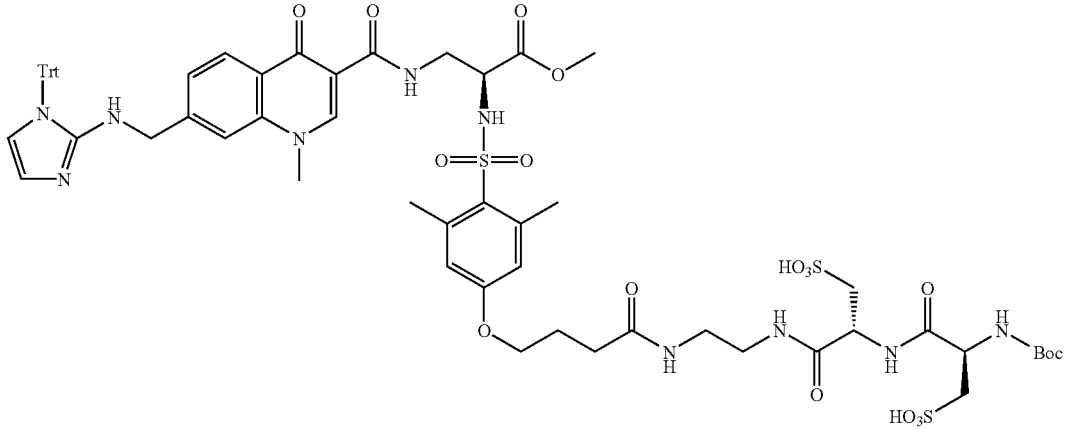

A solution of the product of Part F, above (110 mg, 0.100 mmol), the p-nitrophenyl ester of Boc-L-cysteic acid (82.4 mg, 0.200 mmol), and DIEA (0.104 mL, 0.600 mmol) in anhydrous DMF (5.0 mL) was stirred at ambient temperatures under nitrogen for 48 h. The DMF was removed under vacuum and the resulting amber oil was purified by HPLC on a Vydac C-18 column (50×250 mm) using a 1.12%/min gradient of 9 to 54% ACN containing 0.1% TFA at a flow rate of 80 mL/min. The main product peak eluting at 37.0 min was lyophilized to give the title compound as a colorless solid (96.0 mg, 70.9%). MS: m/e 1355.3 [M+H], 1113.3 [M−Trt+H], 1013.2 [M−Trt−Boc+H].

Part H—Preparation of (2R)-N-[(1R)-1-(N-{2-[4-(4-{[((1S)-1-(Methoxycarbonyl)-2-{[1-methyl-4-oxo-7-({[1-(triphenylmethyl)imidazol-2-yl]amino}methyl)(3-hydroquinolyl)]carbonylamino}ethyl)amino]sulfonyl}-3,5-dimethylphenoxy)butanoylamino]ethyl}carbamoyl)-2-sulfoethyl]-2-aminopropanesulfonic Acid

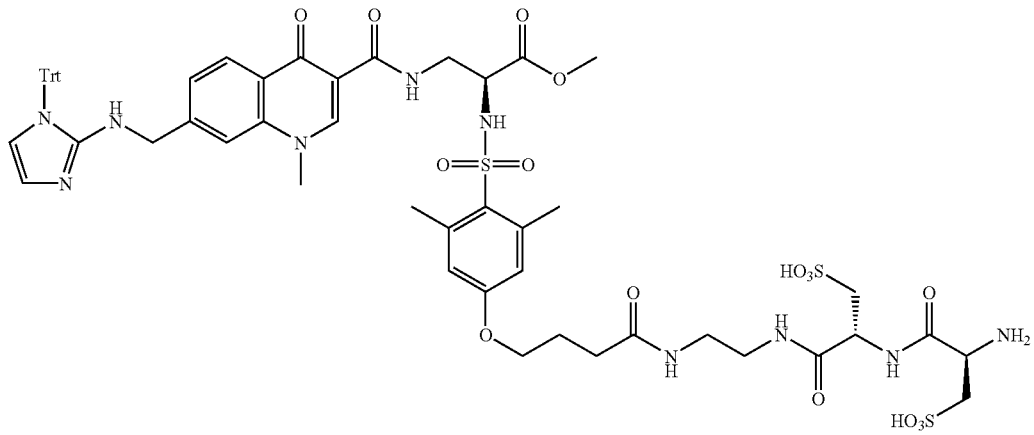

The product of Part G, above (21 mg, 0.0155 mmol) was dissolved in 50/50 TFA/DCM (5.0 mL) and allowed to react at ambient temperatures for 10 min. The solution was concentrated and the residue was taken up in 50% ACN (15 mL) and lyophilized to give the title compound as a colorless solid (18.7 mg, 96.2%). MS: m/e 1255.3 [M+H], 1013.2 [M+H−Trityl]; High Resolution MS: Calcd for $C_{58}H_{67}N_{10}O_{16}S_3$ [M+H]: 1255.3899; Found: 1255.391.

Part I—Preparation of (2R)-N-[(1R)-1-(N-{2-[4-(4-{[((1S)-1-(Methoxycarbonyl)-2-{[1-methyl-4-oxo-7-({[1-(triphenylmethyl)imidazol-2-yl]amino}methyl)(3-hydroquinolyl)]carbonylamino}ethyl)amino]sulfonyl}-3,5-dimethylphenoxy)butanoylamino]ethyl}carbamoyl)-2-sulfoethyl]-2-(2-{1,4,7,10-tetraaza-4,7,10-tris[(tert-butoxycarbonyl)methyl]cyclododecyl}acetylamino) propanesulfonic Acid

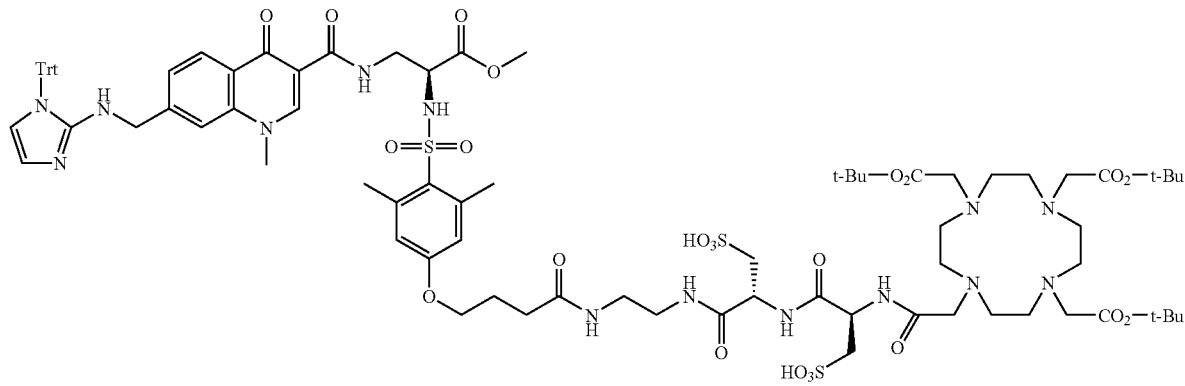

A solution of 2-(1,4,7,10-tetraaza-4,7,10-tris(((tert-butyl)oxycarbonyl)methyl)cyclododecyl)acetic acid (30.0 mg, 0.0327 mmol) (as described in DM-7003), DIEA (0.034 mL, 0.196 mmol), and HBTU (9.3 mg, 0.0245 mmol) in anhydrous DMF (1.5 mL) was stirred under nitrogen at ambient temperatures for 15 min and treated with the product of Part H, above (18.7 mg, 0.0137 mmol). The DMF was removed under vacuum after 75 min and the resulting amber oil was purified by HPLC on a Vydac C-18 column (22×250 mm) using a 0.9%/min gradient of 22.5 to 58.5% ACN containing 0.1% TFA at a flow rate of 20 mL/min. The main product peak eluting at 26.1 min was lyophilized to give the title compound as a colorless fluffy solid (7.5 mg, 53%). MS: m/e 1809.7 [M+H].

Part J—Preparation of (2S)-2-[({2,6-Dimethyl-4-[3-(N-{2-[3-sulfo-2-(3-sulfo-2-{2-[1,4,7,10-tetraaza-4,7,10-tris(carboxymethyl)cyclododecyl]acetylamino}propyl)propyl]ethyl}carbamoyl)propoxy]phenyl}sulfonyl)amino]-3-({7-[(imidazol-2-ylamino)methyl]-1-methyl-4-oxo(3-hydroquinolyl)}carbonylamino)propanoic Acid Trifluoroacetate Salt The product of Step I, above (7.5 mg, 0.0039 mmol) was dissolved in a solution of peroxide-free THF (1.40 mL) and water (0.21 mL), and treated with 3 N LiOH (0.14 mL). The mixture was stirred at ambient temperatures under nitrogen for 1 h, and concentrated to dryness under vacuum. The resulting solid residue was dissolved in 95/5 TFA/Et$_3$SiH (2.0 mL) and heated at 70° C. under nitrogen for 1 h. The solution was concentrated under vacuum and the resulting solid residue was purified by HPLC on a Vydac C-18 column (22×250 mm) using a 0.90%/min gradient of 0 to 27% ACN containing 0.1% TFA at a flow rate of 20 mL/min. The main product peak eluting at 20.5 min was lyophilized to give the title compound as a colorless fluffy solid (4.2 mg, 71.9%). MS: m/e 1385.3 [M+H]; High Resolution MS: Calcd for C$_{54}$H$_{77}$N$_{14}$O$_{23}$S$_3$ [M+H]: 1385.4448; found: 1385.446.

Example 30

Synthesis of DOTA/(2S)-2-{[(4-{3-[N-(2-{2-[(4S)-4-(N-{1-[N-(2-{4-[4-({[(1S)-1-Carboxy-2-({7-[(imidazol-2-ylamino)methyl]-1-methyl-4-oxo(3-hydroquinolyl)}carbonylamino)ethyl]amino}sulfonyl)-3,5-dimethylphenoxy]butanoylamino}ethyl)carbamoyl]-2-sulfoethyl}carbamoyl)-4-aminobutanoylamino]-3-sulfopropyl}ethyl)carbamoyl]propoxy}-2,6-dimethylphenyl)sulfonyl]amino}-3-({7-[(imidazol-2-ylamino)methyl]-1-methyl-4-oxo(3-hydroquinolyl)}-carbonylamino)propanoic Acid Conjugate Bis (trifluoroacetate) Salt

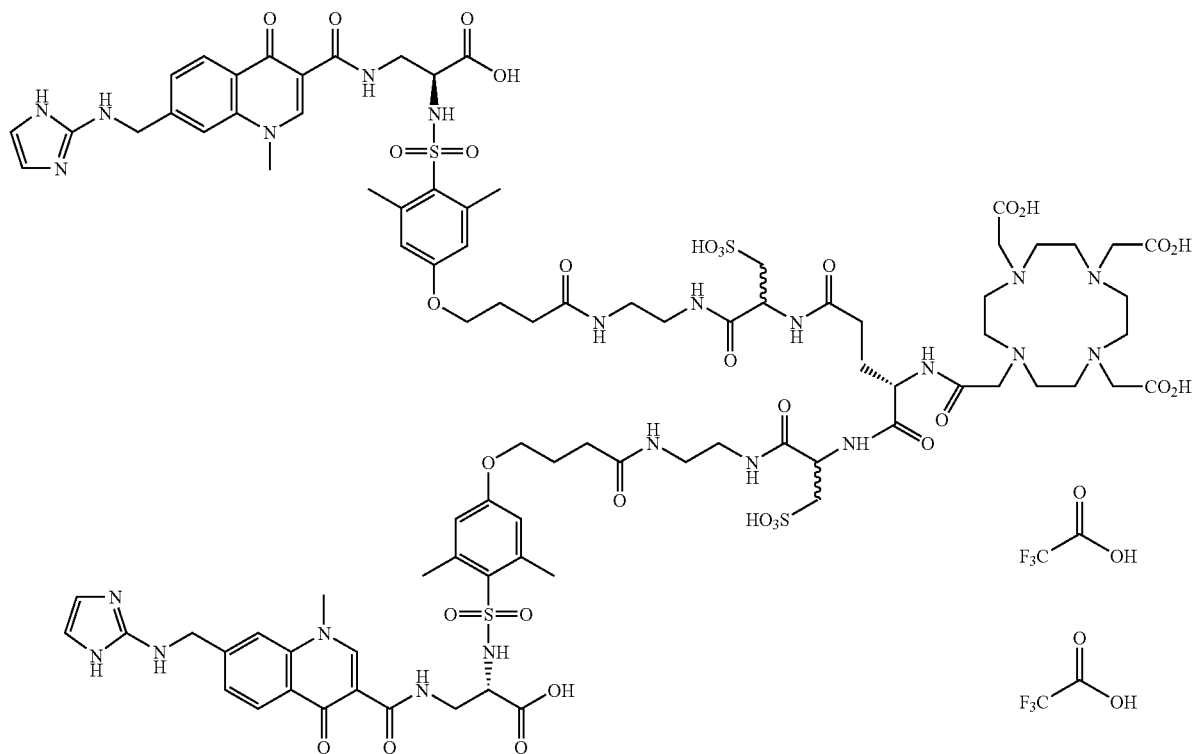

Part A—Preparation of Di-2,3,5,6-tetrafluorophenyl (2S)-2-[(tert-Butoxy)carbonylamino]pentane-1,5-dioate

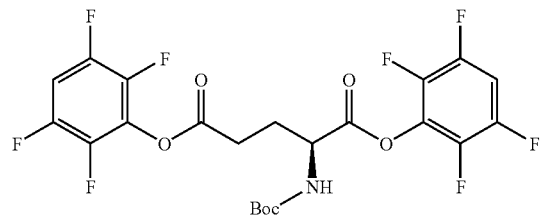

To a solution of Boc-L-Glu-OH (28.9 g, 117 mmol) in DMF (500 mL) at ambient temperatures and under nitrogen, was added a solution of 2,3,5,6-tetrafluorophenol (48.2 g, 290 mmol) in DMF (50 mL). After stirring for 10 min, EDC (55.6 g, 290 mmol) was added and the mixture was stirred for 96 h. The volatiles were removed under vacuum and the residue was triturated with 0.1 N HCl (750 mL). To this mixture was added EtOAc (600 mL) and the layers were separated. The aqueous layer was extracted with EtOAc (3×500 mL), and all EtOAc extracts were combined, washed consecutively with water (300 mL) and saturated NaCl (300 mL), dried (MgSO$_3$), and concentrated to give a tan solid (62 g). The tan solid was washed with ACN to give the title compound (45.5 g, 73.0%) in purified form. MS: m/e 566.0 [M+Na].

Part B—Preparation of (2R)-2-[4-(N-{(1R)-1-[N-(2-{4-[4-({[(1S)-2-({7-[([1-(Triphenylmethyl)imidazol-2-yl]amino)methyl]-1-methyl-4-oxo(3-hydroquinolyl)}carbonylamino)-1-(methoxycarbonyl) ethyl]amino}sulfonyl)-3,5-dimethylphenoxy] butanoylamino}ethyl)carbamoyl]-2-sulfoethyl}carbamoyl)(4S)-4-[(tert-butoxy) carbonylamino]butanoylamino]-N-(2-{4-[4-({[(1S)-2-({7-[(imidazol-2-ylamino)methyl]-1-methyl-4-oxo (3-hydroquinolyl)}carbonylamino)-1-(methoxycarbonyl)ethyl]amino}sulfonyl)-3,5-dimethylphenoxy]butanoylamino}ethyl) propanesulfonic Acid

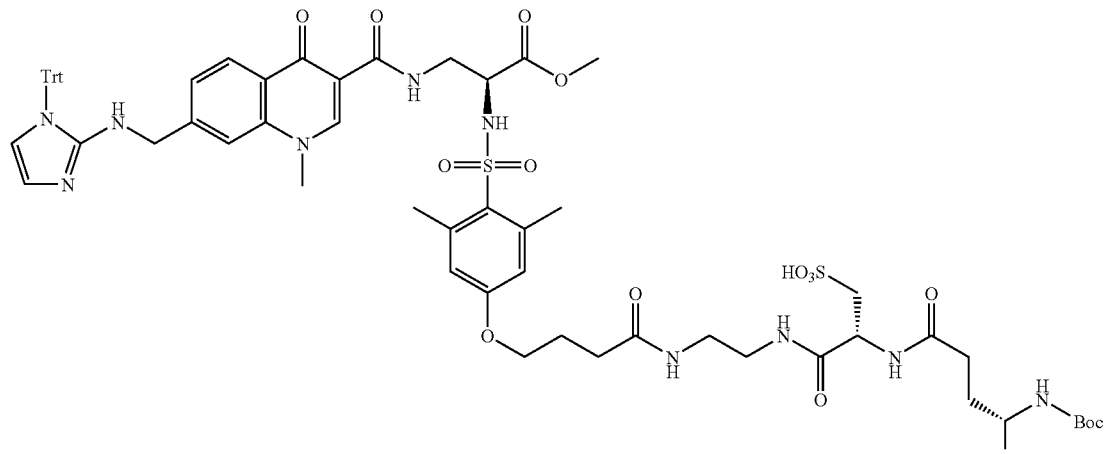

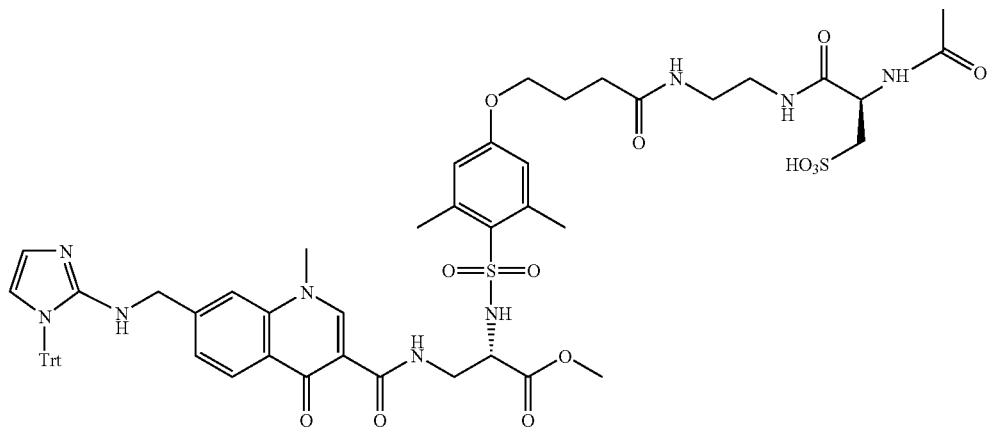

A solution of the product of Example 29, Part F (130 mg, 0.118 mmol), the product of Part A, above (27.2 mg, 0.050 mmol), and DIEA (0.070 mL, 0.40 mmol) in anhydrous DMF (4.0 mL) was stirred at ambient temperatures under nitrogen for 29 h. The DMF was removed under vacuum and the resulting amber oil was purified by HPLC on a Vydac C-18 column (50×250 mm) using a 0.90%/min gradient of 22.5 to 58.5% ACN containing 0.1% TFA at a flow rate of 80 mL/min. The main product peak eluting at 35.7 min was lyophilized to give the title compound as a colorless fluffy solid (108 mg, 89.3%). MS: m/e 2419.6 [M+H], 1210.4 [M+2H].

Part C—Preparation of (2R)-2-[4-(N-{(1R)-1-[N-(2-{4-[4-({[(1S)-2-({7-[([1-(Triphenylmethyl)imidazol-2-yl]amino)methyl]-1-methyl-4-oxo(3-hydroquinolyl)}carbonylamino)-1-(methoxycarbonyl)ethyl]amino}sulfonyl)-3,5-dimethylphenoxy]butanoylamino}ethyl)carbamoyl]-2-sulfoethyl}carbamoyl)(4S)-4-aminobutanoylamino]-N-(2-{4-[4-({[(1S)-2-({7-[(imidazol-2-ylamino)methyl]-1-methyl-4-oxo(3-hydroquinolyl)}carbonylamino)-1-(methoxycarbonyl)ethyl]amino}sulfonyl)-3,5-dimethylphenoxy]butanoylamino}ethyl)propanesulfonic Acid

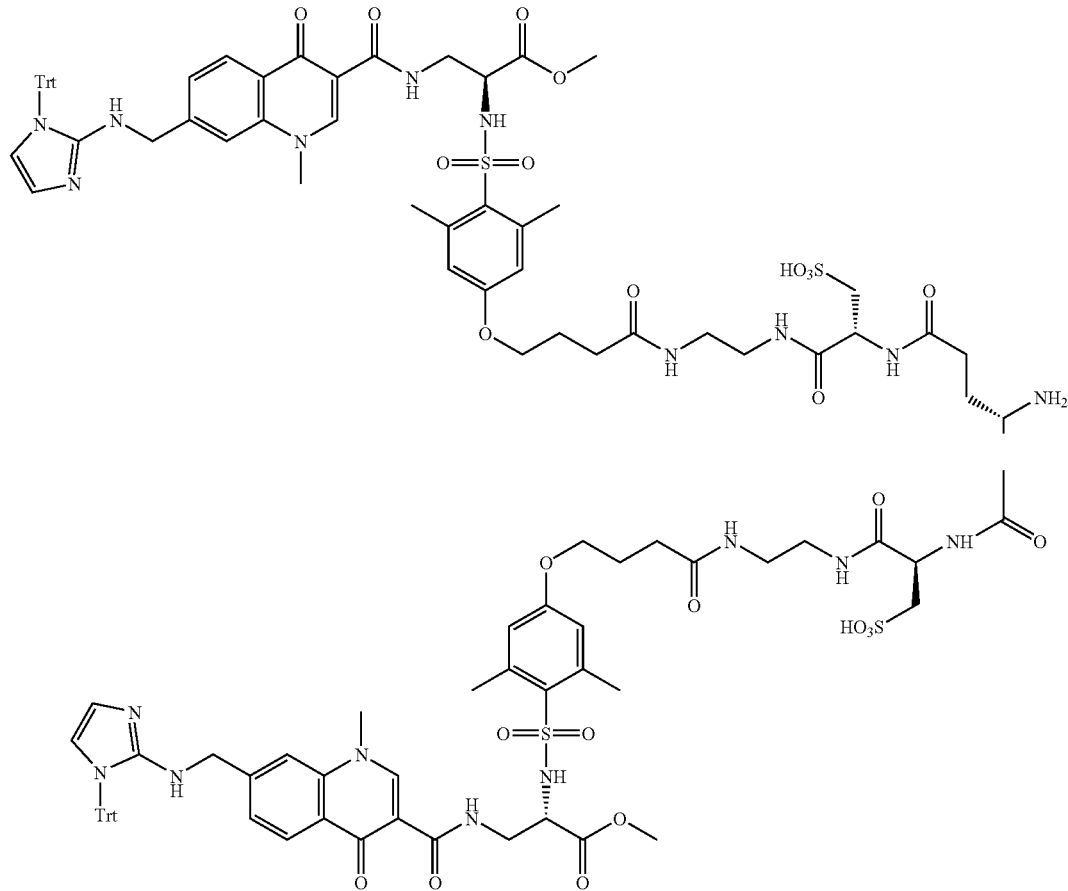

The product of Part B, above (107 mg, 0.0442 mmol) was dissolved in 50/50 TFA/DCM (5.0 mL) and allowed to react at ambient temperatures under nitrogen for 10 min. The solution was concentrated and the resulting amber oil was dissolved in 50% ACN (25 mL) and lyophilized to give the title compound as a pale yellow solid (105 mg, 98.0%). MS: m/e 1159.9 [M+2H], 1039.4 [M+2H−Trt].

Part D—Preparation of DOTA tri-t-Butyl Ester/
(2R)-2-[4-(N-{(1R)-1-[N-(2-{4-[4-({[(1S)-2-({7-
[([1-(Triphenylmethyl)imidazol-2-yl]amino)methyl]-
1-methyl-4-oxo(3-hydroquinolyl)}carbonylamino)-
1-(methoxycarbonyl)ethyl]amino}sulfonyl)-3,5-
dimethylphenoxy]butanoylamino}ethyl)carbamoyl]-
2-sulfoethyl}carbamoyl)(4S)-4-
aminobutanoylamino]-N-(2-{4-[4-({[(1S)-2-({7-
[(imidazol-2-ylamino)methyl]-1-methyl-4-oxo(3-
hydroquinolyl)}carbonylamino)-1-
(methoxycarbonyl)ethyl]amino}sulfonyl)-3,5-
dimethylphenoxy]butanoylamino}ethyl)
propanesulfonic Acid Conjugate A solution of 2-(1,4,7,10-tetraaza-4,7,10-tris(((tert-butyl)oxycarbonyl)methyl)cyclododecyl)acetic acid (31.6 mg, 0.0346 mmol) (as described in DM-7003), DIEA (0.072 mL, 0.416 mmol), and HBTU (9.8 mg, 0.026 mmol) in anhydrous DMF (1.8 mL) was stirred under nitrogen at ambient temperatures for 15 min and treated with the product of Part C, above (40.0 mg, 0.0173 mmol). The DMF was removed under vacuum after 90 min and the resulting pale yellow oil was purified by HPLC on a Vydac C-18 column (50×250 mm) using a 1.01%/min gradient of 22.5 to 63.0% ACN containing 0.1% TFA at a flow rate of 80 mL/min. The main product peak eluting at 27.6 min was lyophilized to give the title compound as a colorless solid (29.0 mg, 62.4%). MS: m/e 1437.6 [M+2H], 1316.6 [M+2H−Trt].

Part E—Preparation of DOTA/(2S)-2-{[(4-{3-[N-
(2-{2-[(4S)-4-(N-{1-[N-(2-{4-[4-({[(1S)-1-Carboxy-
2-({7-[(imidazol-2-ylamino)methyl]-1-methyl-4-oxo
(3-hydroquinolyl)}carbonylamino)ethyl]
amino}sulfonyl)-3,5-dimethylphenoxy]
butanoylamino}ethyl)carbamoyl]-2-
sulfoethyl}carbamoyl)-4-aminobutanoylamino]-3-
sulfopropyl}ethyl)carbamoyl]propoxy}-2,6-
dimethylphenyl)sulfonyl]amino}-3-({7-[(imidazol-
2-ylamino)methyl]-1-methyl-4-oxo(3-
hydroquinolyl)}carbonylamino)propanoic Acid
Conjugate Bis(trifluoroacetate) Salt A mixture of the product of Part D, above (30.0 mg, 0.0104 mmol), peroxide-free THF (3.2 mL), water (0.485 mL), and 3 N LiOH (0.320 mL, 0.96 mmol) was stirred at ambient temperatures under nitrogen for 2 h. The solution was concentrated under vacuum and the resulting solid residue was dissolved in 95/5 TFA/Et₃SiH (5.0 mL). The solution was heated at 70° C. under nitrogen for 1 h and concentrated under vacuum. The resulting oily solid was purified by HPLC on a Vydac C-18 column (22×250 mm) using a 0.90%/min gradient of 0 to 27% ACN containing 0.1% TFA at a flow rate of 20 mL/min. The main product peak eluting at 27.8 min was lyophilized to give the title compound as a colorless fluffy solid (12.8 mg, 48.5%). MS: m/e 1096.8 [M+2H], 731.8 [M+3H]; High Resolution MS: Calcd for $C_{91}H_{122}N_{23}O_{33}S_4$ [M+H]: 2192.7458; Found: 2192.741.

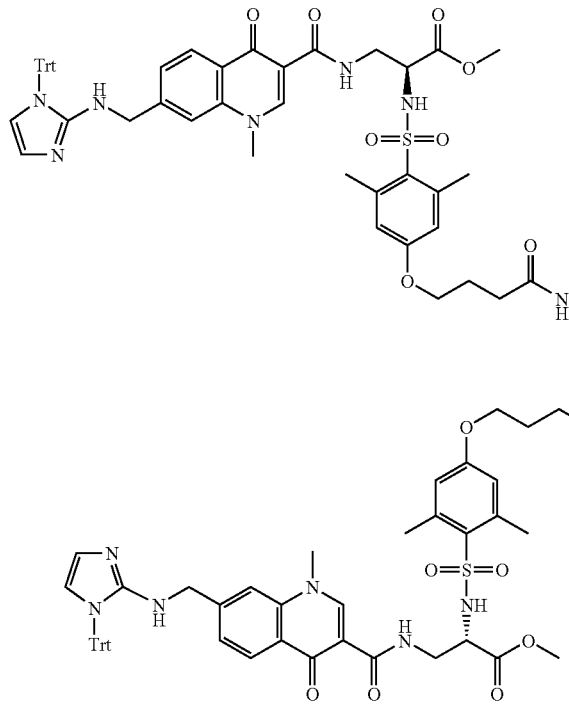
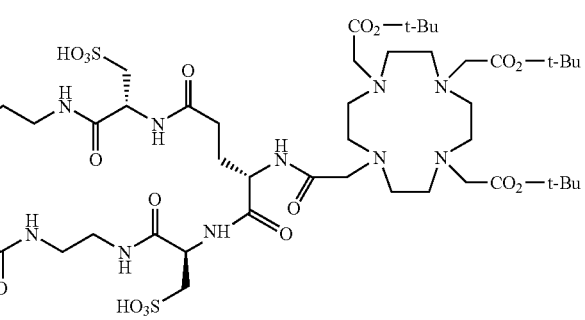

Example 31

Synthesis of 2-[({4-[3-(N-{2-[(2R)-2-((2R)-3-Sulfo-2-{2-[1,4,7,10-tetraaza-4,7,10-tris(carboxymethyl)cyclododecyl]acetylamino}propyl)-3-sulfopropyl]ethyl}carbamoyl)propoxy]-2,6-dimethylphenyl}sulfonyl)amino](2S)-3-({7-[(imidazol-2-ylamino)methyl]-1-methyl-4-oxo(3-hydroquinolyl)}-carbonylamino)propanoic Acid Trifluoroacetate Salt

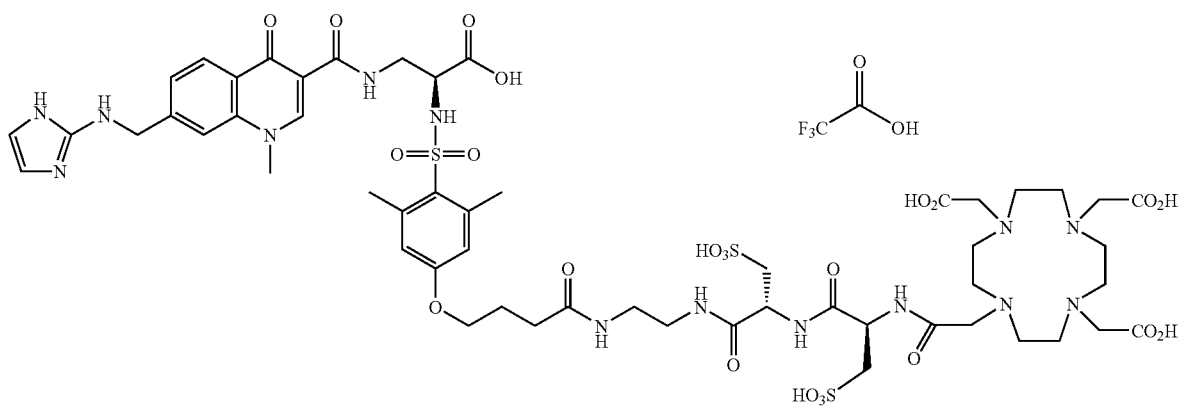

Part A—Preparation of 2-({[4-(3-{N-[2-((2R)-2-Amino-3-sulfopropyl)ethyl]carbamoyl}propoxy)-2,6-dimethylphenyl]sulfonyl}amino)(2S)-3-{[1-methyl-4-oxo-7-({[1-(triphenylmethyl)imidazol-2-yl]amino}methyl)(3-hydroquinolyl)]carbonylamino}propanoic Acid

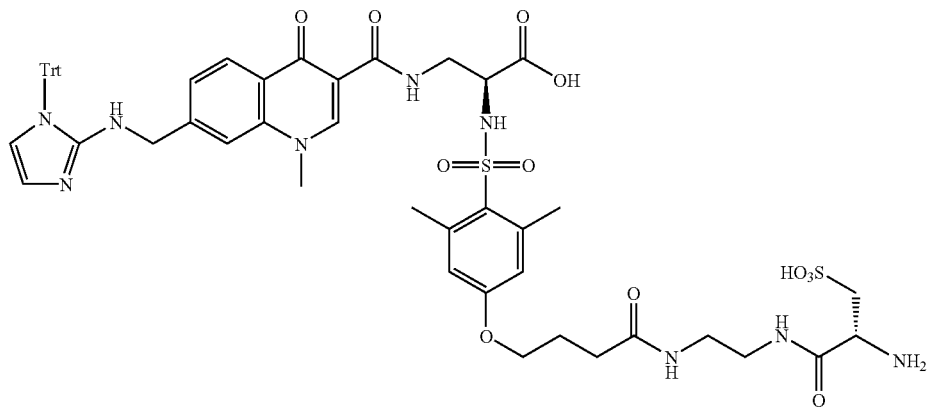

A mixture of the product of Example 29, Part F (125 mg, 0.113 mmol), peroxide-free THF (3.8 mL), water (0.57 mL), and 3 N LiOH (0.38 mL, 1.13 mmol) was stirred at ambient temperatures under nitrogen for 1 h. The mixture was adjusted to pH 1 using 1 N HCl (0.70 mL) and concentrated to dryness under vacuum. The resulting solid was purified by HPLC on a Vydac C-18 column (50×250 mm) using a 0.90%/min gradient of 18 to 54% ACN containing 0.1% TFA at a flow rate of 80 mL/min. The main product peak eluting at 21.0 min was lyophilized to give the title compound as a colorless solid (96.0 mg, 77.9%). MS: m/e 1090.3 [M+H], 848.2 [M+H−Trt]; High Resolution MS: Calcd for $C_{54}H_{60}N_9O_{12}S_2$ [M+H]: 1090.3808; Found: 1090.381.

Part B—Preparation of 2-({[4-(3-{N-[2-((2R)-2-{(2R)-2-[(tert-Butoxy)carbonylamino]-3-sulfopropyl}-3-sulfopropyl)ethyl]carbamoyl}propoxy)-2,6-dimethylphenyl]sulfonyl}amino)(2S)-3-{[1-methyl-4-oxo-7-({[1-(triphenylmethyl)imidazol-2-yl]amino}methyl)(3-hydroquinolyl)]carbonylamino}propanoic Acid

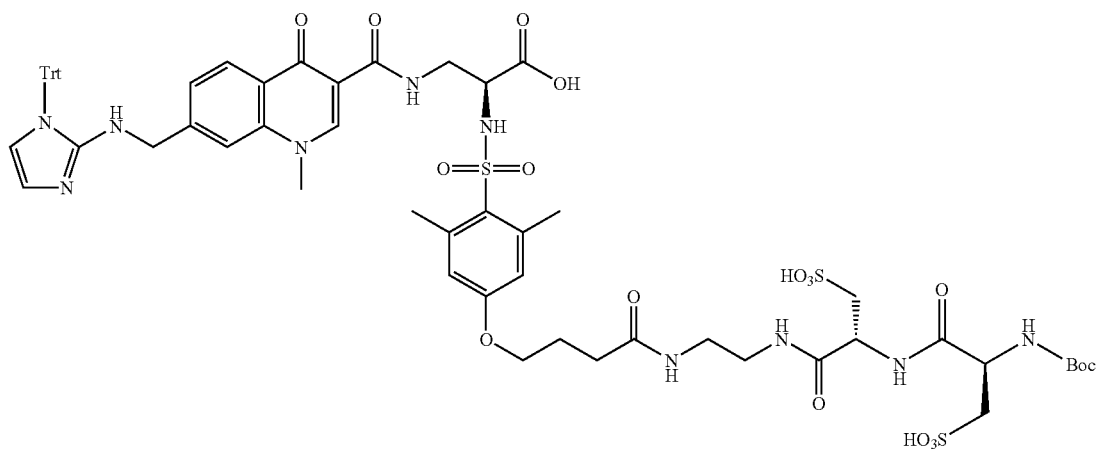

A solution of Boc-L-cysteic acid (37.0 mg, 0.128 mmol), DIEA (0.040 mL, 0.228 mmol), and PyBOP (53.0 mg, 0.102 mmol) in anhydrous DMF (1.0 mL) was stirred at ambient temperatures under nitrogen for 15 min, and added to a solution of the product of Part A, above (93.0 mg, 0.0854 mmol) and DIEA (0.045 mL, 0.256 mmol) in anhydrous DMF (3.0 mL). The resulting solution was stirred at ambient temperatures under nitrogen for 1.5 h and concentrated to a viscous amber oil. Purification by HPLC on a Vydac C-18 column (50×250 mm) using a 0.68%/min gradient of 18 to 45% ACN containing 0.1% TFA at a flow rate of 80 mL/min. The main product peak eluting at 36.4 min was lyophilized to give the title compound as a colorless solid (94.0 mg, 82.1%). MS: m/e 1341.2 [M+H], 1099.1 [M+H−Trt], 999.1 [M+H−Trt−Boc].

Part C—Preparation of 2-{[(4-{3-[N-(2-{(2R)-2-[(2R)-3-Sulfo-2-(2-{1,4,7,10-tetraaza-4,7,10-tris[(tert-butoxycarbonyl)methyl]cyclododecyl}acetylamino)propyl]-3-sulfopropyl}ethyl)carbamoyl]propoxy}-2,6-dimethylphenyl)sulfonyl]amino}(2S)-3-{[1-methyl-4-oxo-7-({[1-(triphenylmethyl)imidazol-2-yl]amino}methyl)(3-hydroquinolyl)]carbonylamino}propanoic Acid

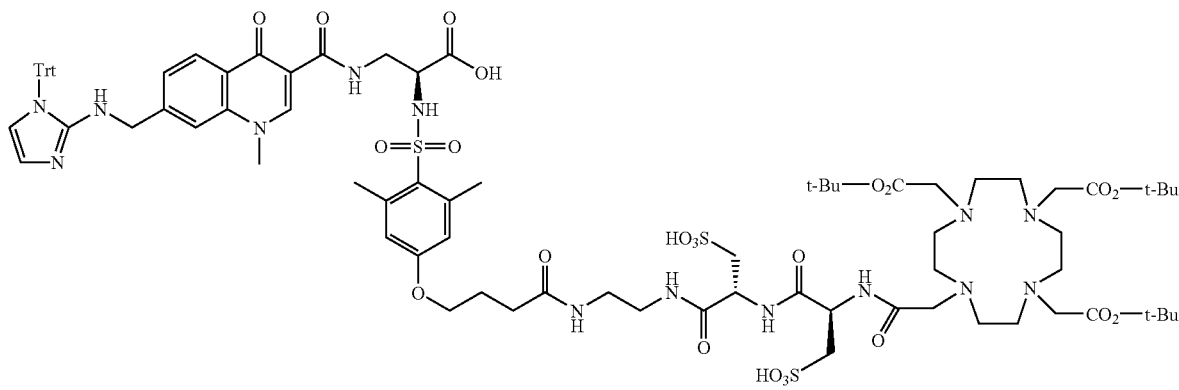

A solution of the product of Part B, above (90.0 mg, 0.0672 mmol) in 50/50 TFA/DCM (10.0 mL) was allowed to react at ambient temperatures under nitrogen for 10 min and concentrated under vacuum to give the intermediate amine as an amber oil. MS: m/e 1241.3 [M+H], 999.3 [M+H−Trt]; High Resolution MS: Calcd for $C_{57}H_{65}N_{10}O_{16}S_3$ [M+H]: 1241.3742; Found: 1241.375.

A solution of 2-(1,4,7,10-tetraaza-4,7,10-tris(((tert-butyl)oxycarbonyl)methyl)cyclododecyl)acetic acid (123 mg, 0.134 mmol) (as described in DM-7003), DIEA (0.092 mL, 0.538 mmol), and PyBOP (52.4 mg, 0.101 mmol) in anhydrous DMF (1.5 mL) was stirred under nitrogen at ambient temperatures for 15 min, and added to a solution of the free amine produced above (90.0 mg, 0.0672 mmol) and DIEA (0.046 mL, 0.269 mmol) in anhydrous DMF (1.5 mL). The DMF was removed under vacuum after 1 h and the resulting amber oil was purified by HPLC on a Vydac C-18 column (50×250 mm) using a 0.288%/min gradient of 30.6 to 45% ACN containing 0.1% TFA at a flow rate of 80 mL/min. The main product peak eluting at 25.8 min was lyophilized to give the title compound as a colorless solid (92.0 mg, 76.3%). MS: m/e 1795.6 [M+H], 1553.5 [M+H–Trt]; High Resolution MS: Calcd for $C_{85}H_{115}N_{14}O_{23}S_3$ [M+H]: 1795.7422; Found: 1795.744.

Part D—Preparation of 2-[({4-[3-(N-{2-[(2R)-2-((2R)-3-Sulfo-2-{2-[1,4,7,10-tetraaza-4,7,10-tris(carboxymethyl)cyclododecyl]acetylamino}propyl)-3-sulfopropyl]ethyl}carbamoyl)propoxy]-2,6-dimethylphenyl}sulfonyl)amino](2S)-3-({7-[(imidazol-2-ylamino)methyl]-1-methyl-4-oxo(3-hydroquinolyl)}-carbonylamino)propanoic Acid Trifluoroacetate Salt A solution of the product of Part C, above (89.0 mg, 0.0496 mmol) in 97/3 TFA/Et$_3$SiH (10.0 mL) was heated at 70° C. under nitrogen for 30 min and concentrated under vacuum. The resulting oily solid was purified by HPLC on a Vydac C-18 column (50×250 mm) using a 0.45%/min gradient of 4.5 to 22.5% ACN containing 0.1% TFA at a flow rate of 80 mL/min. The main product peak eluting at 19.5 min was lyophilized to give steochemically pure title compound as a colorless fluffy solid (65.0 mg, 87.5%). MS: m/e 1385.4 [M+H].

Example 32

Alternative Synthesis of Intermediate 2-({[4-(3-{N-[2-((2R)-2-Amino-3-sulfopropyl)ethyl]carbamoyl}propoxy)-2,6-dimethylphenyl]sulfonyl}amino)(2S)-3-{[1-methyl-4-oxo-7-({[1-(triphenylmethyl)imidazol-2-yl]amino}methyl)(3-hydroquinolyl)]carbonylamino}propanoic Acid

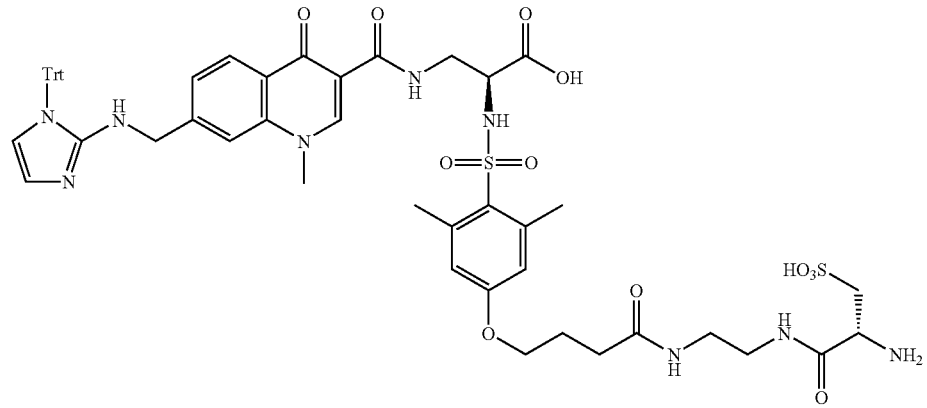

Part A—Preparation of (2S)-2-{[(4-{3-[N-(2-Aminoethyl)carbamoyl]propoxy}-2,6-dimethylphenyl)sulfonyl]amino}-3-{[1-methyl-4-oxo-7-({[1-(triphenylmethyl)imidazol-2-yl]amino}methyl)(3-hydroquinolyl)]carbonylamino}propanoic Acid

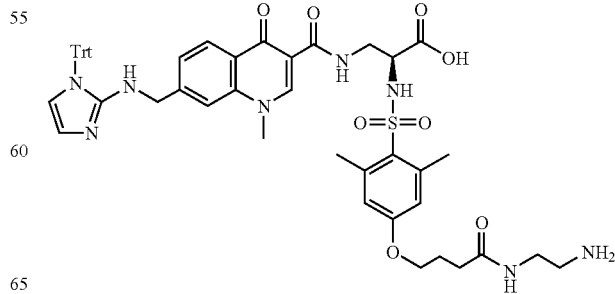

A mixture of the product of Example 29, Part D (956 mg, 1.004 mmol), peroxide-free THF (35 mL), water (5.3 mL), and 3 N LiOH (3.53 mL, 10.6 mmol) was stirred at ambient temperatures under nitrogen for 1 h, and adjusted to pH 5–6 using 1 N HCl (10 mL). The THF was removed under vacuum causing a gummy yellow solid to precipitate. The water layer was removed by decantation and the solid was washed with water (15 mL). The solid was dried under vacuum to give the title compound as a dry yellow solid Part B—Preparation of 2-{[(4-{3-[N-(2-{(2R)-2-[(tert-Butoxy)carbonylamino]-3-sulfopropyl}ethyl)carbamoyl]propoxy}-2,6-dimethylphenyl)sulfonyl]amino}(2S)-3-{[1-methyl-4-oxo-7-({[1-(triphenylmethyl)imidazol-2-yl]amino}methyl)(3-hydroquinolyl)]carbonylamino}propanoic Acid

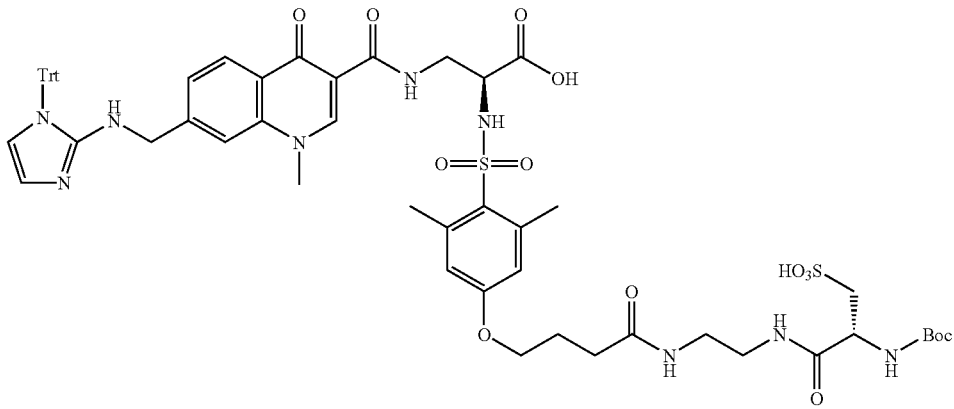

A solution of Boc-L-cysteic acid (175 mg, 0.60 mmol), DIEA (0.208 mL, 1.20 mmol), and PyBOP (250 mg, 0.480 mmol) in anhydrous DMF (5.0 mL) was stirred at ambient temperatures under nitrogen for 17 min, and added to a solution of the product of Part A, above (375 mg, 0.400 mmol) and DIEA (0.070 mL, 0.400 mmol) in anhydrous DMF (4.0 mL). The resulting solution was stirred at ambient temperatures under nitrogen for 45 min and concentrated under vacuum to give an amber oil. Purification by PLC on a Vydac C-18 column (50×250 mm) using a 0.292%/min gradient of 31.5 to 43.2% ACN containing 0.1% TFA at a flow rate of 80 mL/min. The main product peak eluting at 22.0 min was lyophilized to give the title compound as a colorless solid (430 mg, 90.4%). MS: m/e 1190.3 [M+H], 948.3 [M+H−Trt].

Part C—Preparation of 2-({[4-(3-{N-[2-((2R)-2-Amino-3-sulfopropyl)ethyl]carbamoyl}propoxy)-2,6-dimethylphenyl]-sulfonyl}amino)(2S)-3-{[1-methyl-4-oxo-7-({[1-(triphenylmethyl)imidazol-2-yl]amino}methyl)(3-hydroquinolyl)]carbonylamino}propanoic Acid A solution of the product of Part B, above (430 mg, 0.362 mmol) in 50/50 TFA/DCM (15 mL) was allowed to react at ambient temperatures under nitrogen for 10 min and concentrated under vacuum. The resulting amber oil was taken up in 50% ACN (50 mL) and lyophilized to give the title compound as a pale yellow solid (398 mg, 100%). MS: m/e 1090.3 [M+H], 848.2 [M+H−Trt].

Example 33

Synthesis of DOTA/2-{[(4-{3-[N-(2-{(2R)-2-[(2R)-2-(4-{N-[(1R)-1-(N-{(1R)-1-[N-(2-{4-[4-({[(1S)-1-Carboxy-2-({7-[(imidazol-2-ylamino)methyl]-1-methyl-4-oxo(3-hydroquinolyl)}carbonylamino)-1-carboxyethyl]amino}-sulfonyl)-3,5-dimethylphenoxy]butanoylamino}ethyl)carbamoyl]-2-sulfoethyl}carbamoyl)-2-sulfoethyl]carbamoyl}(2S)-2-aminobutanoylamino)-3-sulfopropyl]-3-sulfopropyl}ethyl)carbamoyl]propoxy}-2,6-dimethylphenyl)sulfonyl]amino}(2S)-3-({7-[(imidazol-2-ylamino)methyl]-1-methyl-4-oxo(3-hydroquinolyl)}-carbonylamino)propanoic Acid Conjugate

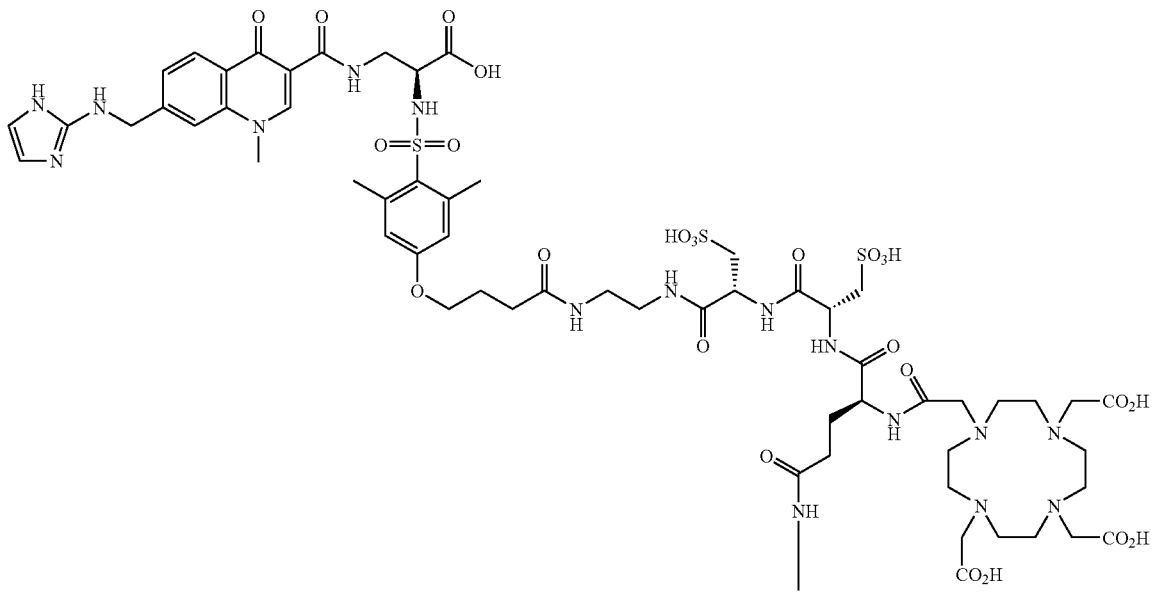

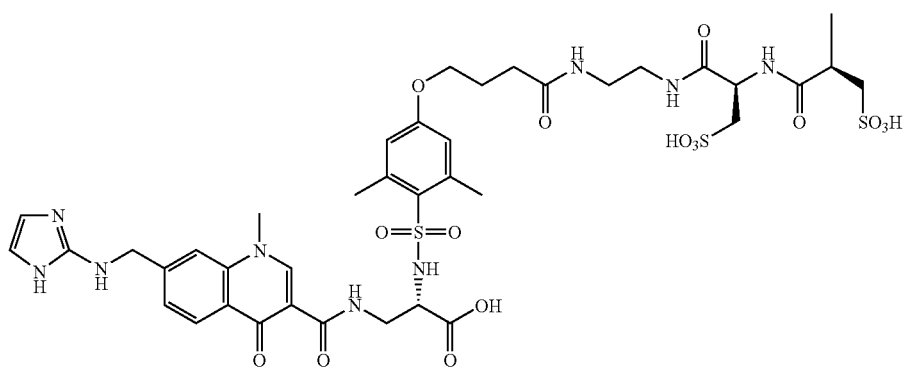

Part A—Preparation of 2-{[(4-{3-[N-(2-{(2R)-2-[(2R)-2-(4-{N-[(1R)-1-(N-{(1R)-1-[N-(2-{4-[4-({[(1S)-1-Carboxy-2-({7-[({1-(triphenylmethyl)imidazol-2-yl}amino)methyl]-1-methyl-4-oxo(3-hydroquinolyl)}carbonylamino)-1-carboxyethyl]amino}sulfonyl)-3,5-dimethylphenoxy]butanoylamino}ethyl)carbamoyl]-2-sulfoethyl}carbamoyl)-2-sulfoethyl]carbamoyl}(2S)-2-[(tert-butoxy)carbonylamino]butanoylamino)-3-sulfopropyl]-3-sulfopropyl}ethyl)carbamoyl]propoxy}-2,6-dimethylphenyl)sulfonyl]amino}(2S)-3-({7-[({1-(triphenylmethyl)imidazol-2-yl}amino)methyl]-1-methyl-4-oxo(3-hydroquinolyl)}carbonylamino)propanoic Acid

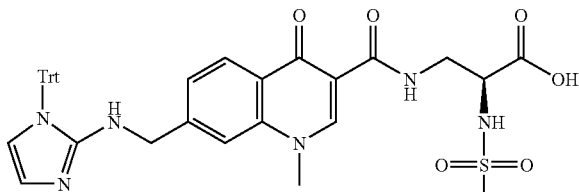
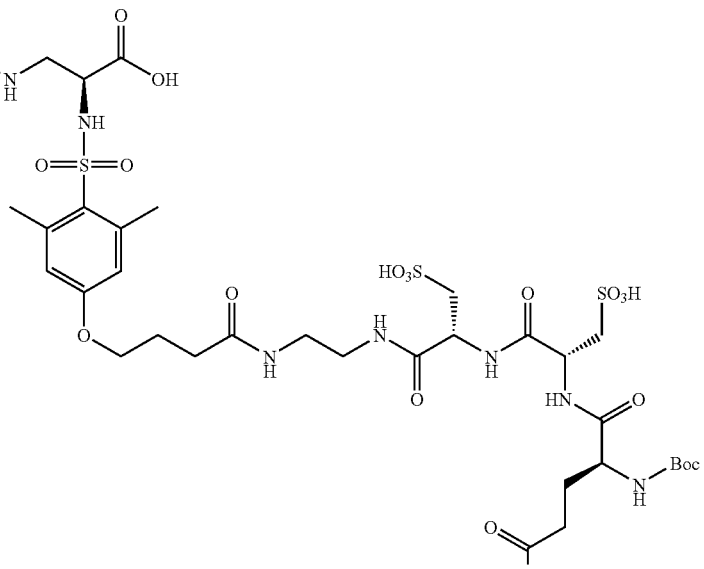
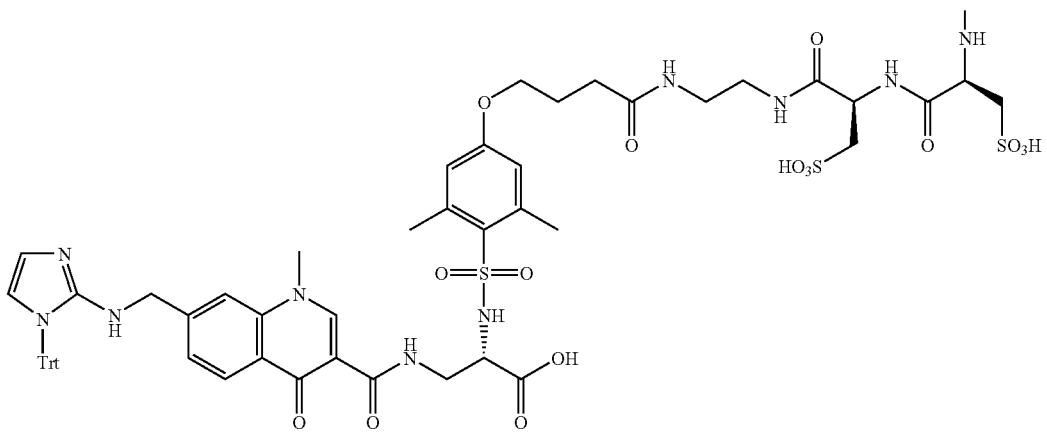

A solution of the product of the first half of Example 31, Part C (136 mg, 0.110 mmol), DIEA (0.076 mL, 0.44 mmol), and the product of Example 30, Part A (26.2 mg, 0.050 mmol) in anhydrous DMF (3.0 mL) was stirred at ambient temperatures under nitrogen for 7 h. The DMF was removed under vacuum and the viscous amber oil was purified by HPLC on a Vydac C-18 column (50×250 mm) using a 0.45%/min gradient of 27 to 45% ACN, followed by a 0.72% gradient of 45–63% ACN containing 0.1% TFA at a flow rate of 80 mL/min. The main product peak eluting at 75.2 min was lyophilized to give the title compound as a colorless solid (129 mg, 47.9%). MS: m/e 1347.3 [M+2H].

Part B—Preparation of DOTA tri-t-Butyl Ester Conjugate of 2-{[(4-{3-[N-(2-{(2R)-2-[(2R)-2-(4-{N-[(1R)-1-(N-{(1R)-1-[N-(2-{4-[4-({[(1S)-1-Carboxy-2-({7-[({1-(triphenylmethyl)imidazol-2-yl}amino)methyl]-1-methyl-4-oxo(3-hydroquinolyl)} carbonylamino)-1-carboxyethyl]amino}sulfonyl)-3,5-dimethylphenoxy]butanoylamino}ethyl)carbamoyl]-2-sulfoethyl}carbamoyl)-2-sulfoethyl]carbamoyl}(2S)-2-aminobutanoylamino)-3-sulfopropyl]-3-sulfopropyl}-ethyl)carbamoyl]propoxy}-2,6-dimethylphenyl)sulfonyl]-amino}(2S)-3-({7-[({1-(triphenylmethyl)imidazol-2-yl}amino)methyl]-1-methyl-4-oxo(3-hydroquinolyl)}-carbonylamino) propanoic Acid

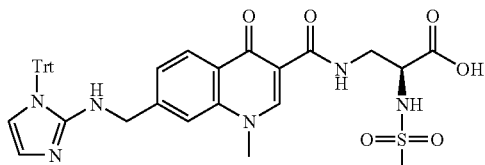

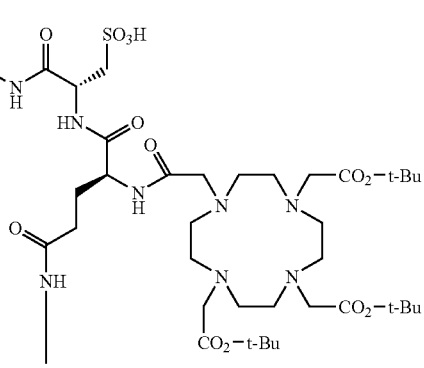

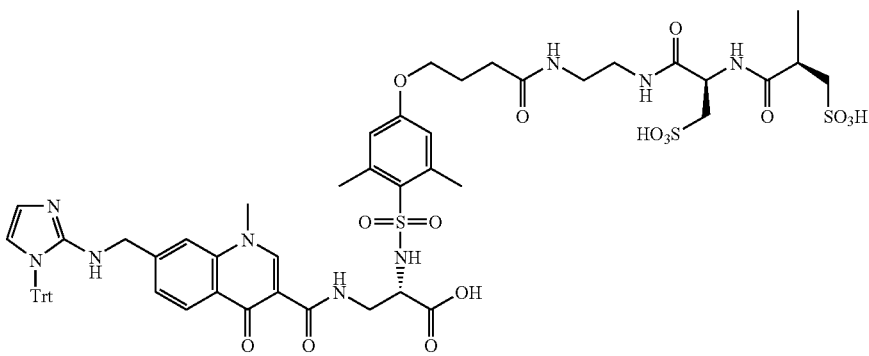

The product of Part A, above (34.0 mg, 0.0126 mmol) was dissolved in 50/50 TFA/DCM (12 mL) and allowed to react at ambient temperatures under nitrogen for 10 min. The solution was concentrated and the resulting amber oil was dried under vacuum.

A solution of 2-(1,4,7,10-tetraaza-4,7,10-tris(((tert-butyl)oxycarbonyl)methyl)cyclododecyl)acetic acid (23.1 mg, 0.0253 mmol), DIEA (0.020 mL, 0.115 mmol), and PyBOP (9.8 mg, 0.019 mmol) in anhydrous DMF (2.0 mL) was stirred under nitrogen at ambient temperatures for 15 min, and added to a solution of the product from the deprotection reaction, above and DIEA (0.020 mL, 0.115 mmol) in anhydrous DMF (2.0 mL). The DMF was removed under vacuum after 2 h, and the resulting residue was purified by HPLC on a Vydac C-18 column (50×250 mm) using a 0.45%/min gradient of 27 to 49.5% ACN containing 0.1% TFA at a flow rate of 80 mL/min. The main product peak eluting at 43.8 min was lyophilized to give the title compound as a colorless solid (16.0 mg, 40.4%). MS: m/e 1574.8 [M+2H], 1453.7 [M+2H−Trt], 1332.2 [M+2H−2Trt].

Part C—Preparation of DOTA/2-{[(4-{3-[N-(2-{(2R)-2-[(2R)-2-(4-{N-[(1R)-1-(N-{(1R)-1-[N-(2-{4-[4-({[(1S)-1-Carboxy-2-({7-[(imidazol-2-ylamino)methyl]-1-methyl-4-oxo(3-hydroquinolyl)}carbonylamino)-1-carboxyethyl]amino}sulfonyl)-3,5-dimethylphenoxy]butanoylamino}ethyl)carbamoyl]-2-sulfoethyl}carbamoyl)-2-sulfoethyl]carbamoyl}(2S)-2-aminobutanoylamino)-3-sulfopropyl]-3-sulfopropyl}-ethyl)carbamoyl]propoxy}-2,6-dimethylphenyl)sulfonyl]-amino}(2S)-3-({7-[(imidazol-2-ylamino)methyl]-1-methyl-4-oxo(3-hydroquinolyl)}carbonylamino)propanoic Acid Conjugate The product of Part B, above (14.0 mg, 0.00445 mmol) was dissolved in 95/5 TFA/Et₃SiH (8.0 mL) and heated at 70° C. under nitrogen for 1 h. The solution was concentrated under vacuum and the resulting yellow solid was purified by HPLC on a Vydac C-18 column (22×250 mm) using a 0.9%/min gradient of 0 to 27% ACN containing 0.1% TFA at a flow rate of 20 mL/min. The main product peak eluting at 24.5 min was lyophilized to give the title compound as a colorless solid (8.2 mg, 73.9%). MS: m/e 1247.7 [M+2H].

Example 34

Synthesis of (2S)-3-{[7-[(Imidazol-2-ylamino)methyl]-4-oxo-1-(3-{2-[1,4,7,10-tetraaza-4,7,10-tris(carboxymethyl)cyclododecyl]acetylamino}propyl)(3-hydroquinolyl)]carbonylamino}-2-{[(2,4,6-trimethylphenyl)sulfonyl]amino}propanoic Acid Tris(trifluoroacetate) Salt

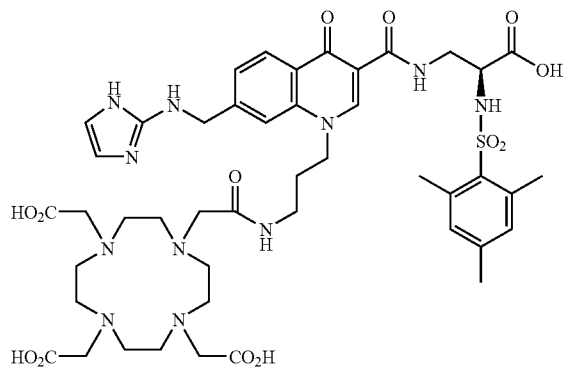

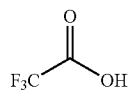

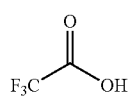

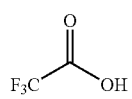

Part A—Preparation of (2S)-3-({7-[(Imidazol-2-ylamino)methyl]-4-oxo-1-[3-(2-{1,4,7,10-tetraaza-4,7,10-tris[(tert-butoxycarbonyl)methyl]cyclododecyl}acetylamino)propyl](3-hydroquinolyl)}carbonylamino)-2-{[(2,4,6-trimethylphenyl)sulfonyl]amino}propanoic Acid Tris(trifluoroacetate) Salt

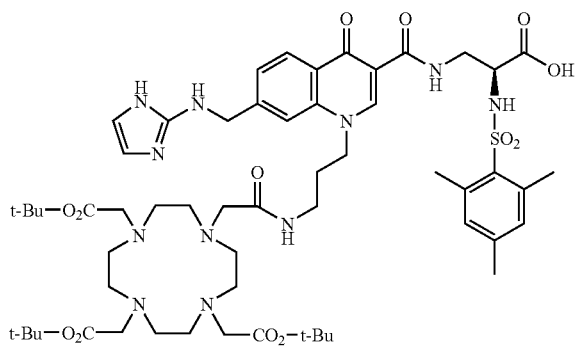

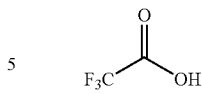

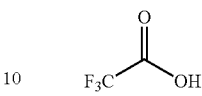

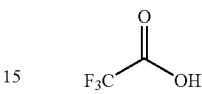

A solution of 2-(1,4,7,10-tetraaza-4,7,10-tris(((tert-butyl)oxycarbonyl)methyl)cyclododecyl)acetic acid (89 mg, 0.0974 mmol) (as described in DM-7003), DIEA (0.103 mL, 0.607 mmol), and HBTU (28.0 mg, 0.0735 mmol) in anhydrous DMF (1.0 mL) was stirred under nitrogen at ambient temperatures for 15 min and treated with a solution of the product of Example 4, Part H (30.0 mg, 0.049 mmol) in anhydrous DMF (1.0 mL). The DMF was removed under vacuum after 3 h and the residue was purified by HPLC on a Vydac C-18 column (22×250 mm) using a 1.08%/min gradient of 18 to 72% ACN containing 0.1% TFA at a flow rate of 20 mL/min. The main product peak eluting at 17.5 min was lyophilized to give the title compound as a colorless solid (48.0 mg, 65.0%). MS: m/e 1164.7 [M+H].

Part B—Preparation of (2S)-3-{[7-[(Imidazol-2-ylamino)methyl]-4-oxo-1-(3-{2-[1,4,7,10-tetraaza-4,7,10-tris(carboxymethyl)cyclododecyl]acetylamino}propyl)(3-hydroquinolyl)]carbonylamino}-2-{[(2,4,6-trimethylphenyl)sulfonyl]amino}propanoic Acid Tris(trifluoroacetate) Salt A solution of the product of Part A, above (48.0 mg, 0.0375 mmol) in 95/5 TFA/Et$_3$SiH (2.1 mL) was stirred at 50° C. under nitrogen for 2 h. The solution was concentrated under vacuum and the oily residue was purified by HPLC on a Vydac C-18 column (22×250 mm) using a 1.2%/min gradient of 0 to 36% ACN containing 0.1% TFA at a flow rate of 20 mL/min. The main product peak eluting at 18.6 min was lyophilized to give the title compound as a colorless solid (25.7 mg, 51.2%). MS: m/e 996.5 [M+H]; High Resolution MS: Calcd for $C_{45}H_{62}N_{11}O_{13}S$ [M+H]: 996.4249; Found: 996.4278.

Example 35

Synthesis of 3-({1-[3-((2R)-3-Sulfo-2-{2-[1,4,7,10-tetraaza-4,7,10-tris(carboxymethyl)cyclododecyl]-acetylamino}propyl)propyl]-7-[(imidazol-2-ylamino)methyl]-4-oxo(3-hydroquinolyl)}carbonylamino)(2S)-2-{[(2,4,6-trimethylphenyl)sulfonyl]amino}propanoic Acid Bis(trifluoroacetate) Salt

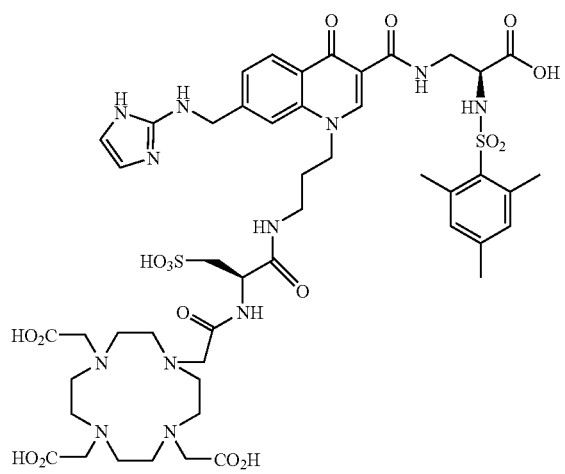

Part A—Preparation of 3-{[1-(3-{(2R)-2-[(tert-Butoxy)carbonylamino]-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid

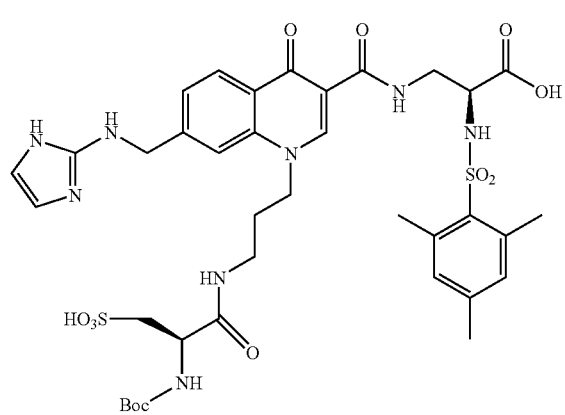

A solution of the product of Example 4, Part H (105 mg, 0.125 mmol), the N-hydroxysuccinimide ester of Boc-Cysteic acid (as described in *Liebigs Ann. Chem.* 1979, 776–783) (146 mg, 0.467 mmol), and DIEA (0.120 mL, 0.69 mmol) in anhydrous DMF (1.5 mL) was stirred at ambient temperatures under nitrogen for 24 h. The DMF was removed under vacuum and the resulting solid residue was purified by HPLC on a Vydac C-18 column (22×250 mm) using a 0.68%/min gradient of 9 to 36% ACN containing 0.1% TFA at a flow rate of 20 mL/min. The main product peak eluting at 30.3 min was lyophilized to give the title compound as a colorless solid (73.0 mg, 67.9%). MS: m/e 861.3 [M+H].

Part B—Preparation of 3-({1-[3-((2R)-2-Amino-3-sulfopropyl)propyl]-7-[(imidazol-2-ylamino)methyl]-4-oxo(3-hydroquinolyl)}carbonylamino)(2S)-2-{[(2,4,6-trimethylphenyl)sulfonyl]amino}propanoic Acid Trifluoroacetate Salt

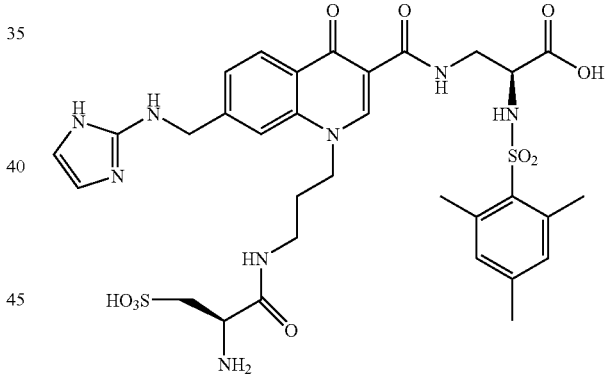

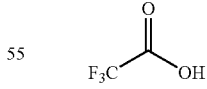

The product of Part B, above (70.0 mg, 0.0814 mmol) was dissolved in 2:1 DCM/TFA (1.5 mL) and allowed to react at ambient temperatures under nitrogen for 30 min. The solution was concentrated under vacuum and the amber oil was dissolved in 50% ACN (25 mL) and lyophilized to give the title compound as a colorless solid (70.8 mg, 99.5%). MS: m/e 761.2 [M+H]; High Resolution MS: Calcd for $C_{32}H_{41}N_8O_{10}S_2$ [M+H]: 761.2387; Found: 761.2393.

Part C—Preparation of 3-[(1-{3-[(2R)-3-Sulfo-2-(2-{1,4,7,10-tetraaza-4,7,10-tris[(tert-butoxycarbonyl)methyl]cyclododecyl}acetylamino)propyl]propyl}-7-[(imidazol-2-ylamino)methyl]-4-oxo(3-hydroquinolyl))carbonylamino](2S)-2-{[(2,4,6-trimethylphenyl)sulfonyl]amino}propanoic Acid Bis(trifluoroacetate) Salt

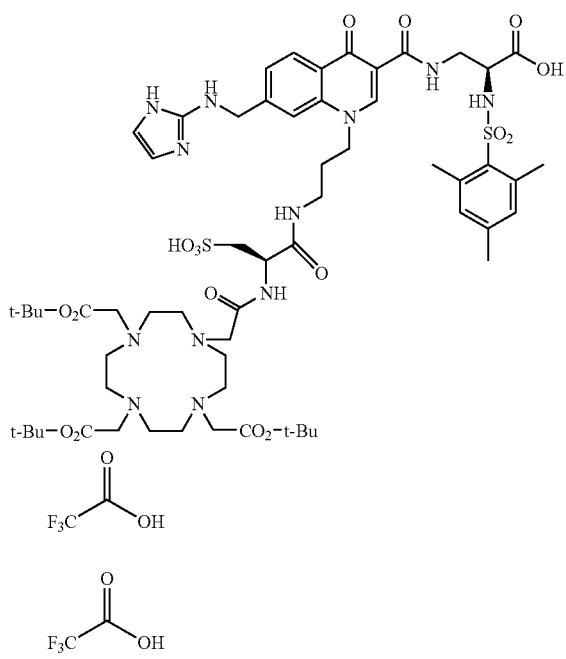

A solution of 2-(1,4,7,10-tetraaza-4,7,10-tris(((tert-butyl)oxycarbonyl)methyl)cyclododecyl)acetic acid (20.8 mg, 0.0228 mmol) (as described in DM-7003), DIEA (0.006 mL, 0.034 mmol), and HBTU (6.5 mg, 0.0171 mmol) in anhydrous DMF (0.5 mL) was stirred under nitrogen at ambient temperatures for 5 min and treated with a solution of the product of Part B, above (10.0 mg, 0.0114 mmol) and DIEA (0.006 mL, 0.034 mmol) in anhydrous DMF (0.5 mL). Stirring was continued at ambient temperatures for 24 h, and the reaction was diluted with water (3.0 mL), treated with concentrated ammonium hydroxide (0.003 mL), and stirred an additional 10 min. The solution was adjusted to pH 3 using 0.1 N HCl (6.0 mL) and diluted further with 10% ACN (5.5 mL). This solution was purified directly by HPLC on a Vydac C-18 column (22×250 mm) using a 0.68%/min gradient of 9 to 36% ACN containing 0.1% TFA at a flow rate of 20 mL/min. The main product peak eluting at 36.0 min was lyophilized to give the title compound as a colorless solid (12.0 mg, 68.3%). MS: m/e 1315.6 [M+H].

Part D—Preparation of 3-({1-[3-((2R)-3-Sulfo-2-{2-[1,4,7,10-tetraaza-4,7,10-tris(carboxymethyl)cyclododecyl]-acetylamino}propyl)propyl]-7-[(imidazol-2-ylamino)methyl]-4-oxo(3-hydroquinolyl)}carbonylamino)(2S)-2-{[(2,4,6-trimethylphenyl)sulfonyl]amino}propanoic Acid Bis(trifluoroacetate) Salt A solution of the product of Part C, above (12.0 mg, 0.00778 mmol) in 95/5 TFA/Et$_3$SiH (1.0 mL) was stirred at ambient temperatures under nitrogen for 18 h. The solution was concentrated under vacuum and the oily residue was purified by HPLC on a Vydac C-18 column (22×250 mm) using a 1.2%/min gradient of 0 to 36% ACN containing 0.1% TFA at a flow rate of 20 mL/min. The main product peak eluting at 21.1 min was lyophilized to give the title compound as a colorless solid (8.1 mg, 75.7%). MS: m/e 1147.3 [M+H]; High Resolution MS: Calcd for C$_{48}$H$_{67}$N$_{12}$O$_{17}$S$_2$ [M+H]: 1147.4189; Found: 1147.418.

Example 36

Synthesis of 3-{[1-(3-{2-[(6-{[(1E)-1-Aza-2-(2-sulfophenyl)vinyl]amino}(3-pyridyl))carbonylamino](2R)-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid

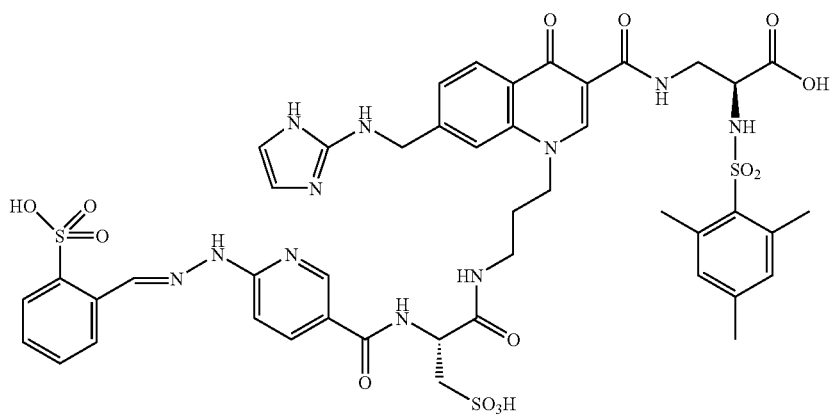

A solution of the product of Example 35, Part B (10.0 mg, 0.0101 mmol), DIEA (0.007 mL, 0.040 mmol), and 2-(2-aza-2-((5-((2,5-dioxopyrrolidinyl)carbonyl)(2-pyridyl))amino)vinyl)benzenesulfonic acid (5.3 mg, 0.0120 mmol) in anhydrous DMF (0.5 mL) was allowed to stand at ambient temperatures under a nitrogen atmosphere for 48 h. Additional 2-(2-aza-2-((5-((2,5-dioxopyrrolidinyl)carbonyl)(2-pyridyl))amino)vinyl)benzenesulfonic acid (2.0 mg, 0.00455 mmol) was added and stirring was continued an additional 48 h. The DMF was removed under vacuum and the residue was purified by HPLC on a Vydac C-18 column (22×250 mm) using a 0.9%/min gradient of 0 to 36% ACN containing 0.1% TFA at a flow rate of 20 mL/min. The main product peak eluting at 30.0 min was lyophilized to give the title compound as a colorless solid (2.5 mg, 23.3%). MS: m/e 1064.3 [M+H]; High Resolution MS: Calcd for $C_{45}H_{50}N_{11}O_{14}S_3$ [M+H]: 1064.27005; Found: 1064.272.

Example 37

Synthesis of 3-{[1-(3-{(2R)-2-[4-(N-{(1R)-1-[N-(3-{3-[N-((2S)-2-Carboxy-2-{[(2,4,6-trimethylphenyl)sulfonyl]-amino}ethyl)carbamoyl]-7-[(imidazol-2-ylamino)methyl]-4-oxohydroquinolyl}propyl)carbamoyl]-2-sulfoethyl}-carbamoyl)(2S)-2-{2-[1,4,7,10-tetraaza-4,7,10-tris(carboxymethyl)cyclododecyl]acetylamino}butanoylamino]-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid Bis(trifluoroacetate) Salt

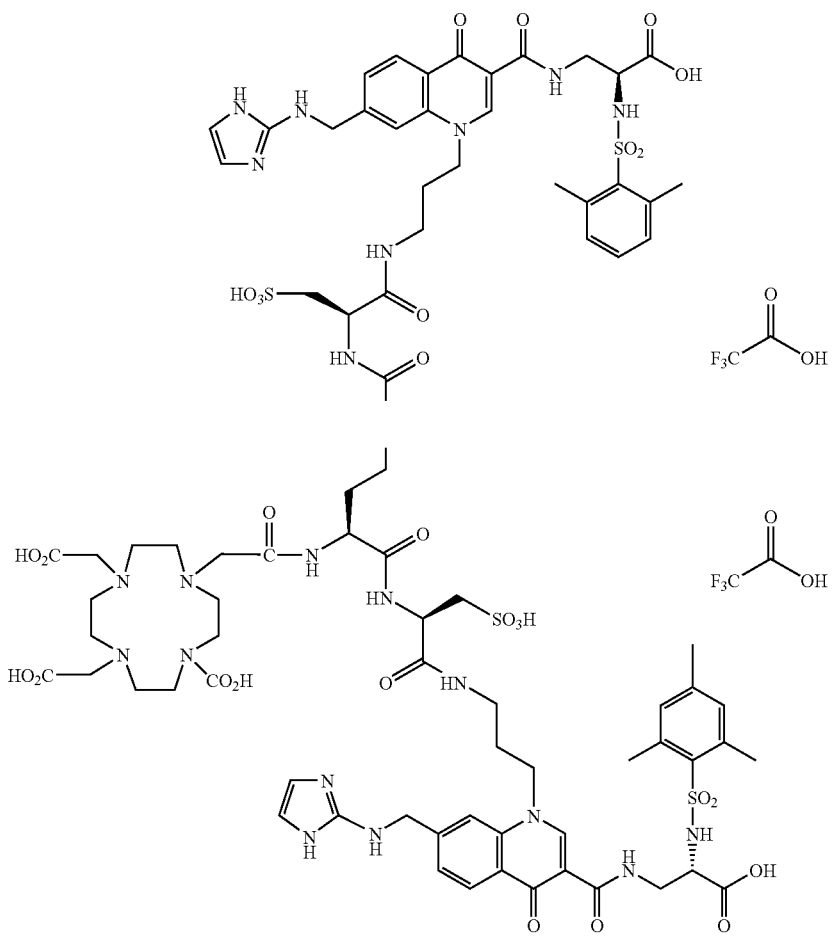

Part A—Preparation of 3-{[1-(3-{(2R)-2-[4-(N-{(1R)-1-[N-(3-{3-[N-((2S)-2-Carboxy-2-{[(2,4,6-trimethylphenyl)sulfonyl]amino}ethyl)carbamoyl]-7-[(imidazol-2-ylamino)methyl]-4-oxohydroquinolyl}propyl)carbamoyl]-2-sulfoethyl}carbamoyl)(2S)-2-[(tert-butoxy)carbonylamino]-butanoylamino]-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid

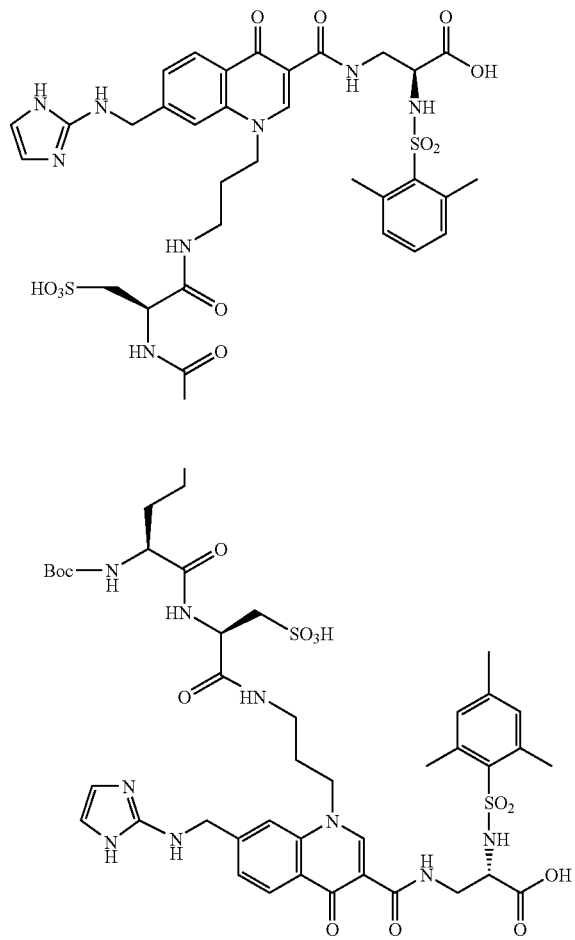

A solution of the product of Example 35, Part B (38.0 mg, 0.0434 mmol), DIEA (0.015 mL, 0.0869 mmol), and the product of Example 30, Part A (10.9 mg, 0.0202 mmol) in anhydrous DMF (1.0 mL) was stirred at ambient temperatures under nitrogen for 48 h. The DMF was removed under vacuum and the amber oil was purified by HPLC on a Vydac C-18 column (22×250 mm) using a 0.68%/min gradient of 9 to 36% ACN containing 0.1% TFA at a flow rate of 20 mL/min. The main product peak eluting at 36.1 min was lyophilized to give the title compound as a colorless solid (13.5 mg, 38.6%). MS: m/e 1732.4 [M+H], 1632.2 [M+H−Boc].

Part B—Preparation of 3-{[1-(3-{(2R)-2-[4-(N-{(1R)-1-[N-(3-{3-[N-((2S)-2-Carboxy-2-{[(2,4,6-trimethylphenyl)sulfonyl]amino}ethyl)carbamoyl]-7-[(imidazol-2-ylamino)methyl]-4-oxohydroquinolyl}propyl)carbamoyl]-2-sulfoethyl}carbamoyl)(2S)-2-aminobutanoylamino]-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid Trifluoroacetate Salt

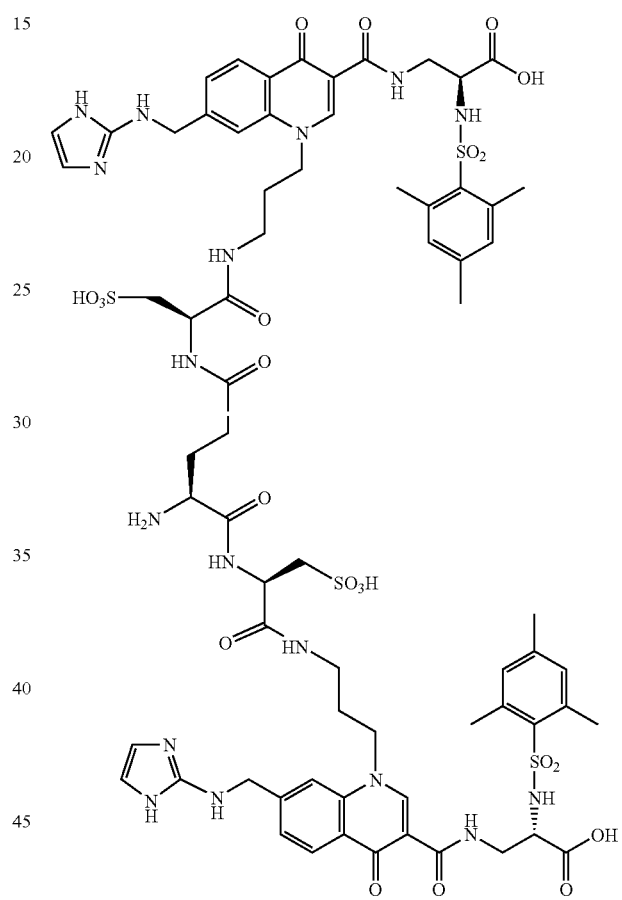

The product of Part A, above (13.5 mg, 0.00779 mmol) was dissolved in 50/50 TFA/DCM (1.0 mL) and allowed to react at ambient temperatures under nitrogen for 45 min. The solution was concentrated under vacuum to give the title compound as a pale amber oil. MS: m/e 1633.3 [M+H].

Part C—Preparation of 3-{[1-(3-{(2R)-2-[4-(N-{(1R)-1-[N-(3-{3-[N-((2S)-2-Carboxy-2-{[(2,4,6-trimethylphenyl)sulfonyl]amino}ethyl)carbamoyl]-7-[(imidazol-2-ylamino)methyl]-4-oxohydroquinolyl}propyl)carbamoyl]-2-sulfoethyl}carbamoyl)(2S)-2-{2-[1,4,7,10-tetraaza-4,7,10-tris[(tert-butoxycarbonyl)methyl]cyclododecyl]acetylamino}-butanoylamino]-3-sulfopropyl}propyl)-7-[(imidazol-2-ylamino)methyl]-4-oxo(3-hydroquinolyl)]carbonylamino}-(2S)-2-{[(2,4,6-trimethylphenyl)sulfonyl]amino}propanoic Acid Bis(trifluoroacetate) Salt

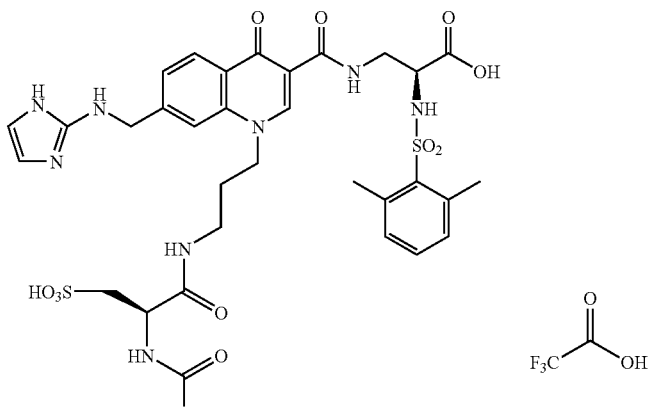

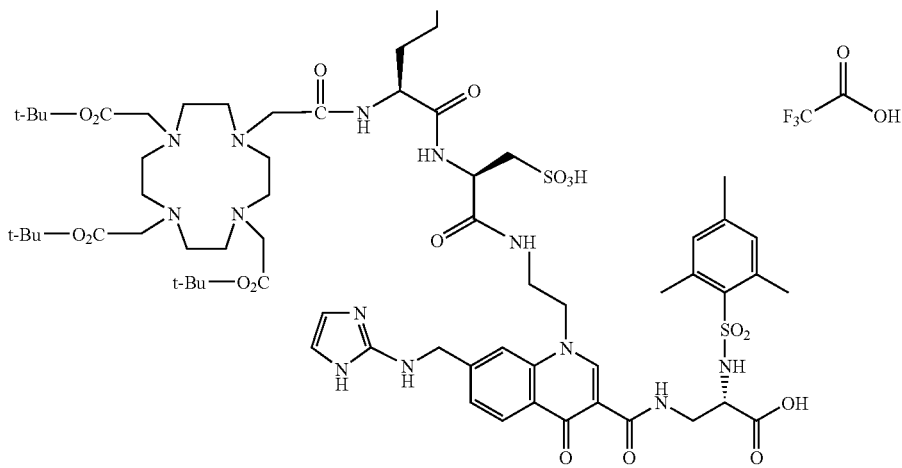

A solution of 2-(1,4,7,10-tetraaza-4,7,10-tris(((tert-butyl)oxycarbonyl)methyl)cyclododecyl)acetic acid (15.0 mg, 0.0164 mmol) (as described in DM-7003), DIEA (0.004 mL), and HBTU (4.7 mg, 0.0124 mmol) in anhydrous DMF (0.5 mL) was stirred under nitrogen at ambient temperatures for 8 min and treated with a solution of the product of Part B, above (0.00779 mmol) and DIEA (0.004 mL) in anhydrous DMF (0.5 mL). The solution was stirred at ambient temperatures for 24 h, treated with 0.1 N NaOH (0.33 mL), stirred an additional 5 min, and adjusted to pH 3 with 0.1 N HCl (0.60 mL). This solution was diluted with water (4.5 mL) and purified directly by HPLC on a Vydac C-18 column (22×250 mm) using a 1.01%/min gradient of 9 to 49.5% ACN containing 0.1% TFA at a flow rate of 20 mL/min. The main product peak eluting at 26.7 min was lyophilized to give the title compound as a colorless solid (7.0 mg, 37.2%). MS: m/e 1094.4 [M+2H]; High Resolution MS: Calcd for $C_{97}H_{136}N_{21}O_{29}S_4$ [M+H]: 2186.8696; Found: 2186.867.

Part D—Preparation of 3-{[1-(3-{(2R)-2-[4-(N-{(1R)-1-[N-(3-{3-[N-((2S)-2-Carboxy-2-{[(2,4,6-trimethylphenyl)sulfonyl]amino}ethyl)carbamoyl]-7-[(imidazol-2-ylamino)methyl]-4-oxohydroquinolyl}propyl)carbamoyl]-2-sulfoethyl}carbamoyl)(2S)-2-{2-[1,4,7,10-tetraaza-4,7,10-tris(carboxymethyl)cyclododecyl]acetylamino}butanoylamino]-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic Acid Bis(trifluoroacetate) Salt A solution of the product of Step C, above (7.0 mg, 0.00290 mmol) in 95/5 TFA/Et₃SiH (1.0 mL) was heated to reflux under nitrogen for 3 h. The solution was concentrated under vacuum and the oily residue was purified by HPLC on a Vydac C-18 column (22×250 mm) using a 1.2%/min gradient of 0 to 36% ACN containing 0.1% TFA at a flow rate of 20 mL/min. The main product peak eluting at 26.5 min was lyophilized to give the title compound as a colorless solid (4.5 mg, 66.1%). High Resolution MS: Calcd for $C_{85}H_{112}N_{21}O_{29}S_4$ [M+H]: 2018.6818; Found: 2018.683.

Example 38

Synthesis of the In-111 Complex of the Conjugate Example 29

To a shielded and crimped 2 cc autosampler vial was added 70 μg of the conjugate of Example 29 dissolved in 140 μl 0.5 M ammonium acetate buffer (pH 4.8) followed by the addition of 2 mg gentisic acid sodium salt and 2.6 mCi (7 μl) In-111 in 0.05M HCl. The reaction mixture (specific activity was heated at 85° C. for 20 minutes and analyzed by HPLC. Yield: 87.9% (total for the two isomers); Ret. Time: 12.5, 13.1 min.

HPLC Method

Column: Zorbax Rx C18, 25 cm×4.6 mm

Column Temperature: Ambient

Flow: 1.0 ml/min

Solvent A: 10 mM ammonium acetate

Solvent B: Acetonitrile

Detector: IN-US β-ram, and UV at 220 nm wavelength.

Gradient

| t (min) | 0 | 25 | 26 | 35 | 36 | 45 |
|---|---|---|---|---|---|---|
| % B | 7 | 7 | 60 | 60 | 7 | 7 |

Example 39

Synthesis of the In-111 Complex of the Conjugate Example 30

To a lead shielded and crimped 2 cc autosampler vial was added 120 μg of the conjugate of Example 30 dissolved in 240 μL ammonium acetate buffer (0.5 M, pH 4.7) followed by the addition of 2 mg of gentisic acid (sodium salt) dissolved in 20 μL of $H_2O$, and 2.3 mCi, (10 μL) In-111 (NEN) in 0.05 N HCl (specific activity: 52 μg/mCi). The reaction mixture was heated at 100° C. for 20 min and analyzed by HPLC. Yield: 94.7% (total for the two isomers), Ret. Time: 16.6 and 17.3 min.

HPLC Method

Column: Zorbax Rx C18, 25 cm×4.6 mm

Column Temperature: Ambient

Flow: 1.0 ml/min

Solvent A: 10 mM ammonium acetate

Solvent B: Acetonitrile

Detector: IN-US β-ram, and UV at 220 nm wavelength.

Gradient

| t (min) | 0 | 25 | 26 | 35 | 36 | 45 |
|---|---|---|---|---|---|---|
| % B | 10 | 15 | 60 | 60 | 10 | 10 |

Example 40

Synthesis of the In-111 Complex of the Conjugate Example 31

To a shielded and crimped 2 cc autosampler vial was added 70 μg of the conjugate of Example 31 dissolved in 140 μl 0.5 M ammonium acetate buffer (pH 4.8) followed by the addition of 2 mg gentisic acid sodium salt and 2.6 mCi (7 μl) In-111 in 0.05M HCl. The reaction mixture (specific activity was heated at 85° C. for 20 minutes and analyzed by HPLC. Yield: 92.2%; Ret. Time: 12.9 min.

HPLC Method

Column: Zorbax Rx C18, 25 cm×4.6 mm

Column Temperature: Ambient

Flow: 1.0 ml/min

Solvent A: 10 mM ammonium acetate

Solvent B: Acetonitrile

Detector: IN-US β-ram, and UV at 220 nm wavelength.

Gradient

| t (min) | 0 | 25 | 26 | 35 | 36 | 45 |
|---|---|---|---|---|---|---|
| % B | 7 | 7 | 60 | 60 | 7 | 7 |

Example 41

Synthesis of the In-111 Complex of the Conjugate Example 33

To a shielded and crimped 2 cc autosampler vial was added 107 μg of the conjugate of Example 33 dissolved in 140 μl 0.5 M ammonium acetate buffer (pH 4.8) followed by the addition of 2 mg gentisic acid sodium salt and 2.6 mCi (7 μl) In-111 in 0.05M HCl. The reaction mixture (specific activity was heated at 85° C. for 20 minutes and analyzed by HPLC. Yield: 77.9%; Ret. Time: 17.8 min.

HPLC Method

Column: Zorbax Rx C18, 25 cm×4.6 mm

Column Temperature: Ambient

Flow: 1.0 ml/min

Solvent A: 10 mM ammonium acetate

Solvent B: Acetonitrile

Detector: IN-US β-ram, and UV at 220 nm wavelength.

Gradient

| t (min) | 0 | 25 | 26 | 35 | 36 | 45 |
|---|---|---|---|---|---|---|
| % B | 9 | 11 | 60 | 60 | 9 | 9 |

Example 42

Synthesis of the In-111 Complex of the Conjugate Example 34

To a lead shielded and crimped autosampler vial was added 25 μg of the conjugate of Example 34 and 1.0 mg gentisic acid, sodium salt dissolved in 50 μL ammonium acetate buffer (0.4 M, pH 4.7) followed by the addition of 1.2 mCi, (5 μL) In-111 in 0.05 N HCl (specific activity: 21 μg/mCi). The reaction mixture was heated at 80° C. for 45 min and analyzed by HPLC and ITLC. 93.5% yield by HPLC, Ret. Time: 16.7 min.

HPLC Method

Column: Zorbax Rx C18, 25 cm×4.6 mm

Column Temperature: Ambient

Flow: 1.0 ml/min

Solvent A: 25 mM sodium phosphate buffer at pH 6

Solvent B: Acetonitrile

Detector: Sodium iodide (NaI) radiometric probe, and UV at 220 nm wavelength.

Gradient

| t (min) | 0  | 25 | 26 | 35 | 36 | 45 |
|---------|----|----|----|----|----|----|
| % B     | 10 | 20 | 60 | 60 | 10 | 10 |

Example 43

Synthesis of the In-111 Complex of the Conjugate Example 35

To a lead shielded and crimped 1 cc autosampler vial was added 40–50 μg of the conjugate of Example 35 dissolved in 100 μL ammonium citrate buffer (0.4 M, pH 4.7) followed by the addition of 2 mCi, (5 μL) In-111 in 0.05 N HCl (specific activity: 25 μg/mCi). The reaction mixture was heated at 90–100 C for 30 min and analyzed by HPLC. Yield: 95%; Ret. Time 12.5 min.

HPLC Method

Column: Zorbax Rx C18, 25 cm×4.6 mm

Column Temperature: Ambient

Flow: 1.0 ml/min

Solvent A: 25 mM sodium phosphate buffer at pH 6

Solvent B: Acetonitrile

Detector: Sodium iodide (NaI) radiometric probe, and UV at 220 nm wavelength.

Gradient

| t (min) | 0  | 25 | 26 | 35 | 36 | 45 |
|---------|----|----|----|----|----|----|
| % B     | 10 | 20 | 60 | 60 | 10 | 10 |

Example 44

Synthesis of the In-111 Complex of the Conjugate Example 37

To a lead shielded and crimped 2 cc autosampler vial was added 150 μg of the conjugate of Example 37 dissolved in 300 μL ammonium citrate buffer (0.3 M, pH 4.8) followed by the addition of 4.5 mCi, (25 μL) In-111 (NEN) in 0.05 N HCl (specific activity: 33 μg/mCi). The reaction mixture was heated at 100° C. for 20 min and analyzed by HPLC. RCP: 80%, Ret. Time: 21 min.

HPLC Method

Column: Zorbax Rx C18, 25 cm×4.6 mm

Column Temperature: Ambient

Flow: 1.0 ml/min

Solvent A: 25 mM sodium phosphate buffer at pH 6

Solvent B: Acetonitrile

Detector: Sodium iodide (NaI) radiometric probe, and UV at 220 nm wavelength.

Gradient

| t (min) | 0  | 25 | 26 | 35 | 36 | 45 |
|---------|----|----|----|----|----|----|
| % B     | 17 | 19 | 60 | 60 | 17 | 17 |

Examples 45–51

Synthesis of Y-90 and Lu-177 Complexes of the Conjugates of Examples 30, 31, 34, 35 and 37

To a clean sealed 5 mL vial was added 0.5–1.0 mL of the appropriate conjugate solution (200 μg/mL in 0.5 M ammonium acetate buffer, pH 7.0–8.0), followed by 0.05 mL of sodium gentisate (10 mg/mL in 0.5 M ammonium acetate buffer, pH 7.0–8.0) solution, and 10–40 μL of $^{90}YCl_3$ or $^{177}LuCl_3$ solution (10–20 mCi) in 0.05 N HCl. The reaction mixture was heated at 100° C. for 5–10 min. After cooling to room temperature, a sample of the resulting solution was analyzed by HPLC and by ITLC.

| Complex Ex # | Isotope | Conjugate Ex. # | Ret. Time (min) | % Yield | HPLC Method |
|--------------|---------|-----------------|-----------------|---------|-------------|
| 45 | Y-90   | 30 | 14.0, 16.0 | 90   | D |
| 46 | Y-90   | 31 | 14.0       | 90.5 | F |
| 47 | Lu-177 | 31 | 13.0       | 85   | D |
| 48 | Y-90   | 34 | 8.0        | 81.9 | A |
| 49 | Y-90   | 35 | 16.0       | 89   | B |
| 50 | Y-90   | 37 | 8.2        | 83.5 | B |
| 51 | Lu-177 | 37 | 14.0       | 70   | G |

HPLC Method A: The HPLC method using a reverse phase $C_{18}$ Zorbax column (4.6 mm×25 cm, 80 Å pore size) at a flow rate of 1.0 mL/min with a gradient mobile phase from 85% A (25 mM pH 6.0 phosphate buffer) and 15% B (acetonitrile) to 75% A and 25% B at 20 min.

HPLC Method B: The HPLC method using a reverse phase $C_{18}$ Zorbax column (4.6 mm×25 cm, 80 Å pore size) at a flow rate of 1.0 mL/min with a gradient mobile phase from 90% A (25 mM pH 6.0 phosphate buffer) and 10% B (acetonitrile) to 80% A and 20% B at 20 min.

HPLC Method D: The HPLC method using a reverse phase $C_{18}$ Zorbax column (4.6 mm×25 cm, 80 Å pore size) at a flow rate of 1.0 mL/min with a gradient mobile phase from 87% A (25 mM pH 6.0 phosphate buffer) and 13% B (acetonitrile) to 86% A and 14% B at 20 min.

HPLC Method F: The HPLC method using a reverse phase $C_{18}$ Zorbax column (4.6 mm×25 cm, 80 Å pore size) at a flow rate of 1.0 mL/min with a gradient mobile phase from 92% A (25 mM ammonium acetate buffer, pH=6.8) and 8% B (acetonitrile) to 90% A and 10% B at 20 min.

HPLC Method G: The HPLC method using a reverse phase $C_{18}$ Zorbax column (4.6 mm×25 cm, 80 Å pore size) at a flow rate of 1.0 mL/min with an isocratic mobile phase of 87% A (25 mM ammonium acetate buffer, pH=6.8) and 13% B (acetonitrile) from 0 to 20 min.

Example 52

Synthesis of $^{99m}$Tc (3-{[1-(3-{2-[(6-(diazenido)(3-pyridyl))carbonylamino](2R)-3-sulfopropyl}propyl)-7-[(imidazol-2-ylamino)methyl]-4-oxo(3-hydroquinolyl)]carbonylamino}(2S)-2-{[(2,4,6-trimethylphenyl)sulfonyl]amino}propanoic acid) (tricine)(TPPTS)

To a lyophilized vial containing 4.84 mg TPPTS, 6.3 mg tricine, 40 mg mannitol, succinic acid buffer, pH 4.8, and 0.1% Pluronic F-64 surfactant, was added 1.1 mL sterile water for injection, 0.2 mL (20 µg) of the conjugate of Example 36 in deionized water or 50% aqueous ethanol, and 0.2 mL of $^{99m}$TcO$_4^-$ (50±5 mCi) in saline. The reconstituted kit was heated in a 100° C. water bath for 15 minutes, and was allowed to cool 10 minutes at room temperature. A sample of the reaction mixture was analyzed by HPLC. The yield was 89.0% and the retention time 12.8, 13.2 min (2 isomers).

HPLC Method

Column: Zorbax C18, 25 cm×4.6 mm

Flow rate: 1.0 mL/min

Solvent A: 10 mM sodium phosphate buffer, pH 6.0

Solvent B: 100% $CH_3CN$

Gradient 0–25% B over 20 min.

Utility

The pharmaceuticals of the present invention are useful for imaging angiogenic tumor vasculature, therapeutic cardiovascular angiogenesis, and cardiac pathologies associated with the expression of vitronectin receptors in a patient or for treating cancer in a patient. The radiopharmaceuticals of the present invention comprised of a gamma ray or positron emitting isotope are useful for imaging of pathological processes involving angiogenic neovasculature, including cancer, diabetic retinopathy, macular degeneration, restenosis of blood vessels after angioplasty, and wound healing, as well as atherosclerotic plaque, myocardial reperfusion injury, and myocardial ischemia, stunning or infarction. The radiopharmaceuticals of the present invention comprised of a beta, alpha or Auger electron emitting isotope are useful for treatment of pathological processes involving angiogenic neovasculature, by delivering a cytotoxic dose of radiation to the locus of the angiogenic neovasculature. The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of pathological processes involving angiogenic neovasculature, as well as atherosclerotic plaque, myocardial reperfusion injury, and myocardial ischemia, stunning or infarction.

The compounds of the present invention comprised of one or more heavy atoms with atomic number of 20 or greater are useful as X-ray contrast agents for X-ray imaging of pathological processes involving angiogenic neovasculature, as well as atherosclerotic plaque, myocardial reperfusion injury, and myocardial ischemia, stunning or infarction.

The compounds of the present invention comprised of an echogenic gas containing surfactant microspheres are useful as ultrasound contrast agents for sonography of pathological processes involving angiogenic neovasculature.

Representative compounds of the present invention were tested in the following in vitro assays and in vivo models and were found to be active.

Immobilized Human Placental avb3 Receptor Assay

The assay conditions were developed and validated using [I-125]vitronectin. Assay validation included Scatchard format analysis (n=3) where receptor number (Bmax) and Kd (affinity) were determined. Assay format is such that compounds are preliminarily screened at 10 and 100 nM final concentrations prior to IC50 determination. Three standards (vitronectin, anti-avB3 antibody, LM609, and anti-avB5, P1F6) and five reference peptides have been evaluated for IC50 determination. Briefly, the method involves immobilizing previously isolated receptors in 96 well plates and incubating overnight. The receptors were isolated from normal, fresh, non-infectious (HIV, hepatitis B and C, syphilis, and HTLV free) human placenta. The tissue was lysed and tissue debris removed via centrifugation. The lysate was filtered. The receptors were isolated by affinity chromatography using the immobilized avb3 antibody. The plates are then washed 3× with wash buffer. Blocking buffer is added and plates incubated for 120 minutes at room temperature. During this time compounds to be tested and [I-125]vitronectin are premixed in a reservoir plate. Blocking buffer is removed and compound mixture pipetted. Competition is carried out for 60 minutes at room temperature. Unbound material is then removed and wells are separated and counted via gamma scintillation.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of echogenic gas containing surfactant microspheres as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 µg/ml] and injected subcutaneously into the mid-abdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus 1 µg bFGF and 4 µg VEGF. The radiopharmaceutical is then injected 7 days later and the images obtained.

This model can also be used to assess the effectiveness of the radiopharmaceuticals of the present invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of the radiopharmaceuticals can be assessed by monitoring the rate of growth of the angiogenic sites in control rabbits versus those in the rabbits administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the angiogenic sites. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the angiogenic sites. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the angiogenic sites in the animal can be imaging using an ultrasound probe held proximate to the tumors. The effectiveness of the contrast agents can be readily seen by comparison to the images obtain from animals that are not administered a contrast agent.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anesthesia. Chemical restraint was continued with ketamine (3 mg/kg)/xylazine (6 mg/kg) titrating as necessary. If required the animals were ventilated with room air via an endotracheal tube (12 strokes/min, 25 ml/kg) during the study. Peripheral veins were catheterized using 20G I.V. catheters, one to serve as an infusion port for compound while the other for exfusion of blood samples. Heart rate and EKG were monitored using a cardiotachometer (Biotech, Grass Quincy, Mass.) triggered from a lead II electrocardiogram generated by limb leads. Blood samples are generally taken at ~10 minutes (control), end of infusion, (1 minute), 15 min, 30 min, 60 min, 90 min, and 120 min for whole blood cell number and counting. Radiopharmaceutical dose was 300 µCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20–90 µCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known µCi. The result is µCi for the ROI.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the size of the tumors over time.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Cardiovascular disease models that can be used to assess the diagnostic radiopharmaceuticals, magnetic resonance, X-ray and ultrasound contrast agents of the present invention are reviewed in J. Nucl. Cardiol., 1998, 5, 167–83. There are several well established rabbit models of atherosclerosis; one model produces predominantly proliferating smooth muscle cells by balloon deendothelialization of infradiaphragmatic abdominal aorta to simulate restenotic lesions; another model that produces simulated advanced human atherosclerotic plaque by balloon deendothelialization followed by a high cholesterol diet.

A model of congestive heart failure is described in Am. J. Physiol., 1998, 274, H1516–23. In general, Yorkshire pigs are randomly assigned to undergo 3 wks of rapid atrial pacing at 240 beats/min. or to be sham controls. The pigs are chronically instrumented to measure left ventricular function in the conscious state. The pigs are anesthetized.

A shielded stimulating electrode is sutured onto the left atrium, connected to a modified programmable pace maker and buried in a subcutaneous pocket. The pericardium is closed loosely, the thoracotomy is closed, and the pleural space is evacuated of air. After a recovery period of 7–10 days, the pacemaker is activated in the animals selected to undergo chronic rapid pacing. The animals are sedated, the pacemaker is deactivated (pacing groups only. After a 30 min stabilization period, indexes of LV function and geometry are determined (by echocardiography as a control) by injecting the radiolabeled compound. For biodistribution, the animals are anesthetized, the heart extirpate and the LV apex and midventricular regions are evaluated.

A rat model of reversible coronary occlusion and reperfusion is described in McNulty et al., J. Am. Physiol., 1996, H2283–9.

Obviously, numerous modifications and variations of the present invention are possible in light of the above teachings. It is therefore to be understood that within the scope of the appended claims, the invention may be practiced otherwise that as specifically described herein.

What is claimed is described below:

1. An MRI contrast agent, comprising:
   a metal, wherein, the metal is a paramagnetic metal ion selected from the group: Gd(III), Dy(III), Fe(III), and Mn(II),
   a chelator capable of chelating the metal, and
   a targeting moiety, wherein the targeting moiety is bound to the chelator, is a quinolone non-peptide and binds to a receptor that is upregulated during angiogenesis and the compound has 0–1 linking groups between the targeting moiety and chelator, the targeting moiety is a quinolone nonpeptide and the linking group is present between the targeting moiety and chelator.

2. A composition according to claim 1, wherein the linking group is present between the targeting moiety and chelator and the receptor is $\alpha_v\beta_3$ or $\alpha_v\beta_5$.

3. A composition according to claim 2, wherein the metal ion is Gd(III).

4. A composition according to claim 3, wherein the contrast agent is

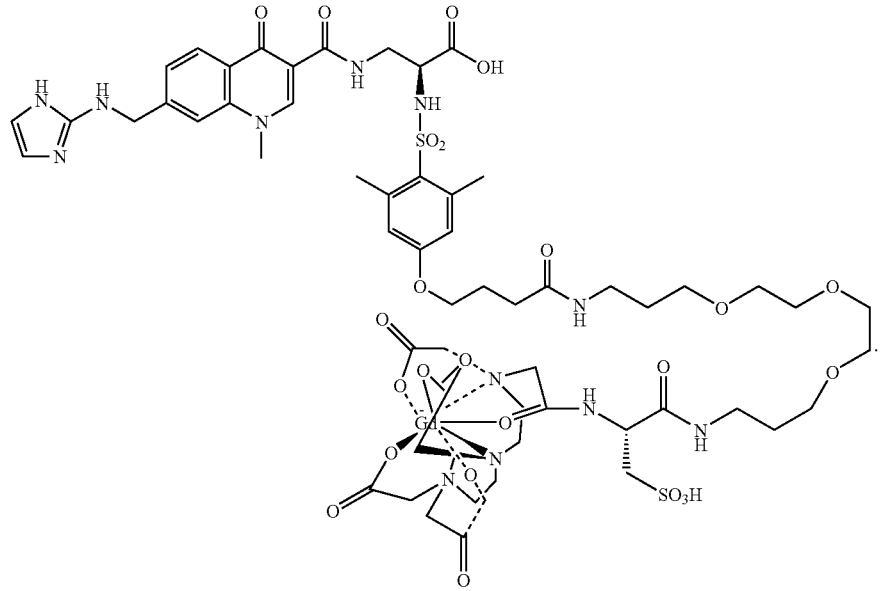

205

5. A compound, comprising: a targeting moiety and a surfactant, wherein the targeting moiety is bound to the surfactant, is a quinolone nonpeptide, and binds to a receptor that is upregulated during angiogenesis and the compound has 0–1 linking groups between the targeting moiety and surfactant.

6. A compound according to claim 5, wherein the linking group is present between the targeting moiety and surfactant.

7. A compound according to claim 6, wherein the receptor is the integrin $\alpha_v\beta_3$ or $\alpha_v\beta_5$ and the compound is of the formula:

$$(Q)_d-L_n-S_f$$

wherein, Q is a compound of Formula (II):

(II)

[Structure of Formula (II): a quinolone core with substituents $R^{1e}-U^e-$, $R^{19e}$, $G^e$, $W^e-Y^e$, $R^{19e}$, $R^{18ae}$ on nitrogen]

including stereoisomeric forms thereof, or mixtures of stereoisomeric forms thereof, or pharmaceutically acceptable salt or prodrug forms thereof wherein:

$R^{1e}$ is selected from:

[Multiple chemical structures shown including amidines, imidazoles, pyridines, benzimidazoles, tetrahydronaphthyridine, and related heterocycles with substituents $NR^{2ae}$, $R^{2ae}-HN$, $N_{2ae}R$, $M^e$, $L^e$, $J^e=K^e$, $NHR^{12e}$, $D^e$, $F^e$, $E^e$, $A^e-()_{re}$, $B^e$, $A^{1e}$, $R^{12e}N$, $R^{2e}$, $R^{3e}$, etc.], and

206

-continued

[Structure: 2-amino-6-methylpyridine fragment with $H_2N$];

$A^e$ is $-CH_2-$ or $-N(R^{10e})-$;
$A^{1e}$ and $B^e$ are independently $-CH_2-$ or $-N(R^{10e})-$;
$D^e$ is $-N(R^{10e})-$ or $-S-$;
$E^e-F^e$ is $-C(R^{2e})=C(R^{3e})-$ or $-C(R^{2e})_2C(R^{3e})_2-$;
$J^e$ is $-C(R^{2e})-$ or $-N-$;
$K^e$, $L^e$ and $M^e$ are independently $-C(R^{2e})-$ or $-C(R^{3e})-$;
$R^{2e}$ and $R^{3e}$ are independently selected from:
H, $C_1-C_4$ alkoxy, $NR^{11e}R^{12e}$, halogen, $NO_2$, CN, $CF_3$, $C_1-C_6$ alkyl, $C_3-C_6$ alkenyl, $C_3-C_7$ cycloalkyl, $C_3-C_7$ cycloalkyl($C_1-C_4$ alkyl), aryl($C_1-C_6$ alkyl)-, ($C_1-C_6$ alkyl)carbonyl, ($C_1-C_6$ alkoxy)carbonyl, arylcarbonyl, and aryl substituted with 0–4 $R^{7e}$,
alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1-C_4$ alkyl, $C_1-C_4$ alkoxy, halo, cyano, amino, $CF_3$ and $NO_2$;

$R^{2ae}$ is selected from:
H, $C_1-C_{10}$ alkyl, $C_2-C_6$ alkenyl, $C_3-C_{11}$ cycloalkyl, $C_3-C_7$ cycloalkyl($C_1-C_4$ alkyl), aryl, aryl($C_1-C_4$ alkyl)-, ($C_2-C_7$ alkyl)carbonyl, arylcarbonyl, ($C_2-C_{10}$ alkoxy)carbonyl, $C_3-C_7$ cycloalkoxycarbonyl, $C_7-C_{11}$ bicycloalkoxycarbonyl, aryloxycarbonyl, aryl ($C_1-C_{10}$ alkoxy)carbonyl, $C_1-C_6$ alkylcarbonyloxy($C_1-C_4$ alkoxy)carbonyl, arylcarbonyloxy($C_1-C_4$ alkoxy)carbonyl, and $C_3-C_7$ cycloalkylcarbonyloxy($C_1-C_4$ alkoxy)carbonyl;

$R^{7e}$ is selected from:
H, hydroxy, $C_1-C_4$ alkyl, $C_1-C_4$ alkoxy, aryl, aryl($C_1-C_4$ alkyl)-, ($C_1-C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:
$-(CH_2)_n{}^e-$, $-(CH_2)_n{}^eO(CH_2)_m{}^e-$, $-(CH_2)_n{}^eN(R^{12})(CH_2)_m{}^e-$, $-NH(CH_2)_n{}^e-$, $-(CH_2)_n{}^eC(=O)(CH_2)_m{}^e-$, $-(CH_2)_n{}^eS(O)_p{}^e(CH_2)_m{}^e-$, $-(CH_2)_n{}^eNHNH(CH_2)_m{}^e-$, $-N(R^{10e})C(=O)-$, $-NHC(=O)(CH_2)_n{}^e-$, $-C(=O)N(R^{10e})-$, and $-N(R^{10e})S(O)_p{}^e-$;

$G^e$ is N or $CR^{19e}$;
$W^e$ is $-C(=O)-N(R^{10e})-(C_1-C_3$ alkylene)-, in which the alkylene group is substituted by $R^{8e}$ and by $R^{9e}$:
$R^{8e}$ and $R^{9e}$ are independently selected from:
H, $CO_2R^{18be}$, $C(=O)R^{18be}$, $CONR^{17}R^{18be}$,
$C_1-C_{10}$ alkyl substituted with 0–1 $R^{6e}$,
$C_2-C_{10}$ alkenyl substituted with 0–1 $R^{6e}$,
$C_2-C_{10}$ alkynyl substituted with 0–1 $R^{6e}$,
$C_3-C_8$ cycloalkyl substituted with 0–1 $R^{6e}$,
$C_5-C_6$ cycloalkenyl substituted with 0–1 $R^{6e}$,
($C_1-C_{10}$ alkyl)carbonyl,
$C_3-C_{10}$ cycloalkyl($C_1-C_4$ alkyl)-,
phenyl substituted with 0–3 $R^{6e}$,
naphthyl substituted with 0–3 $R^{6e}$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$, $C_1$–$C_{10}$ alkoxy substituted with 0–2 $R^{7e}$, hydroxy, nitro, —N($R^{10e}$)$R^{11e}$, —N($R^{16e}$)$R^{17e}$, aryl ($C_0$–$C_6$ alkyl)carbonyl, aryl($C_3$–$C_6$ alkyl), heteroaryl ($C_1$–$C_6$ alkyl), CONR$^{18ae}$R$^{20e}$, SO$_2$R$^{18ae}$, and SO$_2$NR$^{18ea}$R$^{20e}$, providing that any of the above alkyl, cycloalkyl, aryl or heteroaryl groups may be unsubstituted or substituted independently with 1–2 $R^{7e}$;

$R^{6e}$ is selected from:

H, $C_1$–$C_{10}$ alkyl, hydroxy, $C_1$–$C_{10}$ alkoxy, nitro, $C_1$–$C_{10}$ alkylcarbonyl, —N($R^{11e}$)$R^{12e}$, cyano, halo, CF$_3$, CHO, CO$_2$R$^{18be}$, C(=O)R$^{18be}$, CONR$^{17e}$R$^{18be}$, OC(=O)R$^{10e}$, OR$^{10e}$, OC(=O)NR$^{10e}$R$^{11e}$, NR$^{10e}$C(=O)R$^{10e}$, NR$^{10e}$C(=O)OR$^{21e}$, NR$^{10e}$C(=O)NR$^{10e}$R$^{11e}$, NR$^{10e}$SO$_2$NR$^{10e}$R$^{11e}$, NR$^{10e}$SO$_2$R$^{21e}$, S(O)$_p$R$^{11e}$, SO$_2$NR$^{10e}$R$^{11e}$, aryl substituted with 0–3 groups selected from halogen, $C_1$–$C_6$ alkoxy, $C_1$–$C_6$ alkyl, CF$_3$, S(O)$_m^e$Me, and —NMe$_2$, aryl($C_1$–$C_4$ alkyl)-, said aryl being substituted with 0–3 groups selected from halogen, $C_1$–$C_6$ alkoxy, $C_1$–$C_6$ alkyl, CF$_3$, S(O)$_p^e$Me, and —NMe$_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:

H, CF$_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:

H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:

H, $C_1$–$C_6$ alkyl, $C_3$–$C_7$ cycloalkyl, $C_3$–$C_7$ cycloalkyl ($C_1$–$C_4$ alkyl)-, ($C_1$–$C_{10}$ alkyl)carbonyl, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, CF$_3$, and NO$_2$;

alternatively, when $R^{10e}$ and $R^{11e}$ are both substituents on the same nitrogen atom (as in —NR$^{10e}$R$^{11e}$) they may be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;

said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy) carbonyl, $C_1$–$C_6$ alkylsulfonyl, and arylsulfonyl;

$R^{12e}$ is selected from:

H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, CF$_3$, and nitro;

$R^{16e}$ is selected from:

—C(=O)OR$^{18ae}$, —C(=O)R$^{18be}$, —C(=O)N(R$^{18be}$)$_2$, —C(=O)NHSO$_2$R$^{18ae}$, —C(=O)NHC(=O)R$^{18be}$, —C(=O)NHC(=O)OR$^{18ae}$, —C(=O)NHSO$_2$NHR$^{18be}$, —SO$_2$R$^{18ae}$, —SO$_2$N(R$^{18be}$)$_2$, and —SO$_2$NHC(=O)OR$^{18be}$;

$R^{17e}$ is selected from:

H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:

$C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:

H, halogen, CF$_3$, CO$_2$H, CN, NO$_2$, —NR$^{11e}$R$^{12e}$, OCF$_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, CF$_3$, $C_1$–$C_3$ alkyl, and $C_1$–$C_3$ alkoxy;

$R^{20e}$ is selected from:

hydroxy, $C_1$–$C_{10}$ alkyloxy, $C_3$–$C_{11}$ cycloalkyloxy, aryloxy, aryl($C_1$–$C_4$ alkyl)oxy, $C_2$–$C_{10}$ alkylcarbonyloxy($C_1$–$C_2$ alkyl)oxy-, $C_2$–$C_{10}$ alkoxycarbonyloxy($C_1$–$C_2$ alkyl)oxy-, $C_2$–$C_{10}$ alkoxycarbonyl($C_1$–$C_2$ alkyl)oxy-, $C_3$–$C_{10}$ cycloalkylcarbonyloxy($C_1$–$C_2$ alkyl)oxy-, $C_3$–$C_{10}$ cycloalkoxycarbonyloxy($C_1$–$C_2$ alkyl)oxy-, $C_3$–$C_{10}$ cycloalkoxycarbonyl($C_1$–$C_2$ alkyl)oxy-, aryloxycarbonyl($C_1$–$C_2$ alkyl)oxy-, aryloxycarbonyloxy($C_1$–$C_2$ alkyl)oxy-, arylcarbonyloxy($C_1$–$C_2$ alkyl)oxy-, $C_1$–$C_5$ alkoxy($C_1$–$C_5$ alkyl)carbonyloxy($C_1$–$C_2$ alkyl) oxy, (5-($C_1$–$C_5$ alkyl)-1,3-dioxa-cyclopenten-2-one-yl)methyloxy, (5-aryl-1,3-dioxa-cyclopenten-2-one-yl)methyloxy, and ($R^{10e}$)($R^{11e}$)N—($C_1$–$C_{10}$ alkoxy)-;

$R^{21e}$ is selected from:

$C_1$–$C_8$ alkyl, $C_2$–$C_6$ alkenyl, $C_3$–$C_{11}$ cycloalkyl, ($C_3$–$C_{11}$ cycloalkyl) methyl, aryl, aryl($C_1$–$C_4$ alkyl)-, and $C_1$–$C_{10}$ alkyl substituted with 0–2 $R^{7e}$;

$R^{22e}$ is selected from:

—C(=O)—R$^{18be}$, —C(=O)N(R$^{18be}$)$_2$, —C(=O) NHSO$_2$R$^{18ae}$, —C(=O)NHC(=O)R$^{18be}$, —C(=O) NHC(=O)OR$^{18ae}$, and —C(=O)NHSO$_2$NHR$^{18be}$;

209

$Y^e$ is selected from:
—$COR^{20e}$, —$SO_3H$, —$PO_3H$, —$CONHNHSO_2CF_3$, —$CONHSO_2R^{18ae}$, —$CONHSO_2NHR^{18be}$, —NHCOCF_3, —$NHCONHSO_2R^{18ae}$, —$NHSO_2R^{18ae}$, —$OPO_3H_2$, —$OSO_3H$, —$PO_3H_2$, —$SO_2NHCOR^{18ae}$, —$SO_2NHCO_2R^{18ae}$,

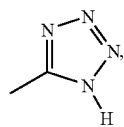 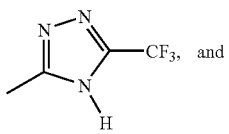 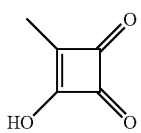

$m^e$ is 0–2;
$n^e$ is 0–4;
$p^e$ is 0–2;
$r^e$ is 0–2;
with the following proviso: $n^e$ and $m^e$ are chosen such that the number of atoms connecting $R^{1e}$ and $Y^e$ is in the range of 8–14;
d is selected from 1, 2, 3, 4, 5, 6, 7, 8, 9, and 10;
$L_n$ is a linking group having the formula:

$((W)_h—(CR^6R^7)_g)_x—(Z)_k—((CR^{6a}R^{7a})_{g'}—(W)_{h'})_{x'}$;

W is independently selected at each occurrence from the group: O, S, NH, NHC(=O), C(=O)NH, $NR^8C$(=O), C(=O)$NR^8$, C(=O), C(=O)O, OC(=O), NHC(=S)NH, NHC(=O)NH, $SO_2$, $SO_2NH$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_{t'}$;
aa is independently at each occurrence an amino acid;
Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;
$R^6$, $R^{6a}$, $R^7$, $R^{7a}$, and $R^8$ are independently selected at each occurrence from the group: H, =O, COOH, $SO_3H$, $PO_3H$, $C_1–C_5$ alkyl substituted with 0–3 $R^{10}$, aryl substituted with 0–3 $R^{10}$, benzyl substituted with 0–3 $R^{10}$, and $C_1–C_5$ alkoxy substituted with 0–3 $R^{10}$, NHC(=O)$R^{11}$, C(=O)$NHR^{11}$, NHC(=O)$NHR^{11}$, $NHR^{11}$, $R^{11}$, and a bond to $S_f$;
$R^{10}$ is independently selected at each occurrence from the group: a bond to $S_f$, $COOR^{11}$, C(=O)$NHR^{11}$, NHC(=O)$R^{11}$, OH, $NHR^{11}$, $SO_3H$, $PO_3H$, —$OPO_3H_2$, —$OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;
$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $S_f$;

210

$R^{12}$ is a bond to $S_f$;
k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5;
x' is selected from 0, 1, 2, 3, 4, and 5;
$S_f$ is a surfactant which is a lipid or a compound of the formula:

$A^9{-}E^1{-}A^{10}$;

$A^9$ is selected from the group: OH and $OR^{27}$;
$A^{10}$ is $OR^{27}$;
$R^{27}$ is C(=O)$C_{1-20}$ alkyl;
$E^1$ is $C_{1-10}$ alkylene substituted with 1–3 $R^{28}$;
$R^{28}$ is independently selected at each occurrence from the group: $R^{30}$, —$PO_3H$—$R^{30}$, =O, —$CO_2R^{29}$, —C(=O)$R^{29}$, —C(=O)$N(R^{29})_2$, —$CH_2OR^{29}$, —$OR^{29}$, —$N(R^{29})_2$, $C_1–C_5$ alkyl, and $C_2–C_4$ alkenyl;
$R^{29}$ is independently selected at each occurrence from the group: $R^{30}$, H, $C_1–C_6$ alkyl, phenyl, benzyl, and trifluoromethyl;
$R^{30}$ is a bond to $L_n$;
and a pharmaceutically acceptable salt thereof.

8. A compound according to claim 7, wherein the compound is of the formula:

$Q{-}L_n{-}S_f$ wherein, Q is a compound of Formula (IV):

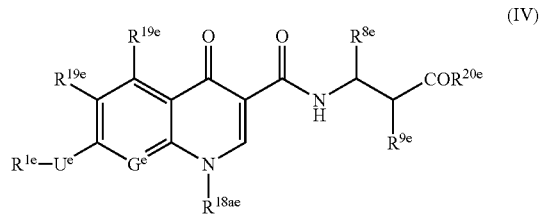

(IV)

including stereoisomeric forms thereof, or mixtures of stereoisomeric forms thereof, or pharmaceutically acceptable salt or prodrug forms thereof wherein:
$R^{1e}$ is selected from:

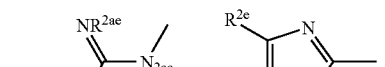 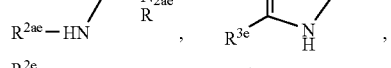 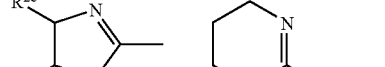 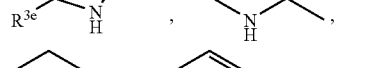 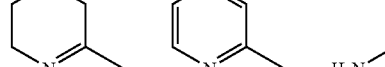 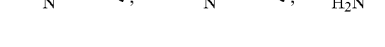

-continued

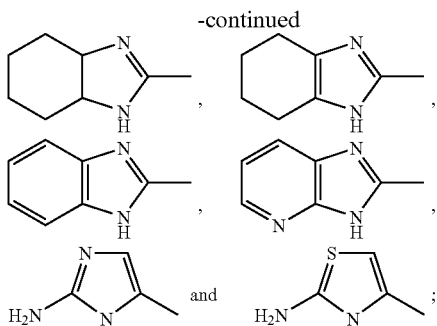

and $R^{2e}$ and $R^{3e}$ are independently selected from:

H, $C_1–C_4$ alkoxy, $NR^{11e}R^{12e}$, halogen, $NO_2$, CN, $CF_3$, $C_1–C_6$ alkyl, $C_3–C_6$ alkenyl, $C_3–C_7$ cycloalkyl, $C_3–C_7$ cycloalkyl($C_1–C_4$ alkyl), aryl($C_1–C_6$ alkyl)-, ($C_1–C_6$ alkyl)carbonyl, ($C_1–C_6$ alkoxy)carbonyl, arylcarbonyl, and aryl substituted with 0–4 $R^{7e}$, alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1–C_4$ alkyl, $C_1–C_4$ alkoxy, halo, cyano, amino, $CF_3$ and $NO_2$;

$R^{2ae}$ is selected from:

H, $C_1–C_{10}$ alkyl, $C_2–C_6$ alkenyl, $C_3–C_{11}$ cycloalkyl, $C_3–C_7$ cycloalkyl($C_1–C_4$ alkyl), aryl, aryl($C_1–C_4$ alkyl)-, ($C_2–C_7$ alkyl)carbonyl, arylcarbonyl, ($C_2–C_{10}$ alkoxy)carbonyl, $C_3–C_7$ cycloalkoxycarbonyl, $C_7–C_{11}$ bicycloalkoxycarbonyl, aryloxycarbonyl, aryl ($C_1–C_{10}$ alkoxy)carbonyl, p1 $C_1–C_6$ alkylcarbonyloxy ($C_1–C_4$ alkoxy)carbonyl, arylcarbonyloxy($C_1–C_4$ alkoxy)carbonyl, and $C_3–C_7$ cycloalkylcarbonyloxy($C_1–C_4$ alkoxy)carbonyl;

$R^{7e}$ is selected from:

H, hydroxy, $C_1–C_4$ alkyl, $C_1–C_4$ alkoxy, aryl, aryl($C_1–C_4$ alkyl)-, ($C_1–C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:

—$(CH_2)_n{}^e$—, —$(CH_2)_n{}^e O(CH_2)_m{}^e$—, —$NH(CH_2)_n{}^e$—, —$N(R^{10e})C(=O)$—, —$NHC(=O)(CH_2)_n{}^e$—, and —$C(=O)N(R^{10e})$—;

$G^e$ is N or $CR^{19e}$;

$R^{8e}$ is selected from:

H, $CO_2R^{18be}$, $C(=O)R^{18be}$, $CONR^{17e}R^{18be}$,
$C_1–C_{10}$ alkyl substituted with 0–1 $R^{6e}$,
$C_2–C_{10}$ alkenyl substituted with 0–1 $R^{6e}$,
$C_2–C_{10}$ alkynyl substituted with 0–1 $R^{6e}$,
$C_3–C_8$ cycloalkyl substituted with 0–1 $R^{6e}$,
$C_5–C_6$ cycloalkenyl substituted with 0–1 $R^{6e}$,
($C_1–C_{10}$ alkyl)carbonyl,
$C_3–C_{10}$ cycloalkyl($C_1–C_4$ alkyl)-,
phenyl substituted with 0–3 $R^{6e}$,
naphthyl substituted with 0–3 $R^{6e}$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{9e}$ is selected from:

$C_1–C_{10}$ alkyl substituted with 0–1 $R^{6e}$,
$C_1–C_{10}$ alkoxy substituted with 0–2 $R^{7e}$, H, nitro, $N(R^{11e})R^{12e}$, $OC(=O)R^{10e}$, $OR^{10e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, hydroxy, $OR^{22e}$, —$N(R^{10e})R^{11e}$, —$N(R^{16e})R^{17e}$, aryl($C_0–C_6$ alkyl)carbonyl, aryl($C_1–C_6$ alkyl), heteroaryl($C_1–C_6$ alkyl), $CONR^{18ae}R^{20e}$, $SO_2R^{18ae}$, and $SO_2NR^{18ae}R^{20e}$, providing that any of the above alkyl, cycloalkyl, aryl or heteroaryl groups may be unsubstituted or substituted independently with 1–2 $R^{7e}$;

$R^{6e}$ is selected from:

H, $C_1–C_{10}$ alkyl, hydroxy, $C_1–C_{10}$ alkoxy, nitro, $C_1–C_{10}$ alkylcarbonyl, —$N(R^{11e})R^{12e}$, cyano, halo, $CF_3$, CHO, $CO_2R^{18be}$, $C(=O)R^{18be}$, $CONR^{17e}R^{18be}$, $OC(=O)R^{10e}$, $OR^{10e}$, $OC(=O)NR^{10e}R^{11e}$, $NR^{10e}C(=O)R^{10e}$, $NR^{10e}C(=O)OR^{21e}$, $NR^{10e}C(=O)NR^{10e}R^{11e}$, $NR^{10e}SO_2NR^{10e}R^{11e}$, $NR^{10e}SO_2R^{21e}$, $S(O)_p{}^e R^{11e}$, $SO_2NR^{10e}R^{11e}$, aryl substituted with 0–3 groups selected from halogen, $C_1–C_6$ alkoxy, $C_1–C_6$ alkyl, $CF_3$, $S(O)_m{}^e Me$, and —$NMe_2$, aryl($C_1–C_4$ alkyl)-, said aryl being substituted with 0–3 groups selected from halogen, $C_1–C_6$ alkoxy, $C_1–C_6$ alkyl, $CF_3$, $S(O)_p{}^e Me$, and —$NMe_2$, and a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:

H, $CF_3$, $C_3–C_6$ alkenyl, $C_3–C_{11}$ cycloalkyl, aryl, ($C_3–C_{11}$ cycloalkyl)methyl, aryl($C_1–C_4$ alkyl), and $C_1–C_{10}$ alkyl substituted with 0–2 $R^{6e}$;

$R^{11e}$ is selected from:

H, hydroxy, $C_1–C_8$ alkyl, $C_3–C_6$ alkenyl, $C_3–C_{11}$ cycloalkyl, ($C_3–C_{11}$ cycloalkyl)methyl, $C_1–C_6$ alkoxy, benzyloxy, aryl, heteroaryl, heteroaryl($C_1–C_4$ alkyl)-, aryl($C_1–C_4$ alkyl), adamantylmethyl, and $C_1–C_{10}$ alkyl substituted with 0–2 $R^{4e}$;

$R^{4e}$ is selected from:

H, $C_1–C_6$ alkyl, $C_3–C_7$ cycloalkyl, $C_3–C_7$ cycloalkyl ($C_1–C_4$ alkyl)-, aryl, heteroaryl, aryl($C_1–C_6$ alkyl)-, and heteroaryl($C_1–C_6$ alkyl)-, wherein said aryl or heteroaryl groups are substituted with 0–2 substituents independently selected from the group consisting of $C_1–C_4$ alkyl, $C_1–C_4$ alkoxy, F, Cl, Br, $CF_3$, and $NO_2$, $R^{12e}$ is selected from:

H, $C_1–C_6$ alkyl, triphenylmethyl, methoxymethyl, methoxyphenyldiphenylmethyl, trimethylsilylethoxymethyl, ($C_1–C_6$ alkyl)carbonyl, ($C_1–C_6$ alkoxy)carbonyl, ($C_1–C_6$ alkyl)aminocarbonyl, $C_3–C_6$ alkenyl, $C_3–C_7$ cycloalkyl, $C_3–C_7$ cycloalkyl($C_1–C_4$ alkyl)-, aryl, heteroaryl($C_1–C_6$ alkyl)carbonyl, heteroarylcarbonyl, aryl ($C_1–C_6$ alkyl)-, ($C_1–C_6$ alkyl)carbonyl, arylcarbonyl, $C_1–C_6$ alkylsulfonyl, arylsulfonyl, aryl($C_1–C_6$ alkyl) sulfonyl, heteroarylsulfonyl, heteroaryl($C_1–C_6$ alkyl) sulfonyl, aryloxycarbonyl, and aryl($C_1–C_6$ alkoxy)carbonyl, wherein said aryl groups are substituted with 0–2 substituents selected from the group consisting of $C_1–C_4$ alkyl, $C_1–C_4$ alkoxy, halo, $CF_3$, and nitro;

$R^{16e}$ is selected from:

—$C(=O)OR^{18ae}$, —$C(=O)R^{18be}$, —$C(=O)N(R^{18be})_2$, —$SO_2R^{18ae}$, and —$SO_2N(R^{18be})_2$;

$R^{17e}$ is selected from:

H, $C_1–C_6$ alkyl, $C_3–C_7$ cycloalkyl, $C_3–C_7$ cycloalkyl ($C_1–C_4$ alkyl)-, aryl, aryl($C_1–C_6$ alkyl)-, and heteroaryl ($C_1–C_6$ alkyl);

$R^{18ae}$ is selected from:
$C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
H, halogen, $CF_3$, $CO_2H$, CN, $NO_2$, —$NR^{11e}R^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-$SO_2$—, heteroaryl, and heteroaryl-$SO^2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
hydroxy, $C_1$–$C_{10}$ alkyloxy, $C_3$–$C_{11}$ cycloalkyloxy, aryloxy, aryl($C_1$–$C_4$ alkyl)oxy,
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl)oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl)oxy,
(5-($C_1$–$C_5$ alkyl)-1,3-dioxa-cyclopenten-2-one-yl)methyloxy,
(5-aryl-1,3-dioxa-cyclopenten-2-one-yl)methyloxy, and
($R^{10e}$)($R^{11e}$)N—($C_1$–$C_{10}$ alkoxy)-;

$R^{21e}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^{7e}$;

$R^{22e}$ is selected from:
—C(=O)—$R^{18be}$, —C(=O)N($R^{18be}$)$_2$, —C(=O)NHSO$_2$$R^{18ae}$,
—C(=O)NHC(=O)$R^{18be}$, —C(=O)NHC(=O)O$R^{18ae}$, and
—C(=O)NHSO$_2$NH$R^{18be}$;

$m^e$ is 0–2;
$n^e$ is 0–4; and
$p^e$ is 0–2;
with the following proviso: $n^e$ and $m^e$ are chosen such that the number of atoms connecting $R^1$ and —$COR^{20e}$ in Formula (IV) is in the range of 8–14;

W is independently selected at each occurrence from the group: O, S, NH, NHC(=O), C(=O)NH, $NR^8$C(=O), C(=O)$NR^8$, C(=O), C(=O)O, OC(=O), NHC(=S) NH, NHC(=O)NH, SO$_2$, SO$_2$NH, (OCH$_2$CH$_2$)$_{20-200}$, (CH$_2$CH$_2$O)$_{20-200}$, (OCH$_2$CH$_2$CH$_2$)$_{20-200}$, (CH$_2$CH$_2$CH$_2$O)$_{20-200}$, and (aa)$_{t'}$;

aa is independently at each occurrence an amino acid;
Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, SO$_3$H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC (=O)$R^{11}$, C(=O)NH$R^{11}$, NHC(=O)NH$R^{11}$, NH$R^{11}$, $R^{11}$, and a bond to $S_f$;

k is 0 or 1;
$S_f$ is a surfactant which is a lipid or a compound of the formula:

$$A^9 \diagdown E^1 \text{—} A^{10};$$

$A^9$ is $OR^{27}$;
$A^{10}$ is $OR^{27}$;
$R^{27}$ is C(=O)$C_{1-15}$ alkyl;
$E^1$ is $C_{1-4}$ alkylene substituted with 1–3 $R^{28}$;
$R^{28}$ is independently selected at each occurrence from the group: $R^{30}$, —PO$_3$H—$R^{30}$, =O, —CO$_2R^{29}$, —C(=O)$R^{29}$, —CH$_2$O$R^{29}$, —O$R^{29}$, and $C_1$–$C_5$ alkyl;
$R^{29}$ is independently selected at each occurrence from the group: $R^{30}$, H, $C_1$–$C_6$ alkyl, phenyl, and benzyl;
$R^{30}$ is a bond to $L_n$;
and a pharmaceutically acceptable salt thereof.

9. An ultrasound contrast agent composition, comprising:
(a) a compound of claim 7, comprising: an quinolone that binds to the integrin $\alpha_v\beta_3$, a surfactant and a linking group between the quinolone and the surfactant;
(b) a parenterally acceptable carrier; and,
(c) an echogenic gas.

10. An ultrasound contrast agent composition of claim 9, further comprising: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

11. An ultrasound contrast agent composition of claim 10, wherein the echogenic gas is a $C_{2-5}$ perfluorocarbon.

12. A method of imaging cancer in a patient comprising: (1) administering, by injection or infusion, a ultrasound contrast agent composition of claim 9 to a patient; and (2) imaging the patient using sonography.

13. A method of imaging formation of new blood vessels in a patient comprising: (1) administering, by injection or infusion, a ultrasound contrast agent composition of claim 9 to a patient; (2) imaging the area of the patient wherein the desired formation of new blood vessels is located.

14. A method of imaging therapeutic angiogenesis in a patient comprising: (1) administering, by injection or infusion, an ultrasound contrast agent composition of claim 9 to a patient; (2) imaging the area of the patient wherein the desired formation of new blood vessels is located.

15. A method of imaging atherosclerosis in a patient comprising: (1) administering, by injection or infusion, an ultrasound contrast agent composition of claim 9 to a patient; (2) imaging the area of the patient wherein the atherosclerosis is located.

16. A method of imaging restenosis in a patient comprising: (1) administering, by injection or infusion, an ultrasound contrast agent composition of claim 9 to a patient; (2) imaging the area of the patient wherein the restenosis is located.

17. A method of imaging cardiac ischemia in a patient comprising: (1) administering, by injection or infusion, an ultrasound contrast agent composition of claim 9 to a patient; (2) imaging the area of the myocardium wherein the ischemic region is located.

18. A method of imaging myocardial reperfusion injury in a patient comprising: (1) administering, by injection or infusion, an ultrasound contrast agent composition of claim 9 to a patient; (2) imaging the area of myocardium wherein the reperfusion injury is located.

19. A kit for treating cancer, comprising a compound comprising a targeting moiety and a chelator, wherein the targeting moiety is bound to the chelator, is a quinolone nonpeptide, and binds to a receptor that is upregulated during angiogenesis and the compound has 0–1 linking groups between the targeting moiety and chelator, wherein the receptor is the integrin $\alpha_v\beta_3$ or $\alpha_v\beta_3$ and the compound is of the formula:

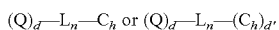

wherein, Q is a compound of Formula (II):

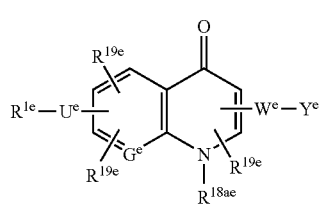

including stereoisomeric forms thereof or mixtures of stereoisomeric forms thereof, or pharmaceutically acceptable salt or prodrug forms thereof wherein:

$R^{1e}$ is selected from:

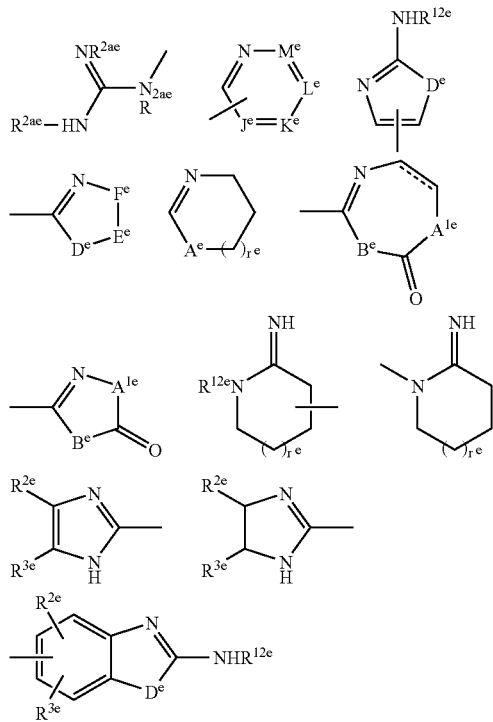

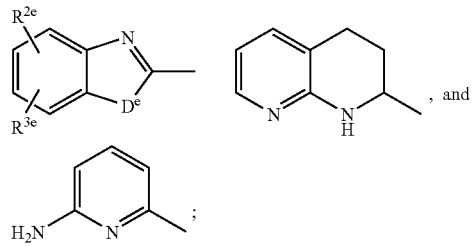

$A^e$ is —$CH_2$— or —$N(R^{10e})$—;

$A^{1e}$ and $B^e$ are independently —$CH_2$— or —$N(R^{10e})$—;

$D^e$ is —$N(R^{10e})$— or —S—;

$E^e$—$F^e$ is —$C(R^{2e})$=$C(R^{3e})$— or —$C(R^{2e})_2C(R^{3e})_2$—;

$J^e$ is —$C(R^{2e})$— or —N—;

$K^e$, $L^e$ and $M^e$ are independently —$C(R^{2e})$— or —$C(R^{3e})$—;

$R^{2e}$ and $R^{3e}$ are independently selected from:

H, $C_1$–$C_4$ alkoxy, $NR^{11e}R^{12e}$, halogen, $NO_2$, CN, $CF_3$, $C_1$–$C_6$ alkyl, $C_3$–$C_6$ alkenyl, $C_3$–$C_7$ cycloalkyl, $C_3$–$C_7$ cycloalkyl($C_1$–$C_4$ alkyl), aryl($C_1$–$C_6$ alkyl)-, ($C_1$–$C_6$ alkyl)carbonyl, ($C_1$–$C_6$ alkoxy)carbonyl, arylcarbonyl, and aryl substituted with 0–4 $R^{7e}$, alternatively, when $R^{2e}$ and $R^{3e}$ are substituents on adjacent atoms, they can be taken together with the carbon atoms to which they are attached to form a 5–7 membered carbocyclic or 5–7 membered heterocyclic aromatic or nonaromatic ring system, said carbocyclic or heterocyclic ring being substituted with 0–2 groups selected from $C_1$–$C_4$ alkyl, $C_1$–$C_4$ alkoxy, halo, cyano, amino, $CF_3$ and $NO_2$;

$R^{2ae}$ is selected from:

H, $C_1$–$C_{10}$ alkyl, $C_2$–$C_6$ alkenyl, $C_3$–$C_{11}$ cycloalkyl, $C_3$–$C_7$ cycloalkyl($C_1$–$C_4$ alkyl), aryl, aryl($C_1$–$C_4$ alkyl)-, ($C_2$–$C_7$ alkyl)carbonyl, arylcarbonyl, ($C_2$–$C_{10}$ alkoxy)carbonyl, $C_3$–$C_7$ cycloalkoxycarbonyl, $C_7$–$C_{11}$ bicycloalkoxycarbonyl, aryloxycarbonyl, aryl($C_1$–$C_{10}$ alkoxy)carbonyl, $C_1$–$C_6$ alkylcarbonyloxy($C_1$–$C_4$ alkoxy)carbonyl, arylcarbonyloxy($C_1$–$C_4$ alkoxy)carbonyl, and $C_3$–$C_7$ cycloalkylcarbonyloxy($C_1$–$C_4$ alkoxy)carbonyl;

$R^{7e}$ is selected from:

H, hydroxy, $C_1$–$C_4$ alkyl, $C_1$–$C_4$ alkoxy, aryl, aryl($C_1$–$C_4$ alkyl)-, ($C_1$–$C_4$ alkyl)carbonyl, $CO_2R^{18ae}$, $SO_2R^{11e}$, $SO_2NR^{10e}R^{11e}$, $OR^{10e}$, and $N(R^{11e})R^{12e}$;

$U^e$ is selected from:

—$(CH_2)_n^e$—, —$(CH_2)_n^eO(CH_2)_m^e$—, —$(CH_2)_n^eN(R^{12})(CH_2)_m^e$—, —$NH(CH_2)_n^e$—, —$(CH_2)_n^eC(=O)(CH_2)_m^e$—,

—$(CH_2)_n^eS(O)_p^e(CH_2)_m^e$—, —$(CH_2)_n^eNHNH(CH_2)_m^e$—,

—$N(R^{10e})C(=O)$—, —$NHC(=O)(CH_2)_n^e$—, —$C(=O)N(R^{10e})$—, and —$N(R^{10e})S(O)_p^e$—;

$G^e$ is N or $CR^{19e}$;

$W^e$ is —$C(=O)$—$N(R^{10e})$—$(C_1$–$C_3$ alkylene)-, in which the alkylene group is substituted by $R^{8e}$ and by $R^{9e}$:

$R^{8e}$ and $R^{9e}$ are independently selected from:

H, $CO_2R^{18be}$, $C(=O)R^{18be}$, $CONR^{17}R^{18be}$, $C_1$–$C_{10}$ alkyl substituted with 0–1 $R^{6e}$, $C_2$–$C_{10}$ alkenyl substituted with 0–1 $R^{6e}$, $C_2$–$C_{10}$ alkynyl substituted with 0–1 $R^{6e}$, $C_3$–$C_8$ cycloalkyl substituted with 0–1 $R^{6e}$, $C_5$–$C_6$ cycloalkenyl substituted with 0–1 $R^{6e}$, ($C_1$–$C_{10}$ alkyl)carbonyl, $C_3$–$C_{10}$ cycloalkyl($C_1$–$C_4$ alkyl)-,
phenyl substituted with 0–3 $R^{6e}$,
naphthyl substituted with 0–3 $R^{6e}$,
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$,
$C_1$–$C_{10}$ alkoxy substituted with 0–2 $R^{7e}$,
hydroxy, nitro, —N($R^{10e}$)$R^{11e}$, —N($R^{16e}$)$R^{17e}$, aryl ($C_0$–$C_6$ alkyl)carbonyl, aryl($C_3$–$C_6$ alkyl), heteroaryl ($C_1$–$C_6$ alkyl), CONR$^{18ae}$R$^{20e}$, SO$_2$R$^{18ae}$, and SO$_2$NR$^{18ae}$R$^{20e}$,
providing that any of the above alkyl, cycloalkyl, aryl or heteroaryl groups may be unsubstituted or substituted independently with 1–2 $R^{7e}$;

$R^{6e}$ is selected from:
H, $C_1$–$C_{10}$ alkyl, hydroxy, $C_1$–$C_{10}$ alkoxy, nitro, $C_1$–$C_{10}$ alkylcarbonyl, —N($R^{11e}$)$R^{12e}$, cyano, halo, $CF_3$, CHO, $CO_2R^{18be}$, C(=O)R$^{18be}$, CONR$^{17e}$R$^{18be}$, OC(=O)R$^{10e}$, OR$^{10e}$, OC(=O)NR$^{10e}$R$^{11e}$, NR$^{10e}$C(=O)R$^{10e}$, NR$^{10e}$C(=O)OR$^{21e}$, NR$^{10e}$C(=O)NR$^{10e}$R$^{11e}$, NR$^{10e}$SO$_2$NR$^{10e}$R$^{11e}$, NR$^{10e}$SO$_2$R$^{21e}$, S(O)$_p$R$^{11e}$, SO$_2$NR$^{10e}$R$^{11e}$,
aryl substituted with 0–3 groups selected from halogen, $C_1$–$C_6$ alkoxy, $C_1$–$C_6$ alkyl, $CF_3$, $S(O)_m^e$Me, and —NMe$_2$,
aryl($C_1$–$C_4$ alkyl)-, said aryl being substituted with 0–3 groups selected from halogen, $C_1$–$C_6$ alkoxy, $C_1$–$C_6$ alkyl, $CF_3$, $S(O)_p^e$Me, and —NMe$_2$, and
a 5–10 membered heterocyclic ring containing 1–3 N, O, or S heteroatoms, wherein said heterocyclic ring may be saturated, partially saturated, or fully unsaturated, said heterocyclic ring being substituted with 0–2 $R^{7e}$;

$R^{10e}$ is selected from:
H, $CF_3$, $C_3$–$C_6$ alkenyl, $C_3$–$C_{11}$ cycloalkyl, aryl, ($C_3$–$C_{11}$ cycloalkyl)methyl, aryl($C_1$–$C_4$ alkyl), and $C_1$–$C_{10}$ alkyl substituted with 0–2 $R^{6e}$;

$R^{11e}$ is selected from:
H, hydroxy, $C_1$–$C_8$ alkyl, $C_3$–$C_6$ alkenyl, $C_3$–$C_{11}$ cycloalkyl, ($C_3$–$C_{11}$ cycloalkyl)methyl, $C_1$–$C_6$ alkoxy, benzyloxy, aryl, heteroaryl, heteroaryl($C_1$–$C_4$ alkyl)-, aryl($C_1$–$C_4$ alkyl), adamantylmethyl, and $C_1$–$C_{10}$ alkyl substituted with 0–2 $R^{4e}$;

$R^{4e}$ is selected from:
H, $C_1$–$C_6$ alkyl, $C_3$–$C_7$ cycloalkyl, $C_3$–$C_7$ cycloalkyl ($C_1$–$C_4$ alkyl)-, ($C_1$–$C_{10}$ alkyl)carbonyl, aryl, heteroaryl, aryl($C_1$–$C_6$ alkyl)-, and heteroaryl($C_1$–$C_6$ alkyl)-, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$,
alternatively, when $R^{10e}$ and $R^{11e}$ are both substituents on the same nitrogen atom (as in —NR$^{10e}$R$^{11e}$) they may be taken together with the nitrogen atom to which they are attached to form a heterocycle selected from: 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl, and 1-piperazinyl;
said heterocycle being substituted with 0–3 groups selected from: $C_1$–$C_6$ alkyl, aryl, heteroaryl, aryl($C_1$–$C_4$ alkyl)-, ($C_1$–$C_6$ alkyl)carbonyl, ($C_3$–$C_7$ cycloalkyl)carbonyl, ($C_1$–$C_6$ alkoxy)carbonyl, aryl($C_1$–$C_4$ alkoxy)carbonyl, $C_1$–$C_6$ alkylsulfonyl, and arylsulfonyl;

$R^{12e}$ is selected from:
H, $C_1$–$C_6$ alkyl, triphenylmethyl, methoxymethyl, methoxyphenyldiphenylmethyl, trimethylsilylethoxymethyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_3$–$C_7$ cycloalkyl($C_1$–$C_4$ alkyl)-, aryl, heteroaryl($C_1$–$C_6$ alkyl)carbonyl, heteroarylcarbonyl, aryl ($C_1$–$C_6$ alkyl)-, ($C_1$–$C_6$ alkyl)carbonyl, arylcarbonyl, $C_1$–$C_6$ alkylsulfonyl, arylsulfonyl, aryl($C_1$–$C_6$ alkyl) sulfonyl, heteroarylsulfonyl, heteroaryl($C_1$–$C_6$ alkyl) sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{16e}$ is selected from:
—C(=O)OR$^{18ae}$, —C(=O)R$^{18be}$, —C(=O)N(R$^{18be}$)$_2$, —C(=O)NHSO$_2$R$^{18ae}$, —C(=O)NHC(=O)R$^{18be}$, —C(=O)NHC(=O)OR$^{18ae}$, —C(=O)NHSO$_2$NHR$^{18be}$, —SO$_2$R$^{18ae}$, —SO$_2$N(R$^{18be}$)$_2$, and —SO$_2$NHC(=O)OR$^{18be}$;

$R^{17e}$ is selected from:
H, $C_1$–$C_6$ alkyl, $C_3$–$C_7$ cycloalkyl, $C_3$–$C_7$ cycloalkyl ($C_1$–$C_4$ alkyl)-, aryl, aryl($C_1$–$C_6$ alkyl)-, and heteroaryl ($C_1$–$C_6$ alkyl);

$R^{18ae}$ is selected from:
$C_1$–$C_8$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, heteroaryl($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl) optionally substituted with a bond to $L_n$, heteroaryl optionally substituted with a bond to $L_n$, phenyl substituted with 3–4 $R^{19e}$ and optionally substituted with a bond to $L_n$, naphthyl substituted with 0–4 $R^{19e}$ and optionally substituted with a bond to $L_n$, and a bond to $L_n$, wherein said aryl or heteroaryl groups are optionally substituted with 0–4 $R^{19e}$;

$R^{18be}$ is H or $R^{18ae}$;

$R^{19e}$ is selected from:
H, halogen, $CF_3$, $CO_2H$, CN, $NO_2$, —NR$^{11e}$R$^{12e}$, $OCF_3$, $C_1$–$C_8$ alkyl, $C_2$–$C_6$ alkenyl, $C_2$–$C_6$ alkynyl, $C_3$–$C_{11}$ cycloalkyl, $C_3$–$C_7$ cycloalkyl($C_1$–$C_4$ alkyl)-, aryl ($C_1$–$C_6$ alkyl)-, $C_1$–$C_6$ alkoxy, $C_1$–$C_4$ alkoxycarbonyl, aryl, aryl-O—, aryl-SO$_2$—, heteroaryl, and heteroaryl-SO$_2$—, wherein said aryl and heteroaryl groups are substituted with 0–4 groups selected from hydrogen, halogen, $CF_3$, $C_1$–$C_3$ alkyl, and $C_1$–$C_3$ alkoxy;

$R^{20e}$ is selected from:
hydroxy, $C_1$–$C_{10}$ alkyloxy, $C_3$–$C_{11}$ cycloalkyloxy, aryloxy, aryl($C_1$–$C_4$ alkyl)oxy, $C_2$–$C_{10}$ alkylcarbonyloxy($C_1$–$C_2$ alkyl)oxy-, $C_2$–$C_{10}$ alkoxycarbonyloxy($C_1$–$C_2$ alkyl)oxy-, $C_2$–$C_{10}$ alkoxycarbonyl($C_1$–$C_2$ alkyl)oxy-, $C_3$–$C_{10}$ cycloalkylcarbonyloxy($C_1$–$C_2$ alkyl)oxy-, $C_3$–$C_{10}$ cycloalkoxycarbonyloxy($C_1$–$C_2$ alkyl)oxy-, $C_3$–$C_{10}$ cycloalkoxycarbonyl($C_1$–$C_2$ alkyl)oxy-, aryloxycarbonyl($C_1$–$C_2$ alkyl)oxy-, aryloxycarbonyloxy($C_1$–$C_2$ alkyl)oxy-, arylcarbonyloxy($C_1$–$C_2$ alkyl)oxy-, $C_1$–$C_5$ alkoxy($C_1$–$C_5$ alkyl)carbonyloxy($C_1$–$C_2$ alkyl) oxy, (5-($C_1$–$C_5$ alkyl)-1,3-dioxa-cyclopenten-2-one-yl)methyloxy, (5-aryl-1,3-dioxa-cyclopenten-2-one-yl)methyloxy, and (R$^{10e}$)(R$^{11e}$)N—(C$_1$–C$_{10}$ alkoxy)-;

$R^{21e}$ is selected from:
$C_1$–$C_8$ alkyl, $C_2$–$C_6$ alkenyl, $C_3$–$C_{11}$ cycloalkyl, ($C_3$–$C_{11}$ cycloalkyl)methyl, aryl, aryl($C_1$–$C_4$ alkyl)-, and $C_1$–$C_{10}$ alkyl substituted with 0–2 $R^{7e}$;

$R^{22e}$ is selected from:
—C(=O)—$R^{18be}$, —C(=O)N($R^{18be}$)$_2$, —C(=O)NHSO$_2R^{18ae}$, —C(=O)NHC(=O)$R^{18be}$, —C(=O)NHC(=O)O$R^{18ae}$, and —C(=O)NHSO$_2$NH$R^{18be}$;

$Y^e$ is selected from:
—COR$^{20e}$, —SO$_3$H, —PO$_3$H, —CONHNHSO$_2$CF$_3$, —CONHSO$_2R^{18ae}$, —CONHSO$_2$NHR$^{18be}$, —NH-COCF$_3$, —NHCONHSO$_2R^{18ae}$, —NHSO$_2R^{18ae}$, —OPO$_3$H$_2$, —OSO$_3$H, —PO$_3$H$_2$, —SO$_2$NHCOR$^{18ae}$, —SO$_2$NHCO$_2R^{18ae}$,

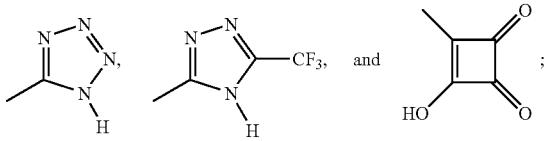

$m^e$ is 0–2;
$n^e$ is 0–4;
$p^e$ is 0–2;
$r^e$ is 0–2;
with the following proviso: $n^e$ and $m^e$ are chosen such that the number of atoms connecting $R^{1e}$ and $Y^e$ is in the range of 8–14;
d is selected from 1, 2, 3, 4, 5, 6, 7, 8, 9, and 10;
d' is 1–100;
$L_n$ is a linking group having the formula:

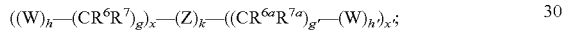

W is independently selected at each occurrence from the group: O, S, NH, NHC(=O), C(=O)NH, NR$^8$C(=O), C(=O)NR$^8$, C(=O), C(=O)O, OC(=O), NHC(=S)NH, NHC(=O)NH, SO$_2$, SO$_2$NH, (OCH$_2$CH$_2$)$_s$, (CH$_2$CH$_2$O)$_s$, (OCH$_2$CH$_2$CH$_2$)$_{s''}$, (CH$_2$CH$_2$CH$_2$O)$_t$, and (aa)$_{t'}$;
aa is independently at each occurrence an amino acid;
Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;
$R^6$, $R^{6a}$, $R^7$, $R^{7a}$, and $R^8$ are independently selected at each occurrence from the group: H, =O, COOH, SO$_3$H, PO$_3$H, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)R$^{11}$, C(=O)NHR$^{11}$, NHC(=O)NHR$^{11}$, NHR$^{11}$, $R^{11}$, and a bond to $C_h$;
$R^{10}$ is independently selected at each occurrence from the group: a bond to $C_h$, COOR$^{11}$, C(=O)NHR$^{11}$, NHC(=O)R$^{11}$, OH, NHR$^{11}$, SO$_3$H, PO$_3$H, —OPO$_3$H$_2$, —OSO$_3$H, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;
$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R_{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $C_h$;
$R^{12}$ is a bond to $C_h$;
k is selected from 0, 1, and 2;
h is selected from 0, 1, and 2;
h' is selected from 0, 1, and 2;
g is selected from 0, 1, 2, 3, 4, 5, 6, 7, 8, 9, and 10;
g' is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
x is selected from 0, 1, 2, 3, 4, and 5;
x' is selected from 0, 1, 2, 3, 4, and 5;
$C_h$ is a metal bonding unit having a formula selected from the group:

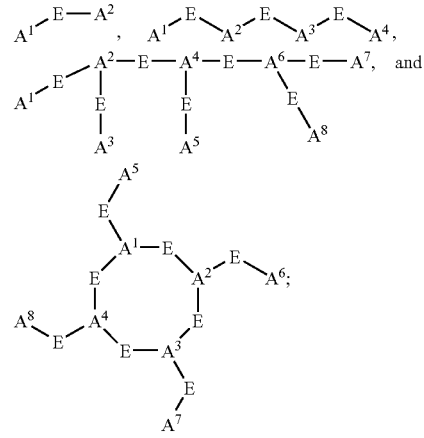

$A^1$, $A^2$, $A^3$, $A^4$, $A^5$, $A^6$, $A^7$, and $A^8$ are independently selected at each occurrence from the group: NR$^{13}$, NR$^{13}$R$^{14}$, S, SH, S(Pg), O, OH, PR$^{13}$, PR$^{13}$R$^{14}$, P(O)R$^{15}$R$^{16}$, and a bond to $L_n$;
E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;
$R^{13}$ and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form $=C(R^{20})(R^{21})$;

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —$C(=O)R^{18}$, —$C(=O)N(R^{18})_2$, —CHO, —$CH_2OR^{18}$, —$OC(=O)R^{18}$, —$OC(=O)OR^{18a}$, —$OR^{18}$, —$OC(=O)N(R^{18})_2$, —$NR^{19}C(=O)R^{18}$, —$NR^{19}C(=O)OR^{18a}$, —$NR^{19}C(=O)N(R^{18})_2$, —$NR^{19}SO_2N(R^{18})_2$, —$NR^{19}SO_2R^{18a}$, —$SO_3H$, —$SO_2R^{18a}$, —$SR^{18}$, —$S(=O)R^{18a}$, —$SO_2N(R^{18})_2$, —$N(R^{18})_2$, —NHC(=S)$NHR^{18}$, =$NOR^{18}$, $NO_2$, —$C(=O)NHOR^{18}$, —$C(O)NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$, and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —$C(=O)R^{25}$, —$C(=O)N(R^{25})_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

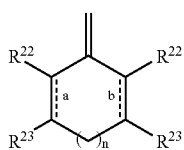

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —$C(=O)R^{25}$, —$C(=O)N(R^{25})_2$, —$N(R^{25})_3^+$, —$CH_2OR^{25}$, —$OC(=O)R^{25}$, —$OC(=O)OR^{25a}$, —$OR^{25}$, —$OC(=O)N(R^{25})_2$, —$NR^{26}C(=O)R^{25}$, —$NR^{26}C(=O)OR^{25a}$, —$NR^{26}C(=O)N(R^{25})_2$, —$NR^{26}SO_2N(R^{25})_2$, —$NR^{26}SO_2R^{25a}$, —$SO_3H$, —$SO_2R^{25a}$, —$SR^{25}$, —$S(=O)R^{25a}$, —$SO_2N(R^{25})_2$, —$N(R^{25})_2$, =$NOR^{25}$, —$C(=O)NHOR^{25}$, —$OCH_2CO_2H$, and 2-(1-morpholino)ethoxy; and, $R^{25}$, $R^{25a}$, and $R^{26}$ are each independently selected at each occurrence from the group: hydrogen and $C_1$–$C_6$ alkyl, or a pharmaceutically acceptable salt thereof, and at least one agent selected from the group consisting of a chemotherapeutic agent and a radiosensitizer agent, or a pharmaceutically acceptable salt thereof, and a pharmaceutically acceptable carrier.

20. A kit according to claim 19 wherein said kit comprises a plurality of separate containers, wherein at least one of said containers contains a compound of claim 2, or a pharmaceutically acceptable salt thereof, and at least another of said containers contains one or more agents selected from the group consisting of a chemotherapeutic agent and a radiosensitizer agent, or a pharmaceutically acceptable salt thereof, and a pharmaceutically acceptable carrier.

21. A kit according to claim 19, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

22. A kit according to claim 19, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, and lisuride.

23. A kit according to claim 19 wherein the chemotherapeutic agent is selected from the group consisting of oxymetholone, tamoxifen, progesterone, mepitiostane, epitiostanol, and formestane.

24. A kit according to claim 19 wherein the chemotherapeutic agent is selected from the group consisting of interferon-alpha, interferon-2 alpha, interferon-beta, interferon-gamma, colony stimulating factor-1, colony stimulating factor-2, denileukin diftitox, interleukin-2, and leutinizing hormone releasing factor.

25. A kit according to claim 19, wherein radiosensitizer agent is selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino- 1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

26. A process for the preparation of diagnostic or therapeutic metallopharmaceutical composition, said process comprising generating a macrostructure from a plurality of molecular components wherein the plurality of components includes a targeting moiety and a chelator, wherein the targeting moiety is a quinolone nonpeptide, which is bound to the chelator, and binds to a receptor that is upregulated during angiogenesis and the compound has 0–1 linking groups between the targeting moiety and chelator.

* * * * *